US 12,337,199 B2

United States Patent
Cao et al.

(10) Patent No.: US 12,337,199 B2
(45) Date of Patent: Jun. 24, 2025

(54) STABLE ANTIBODY FORMULATION

(71) Applicant: REGENERON PHARMACEUTICALS, INC., Tarrytown, NY (US)

(72) Inventors: Yuan Cao, White Plains, NY (US); Dingjiang Liu, Pleasantville, NY (US); Long Xu, Shanghai (CN)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 457 days.

(21) Appl. No.: 17/155,432

(22) Filed: Jan. 22, 2021

(65) Prior Publication Data

US 2021/0252146 A1    Aug. 19, 2021

Related U.S. Application Data

(60) Provisional application No. 62/965,786, filed on Jan. 24, 2020.

(51) Int. Cl.
| | |
|---|---|
| *A61K 39/395* | (2006.01) |
| *A61K 39/42* | (2006.01) |
| *A61K 47/22* | (2006.01) |
| *A61K 47/26* | (2006.01) |
| *A61P 31/12* | (2006.01) |

(52) U.S. Cl.
CPC ........ *A61K 39/39591* (2013.01); *A61K 39/42* (2013.01); *A61K 47/22* (2013.01); *A61K 47/26* (2013.01); *A61P 31/12* (2018.01)

(58) Field of Classification Search
None
See application file for complete search history.

(56) References Cited

U.S. PATENT DOCUMENTS

| | | | |
|---|---|---|---|
| 4,997,423 A | | 3/1991 | Okuda et al. |
| 5,908,686 A | | 6/1999 | Sudo et al. |
| 6,286,699 B1 | | 9/2001 | Sudo |
| 6,629,949 B1 | | 10/2003 | Douglas |
| 6,630,144 B1 | | 10/2003 | Hart et al. |
| 6,645,635 B2 | | 11/2003 | Muraki |
| 6,659,982 B2 | | 12/2003 | Douglas et al. |
| 6,875,433 B2 | | 4/2005 | Hart et al. |
| 7,226,554 B2 | | 6/2007 | Sudo et al. |
| 7,335,356 B2 | | 2/2008 | Hart et al. |
| 8,513,391 B2 | | 8/2013 | Jones et al. |
| 9,771,414 B2 | * | 9/2017 | Kyratsous .............. C07K 16/10 |
| 10,081,670 B2 | * | 9/2018 | Kyratsous ............... A61P 31/14 |
| 10,501,526 B2 | * | 12/2019 | Kyratsous .......... A61K 39/3955 |
| 10,829,544 B2 | * | 11/2020 | Kyratsous ............... A61K 43/00 |
| 11,530,255 B2 | * | 12/2022 | Kyratsous ............... A61P 43/00 |
| 2009/0232795 A1 | * | 9/2009 | Condra ..................... A61P 3/06 |
| | | | 536/23.53 |
| 2016/0215040 A1 | | 7/2016 | Kyratsous et al. |
| 2016/0304607 A1 | | 10/2016 | Sadineni et al. |

FOREIGN PATENT DOCUMENTS

| | | |
|---|---|---|
| EP | 1539238 | 11/2007 |
| WO | WO 2010048615 | 4/2010 |
| WO | WO2012/135408 A1 | 10/2012 |
| WO | WO2014/031718 A1 | 2/2014 |
| WO | WO 2016123019 | 8/2016 |
| WO | WO2018/204405 A1 | 11/2018 |
| WO | WO2019/206987 A1 | 10/2019 |

OTHER PUBLICATIONS

Rudikoff et al, Proc Natl Acad Sci USA 1982 vol. 79 p. 1979-1983.*
Bolton, et al. (2011) "Effect of Protein and Solution Properties on the Donnan Effect During the Ultrafiltration of Proteins", Biotechnol. Prog. 27(1):140-152.
Cao, et al. (2019) "Charge Variants Characterization and Release Assay Development for Co-Formulated Antibodies as a Combination Therapy", mAbs 11(3):489-499.
European Medicines Agency (2008) "Guideline on the Non-Clinical Development of Fixed Combination Medicinal Productions" Version 1:1-6.
European Medicines Agency (2017) "Guideline on Clinical Development of Fixed Combination Medicinal Products" Revision 2:1-12.
FDA (2018) "Combination Product Definition Combination Product Types" https://www.fda.gov/combination-products/about-combination-products/combination-product-definition-combination-product-types#:~:text=Any%20investigational%20drug%2C%20device%2C%20or,use%2C%20indication%2C%20or%20effect.
Glover et al., (2013) "Compatibility and Stability of Pertuzumab and Trastuzumab Admixtures in i.v. Infusion Bags for Coadministration", J Pharm Sci., 102(3):794-812.
Henricks, et al. (2015) "The use of Combinations of Monoclonal Antibodies in Clinical Oncology", Cancer Treatment Reviews, 41:859-867.
Karali "Fixed Dose Combination (FDC) Products Overview" PharmaCircle LLC https://www.pharmacircle.com/presentations/Fixed_Dose.pdf.
Kirschbrown, et al. (2019) "Development of a Subcutaneous Fixed-Dose Combination of Pertuzumab and Trastuzumab: Results From the Phase Ib Dose-Finding Study", The Journal of Clinical Pharmacology, 59(5):702-716.

(Continued)

*Primary Examiner* — Yunsoo Kim
(74) *Attorney, Agent, or Firm* — FisherBroyles, LLP; Cara L. Crowley-Weber; Gabriele Amodeo

(57) ABSTRACT

The present disclosure provides stable pharmaceutical formulations comprising a human antibody that specifically binds to Ebola Virus (EBOV). In certain embodiments, the formulations contain, in addition to an anti-EBOV antibody, a buffer, an amino acid, a non-ionic surfactant, and a stabilizer. The pharmaceutical formulations of the present disclosure exhibit a substantial degree of antibody stability upon stress, for example, agitation during transport, and storage, for example, storage at temperatures greater than 40° C.

63 Claims, 2 Drawing Sheets

Specification includes a Sequence Listing.

(56) References Cited

OTHER PUBLICATIONS

Meehan, et al. (1997) "A Microinfusor Device for the Delivery of Therapeutic Levels of Peptides and Macromolecules", J. Controlled Release, 46:107-116.
Mueller et al. (2018) "Challenges for the Pharmaceutical Technical Development of Protein Coforumulations", Journal of Pharmacy and Pharmacology, 70: 666-674.
Patel, et al. (2018) "Coformulation of Broadly Neutralizing Antibodies 3BNC117 and PGT121: Analytical Challenges During Preformulation Characterization and Storage Stability Studies", Journal of Pharmaceutical Sciences, 107: 3032-3046.
Robinson (2002) "Protein Deamidation", PNAS, 99(8):5283-5288.
Shpilberg & Jackisch (2013) "Subcutaneous Administration of Rituximab (MabThera) and Trastuzumab (Herceptin) Using Hualuronidase", British Journal of Cancer, 109:1556-1561.
Svitel (2019) "Analytical Strategies for Fixed-Dose Coformulated Protein Therapeutics", BioProcess International.
U.S. Department of Health and Human Services (2013) "Guideline for Industry: Codevelopment of Two or More New Investigational Drugs for Use in Combinations" 1-13.
Wang, et al. (2007) "Antibody Structure, Instability, and Formulation", J. Pharma. Sci. 96: 1-26.
Who Drug Information (2003) "Regulatory Challenges" 17(3):174-177.
Woldeyes, et al. (2018) "Viscosities and Protein Interactions of Bispecific Antibodies and Their Monospecific Mixtures", Molecular Pharmaceutics, 15:4745-4755.
Baek, et al. (2016) "Effects of Histidine and Sucrose on the Biophysical Properties of a Monoclonal Antibody", Pharm. Res., 34:629-639.
Falconer (2019) "Advances in Liquid Formulations of Parenteral Therapeutic Proteins", Biotechnology Advances 37 (7):107412, 9pages.
International Search Report and Written Opinion received in PCT/US2021/014524 on May 12, 2021 (16 pages).
Kang, et al. (2016) "Rapid Formulation Development for Monoclonal Antibodies", Internet Link URL: http://www.bioprocessintl.com/manufacturing/formulation/rapid-formulation-development-for-monoclonal-antibodies/.
Dondelinger et al. (2018) "Understanding the Significance and Implications of Antibody Numbering and AntigenBinding Surface/Residue Definition", Frontiers in Immunology, 9(2278): 1-15.

\* cited by examiner

Figure 1: Overlay of H1H17203P, H1H17139P, and H1H17161P RP-UPLC Chromatograms
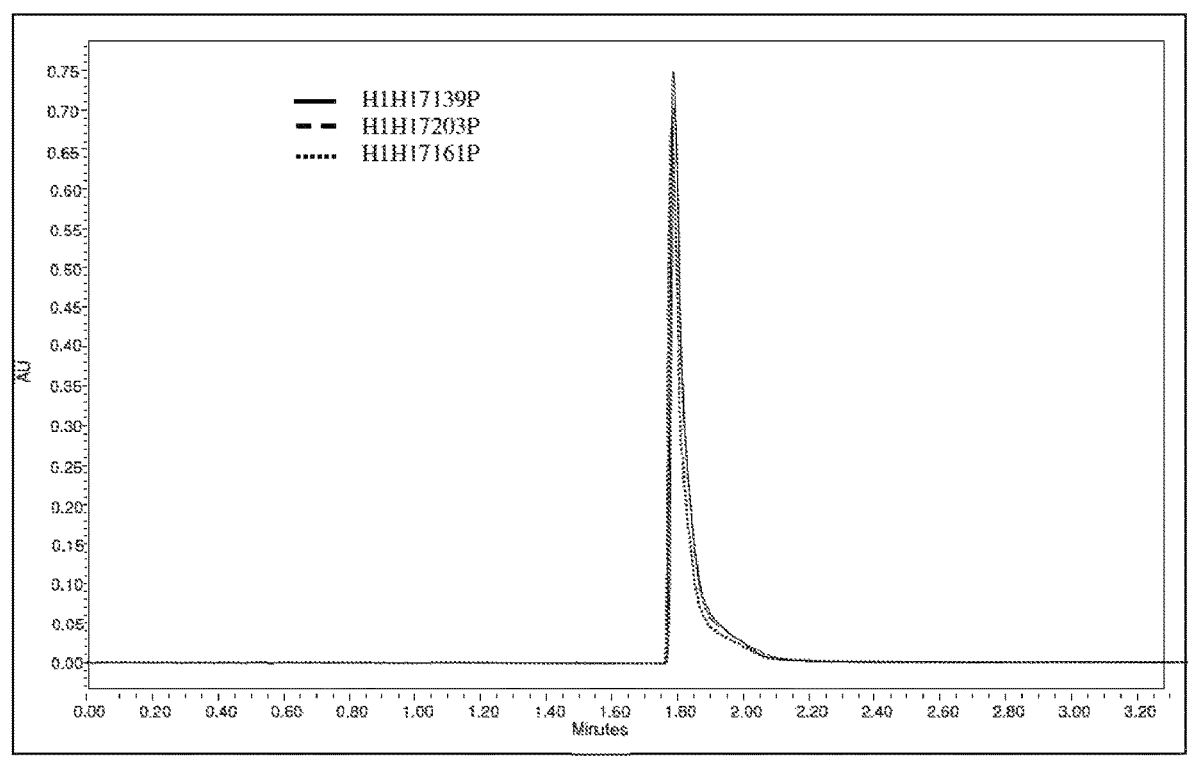
RP-UPLC chromatograms of 50 mg/mL H1H17203P (dashes – –), 50 mg/mL H1H17139P (solid —), and 50 mg/mL H1H17161P (circle dots ······).

Figure 2:   Overlay of H1H17203P, H1H17139P and H1H17161P SE-UPLC Chromatograms
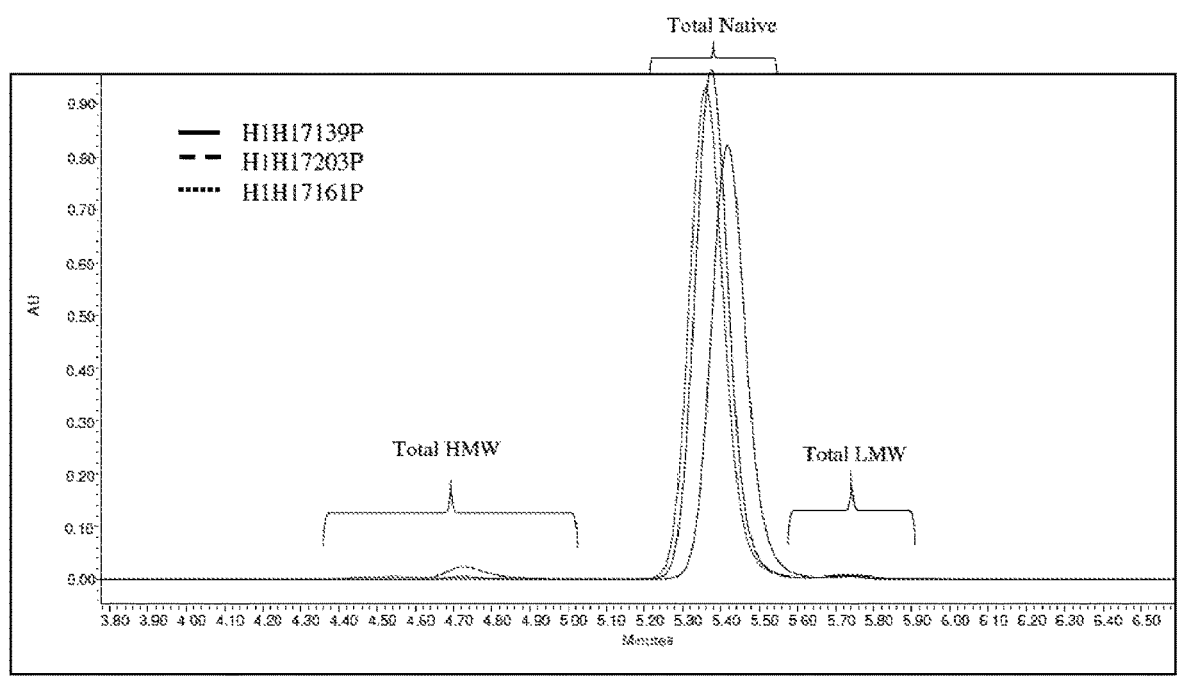
SE-UPLC chromatograms of H1H17203P (dashes— —), H1H17139P (solid ———), H1H17161P (circle dots······ ).

SEQUENCE LISTING

<160> NUMBER OF SEQ ID NOS: 54

<210> SEQ ID NO 1
<211> LENGTH: 348
<212> TYPE: DNA
<213> ORGANISM: Artificial Sequence
<220> FEATURE:
<223> OTHER INFORMATION: Synthetic

<400> SEQUENCE: 1

```
caggtgcagc tggtggagtc tgggggaggc gtggtccagc ctggaggtc cctgagactc        60 tcctgtgcag cgtctggctt caccttcaat aactatggca tgcactgggt ccgccaggct       120
ccaggcatgg ggctggagtg ggtggcagtt atatggcacg atggaagtga taaatactat       180
gcagactccg tgaagggccg attcaccatc tccagagaca attccaagaa cacgctgtat       240
ctgcaaatga acagcctgag agccgaggac acggctgtgt attactgtgc gagaaattgg       300
aacctctttg actactgggg ccagggaacc ctggtcactg tctcctca                    348
```

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Met Gly Leu Glu Trp Val
        35                  40                  45

Ala Val Ile Trp His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Asn Leu Phe Asp Tyr Trp Gly Gln Gly Thr Leu Val
            100                 105                 110
```

Thr Val Ser Ser
    115

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3
ggcttcacct tcaataacta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asn Asn Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
atatggcacg atggaagtga taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Trp His Asp Gly Ser Asp Lys
1               5

<210> SEQ ID NO 7
<211> LENGTH: 27
<212> TYPE: DNA
<213> ORGANISM: Artificial Sequence
<220> FEATURE:
<223> OTHER INFORMATION: Synthetic

<400> SEQUENCE: 7
gcgagaaatt ggaacctctt tgactac                                       27

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Ala Arg Asn Trp Asn Leu Phe Asp Tyr
1               5

<210> SEQ ID NO 9
<211> LENGTH: 324
<212> TYPE: DNA
<213> ORGANISM: Artificial Sequence
<220> FEATURE:
<223> OTHER INFORMATION: Synthetic

<400> SEQUENCE: 9

```
gacatccaga tgacccagtc tccatcctcc ctgtctgcat ctgtaggaga cagaatcacc     60
atcacttgcc gggcaagtca gagcatcagc acctatttac attggtatca gcagaaacca    120
gggaaagccc ctaagctcct gatctatgct gcatccactt tgcagagtgg ggtcccatca    180
aggttcagtg gcagtggatc tgggacagat ttcactctca ccatcagcag tctgcaacct    240
gaagattttg caacttacta ctgtcaacag agtttcagta cccctccgat aaacttcggc    300
caagggacca agctggagat caaa                                           324
```

<210> SEQ ID NO 10
<211> LENGTH: 108
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Thr Tyr
            20                  25                  30

Leu His Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Pro
                85                  90                  95

Ile Asn Phe Gly Gln Gly Thr Lys Leu Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11

```
cagagcatca gcacctat                                                   18
```

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Thr Tyr
1               5

<210> SEQ ID NO 13

-continued

```
<211> LENGTH: 9
<212> TYPE: DNA
<213> ORGANISM: Artificial Sequence
<220> FEATURE:
<223> OTHER INFORMATION: Synthetic

<400> SEQUENCE: 13 gctgcatcc                                                                    9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Ala Ala Ser
1

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
caacagagtt tcagtacccc tccgataaac                                             30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Ser Phe Ser Thr Pro Pro Ile Asn
1               5                   10

<210> SEQ ID NO 17
<211> LENGTH: 446
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Asn Asn Tyr
            20                  25                  30

Gly Met His Trp Val Arg Gln Ala Pro Gly Met Gly Leu Glu Trp Val
        35                  40                  45

Ala Val Ile Trp His Asp Gly Ser Asp Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Trp Asn Leu Phe Asp Tyr Trp Gly Gln Gly Thr Leu Val
            100                 105                 110
```

```
Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 18
<211> LENGTH: 215
<212> TYPE: PRT
<213> ORGANISM: Artificial Sequence
<220> FEATURE:
<223> OTHER INFORMATION: Synthetic

<400> SEQUENCE: 18

Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Ser Ile Ser Thr Tyr
            20                  25                  30
```

Leu His Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Phe Ser Thr Pro Pro
                 85                  90                  95

Ile Asn Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 19
<211> LENGTH: 354
<212> TYPE: DNA
<213> ORGANISM: Artificial Sequence
<220> FEATURE:
<223> OTHER INFORMATION: Synthetic

<400> SEQUENCE: 19
gaggtgcagc tggtggagtc tgggggaggc ttggtacagc ctggggggtc cctgagactc      60
tcctgtgcag cctctggatt caccttcagt agctacgaca tgcactgggt ccgccaagct     120
acaggaaaag gtctggagtg ggtctcagct attggtactg ctggtgacac atactatcca     180
ggctccgtga aggccgatt caccatctcc agagaaaatg ccaaaaactc cttgtatctt     240
caaatgaaca gcctgagagc cggggacacg gctgtgtatt actgtgcaag aacatggttc     300
ggggagcttt actttgacta ctggggccag ggaaccctgg tcaccgtctc ctca          354

<210> SEQ ID NO 20
<211> LENGTH: 118
<212> TYPE: PRT
<213> ORGANISM: Artificial Sequence
<220> FEATURE:
<223> OTHER INFORMATION: Synthetic

<400> SEQUENCE: 20

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Asp Met His Trp Val Arg Gln Ala Thr Gly Lys Gly Leu Glu Trp Val
         35                  40                  45

Ser Ala Ile Gly Thr Ala Gly Asp Thr Tyr Tyr Pro Gly Ser Val Lys
 50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
            85                  90                  95

Arg Thr Trp Phe Gly Glu Leu Tyr Phe Asp Tyr Trp Gly Gln Gly Thr
        100                 105                 110

Leu Val Thr Val Ser Ser
        115

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
ggattcacct tcagtagcta cgac                                    24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Gly Phe Thr Phe Ser Ser Tyr Asp
1               5

<210> SEQ ID NO 23
<211> LENGTH: 21
<212> TYPE: DNA
<213> ORGANISM: Artificial Sequence
<220> FEATURE:
<223> OTHER INFORMATION: Synthetic

<400> SEQUENCE: 23
attggtactg ctggtgacac a                                       21

<210> SEQ ID NO 24
<211> LENGTH: 7
<212> TYPE: PRT
<213> ORGANISM: Artificial Sequence
<220> FEATURE:
<223> OTHER INFORMATION: Synthetic

<400> SEQUENCE: 24

Ile Gly Thr Ala Gly Asp Thr
1               5

<210> SEQ ID NO 25
<211> LENGTH: 36
<212> TYPE: DNA
<213> ORGANISM: Artificial Sequence
<220> FEATURE:
<223> OTHER INFORMATION: Synthetic

<400> SEQUENCE: 25
gcaagaacat ggttcgggga gctttacttt gactac                       36

<210> SEQ ID NO 26
<211> LENGTH: 12
<212> TYPE: PRT

<213> ORGANISM: Artificial Sequence
<220> FEATURE:
<223> OTHER INFORMATION: Synthetic

<400> SEQUENCE: 26

Ala Arg Thr Trp Phe Gly Glu Leu Tyr Phe Asp Tyr
1               5                   10

<210> SEQ ID NO 27
<211> LENGTH: 339
<212> TYPE: DNA
<213> ORGANISM: Artificial Sequence
<220> FEATURE:
<223> OTHER INFORMATION: Synthetic

<400> SEQUENCE: 27

```
gacatcgtga tgacccagtc tccagactcc ctggctgtgt ctctgggcga gagggccacc     60
atcaactgca agtccagcca gagtgtttta tacagctcca acaataagaa ctacttagct    120
tggtaccagc agaaaccagg acagcctcct aagctgctca tttactgggc atctacccgg    180
gaatccgggg tccctgaccg attcagtggc agcgggtctg ggacagaatt cactctcacc    240
atcaccagcc tgcaggctga agatgtggca gtttattact gtcagcaata ttatagtagt    300
ccgctcactt tcggcggagg gaccaaggtg gagatcaaa                            339
```

<210> SEQ ID NO 28
<211> LENGTH: 113
<212> TYPE: PRT
<213> ORGANISM: Artificial Sequence
<220> FEATURE:
<223> OTHER INFORMATION: Synthetic

<400> SEQUENCE: 28

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Glu Phe Thr Leu Thr
65                  70                  75                  80

Ile Thr Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys

<210> SEQ ID NO 29
<211> LENGTH: 36
<212> TYPE: DNA
<213> ORGANISM: Artificial Sequence
<220> FEATURE:
<223> OTHER INFORMATION: Synthetic

<400> SEQUENCE: 29

```
cagagtgttt tatacagctc caacaataag aactac                               36
```

<210> SEQ ID NO 30
<211> LENGTH: 12

```
<212> TYPE: PRT
<213> ORGANISM: Artificial Sequence
<220> FEATURE:
<223> OTHER INFORMATION: Synthetic

<400> SEQUENCE: 30

Gln Ser Val Leu Tyr Ser Ser Asn Asn Lys Asn Tyr
1               5                   10

<210> SEQ ID NO 31
<211> LENGTH: 9
<212> TYPE: DNA
<213> ORGANISM: Artificial Sequence
<220> FEATURE:
<223> OTHER INFORMATION: Synthetic

<400> SEQUENCE: 31 tgggcatct                                                                9

<210> SEQ ID NO 32
<211> LENGTH: 3
<212> TYPE: PRT
<213> ORGANISM: Artificial Sequence
<220> FEATURE:
<223> OTHER INFORMATION: Synthetic

<400> SEQUENCE: 32

Trp Ala Ser
1

<210> SEQ ID NO 33
<211> LENGTH: 27
<212> TYPE: DNA
<213> ORGANISM: Artificial Sequence
<220> FEATURE:
<223> OTHER INFORMATION: Synthetic

<400> SEQUENCE: 33
cagcaatatt atagtagtcc gctcact                                           27

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Gln Gln Tyr Tyr Ser Ser Pro Leu Thr
1               5

<210> SEQ ID NO 35
<211> LENGTH: 448
<212> TYPE: PRT
<213> ORGANISM: Artificial Sequence
<220> FEATURE:
<223> OTHER INFORMATION: Synthetic

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met His Trp Val Arg Gln Ala Thr Gly Lys Gly Leu Glu Trp Val
        35                  40                  45
```

| | | | | | | | | | | | |
|---|---|---|---|---|---|---|---|---|---|---|---|
|Ser|Ala|Ile|Gly|Thr|Ala|Gly|Asp|Thr|Tyr|Tyr|Pro|Gly|Ser|Val|Lys
| |50| | | |55| | | | |60| |

Ser Ala Ile Gly Thr Ala Gly Asp Thr Tyr Tyr Pro Gly Ser Val Lys
       50                55                 60

Gly Arg Phe Thr Ile Ser Arg Glu Asn Ala Lys Asn Ser Leu Tyr Leu
65               70               75               80

Gln Met Asn Ser Leu Arg Ala Gly Asp Thr Ala Val Tyr Tyr Cys Ala
               85               90               95

Arg Thr Trp Phe Gly Glu Leu Tyr Phe Asp Tyr Trp Gly Gln Gly Thr
              100            105            110

Leu Val Thr Val Ser Ser Ala Ser Thr Lys Gly Pro Ser Val Phe Pro
       115               120            125

Leu Ala Pro Ser Ser Lys Ser Thr Ser Gly Gly Thr Ala Ala Leu Gly
130              135               140

Cys Leu Val Lys Asp Tyr Phe Pro Glu Pro Val Thr Val Ser Trp Asn
145              150              155            160

Ser Gly Ala Leu Thr Ser Gly Val His Thr Phe Pro Ala Val Leu Gln
              165            170            175

Ser Ser Gly Leu Tyr Ser Leu Ser Ser Val Val Thr Val Pro Ser Ser
       180               185            190

Ser Leu Gly Thr Gln Thr Tyr Ile Cys Asn Val Asn His Lys Pro Ser
       195               200            205

Asn Thr Lys Val Asp Lys Lys Val Glu Pro Lys Ser Cys Asp Lys Thr
    210              215              220

His Thr Cys Pro Pro Cys Pro Ala Pro Glu Leu Leu Gly Gly Pro Ser
225              230              235            240

Val Phe Leu Phe Pro Pro Lys Pro Lys Asp Thr Leu Met Ile Ser Arg
              245            250            255

Thr Pro Glu Val Thr Cys Val Val Val Asp Val Ser His Glu Asp Pro
       260               265            270

Glu Val Lys Phe Asn Trp Tyr Val Asp Gly Val Glu Val His Asn Ala
              275            280            285

Lys Thr Lys Pro Arg Glu Glu Gln Tyr Asn Ser Thr Tyr Arg Val Val
    290              295              300

Ser Val Leu Thr Val Leu His Gln Asp Trp Leu Asn Gly Lys Glu Tyr
305              310              315            320

Lys Cys Lys Val Ser Asn Lys Ala Leu Pro Ala Pro Ile Glu Lys Thr
              325            330            335

Ile Ser Lys Ala Lys Gly Gln Pro Arg Glu Pro Gln Val Tyr Thr Leu
       340               345            350

Pro Pro Ser Arg Asp Glu Leu Thr Lys Asn Gln Val Ser Leu Thr Cys
       355               360            365

Leu Val Lys Gly Phe Tyr Pro Ser Asp Ile Ala Val Glu Trp Glu Ser
370              375              380

Asn Gly Gln Pro Glu Asn Asn Tyr Lys Thr Thr Pro Pro Val Leu Asp
385              390              395            400

Ser Asp Gly Ser Phe Phe Leu Tyr Ser Lys Leu Thr Val Asp Lys Ser
              405            410            415

Arg Trp Gln Gln Gly Asn Val Phe Ser Cys Ser Val Met His Glu Ala
       420               425            430

Leu His Asn His Tyr Thr Gln Lys Ser Leu Ser Leu Ser Pro Gly Lys
              435            440            445

<210> SEQ ID NO 36
<211> LENGTH: 220
<212> TYPE: PRT

<213> ORGANISM: Artificial Sequence
<220> FEATURE:
<223> OTHER INFORMATION: Synthetic

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Glu Phe Thr Leu Thr
65                  70                  75                  80

Ile Thr Ser Leu Gln Ala Glu Asp Val Ala Val Tyr Tyr Cys Gln Gln
                85                  90                  95

Tyr Tyr Ser Ser Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 37
<211> LENGTH: 354
<212> TYPE: DNA
<213> ORGANISM: Artificial Sequence
<220> FEATURE:
<223> OTHER INFORMATION: Synthetic

<400> SEQUENCE: 37
gaggtgcagc tggtggagtc tgggggaggc ttggtacagc ctggggggtc cctgagactc      60
tcctgtgcag cctctggatt cacctctagc agctatgcca tgaactgggt ccgccaggct     120
ccagggaagg ggctggagtg ggtctcaaca attagtggta tgggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaaggggga     300 tatcccatt cttttgatat ctggggccaa gggacaatgg tcaccgtctc ttca            354

<210> SEQ ID NO 38
<211> LENGTH: 118
<212> TYPE: PRT
<213> ORGANISM: Artificial Sequence
<220> FEATURE:
<223> OTHER INFORMATION: Synthetic

<400> SEQUENCE: 38

-continued

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Met Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Tyr Pro His Ser Phe Asp Ile Trp Gly Gln Gly Thr
            100                 105                 110

Met Val Thr Val Ser Ser
            115

<210> SEQ ID NO 39
<211> LENGTH: 24
<212> TYPE: DNA
<213> ORGANISM: Artificial Sequence
<220> FEATURE:
<223> OTHER INFORMATION: Synthetic

<400> SEQUENCE: 39
ggattcacct ctagcagcta tgcc        24

<210> SEQ ID NO 40
<211> LENGTH: 8
<212> TYPE: PRT
<213> ORGANISM: Artificial Sequence
<220> FEATURE:
<223> OTHER INFORMATION: Synthetic

<400> SEQUENCE: 40

Gly Phe Thr Ser Ser Ser Tyr Ala
1               5

<210> SEQ ID NO 41
<211> LENGTH: 24
<212> TYPE: DNA
<213> ORGANISM: Artificial Sequence
<220> FEATURE:
<223> OTHER INFORMATION: Synthetic

<400> SEQUENCE: 41
attagtggta tgggtggtag caca        24

<210> SEQ ID NO 42
<211> LENGTH: 8
<212> TYPE: PRT
<213> ORGANISM: Artificial Sequence
<220> FEATURE:
<223> OTHER INFORMATION: Synthetic

<400> SEQUENCE: 42

Ile Ser Gly Met Gly Gly Ser Thr
1               5

<210> SEQ ID NO 43
<211> LENGTH: 33
<212> TYPE: DNA

```
<213> ORGANISM: Artificial Sequence
<220> FEATURE:
<223> OTHER INFORMATION: Synthetic

<400> SEQUENCE: 43
gcgaaaaggg gatatcccca ttcttttgat atc                                    33

<210> SEQ ID NO 44
<211> LENGTH: 11
<212> TYPE: PRT
<213> ORGANISM: Artificial Sequence
<220> FEATURE:
<223> OTHER INFORMATION: Synthetic

<400> SEQUENCE: 44

Ala Lys Arg Gly Tyr Pro His Ser Phe Asp Ile
1               5                   10

<210> SEQ ID NO 45
<211> LENGTH: 318
<212> TYPE: DNA
<213> ORGANISM: Artificial Sequence
<220> FEATURE:
<223> OTHER INFORMATION: Synthetic

<400> SEQUENCE: 45
gacatccaga tgacccagtc tccatcctcc ctgtctgcat ctgtaggaga cagagtcacc        60
atcacttgcc gggcaagtca gagcattagc agcttttaa attggtatca gcagaaacca       120
gggaaagccc ctaaactcct gatctatgct gcatccagtt tgcaaagtgg ggtcccatca       180
aggttcagtg gcagtggatc tgggacagat ttcactctca ccatcagcag tctgcaacct      240
gaagattttg caacttacta ctgtcaacag agttacagta ccctcacctt cggccaaggg      300
acacgactgg agattaaa                                                    318

<210> SEQ ID NO 46
<211> LENGTH: 106
<212> TYPE: PRT
<213> ORGANISM: Artificial Sequence
<220> FEATURE:
<223> OTHER INFORMATION: Synthetic

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Thr
                85                  90                  95

Phe Gly Gln Gly Thr Arg Leu Glu Ile Lys
            100                 105

<210> SEQ ID NO 47
<211> LENGTH: 18
<212> TYPE: DNA
<213> ORGANISM: Artificial Sequence
```

<220> FEATURE:
<223> OTHER INFORMATION: Synthetic

<400> SEQUENCE: 47
cagagcatta gcagcttt                                                    18

<210> SEQ ID NO 48
<211> LENGTH: 6
<212> TYPE: PRT
<213> ORGANISM: Artificial Sequence
<220> FEATURE:
<223> OTHER INFORMATION: Synthetic

<400> SEQUENCE: 48

Gln Ser Ile Ser Ser Phe
1               5

<210> SEQ ID NO 49
<211> LENGTH: 9
<212> TYPE: DNA
<213> ORGANISM: Artificial Sequence
<220> FEATURE:
<223> OTHER INFORMATION: Synthetic

<400> SEQUENCE: 49 gctgcatcc                                                               9

<210> SEQ ID NO 50
<211> LENGTH: 3
<212> TYPE: PRT
<213> ORGANISM: Artificial Sequence
<220> FEATURE:
<223> OTHER INFORMATION: Synthetic

<400> SEQUENCE: 50

Ala Ala Ser
1

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
caacagagtt acagtaccct cacc                                             24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gln Gln Ser Tyr Ser Thr Leu Thr
1               5

<210> SEQ ID NO 53
<211> LENGTH: 448
<212> TYPE: PRT
<213> ORGANISM: Artificial Sequence
<220> FEATURE:
<223> OTHER INFORMATION: Synthetic

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ser Ser Ser Tyr
            20                  25                  30

Ala Met Asn Trp Val Arg Gln Ala Pro Gly Lys Gly Leu Glu Trp Val
        35                  40                  45

Ser Thr Ile Ser Gly Met Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Tyr Pro His Ser Phe Asp Ile Trp Gly Gln Gly Thr
            100                 105                 110

Met Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415
```

```
Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 54
<211> LENGTH: 213
<212> TYPE: PRT
<213> ORGANISM: Artificial Sequence
<220> FEATURE:
<223> OTHER INFORMATION: Synthetic

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Thr
                85                  90                  95

Phe Gly Gln Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

STABLE ANTIBODY FORMULATION

RELATED APPLICATIONS

This application claims priority under 35 U.S.C. § 119(e) of U.S. Provisional Application No. 62/965,786, filed Jan. 24, 2020; the disclosure of which is herein incorporated by reference in its entirety.

GOVERNMENT LICENSE RIGHTS

This invention was made with Government support under Agreement HHS0100201500013C and HHS0100201700016C awarded by the U.S. Department of Health and Human Services. The government has certain rights in the invention.

SEQUENCE LISTING

An official copy of the sequence listing is submitted concurrently with the specification electronically via EFS-Web as an ASCII formatted sequence listing with a file name of "10668US01_Sequence_Listing_ST25.txt", a creation date of Jan. 22, 2021, and a size of about 36 KB. The sequence listing contained in this ASCII formatted document is part of the specification and is herein incorporated by reference in its entirety.

FIELD OF THE INVENTION

The present disclosure relates to the field of therapeutic antibody formulations. More specifically, the present disclosure relates to the field of pharmaceutical formulations comprising one or more human antibodies that specifically bind to Ebola virus (EBOV).

BACKGROUND

Therapeutic macromolecules (e.g., antibodies) must be formulated in a manner that not only makes the molecules suitable for administration to patients, but also maintains their stability during storage and subsequent use. For example, therapeutic antibodies in liquid solution are prone to degradation, aggregation or undesired chemical modifications unless the solution is formulated properly. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation, and the visual quality or appeal of the formulation. Thus, when formulating a therapeutic antibody, great care must be taken to arrive at a formulation that remains stable, contains an adequate concentration of antibody, and possesses a suitable viscosity as well as other properties which enable the formulation to be conveniently administered to patients. Antibodies to the Ebola virus (EBOV) are one example of a therapeutically relevant macromolecule that requires proper formulation. Anti-EBOV antibodies are clinically useful for the prevention and/or treatment of Ebola virus infection. Exemplary anti-EBOV antibodies are described, inter alia, in U.S. Pat. Nos. 10,501,526 10,081,670, 9,771,414, 6,630,144, 6,875, 433, 7,335,356, and 8,513,391, and in WO 2016/123019, EP1539238, EP2350270, and EP8513391.

Although anti-EBOV antibodies are known, there remains a need in the art for novel pharmaceutical formulations comprising anti-EBOV antibodies that are sufficiently stable and suitable for administration to patients, including patients located in remote environments or environments lacking access to refrigeration for therapeutics.

BRIEF SUMMARY

The present disclosure satisfies the aforementioned need by providing stable pharmaceutical formulations comprising a human antibody that specifically binds to Ebola virus (EBOV).

In one aspect, a stable liquid pharmaceutical formulation is provided comprising: (a) a stabilizer comprising a sugar; (b) a buffer comprising histidine; (c) an organic cosolvent comprising polysorbate; and (d) at least one antibody which binds specifically to Ebola virus (EBOV).

In various embodiments, the at least one antibody that specifically binds to EBOV is provided at a concentration from about 5±0.75 mg/mL to about 250±37.5 mg/mL. In some embodiments, 250 mg/mL is the maximum protein concentration in the formulation. In some aspects, the 250 mg/mL protein comprises up to three antibodies. In some aspects, a maximum protein concentration in a formulation comprising three antibodies would range from about 5±0.75 mg/mL to about 250 mg/mL±37.5 mg/mL.

The ratio of the two or three antibodies present in the formulation can be modified depending on outcome measurements. In some aspects, the two antibodies are present in a 1:1 ratio. In some aspects, the antibodies are present in a 1:2 ratio. In some aspects, the two antibodies are present in a ratio of about 1 to 10:1. In some aspects, the three antibodies are present in a 1:1:1 ratio. In some aspects, the three antibodies are present in a 1:2:1 ratio. In some aspects, the three antibodies are present in a 2:1:1 ratio. In some aspects, the three antibodies are present in a 1:1:2 ratio. In some aspects, the antibodies are present in a ratio of about 1 to 10:1 to 10:1 to 10.

In some embodiments, the dosage is about 3000 mg, about 2000 mg, about 1500 mg, 1000 mg, about 800 mg, about 750 mg, about 500 mg, about 250 mg, about 200 mg, about 150 mg, about 100 mg, about 75 mg, about 50 mg, or about 25 mg. In some aspects, a dosage comprises one anti-EBOV antibody. In some aspects, a dosage comprises two anti-EBOV antibodies. In some aspects, a dosage comprises three anti-EBOV antibodies. In one embodiment, the co-formulated antibodies are delivered intravenously over a time period of about 2 hours.

In one embodiment, the at least one antibody is provided at a concentration of 12.5 mg/mL±1.85 mg/mL, or about 12.5 mg/mL. In one embodiment, the at least one antibody is provided at a concentration of 25 mg/mL±3.75 mg/mL, or about 25 mg/mL. In another embodiment, the at least one antibody is provided at a concentration of 50 mg/mL±7.5 mg/mL, or about 50 mg/mL. In another embodiment, the at least one antibody is provided at a concentration of 100 mg/mL±15 mg/mL, or about 100 mg/mL. In another embodiment, the at least one antibody is provided at a concentration of 125 mg/mL±18.75 mg/mL, or about 125 mg/mL. In one embodiment, the at least one antibody is provided at a concentration of 150 mg/mL±22.5 mg/mL, or about 150 mg/mL. In another embodiment, the at least one antibody is provided at a concentration of 175 mg/mL±26.25 mg/mL, or about 175 mg/mL. In another embodiment, the at least one antibody is provided at a concentration of 200 mg/mL±30 mg/mL, or about 200 mg/mL. In another embodiment, the at least one antibody is provided at a concentration of 250 mg/mL±37.5 mg/mL, or about 250 mg/mL.

In some embodiments, each antibody is administered at 50 mg/kg of body weight. In one embodiment, three antibodies are co-formulated such that the final formulation provides for each antibody to be administered at 50 mg/kg of body weight. Accordingly, the final dose to be administered to the patient is 150 mg/kg of body weight, with the three antibodies in the formulation at a 1:1:1 ratio. In one embodiment, the co-formulated antibodies are delivered intravenously over a time period of about 2 hours.

In certain embodiments, the formulation comprises any one or more of the anti-EBOV antibodies disclosed in US Patent Application Publication No: 2016/0215040, incorporated herein in its entirety. In certain embodiments, the anti-EBOV antibody comprises (a) a heavy chain variable region (HCVR) comprising heavy chain complementarity determining regions 1, 2 and 3 (HCDR1-HCDR2-HCDR3) each comprising a sequence of SEQ ID NO: 4, SEQ ID NO: 6, and SEQ ID NO: 8, respectively; and (b) a light chain variable region (LCVR) comprising light chain complementarity determining regions 1, 2 and 3 (LCDR1-LCDR2-LCDR3) each comprising a sequence of SEQ ID NO: 12, SEQ ID NO: 14, and SEQ ID NO: 16, respectively. In one embodiment, the antibody comprises a HCVR comprising the amino acid sequence of SEQ ID NO: 2 and a LCVR comprising the amino acid sequence of SEQ ID NO: 10. In one embodiment, the antibody comprises a heavy chain comprising the amino acid sequence of SEQ ID NO: 17 and a light chain comprising the amino acid sequence of SEQ ID NO: 18. In one embodiment, the antibody comprises a HCVR having at least 90% sequence identity to SEQ ID NO: 2. In one embodiment, the antibody comprises a LCVR having at least 90% sequence identity to SEQ ID NO: 10. In one embodiment, the antibody comprises a HCVR having at least 95% sequence identity to SEQ ID NO: 2 and a LCVR having at least 95% sequence identity to SEQ ID NO: 10.

In certain embodiments, the anti-EBOV antibody comprises (a) a heavy chain variable region (HCVR) comprising heavy chain complementarity determining regions 1, 2 and 3 (HCDR1-HCDR2-HCDR3) each comprising a sequence of SEQ ID NO: 22, SEQ ID NO: 24, and SEQ ID NO: 26, respectively; and (b) a light chain variable region (LCVR) comprising light chain complementarity determining regions 1, 2 and 3 (LCDR1-LCDR2-LCDR3) each comprising a sequence of SEQ ID NO: 30, SEQ ID NO: 32, and SEQ ID NO: 34, respectively. In one embodiment, the antibody comprises a HCVR comprising the amino acid sequence of SEQ ID NO: 20 and a LCVR comprising the amino acid sequence of SEQ ID NO: 28. In one embodiment, the antibody comprises a heavy chain comprising the amino acid sequence of SEQ ID NO: 35 and a light chain comprising the amino acid sequence of SEQ ID NO: 36. In one embodiment, the antibody comprises a HCVR having 90% sequence identity to SEQ ID NO: 20. In one embodiment, the antibody comprises a LCVR having 90% sequence identity to SEQ ID NO: 28. In one embodiment, the antibody comprises a HCVR having 95% sequence identity to SEQ ID NO: 20 and a LCVR having 95% sequence identity to SEQ ID NO: 28.

In certain embodiments, the anti-EBOV antibody comprises (a) a heavy chain variable region (HCVR) comprising heavy chain complementarity determining regions 1, 2 and 3 (HCDR1-HCDR2-HCDR3) each comprising a sequence of SEQ ID NO: 40, SEQ ID NO: 42, and SEQ ID NO: 44, respectively; and (b) a light chain variable region (LCVR) comprising light chain complementarity determining regions 1, 2 and 3 (LCDR1-LCDR2-LCDR3) each comprising a sequence of SEQ ID NO: 48, SEQ ID NO: 50, and SEQ ID NO: 52, respectively. In one embodiment, the antibody comprises a HCVR comprising the amino acid sequence of SEQ ID NO: 38 and a LCVR comprising the amino acid sequence of SEQ ID NO: 46. In one embodiment, the antibody comprises a heavy chain comprising the amino acid sequence of SEQ ID NO: 53 and a light chain comprising the amino acid sequence of SEQ ID NO: 54. In one embodiment, the antibody comprises a HCVR having 90% sequence identity to SEQ ID NO: 38. In one embodiment, the antibody comprises a LCVR having 90% sequence identity to SEQ ID NO: 46. In one embodiment, the antibody comprises a HCVR having 95% sequence identity to SEQ ID NO: 38 and a LCVR having 95% sequence identity to SEQ ID NO: 46.

In one embodiment, the pH of the liquid formulation is pH 6.0±0.5, pH 6.0±0.4, pH 6.0±0.3, pH 6.0±0.2, pH 6.0±0.1, pH 6.0±0.05, pH 6.0±0.01, or pH 6.0. In one embodiment, the pH of the liquid formulation is about pH 6.0±0.3.

In one embodiment, the buffer comprises histidine. In certain embodiments, the histidine buffer is at a concentration of from 5 mM±1 mM to 50 mM±10 mM, or from 5 mM±1 mM to 25 mM±5 mM. In one embodiment, the histidine buffer is at a concentration of 10 mM±2 mM or about 10 mM. In one embodiment, the histidine buffer is at a concentration of 20 mM±4 mM or about 20 mM. In one embodiment, the histidine buffer is at a concentration of 40 nM±8 mM or about 40 nM. In certain embodiments, the histidine buffer comprises L-histidine and L-histidine monohydrochloride monohydrate. In one embodiment, L-histidine is at a concentration of from 2 mM±0.4 mM to 25 mM±5 mM, preferably from 4 mM±0.8 mM to 20 mM±4 mM. In one embodiment, L-histidine monohydrochloride monohydrate is at a concentration of from 2 mM±0.4 mM to 25 mM±5 mM, preferably from 4 mM±0.8 mM to 20 mM±4 mM. In one embodiment, the buffer comprises L-histidine at a concentration of 4.8 mM±0.96 mM and L-histidine monohydrochloride monohydrate at a concentration of 5.2 mM±1.04 mM. In one embodiment, the buffer comprises histidine at a concentration of 10 mM±2 mM, wherein the histidine comprises L-histidine at a concentration of 4.8 mM±0.96 mM and L-histidine monohydrochloride monohydrate at a concentration of 5.2 mM±1.04 mM.

In certain embodiments, the organic cosolvent is a nonionic polymer containing a polyoxyethylene moiety. In one embodiment, the organic cosolvent is a surfactant. In some embodiments, the organic cosolvent is any one or more of polysorbate, poloxamer 188 and polyethylene glycol 3350. In one embodiment, the organic cosolvent is polysorbate 80. In one embodiment, the organic cosolvent is polysorbate 20.

In one embodiment, the organic cosolvent is at a concentration of from about 0.01%±0.005% to about 1%±0.5% "weight to volume" or "w/v", wherein, e.g., 0.1 g/ml=10% and 0.01 g/ml=1%. In certain embodiments, the organic cosolvent is polysorbate at a concentration of from 0.05%±0.025% to 0.5%±0.25% (w/v). In one embodiment, the organic cosolvent is polysorbate 80, which is at a concentration of 0.2%±0.1% w/v, or about 0.2%. In another embodiment, the organic cosolvent is polysorbate 80, which is at a concentration of 0.1%±0.05% w/v or about 0.1% w/v. In one embodiment, the organic cosolvent is polysorbate 20, which is at a concentration of 0.2%±0.1% w/v, or about 0.2%. In another embodiment, the organic cosolvent is polysorbate 20, which is at a concentration of 0.1%±0.05% w/v or about 0.1% w/v.

In certain embodiments, the stabilizer is a sugar. In one embodiment, the sugar is sucrose. In various embodiments, the stabilizer is at a concentration of from 1%±0.2% w/v to 20%±4% w/v, from 5%±1% w/v to 15%±3% w/v, or from 1%±0.2% to 10%±2% w/v. In one embodiment, the stabilizer is sucrose at a concentration of 5%±1% w/v or about 5% w/v. In another embodiment, the stabilizer is sucrose at a concentration of 9%±1.8% w/v or about 9% w/v. In another embodiment, the stabilizer is sucrose at a concentration of 10%±2% w/v or about 10% w/v.

In certain embodiments, the formulation does not need a viscosity modifier, i.e. the formulation lacks a viscosity modifier. In certain embodiments, the formulation comprises a viscosity modifier. In one embodiment, the formulation comprises a viscosity modifier and the viscosity modifier is an amino acid or a salt. In one embodiment, the viscosity modifier is L-proline. In certain embodiments, the viscosity modifier is at a concentration of from 1%±0.2% to 5%±1% w/v. In one embodiment, the viscosity modifier is proline at a concentration of 1.5%±0.3% or about 1.5%. In one embodiment, the viscosity modifier is proline at a concentration of 3%±0.6%, or about 3%.

In certain embodiments, the viscosity of the liquid pharmaceutical formulation at 25° C. is less than or equal to about 15 cPoise±10%. In certain embodiments, the viscosity at 25° C. is between 1.0 cPoise±10% and 20 cPoise±10%. In certain embodiments, the viscosity of the liquid pharmaceutical formulation is ≤20 cPoise. In certain embodiments, the viscosity of the liquid pharmaceutical formulation is ≤15 cPoise. In certain embodiments, the viscosity of the liquid pharmaceutical formulation is ≤10 cPoise. In certain embodiments, the viscosity of the liquid pharmaceutical formulation is ≤5 cPoise. In certain embodiments, the viscosity of the liquid pharmaceutical formulation is ≤2.5 cPoise. In certain embodiments, the viscosity at 25° C. is about 2 cPoise±10%, 5 cPoise±10%, 6.0 cPoise±10%, 7.0 cPoise±10%, 7.1 cPoise±10%, 7.2 cPoise±10%, 7.9 cPoise±10%, 8.3 cPoise±10%, 9.0 cPoise±10%, 9.6 cPoise±10%, 10.0 cPoise±10%, 10.6 cPoise±10%, 11.4 cPoise±10%, 11.6 cPoise±10%, 11.8 cPoise±10%, 12.0 cPoise±10%, 13.0 cPoise±10%, 14.0 cPoise±10%, 15.0 cPoise±10%, or 16 cPoise±10%. In certain embodiments, the viscosity at 25° C. is about 2.2 cPoise.

In one aspect, a stable liquid pharmaceutical formulation is provided, comprising: (a) from 5%±1% to 15%±3% w/v sucrose, (b) from 5 mM±1 mM to 20 mM±4 mM histidine buffer, (c) from 0.01%±0.005% to 0.5%±0.25% w/v polysorbate, e.g. about 0.05%±0.025% to about 0.2%±0.1% w/v polysorbate, and (d) 50 mg/mL±7.5 mg/mL total anti-EBOV antibody, at pH 6.0±0.3. In another aspect, a stable liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody, at pH 6.0±0.3. In another aspect, a stable liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±5 g/mL total antibody, at pH 6.0±0.3.

In one aspect, a stable liquid pharmaceutical formulation is provided, comprising: (a) from 5%±1% to 15%±3% w/v sucrose, (b) from 5 mM±1 mM to 20 mM±4 mM histidine buffer, (c) from 0.01%±0.005% to 0.5%±0.25% w/v polysorbate, and (d) 100 mg/mL±15 mg/mL total antibody, at pH 6.0±0.3. In another aspect, a stable liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody, at pH 6.0±0.3. In another aspect, a stable liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±10 mg/mL total antibody, at pH 6.0±0.3.

The anti-EBOV antibody comprises at least one antibody comprising three heavy chain complementarity determining regions (CDRs) (HCDR1, HCDR2 and HCDR3) and three light chain CDRs (LCDR1, LCDR2 and LCDR3) contained in a heavy chain variable region/light chain variable region (HCVR/LCVR) amino acid sequence pair selected from the group consisting of (i) SEQ ID NOs: 2/10, (ii) SEQ ID NOs: 20/28, and (iii) SEQ ID NOs: 38/46. In some aspects, the formulation comprises the following: (i), (ii), (iii), (i)+(ii), (i)+(iii), (ii)+(iii), or (i)+(ii)+(iii), and the total anti-EBOV antibody present in the formulation is 50 mg/mL±7.5 mg/mL. In some aspects, the formulation comprises the following: (i), (ii), (iii), (i)+(ii), (i)+(iii), (ii)+(iii), or (i)+(ii)+(iii), and the total anti-EBOV antibody present in the formulation is 100 mg/mL±15 mg/mL.

In some embodiments, the at least one anti-EBOV antibody comprises a heavy chain variable region (HCVR) and a light chain variable region (LCVR) such that the HCVR/LCVR combination comprises heavy and light chain complementarity determining regions (HCDR1-HCDR2-HCDR3/LCDR1-LCDR2-LCDR3), which comprise the amino acid sequences selected from the group consisting of SEQ ID NOs: 4-6-8/12-14-16, respectively; SEQ ID NOs: 22-24-26/30-32-34, respectively; and SEQ ID NOs: 40-42-44/48-50-52, respectively. In one embodiment, the anti-EBOV antibody comprises a heavy chain variable region (HCVR)/light chain variable region (LCVR) amino acid sequence pair selected from the group consisting of SEQ ID NOs: 2/10, 20/28, and 38/46. In certain embodiments, the anti-EBOV antibody comprises a Fc region elected from the group consisting of human IgG1, IgG2, IgG3, and IgG4 isotypes. In one embodiment, the antibody comprises a human IgG1 isotype. In one embodiment, the antibody comprises a heavy chain comprising the amino acid sequence selected from the group consisting of SEQ ID NOs: 17, 35, and 53; and a light chain comprising the amino acid sequence selected from the group consisting of SEQ ID NOs: 18, 36, and 54. In one embodiment, the antibody has a molecular weight of 145 kDa±15 kDa, for example, 144,804 Da, 145,905 Da, or 143,689 Da.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10. In one embodiment, the anti-EBOV antibody comprises a HCVR comprising the amino acid sequence of SEQ ID NO: 2 and a LCVR comprising the amino acid sequence of SEQ ID NO: 10. In one embodiment, the anti-EBOV antibody comprises a heavy chain comprising the amino acid sequence of SEQ ID NO: 17; and a light chain comprising the amino acid sequence of SEQ ID NO: 18.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the anti-EBOV antibody comprises a HCVR comprising the amino acid sequence of SEQ ID NO: 20 and a LCVR comprising the amino acid sequence of SEQ ID NO: 28. In one embodiment, the anti-EBOV antibody comprises a heavy chain comprising the amino acid sequence of SEQ ID NO: 35; and a light chain comprising the amino acid sequence of SEQ ID NO: 36.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the anti-EBOV antibody comprises a HCVR comprising the amino acid sequence of SEQ ID NO: 38 and a LCVR comprising the amino acid sequence of SEQ ID NO: 46. In one embodiment, the anti-EBOV antibody comprises a heavy chain comprising the amino acid sequence of SEQ ID NO: 53; and a light chain comprising the amino acid sequence of SEQ ID NO: 54.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the first anti-EBOV antibody comprises a HCVR comprising the amino acid sequence of SEQ ID NO: 2 and a LCVR comprising the amino acid sequence of SEQ ID NO: 10; and the second anti-EBOV antibody comprises an HCVR comprising the amino acid sequence of SEQ ID NO: 20 and an LCVR comprising the amino acid sequence of SEQ ID NO: 28.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises a HCVR comprising the amino acid sequence of SEQ ID NO: 2 and a LCVR comprising the amino acid sequence of SEQ ID NO: 10; and the second anti-EBOV antibody comprises an HCVR comprising the amino acid sequence of SEQ ID NO: 38 and an LCVR comprising the amino acid sequence of SEQ ID NO: 46.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises a HCVR comprising the amino acid sequence of SEQ ID NO: 20 and a LCVR comprising the amino acid sequence of SEQ ID NO: 28; and the second anti-EBOV antibody comprises an HCVR comprising the amino acid sequence of SEQ ID NO: 38 and an LCVR comprising the amino acid sequence of SEQ ID NO: 46.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises a HCVR comprising the amino acid sequence of SEQ ID NO: 2 and a LCVR comprising the amino acid sequence of SEQ ID NO: 10; the second anti-EBOV antibody comprises an HCVR comprising the amino acid sequence of SEQ ID NO: 20 and an LCVR comprising the amino acid sequence of SEQ ID NO: 28; and the third anti-EBOV antibody comprises an HCVR comprising the amino acid sequence of SEQ ID NO: 38 and a LCVR comprising the amino acid sequence of SEQ ID NO: 46.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10. In one embodiment, the anti-EBOV antibody comprises a HCVR comprising the amino acid sequence of SEQ ID NO: 2 and a LCVR comprising the amino acid sequence of SEQ ID NO: 10. In one embodiment, the anti-EBOV antibody comprises a heavy chain comprising the amino acid sequence of SEQ ID NO: 17; and a light chain comprising the amino acid sequence of SEQ ID NO: 18.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the anti-EBOV antibody comprises a HCVR comprising the amino acid sequence of SEQ ID NO: 20 and a LCVR comprising the amino acid sequence of SEQ ID NO: 28. In one embodiment, the anti-EBOV antibody comprises a heavy chain comprising the amino acid sequence of SEQ ID NO: 35; and a light chain comprising the amino acid sequence of SEQ ID NO: 36.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the anti-EBOV antibody comprises a HCVR comprising the amino acid sequence of SEQ ID NO: 38 and a LCVR comprising the amino acid sequence of SEQ ID NO: 46. In one embodiment, the anti-EBOV antibody comprises a heavy chain comprising the amino acid sequence of SEQ ID NO: 53; and a light chain comprising the amino acid sequence of SEQ ID NO: 54.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the first anti-EBOV antibody comprises a HCVR comprising the amino acid sequence of SEQ ID NO: 2 and a LCVR comprising the amino acid sequence of SEQ ID NO: 10; and the second anti-EBOV antibody comprises an HCVR comprising the amino acid sequence of SEQ ID NO: 20 and an LCVR comprising the amino acid sequence of SEQ ID NO: 28.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises a HCVR comprising the amino acid sequence of SEQ ID NO: 2 and a LCVR comprising the amino acid sequence of SEQ ID NO: 10; and the second anti-EBOV antibody comprises an HCVR comprising the amino acid sequence of SEQ ID NO: 38 and an LCVR comprising the amino acid sequence of SEQ ID NO: 46.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises a HCVR comprising the amino acid sequence of SEQ ID NO: 20 and a LCVR comprising the amino acid sequence of SEQ ID NO: 28; and the second anti-EBOV antibody comprises an HCVR comprising the amino acid sequence of SEQ ID NO: 38 and an LCVR comprising the amino acid sequence of SEQ ID NO: 46.

In certain embodiments, a stable, liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody that specifically binds to EBOV, at pH 6.0±0.3; wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises a HCVR comprising the amino acid sequence of SEQ ID NO: 2 and a LCVR comprising the amino acid sequence of SEQ ID NO: 10; the second anti-EBOV antibody comprises an HCVR comprising the amino acid sequence of SEQ ID NO: 20 and an LCVR comprising the amino acid sequence of SEQ ID NO: 28; and the third anti-EBOV antibody comprises an HCVR comprising the amino acid sequence of SEQ ID NO: 38 and a LCVR comprising the amino acid sequence of SEQ ID NO: 46.

In certain embodiments, the formulation of any of the preceding aspects has an attribute selected from the group consisting of: (i) the formulation is stable to long-term storage at 60° C., 55° C., 50° C., 45° C., 40° C., 35° C., 30° C., 25° C., 5° C., −20° C., −30° C. and −80° C., as described herein; (ii) the formulation is stable to agitation stress as described herein; (iii) the formulation is stable to heat stress as described herein; (iv) the formulation is low-viscosity (viscosity less than 20 cPoise, preferably less than 15 cPoise); (v) the formulation is stable even with up to ±50% variation in the formulation excipient concentrations, as described herein; (vi) the formulation is iso-osmolar to physiologic conditions; (vii) the formulation is stable to and compatible with intravenous delivery devices and procedures; and (viii) the formulation is stable to long-term storage in a glass vial or in a prefilled syringe.

In certain embodiments, the formulation of any of the preceding aspects has an attribute selected from the group consisting of: (i) the formulation has viscosity of less than 10 cP; (ii) the formulation has a viscosity of less than 5 cP; (iii) the formulation has a viscosity of less than about 2.5; (iv) at least 90% of the antibody is the native species after 28 days at 45° C.; (v) at least 18% of the antibody is the main charge variant of the antibody after 28 days at 45° C.; (vi) at least 96% of the antibody is the native species after three months at 25° C.; (vii) at least 30% of the antibody is the main charge variant of the antibody after three months at 25° C.; (viii) at least 96% of the antibody is the native species after 36 months at 5° C.; (ix) at least 34% of the antibody is the main charge variant of the antibody after 36 months at 5° C.; (x) at least 97% of the antibody is the native species after 120 minutes agitation; (xi) at least 35% of the antibody is the main charge variant of the antibody after 120 minutes agitation; (xii) at least 97% of the antibody is the native species after 8 freeze thaw cycles; and/or (xiii) at least 35% of the antibody is the main charge variant of the antibody after 8 freeze thaw cycles.

In certain embodiments, an antibody within the formulation of any of the preceding aspects has an attribute selected from the group consisting of: (i) the antibody retains ADCC activity of at least about 90% after storage at −80° C. for 12 months relative to the activity of the same antibody prior to storage; (ii) the antibody retains ADCC activity of at least about 80%, or at least about 90%, after storage at −30° C. for 12 months relative to the activity of the same antibody prior to storage; (iii) the antibody retains ADCC activity of at least about 90%, or at least about 95%, after storage at −20° C. for 3 months relative to the activity of the same antibody prior to storage; (iv) the antibody retains ADCC activity of at least about 90%, or at least about 95%, after storage at 5° C. for 56 days relative to the activity of the same antibody prior to storage; (v) the antibody retains ADCC activity of at least about 90%, or at least about 95%, after storage at 25° C./60% relative humidity (RH) for 28 days relative to the activity of the same antibody prior to storage; (vi) the antibody retains ADCC activity of at least about 90%, or at least about 95%, after storage at 40° C./75% RH for 28 days relative to the activity of the same antibody prior to storage; (vii) the antibody retains ADCC activity of at least about 90%, or at least about 95%, after agitation for 120 minutes, or 8 freeze/thaw cycles, relative to the activity of the same antibody prior to agitation or freeze/thaw, respectively.

In certain embodiments, an antibody within the formulation of any of the preceding aspects has an attribute selected from the group consisting of: (i) the antibody retains pseudovirus neutralization activity of at least about 90%, or at least about 95%, after storage at −80° C. for 12 months relative to the activity of the same antibody prior to storage; (ii) the antibody retains pseudovirus neutralization activity of at least about 90%, or at least about 95%, after storage at −30° C. for 12 months relative to the activity of the same antibody prior to storage; (iii) the antibody retains pseudovirus neutralization activity of at least about 90%, or at least about 95%, after storage at −20° C. for 3 months relative to the activity of the same antibody prior to storage; (iv) the antibody retains pseudovirus neutralization activity of at least about 80%, or at least about 85%, or at least about 90%, or at least about 95%, after storage at 5° C. for 56 days relative to the activity of the same antibody prior to storage; (v) the antibody retains pseudovirus neutralization activity of at least about 80%, or at least about 85%, or at least about 90%, or at least about 95%, after storage at 25° C./60% relative humidity (RH) for 28 days relative to the activity of the same antibody prior to storage; (vi) the antibody retains pseudovirus neutralization activity of at least about 80%, or at least about 85%, or at least about 90%, or at least about 95%, after storage at 40° C./75% RH for 28 days relative to the activity of the same antibody prior to storage; (vii) the antibody retains pseudovirus neutralization activity of at least about 90%, or at least about 95%, after agitation for 120 minutes, or 8 freeze/thaw cycles, relative to the activity of the same antibody prior to agitation or freeze/thaw, respectively.

In certain embodiments of this aspect, a stable liquid formulation is provided, comprising: (a) at least one antibody that binds specifically to EBOV, wherein the at least one antibody comprises a heavy chain variable region/light chain variable region (HCVR/LCVR) amino acid sequence pair selected from the group consisting of (i) SEQ ID NOs: 2/10, (ii) SEQ ID NOs: 20/28, and (iii) SEQ ID NOs: 38/46, and wherein the total antibody comprises 50 mg/mL±7.5 mg/mL, (b) 10 mM±2 mM histidine buffer, pH 6.0±0.3, (c) 0.1%±0.05% w/v polysorbate 80, and (d) 10%±2% w/v sucrose. In one embodiment according to this aspect, at least 96% of the antibody is the native species after 36 months at 5° C. In one embodiment according to this aspect, at least 97% of the antibody is the native species after 120 minutes agitation. In one embodiment according to this aspect, at least 97% of the antibody is the native species after 8 freeze thaw cycles. In some aspects, the pharmaceutical formulation consists of: (a) 50 mg/mL±7.5 mg/mL total antibody, (b) 10 mM±2 mM histidine buffer, (c) 0.1%±0.05% w/v polysorbate 80, and (d) 10%±2% w/v sucrose, in water at pH 6.0±0.3.

In certain embodiments of this aspect, a stable liquid formulation is provided, comprising: (a) at least two antibodies that bind specifically to EBOV, wherein the at least two antibodies comprise a heavy chain variable region/light chain variable region (HCVR/LCVR) amino acid sequence pair selected from the group consisting of (i) SEQ ID NOs: 2/10, (ii) SEQ ID NOs: 20/28, and (iii) SEQ ID NOs: 38/46, and wherein the total antibody comprises 50 mg/mL±7.5 mg/mL, (b) 10 mM±2 mM histidine buffer, pH 6.0±0.3, (c) 0.1%±0.05% w/v polysorbate 80, and (d) 10%±2% w/v sucrose. In one embodiment according to this aspect, at least 96% of the antibody is the native species after 12 months at 5° C. In one embodiment according to this aspect, at least 97% of the antibody is the native species after 120 minutes agitation. In one embodiment according to this aspect, at least 97% of the antibody is the native species after 8 freeze thaw cycles. In some aspects, the pharmaceutical formulation consists of: (a) 50 mg/mL±7.5 mg/mL total antibody, (b) 10 mM±2 mM histidine buffer, (c) 0.1%±0.05% w/v polysorbate 80, and (d) 10%±2% w/v sucrose, in water at pH 6.0±0.3.

In certain embodiments of this aspect, a stable liquid formulation is provided, comprising: (a) a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46, and wherein the total antibody comprises 50 mg/mL±7.5 mg/mL, (b) 10 mM±2 mM histidine buffer, pH 6.0±0.3, (c) 0.1%±0.05% w/v polysorbate 80, and (d) 10%±2% w/v sucrose. In one embodiment according to this aspect, at least 96% of the antibody is the native species after 12 months at 5° C. In one embodiment according to this aspect, at least 97% of the antibody is the native species after 120 minutes agitation. In one embodiment according to this aspect, at least 97% of the antibody is the native species after 8 freeze thaw cycles. In some aspects, the pharmaceutical formulation consists of: (a) 50 mg/mL±7.5 mg/mL total antibody, (b) 10 mM±2 mM histidine buffer, (c) 0.1%±0.05% w/v polysorbate 80, and (d) 10%±2% w/v sucrose, in water at pH 6.0±0.3.

In certain embodiments of this aspect, a stable liquid formulation is provided, comprising: (a) at least one antibody that binds specifically to EBOV, wherein the at least one antibody comprises a heavy chain variable region/light chain variable region (HCVR/LCVR) amino acid sequence pair selected from the group consisting of (i) SEQ ID NOs: 2/10, (ii) SEQ ID NOs: 20/28, and (iii) SEQ ID NOs: 38/46, and wherein the total antibody comprises 100 mg/mL±15 mg/mL, (b) 10 mM±2 mM histidine buffer, pH 6.0±0.3, (c) 0.1%±0.05% w/v polysorbate 80, and (d) 10%±2% w/v sucrose. In one embodiment according to this aspect, at least 96% of the antibody is the native species after 12 months at 5° C. In one embodiment according to this aspect, at least 97% of the antibody is the native species after 120 minutes agitation. In one embodiment according to this aspect, at least 97% of the antibody is the native species after 8 freeze thaw cycles. In some aspects, the pharmaceutical formulation consists of: (a) 100 mg/mL±15 mg/mL total antibody, (b) 10 mM±2 mM histidine buffer, (c) 0.1%±0.05% w/v polysorbate 80, and (d) 10%±2% w/v sucrose, in water at pH 6.0±0.3.

In certain embodiments of this aspect, a stable liquid formulation is provided, comprising: (a) at least two antibodies that bind specifically to EBOV, wherein the at least two antibodies comprise a heavy chain variable region/light chain variable region (HCVR/LCVR) amino acid sequence pair selected from the group consisting of (i) SEQ ID NOs: 2/10, (ii) SEQ ID NOs: 20/28, and (iii) SEQ ID NOs: 38/46, and wherein the total antibody comprises 100 mg/mL±15 mg/mL, (b) 10 mM±2 mM histidine buffer, pH 6.0±0.3, (c) 0.1%±0.05% w/v polysorbate 80, and (d) 10%±2% w/v sucrose. In one embodiment according to this aspect, at least 96% of the antibody is the native species after 12 months at 5° C. In one embodiment according to this aspect, at least 97% of the antibody is the native species after 120 minutes agitation. In one embodiment according to this aspect, at least 97% of the antibody is the native species after 8 freeze thaw cycles. In some aspects, the pharmaceutical formulation consists of: (a) 100 mg/mL±15 mg/mL total antibody, (b) 10 mM±2 mM histidine buffer, (c) 0.1%±0.05% w/v polysorbate 80, and (d) 10%±2% w/v sucrose, in water at pH 6.0±0.3.

In certain embodiments of this aspect, a stable liquid formulation is provided, comprising: (a) a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46, and wherein the total antibody comprises 100 mg/mL±15 mg/mL, (b) 10 mM±2 mM histidine buffer, pH 6.0±0.3, (c) 0.1%±0.05% w/v polysorbate 80, and (d) 10%±2% w/v sucrose. In one embodiment according to this aspect, at least 96% of the antibody is the native species after 12 months at 5° C. In one embodiment according to this aspect, at least 97% of the antibody is the native species after 120 minutes agitation. In one embodiment according to this aspect, at least 97% of the antibody is the native species after 8 freeze thaw cycles. In some aspects, the pharmaceutical formulation consists of: (a) 100 mg/mL±15 mg/mL total antibody, (b) 10 mM±2 mM histidine buffer, (c) 0.1%±0.05% w/v polysorbate 80, and (d) 10%±2% w/v sucrose, in water at pH 6.0±0.3.

In one embodiment, the stable liquid formulation comprises 50 mg/mL±7.5 mg/mL total antibody that specifically binds to EBOV and has a viscosity less than 3 cP at 25° C. In one embodiment, ≥90% of the antibodies have a molecular weight of 146 kDa±5 kDa, for example, 144,804 Da, 145,905 Da, or 143,689 Da. In one embodiment, the pharmaceutical formulation has a viscosity of less than 5 cP, less than 4 cP, or less than 3 cP at 25° C. In one embodiment, at least 90% of the antibody is the native species after 28 days at 45° C. In one embodiment, at least 18% of the antibody is the main charge variant of the antibody after 28 days at 45° C. In one embodiment, at least 96% of the antibody is the native species after three months at 25° C. In one embodiment, at least 30% of the antibody is the main charge variant of the antibody after three months at 25° C. In one embodiment, at least 96% of the antibody is the native species after 12 months at 5° C. In one embodiment, at least 34% of the antibody is the main charge variant of the antibody after 12 months at 5° C. In one embodiment, at least 97% of the antibody is the native species after 120 minutes agitation. In one embodiment, at least 35% of the antibody is the main charge variant of the antibody after 120 minutes agitation. In one embodiment, at least 97% of the antibody is the native species after 8 freeze thaw cycles. In one embodiment, at least 35% of the antibody is the main charge variant of the antibody after 8 freeze thaw cycles.

In one embodiment, the stable liquid formulation comprises 100 mg/mL±15 mg/mL total antibody and has a viscosity less than 5 cP at 20° C. In one embodiment, 90% of the antibodies have a molecular weight of 145 kDa±2 kDa, for example, 144,804 Da, 145,905 Da, or 143,689 Da. In one embodiment, the pharmaceutical formulation has a viscosity of less than 6 cP or less than 5 cP at 20° C. In one embodiment, at least 90% of the antibody is the native species after 28 days at 45° C. In one embodiment, at least 18% of the antibody is the main charge variant of the antibody after 28 days at 45° C. In one embodiment, at least 96% of the antibody is the native species after three months at 25° C. In one embodiment, at least 30% of the antibody is the main charge variant of the antibody after three months at 25° C. In one embodiment, at least 96% of the antibody is the native species after 12 months at 5° C. In one embodiment, at least 34% of the antibody is the main charge variant of the antibody after 12 months at 5° C. In one embodiment, at least 97% of the antibody is the native species after 120 minutes agitation. In one embodiment, at least 35% of the antibody is the main charge variant of the antibody after 120 minutes agitation. In one embodiment, at least 97% of the antibody is the native species after 8 freeze thaw cycles. In one embodiment, at least 35% of the antibody is the main charge variant of the antibody after 8 freeze thaw cycles.

In certain embodiments of this aspect, a stable liquid formulation is provided, comprising: (a) a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46, and wherein the total antibody comprises 50 mg/mL±7.5 mg/mL, (b) 10 mM±2 mM histidine buffer, pH 6.0±0.3, (c) 0.1%±0.05% w/v polysorbate 80, and (d) 10%±2% w/v sucrose. In one embodiment of this particular formulation, the viscosity is less than 3 cPoise.

In certain embodiments of this aspect, a stable liquid formulation is provided, comprising: (a) a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46, and wherein the total antibody comprises 100 mg/mL±15 mg/mL, (b) 10 mM±2 mM histidine buffer, pH 6.0±0.3, (c) 0.1%±0.05% w/v polysorbate 80, and (d) 10%±2% w/v sucrose. In one embodiment of this particular formulation, the viscosity is less than 5 cPoise.

In one aspect, the present disclosure provides a stable liquid pharmaceutical formulation, comprising: (a) from 5%±1% to 15%±3% w/v sucrose, (b) from 5 mM±1 mM to 20 mM±4 mM histidine buffer, (c) from 0.01%±0.005% to 0.5%±0.25% w/v polysorbate, and (d) up to 100 mg/mL±15 mg/mL total anti-EBOV antibody, at pH 6.0±0.3. In another aspect, a stable liquid pharmaceutical formulation is provided, comprising: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3. The anti-EBOV antibody, according to this aspect, comprises a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46.

In one aspect, a stable liquid pharmaceutical formulation is provided, comprising: (a) from 5%±1% to 15%±3% w/v sucrose, (b) from 5 mM±1 mM to 20 mM±4 mM histidine buffer, (c) from 0.01%±0.005% to 0.5%±0.25% w/v polysorbate, and (d) 100 mg/mL±15 mg/mL total anti-EBOV antibody, at pH 6.0±0.3. In another aspect, a stable liquid pharmaceutical formulation is provided, comprising: (a) 10%±2% w/v sucrose, (b) 10 mM±2 mM histidine buffer, (c) 0.1%±0.05% w/v polysorbate, and (d) 100 mg/mL±15 mg/mL total antibody, at pH 6.0±0.3. The anti-EBOV antibody, according to this aspect, comprises a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46.

In one embodiment, the stable liquid formulation comprises 150 mg/mL total anti-EBOV antibody. In one embodiment, the stable liquid formulation comprises 100 mg/mL total anti-EBOV antibody. In one embodiment, the stable liquid formulation comprises 50 mg/mL total anti-EBOV antibody. In one embodiment, the stable liquid formulation comprises 10 mM±2 mM histidine buffer. In one embodiment, the stable liquid formulation comprises 10% sucrose. In one embodiment, the stable liquid formulation comprises 9% sucrose. In one embodiment, the stable liquid formulation comprises 8% sucrose. In one embodiment, the stable liquid formulation comprises 5% sucrose. In one embodiment, the stable liquid formulation comprises 0.1% polysorbate. In one embodiment, the stable liquid formulation comprises 0.2% polysorbate. In one embodiment, the polysorbate is polysorbate 80 or polysorbate 20.

In one embodiment, the stable liquid formulation comprises 33.3 mg/mL antibody comprising a heavy chain variable region/light chain variable region (HCVR/LCVR) amino acid sequence pair of SEQ ID NOs: 2/10, 33.3 mg/mL antibody comprising an HCVR/LCVR amino acid sequence pair of SEQ ID NOs: 20/28, and 33.3 mg/mL antibody comprising an HCVR/LCVR amino acid sequence pair of SEQ ID NOs: 38/46, in an aqueous buffered solution, pH 6.0, containing 10 mM L-histidine, 10% (w/v) sucrose, and 0.1% (w/v) polysorbate 80. In one embodiment, the stable liquid formulation maintains ADCC potency of at least about 90%, or at least about 95%, in an ADCC bioassay after storage at 5° C. for 6 months, relative to the same liquid formulation prior to storage at 5° C. for 6 months. In one embodiment, the stable liquid formulation maintains pseudovirus neutralization activity of at least about 95% after storage at 5° C. for 6 months, relative to the same liquid formulation prior to storage at 5° C. for 6 months. In one embodiment, the stable liquid formulation maintains ADCC potency of at least about 80%, or at least about 85%, in an ADCC bioassay after storage at 25° C./60% RH for 6 months, relative to the same liquid formulation prior to storage at 25° C./60% RH for 6 months. In one embodiment, the stable liquid formulation maintains pseudovirus neutralization activity of at least about 95% after storage at 25° C./60% RH for 6 months, relative to the same liquid formulation prior to storage at 25° C./60% RH for 6 months. In one embodiment, the stable liquid formulation maintains pseudovirus neutralization activity of at least about 95% after storage at 40° C./75% RH for 6 months, relative to the same liquid formulation prior to storage at 40° C./75% RH for 6 months. In one embodiment, the stable liquid formulation maintains ADCC potency of at least about 95% in an ADCC bioassay after agitation for 120 minutes, relative to the same liquid formulation prior to agitation for 120 minutes. In one embodiment, the stable liquid formulation maintains ADCC potency of at least about 85% in an ADCC bioassay after 8 freeze/thaw cycles, relative to the same liquid formulation prior to 8 freeze/thaw cycles. In one embodiment, the stable liquid formulation maintains pseudovirus neutralization activity of at least about 95% after agitation for 120 minutes, relative to the same liquid formulation prior to agitation for 120 minutes. In one embodiment, the stable liquid formulation maintains pseudovirus neutralization activity of at least about 95% after 8 freeze/thaw cycles, relative to the same liquid formulation prior 8 freeze thaw cycles.

In one aspect, a stable liquid pharmaceutical formulation of any of the preceding aspects is provided in a container. In one embodiment, the container is a vial. In one embodiment, the container is a polycarbonate vial. In one embodiment, the container is a glass vial. In one embodiment, the glass vial is a type 1 clear glass vial. In one embodiment, the glass vial is a type 1 borosilicate glass vial with a fluorocarbon-coated butyl rubber stopper. In one embodiment, the container is a microinfuser. In one embodiment, the container is a syringe. In one embodiment, the container is a prefilled syringe. In one embodiment, the syringe comprises low-tungsten glass. In one embodiment, the syringe comprises an autoinjector. In one embodiment, the syringe comprises a fluorocarbon-coated plunger. In certain embodiments, the syringe is a 1 mL or 2.25 mL long glass syringe containing less than about 500 parts per billion of tungsten equipped with a 27-G needle, a fluorocarbon-coated butyl rubber stopper, and a latex-free, non-cytotoxic rubber tip cap. In one embodiment, the syringe is a 1 mL long glass syringe equipped with a 27-G thin wall needle, a FLUROTEC-coated 4023/50 rubber stopper, and a FM 27 rubber tip cap. In one embodiment, the syringe is a 1 mL, 2 mL, 3 mL, 5 mL or 10 mL plastic syringe fitted with a needle.

In one aspect, a kit comprising a stable pharmaceutical composition of any one of the preceding aspects, a container, and instructions is provided. In one embodiment, the container is a glass vial. In one embodiment, the container is a prefilled syringe. In one embodiment, the container is an autoinjector. In one embodiment, the syringe is a 1 mL or 2.25 mL long glass syringe equipped with a 27-G thin wall needle, a FLUROTEC-coated 4023/50 rubber stopper, and a FM 27 rubber tip cap. In one embodiment, the syringe is a 1 mL, 2 mL, 3 mL, 5 mL or 10 mL plastic syringe fitted with a needle.

In certain embodiments, the present disclosure provides a prefilled syringe comprising a stable liquid pharmaceutical formulation comprising: (i) from 5±0.75 mg/ml to 250±37.5 mg/ml of at least one human antibody that specifically binds to EBOV; (ii) from 5 mM±1 mM to 20±4 mM histidine buffer; (iii) from 0.05%±0.025% to 0.3%±0.15% (w/v) polysorbate 80; and (iv) from 1%±0.2% to 10%±2% (w/v) sucrose, at a pH of 6.0±0.3, wherein the at least one human anti-EBOV antibody is selected from the group consisting of a first antibody comprising three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody comprising three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody comprising three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In some aspects, the formulation has an attribute selected from the group consisting of: at least 90% of the antibody is the native species after 28 days at 45° C.; at least 18% of the antibody is the main charge variant of the antibody after 28 days at 45° C.; at least 96% of the antibody is the native species after three months at 25° C.; at least 30% of the antibody is the main charge variant of the antibody after three months at 25° C.; at least 96% of the antibody is the native species after 12 months at 5° C.; at least 34% of the antibody is the main charge variant of the antibody after 12 months at 5° C.; at least 97% of the antibody is the native species after 120 minutes agitation; at least 35% of the antibody is the main charge variant of the antibody after 120 minutes agitation; at least 97% of the antibody is the native species after 8 freeze thaw cycles; at least 35% of the antibody is the main charge variant of the antibody after 8 freeze thaw cycles; over 90% of the antibodies have a molecular weight of 145 kDa±2 kDa, for example, 144,804 Da, 145,905 Da, or 143,689 Da; and the pharmaceutical formulation has a viscosity of less than 20 cP, less than 15 cP, less than 10 cP, less than 5 cP, or less than 3 cP.

In certain embodiments the present disclosure provides a glass vial comprising a stable liquid pharmaceutical formulation comprising: (a) 10%±2% w/v sucrose, (b) 10 mM±2 mM histidine buffer, (c) 0.1%±0.05% w/v polysorbate, and (d) from 5 mg/mL±0.75 mg/mL to 250 mg/mL±37.5 mg/mL total anti-EBOV antibody, at pH 6.0±0.3; wherein the at least one anti-EBOV antibody is selected from the group consisting of: a first antibody comprising three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody comprising three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody comprising three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In some aspects, the formulation has an attribute selected from the group consisting of: the formulation is stable to storage and stress in a glass vial; the formulation is stable to and compatible for use in IV delivery devices; the formulation is chemically and physically stable to dilution with standard diluents known in the art (e.g., 0.9% sodium chloride or 5% dextrose or Lactated Ringer's); the formulation is stable to IV bags made of glass or polymer plastics (e.g., polyvinyl chloride, phthalates, polyolefins or polypropylene); the formulation is compatible with standard infusion pumps (e.g., peristaltic pump, fluid displacement pump); at least 90% of the antibody is the native species after 28 days at 45° C.; at least 18% of the antibody is the main charge variant of the antibody after 28 days at 45° C.; at least 96% of the antibody is the native species after three months at 25° C.; at least 30% of the antibody is the main charge variant of the antibody after three months at 25° C.; at least 96% of the antibody is the native species after 12 months at 5° C.; at least 34% of the antibody is the main charge variant of the antibody after 12 months at 5° C.; at least 97% of the antibody is the native species after 120 minutes agitation; at least 35% of the antibody is the main charge variant of the antibody after 120 minutes agitation; at least 97% of the antibody is the native species after 8 freeze thaw cycles; at least 35% of the antibody is the main charge variant of the antibody after 8 freeze thaw cycles; over 90% of the antibodies have a molecular weight of 145 kDa±2 kDa, for example, 144,804 Da, 145,905 Da, or 143,689 Da; and the pharmaceutical formulation has a viscosity of less than 20 cP, less than 15 cP, less than 10 cP, less than 5 cP, or less than 3 cP. In some aspects, the formulation is stable for shipping at temperatures of about 2° C. to about 8° C. In some aspects, the formulation is stable when stored at about 2° C. to about 8° C. Stability studies have been performed to support potential excursions from storage conditions. In some aspects, the formulation is stable at room temperature for at least about 6 months. In some aspects, the formulation is physically and chemically stable against agitation and freeze/thaw cycles. In some aspects, the antibodies within the formulation maintain biological activity, e.g. ADCC activity or pseudovirus neutralization activity, after exposure to temperatures up to 25° C., or up to 30° C., or after agitation or freeze/thaw cycles.

Other embodiments will become apparent from a review of the ensuing detailed description.

BRIEF DESCRIPTION OF FIGURES

FIG. 1 shows an overlay of RP-UPLC chromatograms from H1H17203P, H1H17139P, and H1H17161P.

FIG. 2 shows an overlay of H1H17203P, H1H17139P, and H1H17161P SE-UPLC Chromatograms.

DETAILED DESCRIPTION

Therapeutic drugs such as biologics are typically formulated as individual drugs in formulations providing stability of the therapeutic for long-term storage at cool temperatures. Packaged biologics are treated with care, often maintained in lyophilized form just until prior to use in order to minimize aggregation and damage to the large molecules. Lyophilized formulations are typically more stable than liquid formulations. In addition, packaged biologics are kept cool, if not frozen, during transport and storage.

Provided herein are stable pharmaceutical formulations comprising antibodies for the treatment of Ebola virus (EBOV) infection or prophylactic treatment for EBOV exposure. These formulations are stable liquid antibody formulations prepared to withstand rigorous transport and storage while maintaining stability. The therapeutics are prepared in a manner to facilitate use in remote areas where Ebola outbreaks occur such as Congo and Sudan. As such, the formulations are in liquid form to avoid reconstitution steps required prior to using a drug in lyophilized form, avoiding possible contamination of the drug product. The liquid pharmaceutical formulations are stable even when transported long distances and subjected to stress, for example, temperature cycles, extreme temperatures, agitation during transport, etc., conditions a therapeutic would be exposed to in transit from a manufacturing facility to remote field clinics where Ebola exposure has occurred and/or Ebola patients exist.

In some aspects, the stable liquid formulation comprises more than one antibody, e.g. is a cocktail comprising, for example, two or three anti-EBOV antibodies. Stable antibody cocktails formulations are difficult. Exposure of protein therapeutics in IV bags to ambient temperature and visible light are short term, so those mild conditions typically do not induce product degradation. However, during long term storage individual proteins typically undergo some degradation processes including enhanced attractive intermolecular protein-protein interactions, increased viscosity, and compromised structural integrity. Stress conditions present during coformulation manufacturing, transport, storage, handling and patient administration can affect what becomes a critical product liability: aggregation, deamidation, oxidation, etc. In addition, coformulation conditions can lead to formation of heterogeneous aggregates. See Svitel et al., BioProcess International, 2019; Patel et al, Journal of Pharmaceutical Sciences, 107: 3032-3046, 2018; and Mueller et al., Journal of Pharmacy and Pharmacology, 70: 666-674, 2018.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.). Although any methods and materials similar or equivalent to those described herein can be used in the practice or testing of the present disclosure, preferred methods and materials are now described. All publications mentioned herein are incorporated herein by reference in their entirety.

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient which, when combined with the active ingredient or one or more additional inactive ingredients, is suitable for therapeutic administration to a human or non-human animal. The term "formulation", as used herein, means "pharmaceutical formulation" unless specifically indicated otherwise. The present disclosure provides pharmaceutical formulations comprising at least one therapeutic polypeptide. According to certain embodiments of the present disclosure, the therapeutic polypeptide is an antibody, or an antigen-binding fragment thereof, which binds specifically to Ebola Virus (EBOV). More specifically, the present disclosure includes stable pharmaceutical formulations that comprise: (i) one or more human antibodies that specifically bind to EBOV (ii) a histidine buffer; (iii) an organic cosolvent that is a non-ionic surfactant; and (iv) a stabilizer that is a carbohydrate. In one particular embodiment, the stable pharmaceutical formulation comprises: (i) three human antibodies that specifically bind to EBOV (ii) a histidine buffer; (iii) an organic cosolvent that is a non-ionic surfactant; and (iv) a stabilizer that is a carbohydrate. Specific exemplary components and formulations included within the present disclosure are described in detail below.

Antibodies that Bind Specifically to EBOV

The pharmaceutical formulations of the present disclosure may comprise a human antibody, or an antigen-binding fragment thereof, that binds specifically to EBOV. As used herein, the term "EBOV" means Ebola Virus. Antibodies to EBOV are described in, for example, U.S. Pat. Nos. 10,501,526 10,081,670, 9,771,414, 6,630,144, 6,875,433, 7,335,356, and 8,513,391, and in WO 2016/123019, EP1539238, EP2350270, and EP8513391

The term "antibody", as used herein, is generally intended to refer to immunoglobulin molecules comprising four polypeptide chains, two heavy (H) chains and two light (L) chains inter-connected by disulfide bonds, as well as multimers thereof (e.g., IgM); however, immunoglobulin molecules consisting of only heavy chains (i.e., lacking light chains) are also encompassed within the definition of the term "antibody". Each heavy chain comprises a heavy chain variable region (abbreviated herein as HCVR or $V_H$) and a heavy chain constant region. The heavy chain constant region comprises three domains, CH1, CH2 and CH3. Each light chain comprises a light chain variable region (abbreviated herein as LCVR or $V_L$) and a light chain constant region. The light chain constant region comprises one domain (CL1). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Unless specifically indicated otherwise, the term "antibody", as used herein, shall be understood to encompass complete antibody molecules as well as antigen-binding fragments thereof. The term "antigen-binding portion" or "antigen-binding fragment" of an antibody (or simply "antibody portion" or "antibody fragment"), as used herein, refers to one or more fragments of an antibody that retain the ability to specifically bind to EBOV or an epitope thereof.

An "isolated antibody", as used herein, is intended to refer to an antibody that is substantially free of other antibodies having different antigenic specificities (e.g., an isolated antibody that specifically binds EBOV is substantially free of antibodies that specifically bind antigens other than EBOV).

The term "specifically binds", or the like, means that an antibody or antigen-binding fragment thereof forms a complex with an antigen that is relatively stable under physiologic conditions. Specific binding can be characterized by a dissociation constant of at least about $1 \times 10^{-8}$ M or greater.

Methods for determining whether two molecules specifically bind are well known in the art and include, for example, equilibrium dialysis, surface plasmon resonance, and the like. In the context of the present disclosure, multispecific (e.g., bispecific) antibodies that bind to EBOV as well as one or more additional antigens are deemed to "specifically bind" EBOV. Moreover, an isolated antibody may be substantially free of other cellular material or chemicals.

Exemplary anti-EBOV antibodies that may be included in the pharmaceutical formulations of the present disclosure are set forth in patent application publications US 2016/0215040, and WO 2016/123019, the disclosures of which are incorporated by reference in their entirety. Of particular interest are the three antibodies H1H17203P, H1H17139P, and H1H17161P disclosed therein and formulated independently or in any combination in a stable pharmaceutical formulation.

According to certain embodiments of the present disclosure, the anti-EBOV antibody, or antigen-binding fragment thereof, comprises a heavy chain complementarity determining region (HCDR) 1 of SEQ ID NO: 4, an HCDR2 of SEQ ID NO: 6, and an HCDR3 of SEQ ID NO: 8. In certain embodiments, the anti-EBOV antibody, or antigen-binding fragment thereof, comprises an HCVR of SEQ ID NO: 2.

According to certain embodiments of the present disclosure, the anti-EBOV antibody, or antigen-binding fragment thereof, comprises a light chain complementarity determining region (LCDR) 1 of SEQ ID NO: 12, an LCDR2 of SEQ ID NO: 14, and an LCDR3 of SEQ ID NO: 16. In certain embodiments, the anti-EBOV antibody, or antigen-binding fragment thereof, comprises an LCVR of SEQ ID NO: 10.

According to certain embodiments of the present disclosure, the anti-EBOV antibody, or antigen-binding fragment thereof, comprises a HCVR having 90%, 95%, 98% or 99% sequence identity to SEQ ID NO: 2.

According to certain embodiments of the present disclosure, the anti-EBOV antibody, or antigen-binding fragment thereof, comprises a LCVR having 90%, 95%, 98% or 99% sequence identity to SEQ ID NO: 10.

According to certain embodiments of the present disclosure, the anti-EBOV antibody, or antigen-binding fragment thereof, comprises a HCVR comprising an amino acid sequence of SEQ ID NO: 2 having no more than 5 amino acid substitutions.

According to certain embodiments of the present disclosure, the anti-EBOV antibody, or antigen-binding fragment thereof, comprises a LCVR comprising an amino acid sequence of SEQ ID NO: 10 having no more than 2 amino acid substitutions.

According to certain embodiments of the present disclosure, the anti-EBOV antibody, or antigen-binding fragment thereof, comprises a heavy chain complementarity determining region (HCDR) 1 of SEQ ID NO: 22, an HCDR2 of SEQ ID NO: 24, and an HCDR3 of SEQ ID NO: 26. In certain embodiments, the anti-EBOV antibody, or antigen-binding fragment thereof, comprises an HCVR of SEQ ID NO: 20.

According to certain embodiments of the present disclosure, the anti-EBOV antibody, or antigen-binding fragment thereof, comprises a light chain complementarity determining region (LCDR)1 of SEQ ID NO: 30, an LCDR2 of SEQ ID NO: 32, and an LCDR3 of SEQ ID NO: 34. In certain embodiments, the anti-EBOV antibody, or antigen-binding fragment thereof, comprises an LCVR of SEQ ID NO: 28.

According to certain embodiments of the present disclosure, the anti-EBOV antibody, or antigen-binding fragment thereof, comprises a HCVR having 90%, 95%, 98% or 99% sequence identity to SEQ ID NO: 20.

According to certain embodiments of the present disclosure, the anti-EBOV antibody, or antigen-binding fragment thereof, comprises a LCVR having 90%, 95%, 98% or 99% sequence identity to SEQ ID NO: 28.

According to certain embodiments of the present disclosure, the anti-EBOV antibody, or antigen-binding fragment thereof, comprises a HCVR comprising an amino acid sequence of SEQ ID NO: 20 having no more than 5 amino acid substitutions.

According to certain embodiments of the present disclosure, the anti-EBOV antibody, or antigen-binding fragment thereof, comprises a LCVR comprising an amino acid sequence of SEQ ID NO: 28 having no more than 2 amino acid substitutions.

According to certain embodiments of the present disclosure, the anti-EBOV antibody, or antigen-binding fragment thereof, comprises a heavy chain complementarity determining region (HCDR) 1 of SEQ ID NO: 40, an HCDR2 of SEQ ID NO: 42, and an HCDR3 of SEQ ID NO: 44. In certain embodiments, the anti-EBOV antibody, or antigen-binding fragment thereof, comprises an HCVR of SEQ ID NO: 38.

According to certain embodiments of the present disclosure, the anti-EBOV antibody, or antigen-binding fragment thereof, comprises a light chain complementarity determining region (LCDR)1 of SEQ ID NO: 48, an LCDR2 of SEQ ID NO: 50, and an LCDR3 of SEQ ID NO: 52. In certain embodiments, the anti-EBOV antibody, or antigen-binding fragment thereof, comprises an LCVR of SEQ ID NO: 46.

According to certain embodiments of the present disclosure, the anti-EBOV antibody, or antigen-binding fragment thereof, comprises a HCVR having 90%, 95%, 98% or 99% sequence identity to SEQ ID NO: 38.

According to certain embodiments of the present disclosure, the anti-EBOV antibody, or antigen-binding fragment thereof, comprises a LCVR having 90%, 95%, 98% or 99% sequence identity to SEQ ID NO: 46.

According to certain embodiments of the present disclosure, the anti-EBOV antibody, or antigen-binding fragment thereof, comprises a HCVR comprising an amino acid sequence of SEQ ID NO: 38 having no more than 5 amino acid substitutions.

According to certain embodiments of the present disclosure, the anti-EBOV antibody, or antigen-binding fragment thereof, comprises a LCVR comprising an amino acid sequence of SEQ ID NO: 46 having no more than 2 amino acid substitutions.

According to certain embodiments of the present disclosure, a stable liquid pharmaceutical formulation comprises one or more of the anti-EBOV antibodies, or antigen-binding fragments thereof, as described above.

Sequence identity may be measured by any method known in the art (e.g., GAP, BESTFIT, and BLAST).

The present disclosure also includes stable liquid formulations comprising anti-EBOV antibodies, wherein the anti-EBOV antibodies comprise variants of any of the HCVR, LCVR and/or CDR amino acid sequences disclosed herein having one or more amino acid substitutions, for example, conservative amino acid substitutions. Illustratively, the present disclosure includes formulations comprising anti-EBOV antibodies having HCVR, LCVR and/or CDR amino acid sequences with, e.g., 10 or fewer, 8 or fewer, 6 or fewer, 4 or fewer, etc. amino acid substitutions, e.g. conservative amino acid substitutions, relative to any of the HCVR, LCVR and/or CDR amino acid sequences disclosed herein.

In certain embodiments, the anti-EBOV antibody comprises a Fc region elected from the group consisting of human IgG1, IgG2, IgG3, and IgG4 isotypes.

According to certain embodiments of the present disclosure, the anti-EBOV, or antigen-binding fragment thereof, comprises a heavy chain of SEQ ID NO: 17 and a light chain of SEQ ID NO: 18.

According to certain embodiments of the present disclosure, the anti-EBOV, or antigen-binding fragment thereof, comprises a heavy chain of SEQ ID NO: 35 and a light chain of SEQ ID NO: 36.

According to certain embodiments of the present disclosure, the anti-EBOV, or antigen-binding fragment thereof, comprises a heavy chain of SEQ ID NO: 53 and a light chain of SEQ ID NO: 54.

It is well known in the art that terminal cleavage of amino acids can occur during production of antibodies (see, for example, Wang et al 2007, J. Pharma. Sci. 96: 1-26). Accordingly, in certain embodiments, the anti-EBOV antibody comprises a heavy chain and a light chain, wherein the heavy chain comprises the amino acid sequence of SEQ ID NO: 17, wherein the heavy chain comprises the amino acid sequence of SEQ ID NO: 35, or wherein the heavy chain comprises the amino acid sequence of SEQ ID NO: 53. In some aspects, the heavy chain is missing the C-terminal lysine from the amino acid sequence of SEQ ID NO: 17. In some aspects, the heavy chain is missing the C-terminal lysine from the amino acid sequence of SEQ ID NO: 35. In some aspects, the heavy chain amino is missing the C-terminal lysine from the amino acid sequence of SEQ ID NO: 53. In certain embodiments, formulations of the present disclosure contain about 50%, about 60%, about 70%, about 80%, about 90%, about 95%, about 98% or more of the anti-EBOV antibody wherein the C-terminal lysine is absent.

The amount of antibody, antibody combination, or antigen-binding fragment(s) thereof, contained within the stable liquid pharmaceutical formulations of the present disclosure may vary depending on the specific properties desired of the formulations, as well as the particular circumstances and purposes for which the formulations are intended to be used. For example, it may be necessary to ship formulations comprising one or more anti-EBOV antibodies from the site of manufacture to remote areas of the world, e.g. Congo or other parts of Africa, where the formulations may be exposed to agitation during transit and/or high temperatures during transit or at point-of-care.

In certain embodiments, the pharmaceutical formulations are stable liquid formulations that may contain 5±0.75 mg/mL to 250±37.5 mg/mL total antibody; 10±1.5 mg/mL to 240±36 mg/mL total antibody; 20±3.0 mg/mL to 230±34.5 mg/mL total antibody; 25±3.75 mg/mL to 240±36 mg/mL total antibody; 50±7.5 mg/mL to 230±34.5 mg/mL total antibody; 60±9 mg/mL to 240±36 mg/mL total antibody; 70±10.5 mg/mL to 230±34.5 mg/mL total antibody; 80±12 mg/mL to 220±33 mg/mL total antibody; 90±13.5 mg/mL to 210±31.5 mg/mL total antibody; 100±15 mg/mL to 200±30 mg/mL total antibody; 110±16.5 mg/mL to 190±28.5 mg/mL total antibody; 120±18 mg/mL to 180±27 mg/mL total antibody; 130±19.5 mg/mL to 170±25.5 mg/mL total antibody; 140±21 mg/mL to 160±24 mg/mL total antibody; 150±22.5 mg/mL total antibody; or 175±26.25 mg/ml. For example, the formulations of the present disclosure may comprise about 5 mg/mL; about 10 mg/mL; about 15 mg/mL; about 20 mg/mL; about 25 mg/mL; about 30 mg/mL; about 35 mg/mL; about 40 mg/mL; about 45 mg/mL; about 50 mg/mL; about 55 mg/mL; about 60 mg/mL; about 65 mg/mL; about 70 mg/mL; about 75 mg/mL; about 80 mg/mL; about 85 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; about 200 mg/mL; about 205 mg/mL; about 210 mg/mL; about 215 mg/mL; about 220 mg/mL; about 225 mg/mL; about 230 mg/mL; about 235 mg/mL; about 240 mg/mL; about 245 mg/mL; or about 250 mg/mL total antibody or antigen-binding fragment(s) thereof, that bind specifically to EBOV.

Excipients and pH

The pharmaceutical formulations of the present disclosure comprise one or more excipients. The term "excipient", as used herein, means any non-therapeutic agent added to the formulation to provide a desired consistency, viscosity or stabilizing effect.

In certain embodiments, the pharmaceutical formulation disclosed herein comprises at least one organic cosolvent in a type and in an amount that stabilizes the EBOV antibody under conditions of rough handling or agitation, such as, e.g., vortexing, orbital shaking and shocking. In some embodiments, what is meant by "stabilizes" is the prevention of the formation of aggregated antibody, for example, prevention of the formation of more than 0% aggregated antibody, or more than 1% aggregated antibody, or more than 3% aggregated antibody of the total amount of antibody (on a molar basis) over the course of rough handling. In some embodiments, the cosolvent stabilizes the formulation to prevent the formation of 0% to 3% aggregated antibody. In some embodiments, the cosolvent stabilizes the formulation to prevent the formation of more than 0% aggregated antibody. In some embodiments, rough handling is vortexing a solution containing the antibody and the organic cosolvent for about 60 minutes or about 120 minutes.

In certain embodiments, the organic cosolvent is a non-ionic surfactant, such as an alkyl poly(ethylene oxide). Specific non-ionic surfactants that can be included in the formulations of the present disclosure include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN 20, sorbitan monolaurate and polyoxyethylenesorbitan monolaurate. Poloxamer 188 is also known as PLURONIC F68.

The amount of non-ionic surfactant contained within the pharmaceutical formulations of the present disclosure may vary depending on the specific properties desired of the formulations, as well as the particular circumstances and purposes for which the formulations are intended to be used. In certain embodiments, the formulations may contain 0.01%±0.005% to 0.5%±0.25% surfactant. For example, the formulations of the present disclosure may comprise about 0.005%; about 0.01%; about 0.02%; about 0.03%; about 0.04%; about 0.05%; about 0.06%; about 0.07%; about 0.08%; about 0.09%; about 0.1%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; about 0.30%; about 0.35%; about 0.40%; about 0.45%; about 0.46%; about 0.47%; about 0.48%; about 0.49%; about 0.50%; about 0.55%; or about 0.575% polysorbate 20 or polysorbate 80.

The pharmaceutical formulations of the present disclosure may also comprise one or more stabilizers in a type and in an amount that stabilizes the EBOV antibody under conditions of thermal stress. In some embodiments, what is meant by "stabilizes" is maintaining greater than about 91% of the antibody in a native conformation when the solution containing the antibody and the thermal stabilizer is kept at about 45° C. for at least about 28 days. In some embodiments, what is meant by "stabilizes" is wherein less than about 6% of the antibody is aggregated when the solution containing the antibody and the thermal stabilizer is kept at about 45° C. for at least about 28 days. As used herein, "native" means the major form of the antibody by size exclusion, which is generally an intact monomer of the antibody. The term "native" also refers to non-aggregated and non-degraded form of the antibody.

In some embodiments, the thermal stabilizer is a polyol. In some embodiments, the thermal stabilizer is an amino acid. In some aspects, the thermal stabilizer is a sugar such as sucrose. The amount of stabilizer contained within the formulation can vary depending on the specific circumstances and intended purposes for which the formulation is used. In certain embodiments, the formulations may contain about 1% to about 15% sugar; about 2% to about 14% sugar; about 3% to about 13% sugar; about 4% to about 12% sugar; about 5% to about 12% sugar; about 6% to about 11% sugar; about 7% to about 10% sugar; about 8% to about 11% sugar; or about 9% to about 11% sugar. For example, the pharmaceutical formulations of the present disclosure may comprise 4%±0.8%; 5%±1%; 6%±1.2%; 7%±1.4%; 8%±1.6%; 9%±1.8%; 10% 2%; 11%±2.2%; 12% 2.4%; 13% 2.6%; or about 14%±2.8% sugar (e.g., sucrose).

The pharmaceutical formulations of the present disclosure may also comprise a buffer or buffer system, which serves to maintain a stable pH and to help stabilize the EBOV antibody. The term "buffer" as used herein denotes a pharmaceutically acceptable buffer which maintains a stable pH or resists changes in pH of the solution. In preferred embodiments, the buffer comprises histidine. In the context of this disclosure, "histidine buffer" or "buffer comprising histidine" is a buffer comprising the amino acid histidine. Examples of histidine buffers include histidine chloride, histidine acetate, histidine phosphate, and histidine sulfate. In one embodiment, the histidine buffer is prepared by dissolving L-histidine and L-histidine hydrochloride (e.g. as monohydrate) in a defined amount and ratio. In one embodiment, the histidine buffer is prepared by titrating L-histidine (free base, solid) with diluted hydrochloric acid. The term "histidine" is used interchangeably with "histidine buffer" throughout this disclosure. In some embodiments, what is meant by "stabilizes" is wherein less than 10%±0.5% of the antibody is aggregated when the solution containing the antibody and the buffer is kept at about 45° C. for at least about 28 days. In some embodiments, what is meant by "stabilizes" is wherein less than 5%±0.5% or less than 4%±0.5% of the antibody is aggregated when the solution containing the antibody and the buffer is kept at about 25° C. for up to about three months. In some embodiments, what is meant by "stabilizes" is wherein less than 5%±0.5% or less than 4%±0.5% of the antibody is aggregated when the solution containing the antibody and the buffer is kept at about 5° C. for up to about 36 months. In some embodiments, what is meant by "stabilizes" is wherein at least 90%±0.5% or at least 94%±0.5% of the antibody is in its native conformation as determined by size exclusion chromatography when the solution containing the antibody and the buffer is kept at about 45° C. for at least about 28 days. In some embodiments, what is meant by "stabilizes" is wherein at least 95%±0.5% or at least 96%±0.5% of the antibody is in its native conformation as determined by size exclusion chromatography when the solution containing the antibody and the buffer is kept at about 25° C. for up to about 3 months. In some embodiments, what is meant by "stabilizes" is wherein at least 95%±0.5% or at least 96%±0.5% of the antibody is in its native conformation as determined by size exclusion chromatography when the solution containing the antibody and the buffer is kept at about 5° C. for up to about 12 months. By "native" or "native conformation", what is meant is the antibody fraction that is not aggregated or degraded. This is generally determined by an assay that measures the relative size of the antibody entity, such as a size exclusion chromatographic assay. The non-aggregated and non-degraded antibody elutes at a fraction that equates to the native antibody, and is generally the main elution fraction. Aggregated antibody elutes at a fraction that indicates a size greater than the native antibody. Degraded antibody elutes at a fraction that indicates a size less than the native antibody.

In some embodiments, what is meant by "stabilizes" is wherein at least 18%±0.5% of the antibody is in its main charge form as determined by cation exchange chromatography when the solution containing the antibody and the buffer is kept at about 45° C. for at least about 28 days, or at least about a month. In some embodiments, what is meant by "stabilizes" is wherein at least 30%±0.5% or at least 35%±0.5% of the antibody is in its main charge form as determined by cation exchange chromatography when the solution containing the antibody and the buffer is kept at about 25° C. for up to about 3 months. In some embodiments, what is meant by "stabilizes" is wherein at least 30%±0.5% or at least 34%±0.5% of the antibody is in its main charge form as determined by cation exchange chromatography when the solution containing the antibody and the buffer is kept at about 5° C. for up to about 12 months. By "main charge" or "main charge form", what is meant is the fraction of antibody that elutes from an ion exchange resin in the main peak, which is generally flanked by more "basic" peaks on one side and more "acidic" peaks on the other side.

The pharmaceutical formulations of the present disclosure may have a pH of from about 5.2 to about 6.4. For example, the formulations of the present disclosure may have a pH of about 5.5; about 5.6; about 5.7; about 5.8; about 5.9; about 6.0; about 6.1; about 6.2; about 6.3; about 6.4; or about 6.5. In some embodiments, the pH is 6.0±0.4; 6.0±0.3; 6.0±0.2; 6.0±0.1; about 6.0; or 6.0.

In some embodiments, the buffer or buffer system comprises at least one buffer that has a buffering range that overlaps fully or in part the range of pH 5.5-7.4. In certain embodiments, the buffer comprises a histidine buffer. In certain embodiments, the histidine buffer is present at a concentration of 5 mM±1 mM to 15 mM±3 mM; 6 mM±1.2 mM to 14 mM 2.8 mM; 7 mM±1.4 mM to 13 mM±2.6 mM; 8 mM±1.6 mM to 12 mM±2.4 mM; 9 mM±1.8 mM to 11 mM±2.2 mM; 10 mM±2 mM; or about 10 mM. In certain embodiments, the buffer system comprises histidine at 10 mM±2 mM, at a pH of 6.0±0.3. In certain embodiments, the histidine buffer comprises L-histidine and L-histidine monohydrochloride monohydrate. In one embodiment, the histidine buffer comprises L-histidine at a concentration of 4.8 mM±0.96 mM. In one embodiment, the histidine buffer comprises L-histidine monohydrochloride monohydrate at a concentration of 5.2 mM±1.04 mM. In one embodiment, the histidine buffer comprises L-histidine at a concentration of 4.8 mM±0.96 mM and L-histidine monohydrochloride monohydrate at a concentration of 5.2 mM±1.04 mM.

The pharmaceutical formulations of the present disclosure may also comprise one or more excipients that serve to maintain a reduced viscosity or to lower the viscosity of formulations containing a high concentration of anti-EBOV antibody drug substance (e.g., generally ≥150 mg/ml of antibody). In certain embodiments, the viscosity modifier is an amino acid such as proline or histidine.

During the antibody purification process it may be desired or necessary to exchange one buffer for another to achieve appropriate excipient concentrations, antibody concentration, pH, etc. Buffer exchange can be accomplished, e.g., by ultrafiltration/diafiltration (UF/DF) using, e.g., a semi-permeable tangential flow filtration membrane. Use of such techniques, however, has the potential to cause the Gibbs-Donnan effect [Bolton et al., 2011, Biotechnol. Prog. 27(1): 140-152]. The buildup of positive charge on the product side of the membrane during protein concentration is counterbalanced electrically by the preferential movement of positive ions to the opposite side of the membrane. The potential consequence of this phenomenon is that the final concentrations of certain components (e.g., histidine, etc.) may be lower than the intended target concentrations of these components due to the electrostatic repulsion of positively charged diafiltration buffer excipients to the positively charged antibody protein during the UF/DF step. Thus, the present disclosure includes formulations in which the concentration of, e.g., histidine vary from the recited amounts or ranges herein due to the Gibbs-Donnan effect.

Volume exclusion describes the behavior of highly concentrated samples in which a significant portion of the total volume of the solution is taken up by the solute, especially large molecules such as proteins, excluding the cosolvent from this space. This then decreases the total volume of cosolvent available for other solutes to be dissolved in, which may result in unequal partition across the ultrafiltration membrane. Thus, the present disclosure includes formulations in which the concentration of, e.g., histidine may vary from the recited amounts or ranges herein due to the volume exclusion effect.

During the manufacture of the formulations of the present disclosure, variations in the composition of the formulation may occur. These variations may include the concentration of the active ingredient, the concentration of the excipients, and/or the pH of the formulation. Because changes in any of these parameters could potentially impact the stability or potency of the drug product, formulation robustness studies were conducted to assess whether variations in the composition, within the defined ranges, would impact the stability or potency of the antibody. Accordingly, the present disclosure includes formulations comprising anti-EBOV antibodies which are stable and retain potency with up to 50% variation in the excipient concentration. For example, included herein are anti-EBOV antibody formulations, wherein stability and potency of said formulations is unaffected by ±10%, ±20%, ±30%, ±40% or ±50% variation in the concentration of antibody, sucrose, histidine buffer and/or polysorbate.

Stability and Viscosity of the Pharmaceutical Formulations

As illustrated in the examples below, the present inventors have made the surprising discovery that stable liquid formulations comprising high concentrations of one or more anti-EBOV antibody (e.g., about 50 mg/mL or about 100 mg/mL) can be obtained by formulating the antibody with about 0.1% polysorbate 80, about 10% sucrose, and about 10 mM histidine buffer. In some aspects, the stable liquid formulations comprise three anti-EBOV antibodies at total antibody concentrations of 50 mg/mL or 100 mg/mL, 0.1% polysorbate 80, 10% sucrose, and about 10 nM histidine buffer at a pH of about 6. Such formulations, even those containing three different antibodies, are stable to stress during rough handling and to storage at temperatures ranging from −80° C. to 45° C., such as −30° C., −20° C., 5° C., 25° C., (shown herein) and have low viscosity (have viscosity below 5 cP).

The pharmaceutical formulations of the present disclosure typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of about 90%, about 95%, about 96%, about 97%, about 98% or about 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion ultra performance liquid chromatography [SE-UPLC]), such that native means non-aggregated and non-degraded. An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 60° C., e.g., storage at about −80° C., about −30° C., about −20° C., about 0° C., about 4°-8° C., about 5° C., about 25° C., about 35° C., about 37° C., about 40° C., or about 45° C. For example, a pharmaceutical formulation may be deemed stable if after 28 days of storage at 40° C./75% humidity (RH), greater than about 95%, 96%, 97% or 98% of native antibody is detected by SE-UPLC. A pharmaceutical formulation may be deemed stable if after 12 months of storage at 5° C., greater than about 95%, 96%, 97% or 98% of native antibody is detected by SE-UPLC. A pharmaceutical formulation may also be deemed stable if after 3 months of storage at 25° C., greater than about 95%, 96%, 97% or 98% of native antibody is detected by SE-UPLC. A pharmaceutical formulation may also be deemed stable if after 28 days of storage at 45° C., greater than about 89%, 90%, 91%, 92%, 93%, 94%, 95% or 96% of native antibody is detected by SE-UPLC. A pharmaceutical formulation may also be deemed stable if after 12 months of storage at −20° C., greater than about 96%, 97%, or 98% of native antibody is detected by SE-UPLC. A pharmaceutical formulation may also be deemed stable if after 12 months of storage at −30° C., greater than about 96%, 97% or 98% of native antibody is detected by SE-UPLC. A pharmaceutical formulation may also be deemed stable if after 12 months of storage at −80° C., greater than about 96%, 97% or 98% of native antibody is detected by SE-UPLC.

Stability can be measured, inter alia, by determining the percentage of antibody that forms in an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion ultra performance liquid chromatography [SE-UPLC]). An "acceptable degree of stability", as that phrase is used herein, means that at most 5% of the antibody is in an aggregated form (also denoted as the high molecular weight—HMW—form) detected in the formulation after storage for a defined amount of time at a given temperature. In certain embodiments an acceptable degree of stability means that at most about 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C., about 40° C., or about 45° C. For example, a pharmaceutical formulation may be deemed stable if after 12 months of storage at 5° C., less than about 2%, 1%, 0.5%, or 0.1% of the antibody is detected in an aggregated form. A pharmaceutical formulation may also be deemed stable if after three months of storage at 25° C., less than about 4%, 3%, 2%, 1%, 0.5%, or 0.1% of the antibody is detected in an aggregated form. A pharmaceutical formulation may also be deemed stable if after 28 days of storage at 40° C./75% RH, less than about 4%, 3%, 2%, 1%, 0.5%, or 0.1% of the antibody is detected in an aggregated form. A pharmaceutical formulation may also be deemed stable if after 28 days of storage at 45° C., less than about 10%, 9%, 8%, 7%, 6%, 5%, 4%, 3%, 2%, 1%, or 0.5%, of the antibody is detected in an aggregated form. A pharmaceutical formulation may also be deemed stable if after three months of storage at −20° C., −30° C., or −80° C. less than about 3%, 2%, 1%, 0.5%, or 0.1% of the antibody is detected in an aggregated form.

Stability can be measured, inter alia, by determining the percentage of antibody that migrates in a more acidic fraction during ion exchange ("acidic form") than in the main fraction of antibody ("main charge form"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, PNAS, Apr. 16, 2002, 99(8):5283-5288). The percentage of "acidified" antibody can be determined by, inter alia, ion exchange chromatography (e.g., cation exchange ultra performance liquid chromatography [CEX-UPLC]). An "acceptable degree of stability", as that phrase is used herein, means that at most 45% of the antibody is in a more acidic form detected in the formulation after storage for a defined amount of time at a defined temperature. In certain embodiments an acceptable degree of stability means that at most about 40%, 35%, 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. In one embodiment, an acceptable degree of stability means that less than 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., or about 45° C. For example, a pharmaceutical formulation may be deemed stable if after three months of storage at −80° C., −30° C., or −20° C. less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 12 months of storage at 5° C., less than about 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 3 months of storage at 25° C., less than about 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 45° C., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody can be detected in a more acidic form.

Other methods may be used to assess the stability of the formulations of the present disclosure such as, e.g., differential scanning calorimetry (DSC) to determine thermal stability, controlled agitation to determine mechanical stability, and absorbance at about 350 nm or about 405 nm to determine solution turbidities. For example, a formulation of the present disclosure may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

Measuring the biological activity or binding affinity of the antibody to its target may also be used to assess stability. For example, a formulation of the present disclosure may be regarded as stable if, after storage at e.g., 5° C., 25° C., 45° C., etc. for a defined amount of time (e.g., 1 to 36 months), the anti-EBOV antibody contained within the formulation binds to EBOV with an affinity that is at least 90%, 95%, or more of the binding affinity of the antibody prior to said storage. Binding affinity may be determined by e.g., ELISA or surface plasmon resonance. Biological activity may be determined by a EBOV activity assay, such as e.g., contacting a cell infected with EBOV with the formulation comprising the anti-EBOV antibody. The binding of the antibody to such a cell may be measured directly, such as e.g., via FACS analysis. Alternatively, activity of antibody can be determined by a decrease in viral load in vitro or in vivo, or by an increase in survival of a mammal infected with EBOV.

Additionally, measuring the relative potency of the antibody in an antibody-dependent cellular cytotoxicity assay (ADCC assay) can be used to assess stability. For example, a formulation of the present disclosure may be regarded as stable if, after storage at e.g., −80° C., −30° C., −20° C., 5° C., 25° C., 40° C., 45° C., etc. for a defined amount of time (e.g., 1 to 36 months), the anti-EBOV antibody contained within the formulation retains 90%, 95%, or more relative ADCC potency compared to the antibody prior to storage.

Similarly, measuring the relative potency of the antibody in pseudovirus neutralization assay can be used to assess stability. For example, a formulation of the present disclosure may be regarded as stable if, after storage at e.g., −80° C., −30° C., −20° C., 5° C., 25° C., 40° C., 45° C., etc. for a defined amount of time (e.g., 1 to 36 months), the anti-EBOV antibody contained within the formulation retains 90%, 95%, or more relative pseudovirus neutralization compared to the antibody prior to storage.

Additional methods for assessing the stability of an antibody in formulation are demonstrated in the Examples presented below.

The liquid pharmaceutical formulations of the present disclosure may, in certain embodiments, exhibit low to moderate levels of viscosity. "Viscosity" as used herein may be "kinematic viscosity" or "absolute viscosity". "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, a low level of viscosity, in reference to a fluid formulation of the present disclosure, will exhibit an absolute viscosity of less than about 20 cPoise (cP). For example, a fluid formulation disclosed herein will be deemed to have "low viscosity", if, when measured using standard viscosity measurement techniques, the formulation exhibits an absolute viscosity of about 20 cP, about 19 cP, about 18 cP, about 15 cP, about 12 cP, about 10 cP, about 9 cP, about 8 cP, or less. As used herein, a moderate level of viscosity, in reference to a fluid formulation of the present disclosure, will exhibit an absolute viscosity of between about 35 cP and about 20 cP. For example, a fluid formulation disclosed herein will be deemed to have "moderate viscosity", if when measured using standard viscosity measurement techniques, the formulation exhibits an absolute viscosity of about 34 cP, about 33 cP, about 32 cP, about 31 cP, about 30 cP, about 29 cP, about 28 cP, about 27 cP, about 26 cP, about 25 cP, about 24 cP, about 23 cP, about 22 cP, about 21 cP, about 20 cP, about 19 cP, 18 cP, about 17 cP, about 16 cP, or about 15 cP. Formulations provided herein can have a low viscosity, for example, a viscosity of about 2 cP.

Exemplary Formulations

According to one aspect of the present disclosure, the pharmaceutical formulation is a stable, low viscosity, generally physiologically isotonic liquid formulation, which comprises: (i) a human antibody that specifically binds to EBOV (e.g., H1H17203P, H1H17139P, and/or H1H17161P), at a concentration of up to 250 mg/mL±45 mg/mL; (ii) a histidine buffer system that provides sufficient buffering at about pH 6.0±0.3; (iii) an organic cosolvent, which protects the structural integrity of the antibody; and (iv) a stabilizer that is a sugar.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein the antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10. In one embodiment, the anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein the antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein the antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the first anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16; and the second anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16; and the second anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34; and the second anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 50 mg/mL±7.5 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16; the second anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34; and the third anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein the antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10. In one embodiment, the anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein the antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein the antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28. In one embodiment, the first anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16; and the second anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16; and the second anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34; and the second anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

According to one embodiment, the stable, liquid pharmaceutical formulation comprises: (a) 10%±2% w/v sucrose, (b) 10 mM±2 mM histidine buffer, (c) 0.1%±0.05% w/v polysorbate, and (d) 100 mg/mL±15 mg/mL total anti-EBOV antibody, at pH 6.0±0.3; wherein a first antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody is a human IgG1 antibody that comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46. In one embodiment, the first anti-EBOV antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16; the second anti-EBOV antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34; and the third anti-EBOV antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

Additional non-limiting examples of pharmaceutical formulations encompassed by the present disclosure are set forth elsewhere herein, including the working Examples presented below.

Containers and Methods of Administration

The pharmaceutical formulations of the present disclosure may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present disclosure including, e.g., clear and opaque (e.g., amber) glass or plastic vials. Likewise, any type of syringe can be used to contain or administer the pharmaceutical formulations of the present disclosure.

The pharmaceutical formulations of the present disclosure may be contained within "normal tungsten" syringes or "low tungsten" syringes. As will be appreciated by persons of ordinary skill in the art, the process of making glass syringes generally involves the use of a hot tungsten rod which functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present disclosure, can contain less than about 490, 480, 470, 460, 450, 440, 430, 420, 410, 390, 350, 300, 250, 200, 150,100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present disclosure, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present disclosure are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present disclosure are commercially available under the tradename "FluroTec®", available from West Pharmaceutical Services, Inc. (Lionville, PA). FluroTec® is an example of a fluorocarbon coating used to minimize or prevent drug product from adhering to the rubber surfaces.

According to certain embodiments of the present disclosure, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present disclosure. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ 1, ∥ and Ill (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present disclosure include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park, IL).

The use of a microinfusor to deliver the pharmaceutical formulations of the present disclosure is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J.* *Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In certain embodiments, the stable liquid pharmaceutical formulation of any of the preceding aspects is contained in a sterile glass vial and is administered as an IV infusion. Exemplary dosages include 30,000 mg, 25,000 mg, 20,000 mg, 15,000 mg, 13,500 mg, 12,500 mg, 10,000 mg, 7,500 mg, 5000 mg, 2500 mg, 1450 mg, 1000 mg, 725 mg, 600 mg, 500 mg, 250 mg, 200 mg, 150 mg, 100 mg, 75 mg, 50 mg, or 25 mg.

In one embodiment, the container is a 20 mL type 1 clear borosilicate glass vial. In certain embodiments, the container is a 2 mL, 5 mL or 10 mL type 1 borosilicate glass vial with a chlorobutyl stopper, with a FluroTec® coating.

In one embodiment, the liquid pharmaceutical formulation of the present disclosure comprising about 25 mg/mL, 50 mg/mL, 100 mg/mL, or 150 mg/mL anti-EBOV antibody is administered intravenously and may be contained in a glass vial. In some embodiments, the present disclosure provides a glass vial comprising a stable liquid formulation comprising 50 mg/mL, 100 mg/mL, or 150 mg/mL total anti-EBOV antibody, 10 mM of histidine, at pH of about 6.0, 10% sucrose, and 0.1% polysorbate 80.

In some embodiments, each antibody is administered at 50 mg/kg of body weight. In one embodiment, two antibodies are co-formulated such that the final formulation provides for each antibody to be administered at 50 mg/kg of body weight. Accordingly, the final dose to be administered to the patient is 100 mg/kg of body weight, with the two antibodies in the formulation at a 1:1 ratio. In one embodiment, the co-formulated antibodies are delivered intravenously over a time period of about 2 hours.

In some embodiments, three antibodies are co-formulated such that the final formulation provides for each antibody to be administered at 50 mg/kg of body weight. Accordingly, the final dose to be administered to the patient is 150 mg/kg of body weight, with the three antibodies in the formulation at a 1:1:1 ratio. In one embodiment, the co-formulated antibodies are delivered intravenously over a time period of about 2 hours.

In some aspects, a patient weighing about 90 kg receiving 150 mg/kg dose would get dose of about 13,500 mg dose. In some aspects, a patient weighing about 45 kg person receiving 150 mg/kg would get dose of about 6,750 mg. In some aspects, a patient might receive as much as 30,000 mg.

In certain embodiments, the three antibodies are prepared in a glass vial. In certain embodiments, each vial may contain 725 mg of total antibody, i.e. three antibodies at a 1:1:1 ratio in a volume of 14.5 mL, giving a final antibody concentration of 50 mg/mL. This may be administered intravenously to a patient in a time period of two hours.

In certain embodiments, the three antibodies are prepared in a glass vial. In certain embodiments, each vial may contain 1450 mg of total antibody, i.e. three antibodies at a 1:1:1 ratio in a volume of 14.5 mL, giving a final antibody concentration of 100 mg/mL. This may be administered intravenously to a patient in a time period of two hours.

In certain embodiments, the present disclosure provides an autoinjector comprising any of the liquid formulations described herein. In some embodiments, the present disclosure provides an autoinjector comprising a stable liquid formulation comprising about 50 mg/mL, about 100 mg/mL, about 150 mg/mL or about 175 mg/mL total anti-EBOV antibody, about 10 mM of histidine, at pH of about 6.0, about 10% sucrose, and about 0.1% polysorbate 80.

In certain embodiments, the present disclosure provides an autoinjector comprising any of the liquid formulations described herein. In some embodiments, the present disclosure provides an autoinjector comprising a stable liquid formulation comprising 50 mg/mL or 100 mg/mL total anti-EBOV antibody, 10 mM of histidine, at pH of about 6.0, 10% sucrose, and 0.1% polysorbate 80.

In certain embodiments, the present disclosure provides a prefilled syringe comprising any of the liquid formulations described herein. In some embodiments, the present disclosure provides a prefilled syringe comprising a stable liquid formulation comprising about 50 mg/mL, about 100 mg/mL, about 150 mg/mL or about 175 mg/mL anti-EBOV antibody, about 10 mM of histidine, at pH of about 6.0, about 10% sucrose, and about 0.1% polysorbate 80. In certain embodiments, the syringe is a 1 mL or 2.25 mL long glass syringe filled with a 27-gauge thin wall needle, a fluorocarbon coated rubber plunger and a rubber needle shield.

In one embodiment, the liquid pharmaceutical formulation containing about 100 mg/mL±15 mg/mL total anti-EBOV antibody is administered in a volume of approximately up to 2 mL in a prefilled syringe. In certain embodiments, the syringe is a 1 mL or 2.25 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FLUROTEC® coated 4023/50 rubber plunger.

In one embodiment, the liquid pharmaceutical formulation containing about 50 mg/mL±7.5 mg/mL anti-EBOV antibody is administered in a volume of approximately up to 2 mL in a prefilled syringe. In one embodiment, the syringe is a 1 mL or 2.25 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FLUROTEC® coated 4023/50 rubber plunger.

Compatibility

In one embodiment, the stable formulation is a liquid solution containing 50 mg/mL total anti-EBOV antibody (e.g. 16.7 mg/mL each of H1H17203P, H1H17139P, and/or H1H17161P; or about 25 mg/mL each of any two of H1H17203P, H1H17139P, and H1H17161P) for IV administration. In some aspects, the IV admixture solution has compatibility (including in-use stability) with diluents and materials used in the dosing system (IV bags, sets, and filters), including 0.9% Sodium Chloride, 5% Dextrose or Lactate Ringer's solution, PVC (polyvinyl chloride) and polyethylene.

Exemplary dosages include 10 mg/kg, 30 mg/kg, 50 mg/kg, and 150 mg/kg. In-use stability of the anti-EBOV formulation during IV delivery supports administration of the clinical doses. The 0.9% Sodium Chloride PVC IV bags, containing the diluted antibodies, in some embodiments, can be initially held for 24 hours at 5° C., then incubated for at least 8 hours at 25° C. After these incubations, each of the infusion sets can be connected to IV bags, primed with the diluted DP and held for 1 hour at ambient room temperature. The diluted DP solutions can be then pumped through the respective infusion sets at 25 mL/hr and 500 mL/hr. These infusion sets contain the basic materials (PVC with DEHP, PVC with TOTM and polyethylene) that comprise infusion sets used for IV delivery of the antibody combination in clinical uses. The infusion sets can contain a 0.2 μm polyethersulfone inline filter.

In some aspects, a 50 mg/mL anti-EBOV formulation comprising at least one anti-EBOV antibody, diluted in 0.9% Sodium Chloride Injection to concentrations of either 2.2 mg/mL or 23.7 mg/mL, is physically and chemically stable when tested under these conditions within the proposed dose ranges and administration conditions. The anti-EBOV formulation can, in some aspects, exhibit no meaningful change in quality attributes after dilution in IV bags, storage in IV bag for 24 hours at 2-8° C. and at least 8 hours at 25° C., infusion set hold for one hour, or delivery with pumping rates between 25 mL/hour to 500 mL/hour.

In some aspects, the additional flexibility of using different diluents for dose preparation of a co-formulated antibody formulation and to support temperature excursion (higher than 25° C.) which may occur during IV administration is provided. When the anti-EBOV antibodies are diluted with 0.9% Sodium Chloride, 5% Dextrose or Lactated Ringer's at 40° C. the formulation continued to exhibit stability. The IV bags containing diluted antibodies can be held initially for 24 hours at 5° C.; then incubated for at least 6 hours at 40° C. After incubations, each of the infusion sets can be connected to the IV bags, primed with the diluted antibodies and held for 1 hour at ambient room temperature. The diluted antibody solutions can then be pumped through the respective infusion sets.

In some aspects, a 50 mg/mL anti-EBOV antibody formulation comprising at least one anti-EBOV antibody, diluted in 0.9% Sodium Chloride Injection, 5% Dextrose or lactated ringer's to concentrations of either 1.6 mg/mL or 27.9 mg/mL can be physically and chemically stable under the conditions tested within the proposed dose ranges and administration conditions. The anti-EBOV formulation can, in some aspects, exhibit no meaningful change in quality attributes after dilution in IV bags, storage in IV bag for 24 hours at 2-8° C. and at least 6 hours at 40° C., infusion set hold for one hour.

The IV compatibility characteristics (including in-use stability) of the stable liquid pharmaceutical formulations support the following conclusions pertaining to dose preparation and IV administration (50 mg/mL):

- 0.9% Sodium Chloride Injection, 5% Dextrose Injection and Lactate Ringer's IV bags made of PVC are compatible with IV administration of the formulation containing at least one anti-EBOV antibody;
- The anti-EBOV antibody formulation can be diluted to antibody concentrations as low as 2.2 mg/mL and as high as 23.7 mg/mL in the PVC IV bags containing IV diluent of 0.9% Sodium Chloride, 5% Dextrose or Lactated Ringer's for IV administration;
- Diluted co-formulated antibodies prepared with 0.9% Sodium Chloride Injection can be stored at room temperature up to 25° C. for at least about 8 hours from the time of preparation to the end of the infusion or at 2° C. to 8° C. for at least about 24 hours from the time of preparation to the end of infusion;
- Diluted co-formulated antibodies prepared with 5% Dextrose or Lactate Ringer's can be stored at room temperature up to 25° C. for at least about 4 hours from the time of preparation to the end of the infusion or at 2° C. to 8° C. for at least about 24 hours from the time of preparation to the end of infusion;

Diluted co-formulated antibodies (2.2 mg/mL to 23.7 mg/mL) prepared with 0.9% Sodium Chloride, 5% Dextrose or Lactate Ringer's solution is stable for 6 hours at 40° C.;

Diluted co-formulated antibodies can be administered with an infusion set composed of either PVC containing DEHP, PVC containing TOTM, or polyethylene lined PVC;

Diluted co-formulated antibodies are compatible with the use of an inline 0.2 μm polyethersulfone filter.

Therapeutic Uses of the Pharmaceutical Formulations

The pharmaceutical formulations of the present disclosure are useful, inter alia, for the treatment, prevention or amelioration of EBOV or any symptom related thereto.

EXAMPLES

The following examples are presented so as to provide those of ordinary skill in the art with a complete disclosure and description of how to make and use the methods and compositions disclosed herein, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by mole, molecular weight is average molecular weight, temperature is in degrees Centigrade, and pressure is at or near atmospheric pressure.

Example 1: Development of an Anti-EBOV Antibody Formulation

The goals of the formulation activities were to develop a formulation with the following attributes:

A liquid formulation that is stable after being subjected to stress, for example temperature cycles, extreme temperatures, agitation during transport, etc., conditions a therapeutic would be exposed to in transit from a manufacturing facility to remote field clinics where Ebola exposure has occurred and/or Ebola patients exist;

A liquid formulation with a concentration of the anti-EBOV antibody sufficient to deliver a dose of 25 mg to 30,000 mg, for example about 7500 mg, about 5000 mg, about 3000 mg, about 2000 mg, about 1500 mg, 1000 mg, about 800 mg, about 750 mg, about 500 mg, about 250 mg, about 200 mg, about 150 mg, about 100 mg, about 75 mg, about 50 mg, or about 25 mg, by intravenous infusion;

A near iso-osmolar formulation that is stable upon dilution with commonly used diluents, e.g., 0.9% sodium chloride injection or 5% dextrose injection or Lactated Ringer's injection, for intravenous infusion;

A formulation that is compatible with and stable in Type 1 clear glass vial and standard serum stopper as packaging; and A sterile drug product (DP) solution that supports long-term stability;

A formulation that minimizes antibody high molecular weight (HMW) species when subjected to handling and thermal stresses;

A formulation that minimizes changes in the relative distribution of antibody charged species when subjected to thermal stress; and A formulation that maintains biological activity when subjected to rough transit and thermal stress in extreme environments.

Throughout formulation development, three primary protein stress conditions (representing extreme handling conditions which the antibody drug product could be subjected to during handling, manufacturing, shipping, storing, and labeling) were employed to develop and optimize the antibody formulations and to evaluate the effects of potential real-world stresses on the stability of the drug product used in remote regions of the world. These stress conditions included:

Agitation (vortexing) of the protein solution at room temperature. Vortexing in glass vials exceeds the agitation that occurs during the handling and manufacturing of the protein.

Incubating the protein solution at elevated temperature (37° C., 40° C. or 45° C.) relative to the proposed DP storage condition (2° C.-8° C.).

Subjecting the protein to multiple freeze thaw cycles. Since the protein will undergo at least one freeze thaw cycle during the manufacture of DP, multiple freeze thaw cycles simulate and exceed the actual stress the protein is expected to experience.

There were several main goals of the initial formulation development work:

1. Selection of buffer and pH for each of three anti-EBOV antibodies: The choice of buffer and pH can have a large effect on the stability of proteins, hence deciding on the optimal buffer species and pH is an important process. Studies are presented in these sections that demonstrate the rationale for choice of the optimal buffer and pH for each antibody.

2. Selection of surfactant or organic cosolvent for each of three anti-EBOV antibodies: A surfactant or organic cosolvent, such as polysorbate, is typically required to prevent precipitation or aggregation of proteins when agitated. Soluble protein may be subjected to agitation when handled, filtered, mixed, manufactured, shipped, and administered. The antibody drug substance in a simple buffered solution can become visibly cloudy with excess agitation. Therefore, it was determined that stabilizing each of the proteins to handling and agitation was important.

3. Identification/selection of stabilizing/tonicifying excipients: The addition of sugars, salts, and amino acids were examined for their ability to improve the stability of each of the three antibodies to thermal stress and to increase the shelf life of the drug product (DP). The rationale for inclusion of these thermal stabilizers, as well as studies identifying the optimal concentrations in the final formulation are presented herein.

4. Selection of antibody concentration: The effect of antibody concentration on the stability of the drug product with the selected excipients was examined.

5. Co-formulating three anti-EBOV antibodies: The three anti-EBOV antibodies were co-formulated into a liquid formulation at two concentrations, and buffer and pH were selected for the combination, surfactant or organic cosolvent were selected, additional excipients tested, and stabilizers were identified and selected.

Initial formulation development activities were conducted using 100 mg/mL of each anti-EBOV antibody separately formulated, and involved screening organic cosolvents, thermal stabilizers, and buffers in liquid formulations of each of the anti-EBOV antibodies to identify excipients that are compatible with the protein and enhance its stability, while maintaining near physiologic osmolality and low viscosity for intravenous and subcutaneous injection. Buffer conditions were also examined to determine the optimal pH for maximum protein stability (described in Example 6 herein).

Results from this initial formulation development work were used to develop an initial formulation that was suitable for clinical studies.

With the knowledge gained from the initial formulation development, the late stage formulation development activities involved co-formulating the three antibodies at two concentrations, confirming pH, surfactant concentration, and stabilizers to identify excipients that enhance protein stability at both low and high protein concentrations and when exposed to stress such as high temperatures and agitation (described in Examples 4-9).

Throughout formulation development, the formulations were assessed for stress and storage stability. The methods used to assess stability in the formulation development studies are described in Example 3 herein. Examples 4 through 9 describe the storage and stress stability of the formulations.

Results generated from these studies were used to develop stable liquid formulations suitable for clinical use, for intravenous (IV) administration. Such formulations exhibited stability when exposed to thermal or agitational stress.

Other attributes of the formulations will be apparent from the description herein.

Anti-EBOV Antibodies:

Anti-EBOV antibodies are described in US 2016/0215040, incorporated herein in its entirety. The exemplary antibodies used in the Examples below are fully human anti-EBOV antibodies H1H17203P (REGN3470; having an HCVR amino acid sequence of SEQ ID NO: 2 and an LCVR amino acid sequence of SEQ ID NO: 10), H1H17139P (REGN3471; having an HCVR amino acid sequence of SEQ ID NO: 20 and an LCVR amino acid sequence of SEQ ID NO: 28), and H1H17161P (REGN3479; having an HCVR amino acid sequence of SEQ ID NO: 38 and an LCVR amino acid sequence of SEQ ID NO: 46) comprising the sequences described in detail above.

Example 2: Exemplary Formulations

In certain embodiments, the anti-EBOV antibodies are individually formulated or co-formulated as an aqueous buffered formulation comprising: (a) from 5%±1% to 15%±3% w/v sucrose, (b) from 5 mM±1 mM to 20 mM±4 mM histidine buffer, (c) from 0.01%±0.005% to 0.5%±0.25% w/v polysorbate, and (d) 50 mg/mL±7.5 mg/mL total anti-EBOV antibody, at pH 6.0±0.3. In certain embodiments, the anti-EBOV antibodies are individually formulated or co-formulated as an aqueous buffered formulation comprising: (a) 10%±2% w/v sucrose, (b) 10 mM±2 mM histidine buffer, (c) 0.1%±0.05% w/v polysorbate, and (d) 50 mg/mL±7.5 mg/mL total antibody, at pH 6.0±0.3. When co-formulated, the anti-EBOV antibodies are present in a 1:1:1 ratio.

In certain embodiments, the anti-EBOV antibodies are individually formulated or co-formulated as an aqueous buffered formulation comprising: (a) from 5%±1% to 15%±3% w/v sucrose, (b) from 5 mM±1 mM to 20 mM±4 mM histidine buffer, (c) from 0.01%±0.005% to 0.5%±0.25% w/v polysorbate, and (d) 100 mg/mL±15 mg/mL total antibody, at pH 6.0±0.3. In certain embodiments, the anti-EBOV antibodies are individually formulated or co-formulated as an aqueous buffered formulation comprising: (a) 10%±2% w/v sucrose, (b) 10 mM±2 mM histidine buffer, (c) 0.1%±0.05% w/v polysorbate, and (d) 100 mg/mL±15 mg/mL total antibody, at pH 6.0±0.3. When co-formulated, the anti-EBOV antibodies are present in a 1:1:1 ratio.

Exemplary formulations include:

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL H1H17203P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL, H1H17139P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL total H1H17203P and H1H17139P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL total H1H17203P and H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL total H1H17139P and H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 50 mg/mL±7.5 mg/mL total H1H17203P, H1H17139P, and H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±10 mg/mL H1H17203P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±15 mg/mL, H1H17139P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±15 mg/mL H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±15 mg/mL total H1H17203P and H1H17139P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±15 mg/mL total H1H17203P and H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±15 mg/mL total H1H17139P and H1H17161P anti-EBOV antibody, at pH 6.0±0.3.

A stable liquid pharmaceutical formulation comprising: (a) 10%±2% w/v sucrose, (b) 10 mM±2 mM histidine buffer, (c) 0.1%±0.05% w/v polysorbate, and (d) 100 mg/mL±15 mg/mL total H1H17203P, H1H17139P, and H1H17161P anti-EBOV antibody, at pH 6.0±0.3.

Example 3: Methods Used to Assess Formulation Stability

The following assays were applied to assess formulation stability:

Color and appearance by visual inspection pH

Turbidity measured by increase in OD at 405 nm, or by nephelometry

Particulate matter analysis performed by microflow imaging (MFI) (reported as particle counts obtained as is), and light obscuration (HIAC)

Protein concentration by reverse phase-ultra performance liquid chromatography (RP-UPLC)

Purity by size exclusion—ultra performance liquid chromatography (SE-UPLC), or by reduced and non-reduced microchip capillary electrophoresis sodium dodecyl sulfate (MCE-SDS) PAGE Charge variant analysis by cation exchange chromatography-ultra performance liquid chromatography (CEX-UPLC), or by imaged capillary isoelectric focusing (iCIEF)

Potency by bioassay: The relative potency of each sample is determined using a bioassay and is defined as: ($IC_{50}$ reference sample/$IC_{50}$ sample)*100%. The measured potency of storage stability samples must be within 50% to 150% of the measured potency of the reference standard.

The physical stability of a formulation refers to properties such as color, appearance, pH, turbidity, and protein concentration. The presence of visible particulates in solution can be detected by visual inspection. A solution passes visual inspection if it is clear to slightly opalescent, essentially free from visible particulates, and colorless to pale yellow. In addition, turbidity, measured by OD at 405 nm, can also be used to detect particulates in solution. An increase in OD at 405 nm may indicate the presence of particulates, an increase in opalescence, or color change of the test articles. MFI is used to measure subvisible particulates that are ≥2 μm in size. The anti-EBOV antibody protein concentration is measured by a RP-UPLC assay and reported as percent protein recovery relative to the starting material. In the RP-UPLC assay, anti-EBOV antibody is eluted from the RP column as a single peak. The protein concentration is determined from the antibody total peak area by comparing it with a calibration curve generated using antibody standards. Percent of recovery is calculated based on the measured protein concentration relative to the starting protein concentration.

Chemical stability refers to the formation of covalently modified forms (e.g. covalent aggregates, cleavage products, or charge variant forms) and non-covalently modified forms (e.g. non-covalent aggregates) of protein. Higher and lower molecular weight degradation products can be separated from native antibody by SE-UPLC and MCE-SDS methods. The percentage of degraded anti-EBOV antibody in the SE-UPLC and MCE-SDS methods is calculated from the ratio of the area of all non-native peaks to the total area of all anti-EBOV antibody peaks. Charge variant forms of anti-EBOV antibodies are resolved using CEX-UPLC and iCIEF. In the CEX-UPLC method, peaks with retention times earlier than that of the main peak are labeled as "acidic" peaks; the peaks with retention times later than that of the main peak are labeled as "basic" peaks. In the iCIEF method, peaks that are focused to a pl lower than that of the main peak are labeled "acidic" peaks, whereas those focused to a pl higher than that of the main peak are labeled "basic" peaks.

Example 4: Stability Studies for Aqueous Formulations of Anti-EBOV Antibodies

All studies outlined in this section in this Example refer to research stability studies performed on H1H17203P Drug Product (DP), H1H17139P DP, and H1H17161P DP. Each DP was formulated and filled separately to provide stability data under real time, accelerated, and stress stability conditions. The Drug Substance (DS) lots used for these studies are representative of the DS manufactured for clinical use.

Formulation Development

H1H17203P, H1H17139P and H1H17161P antibodies are formulated for delivery by intravenous (IV) injection for a first-in-human study. The stability of individually formulated and filled H1H17203P, H1H17139P, and H1H17161P drug products were assessed in the clinical formulation; the analytical characterization results indicated that this formulation provided adequate stability for H1H17203P, H1H17139P, and H1H17161P antibodies under all conditions examined. The H1H17203P, H1H17139P, and H1H17161P antibody formulation contains 10 mM histidine, pH 6.0, 0.1% (w/v) polysorbate 80, and 10% (w/v) sucrose.

Research Stability

All FDS (Formulated Drug Substance) and DP (Drug Product) studies outlined in this section refer to research stability studies performed on individually formulated and filled H1H17203P, H1H17139P, and H1H17161P antibodies, manufactured for developmental use. Formal stability studies examining H1H17203P, H1H17139P, and H1H17161P antibodies manufactured for clinical use are discussed below.

Stability studies have been initiated to determine the storage, accelerated, and stress stability of individually formulated and filled research lots of 50 mg/mL H1H17203P DP, 50 mg/mL H1H17139P DP and 50 mg/mL H1H17161P DP. The DS lots used for these studies are representative of the DS manufactured for clinical use. The DP was incubated under several elevated temperature conditions, relative to storage temperature conditions. These accelerated conditions were selected to simulate the conditions beyond which the DP may not be subjected during manufacturing and handling and to elucidate the degradation pathways for H1H1723P DP, H1H17139P DP and H1H17161P DP. An outline of the storage, accelerated and stress stability conditions for the H1H17203P DP, H1H17139P DP, and H1H17161P DP are presented in Table and the analysis plans are presented in Table 2.

TABLE 1

Research Stability Studies for H1H17203P DP,
H1H17139P DP, and H1H17161P DP

| Storage Stability | | Container/Closure |
|---|---|---|
| Storage Temperature | Length of Storage (months) | Type 1 borosilicate glass with FluroTec® coated 4432/50 butyl rubber stopper |
| 5° C. | 0, 1, 3, 6, 9, 12 | |
| Accelerated Stability | | |
| Incubation Condition | Length of Incubation | |
| 25° C. | 0, 0.5, 1, and 3 months | |
| 45° C. | 0, 7, 14, and 28 days | |
| Stress Stability | | |
| Stress | Duration of Stress | |
| Agitation (vortex) | 0, 60, and 120 minutes | |
| Freeze/Thaw[a] | 0, 4, and 8 cycles | |

[a]Frozen at −80° C. and thawed at room temperature.

TABLE 2

Research Stability Studies Analysis Plan for H1H17203P DP,
H1H17139P DP, and H1H17161P DP

| Assay | Samples to be Analyzed |
|---|---|
| Color and Appearance | All Samples |
| pH | All Samples |
| Turbidity (Increase in OD at 405 nm) | All Samples |
| % Protein Recovered by RP-UPLC | All Samples |
| % Purity by Non-Reduced and Reduced MCE-SDS | t = 0, 6, 12, 24 and 36 months at 5° C.; 3 months at 25° C.; 28 days at 45° C. 120 min Agitation, 8X Freeze/Thaw |
| % Purity by SE-UPLC | All Samples |
| Charge Variant Analysis by CEX-UPLC | All Samples |
| Charge Variant Analysis by iCIEF | t = 0, 6, 12 at 5° C.; 3 months at 25° C.; 28 days at 45° C. 120 min Agitation, 8X Freeze/Thaw |
| Particulate Matter Analysis by MFI | t = 0, 6, 12, 24 and 36 months at 5° C.; 3 months at 25° C.; 28 days at 45° C. 120 min Agitation, 8X Freeze/Thaw |

Research Stability for 50 mg/mL H1H17203P DP
Research Storage Stability for 50 mg/mL H1H17203P DP Three months of research stability data are shown for the 50 mg/mL H1H17203P DP. The 50 mg/mL H1H17203P DP was physically and chemically stable when stored at 5° C. for 3 months (Table 3). No appreciable change in the physical or chemical stability was detected in any of the monitored attributes.

Research Accelerated Stability for 50 mg/mL H1H17203P DP

Results from the analysis of the 50 mg/mL H1H17203P DP following incubation under accelerated conditions are provided in Table 6. After H1H17203P DP was incubated for 28 days at 45° C., 2.1% and 1.6% increases in the relative amount of HMW and LMW species (SE-UPLC), and 15.1% and 13.5% increases in the percentage of acidic charge variant species, determined by CEX-UPLC and iCIEF, respectively, were observed. After H1H17203P DP was incubated for 3 months at 25° C., a 0.3% increase in the amount of both HMW and LMW species (SE-UPLC) and 2.9% and 3.0% increases in the percentage of acidic charge variant species, determined by CEX-UPLC and iCIEF, respectively, were observed. The results from accelerated stability testing demonstrated that an increase in the relative amount of HMW and LMW species and the formation of acidic charge variants were the main degradation pathways for 50 mg/mL H1H17203P DP.

Research Stress Stability for 50 mg/mL H1H17203P DP

Results from the research stress stability studies are presented in Table 9. H1H17203P DP was physically and chemically stable when agitated (vortexed at ambient temperature) for 120 minutes. No appreciable change in the physical or chemical stability was detected in any of the monitored attributes. H1H17203P DP was physically and chemically stable when subjected to 8 freeze/thaw cycles (freezing at −80° C. and thawing at room temperature). No appreciable change in the physical or chemical stability was detected in any of the monitored attributes.

Research Stability for 50 mg/mL H1H17139P DP
Research Storage Stability for 50 mg/mL H1H17139P DP Three months of research stability data are shown for the 50 mg/mL H1H17139P DP. The 50 mg/mL H1H17139P DP was physically and chemically stable when stored at 5° C. for 3 months (Table 4). No appreciable change in the physical or chemical stability was detected in any of the monitored attributes. The 50 mg/mL H1H17139P DP maintained potency over the three-month assessment interval as determined by bioassay analysis.

Research Accelerated Stability for 50 mg/mL H1H17139P DP

Results from the analysis of the 50 mg/mL H1H17139P DP following incubation under accelerated conditions are provided in Table 7. After H1H17139P DP was incubated for 28 days at 45° C., 0.8% and 1.8% increases in the relative amount of HMW and LMW species (SE-UPLC), and 13.8% and 12.9% increases in the percentage of acidic charge variant species, determined by CEX-UPLC and iCIEF, respectively, were observed. After H1H17139P DP was incubated for 3 months at 25° C., 0.4% and 0.5% increases in the amount of HMW and LMW species (SE-UPLC) and 2.6% and 3.1% increases in the percentage of acidic charge variant species, determined by CEX-UPLC and iCIEF, respectively, were observed. H1H17139P maintained potency, as determined by bioassay analysis, after incubation under each of the accelerated conditions. The results from accelerated stability testing demonstrated that an increase in the relative amount of HMW and LMW species and the formation of acidic charge variants were the main degradation pathways for 50 mg/mL H1H17139P DP.

Research Stress Stability for 50 mg/mL H1H17139P DP

Results from the research stress stability studies are presented in Table 10. H1H17139P DP was physically and chemically stable when agitated (vortexed at ambient temperature) for 120 minutes. No appreciable change in the physical or chemical stability was detected in any of the monitored attributes. H1H17139P DP was physically and chemically stable when subjected to 8 freeze/thaw cycles (freezing at −80° C. and thawing at room temperature). No appreciable change in the physical or chemical stability was detected in any of the monitored attributes.

Research Stability for 50 mg/mL H1H17161P DP
Research Storage Stability for 50 mg/mL H1H17161P DP Three months of research stability data are shown for 50 mg/mL H1H17161P DP. The 50 mg/mL H1H17161P DP was physically and chemically stable when stored at 5° C. for 3 months (Table 5). No appreciable change in the physical or chemical stability was detected in any of the monitored attributes. The 50 mg/mL H1H17161P DP maintained potency over the three-month assessment interval as determined by bioassay analysis.

Research Accelerated Stability for 50 mg/mL H1H17161P DP

Results from the analysis of 50 mg/mL H1H17161P DP following incubation under accelerated conditions are provided in Table 8. After H1H17161P DP was incubated for 28 days at 45° C., 1.0% and 1.8% increases in the relative amount of HMW and LMW species (SE-UPLC), and 15.6% and 13.2% increases in the percentage of acidic charge variant species, determined by CEX-UPLC and iCIEF, respectively, were observed. After H1H17161P DP was incubated for 3 months at 25° C., 0.7% and 0.5% increases in the amount of HMW and LMW species (SE-UPLC) and 4.2% and 3.4% increases in the percentage of acidic charge variant species, determined by CEX-UPLC and iCIEF, respectively, were observed. H1H17161P maintained potency, as determined by bioassay analysis, after incubation under each of the accelerated conditions. The results from accelerated stability testing demonstrated that an increase in the relative amount of HMW and LMW species and the formation of acidic charge variants were the main degradation pathways for 50 mg/mL H1H17161P DP.

Research Stress Stability for 50 mg/mL H1H17161P DP

Results from the research stress stability studies are presented in Table 11. H1H17161P DP was physically and chemically stable when agitated (vortexed at ambient temperature) for 120 minutes. No appreciable change in the physical or chemical stability was detected in any of the monitored attributes. H1H17161P DP was physically and chemically stable when subjected to 8 freeze/thaw cycles (freezing at −80° C. and thawing at room temperature). No appreciable change in the physical or chemical stability was detected in any of the monitored attributes.

Research Stability Conclusions for H1H17203P DP, H1H17139P DP, and H1H17161P DP

The results from the DP storage, accelerated, and stress stability studies indicate that H1H17203P DP, H1H17139P DP, and H1H17161P DP formulations can withstand limited exposures to room temperature without compromising physical or chemical stability. In addition, the results from H1H17203P, H1H17139P, and H1H17161P formulation studies indicate H1H17203P DP, H1H17139P DP, and H1H17161P DP are stable when stored at 5° C. for at least 3 months. H1H17203P DP, H1H17139P DP, and H1H17161P DP should be stored at 2° C. to 8° C. and exposure to temperatures greater than 8° C. should be limited.

TABLE 3

Research Stability of 50 mg/mL H1H17203P Drug Product Stored at 5° C.

| | |
|---|---|
| Stability Study Number | H1H17203-SS004 |
| Source DS Lot Number | 9018800002 |
| Formulation Lot Number | L15-0397 |
| Formulation | 50 mg/mL H1H17203P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 GRY B2-40 stopper |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.1 | 6.1 | 6.1 | 6.1 | 6.1 | 6.1 |
| % Total H1H17203P Recovered by RP-UPLC | | 100 | 101 | 102 | 109 | 100 | 99 |
| Purity by MCE-SDS | Non-reduced; % main peak | 100 | NR | NR | NA | NR | NA |
| | Reduced; % heavy + light chain | 99.6 | NR | NR | NA | NR | NA |
| Purity by SE-UPLC | % HMW | 0.6 | 0.6 | 0.7 | 0.8 | 0.8 | 0.9 |
| | % Native | 98.3 | 98.5 | 98.4 | 98.2 | 97.9 | 97.7 |
| | % LMW | 1.2 | 0.9 | 0.9 | 1.0 | 1.3 | 1.5 |
| Charge Variant Analysis by CEX-UPLC | % Acidic | 42.2 | 42.2 | 41.2 | 41.5 | 41.8 | 41.9 |
| | % Main | 46.5 | 46.9 | 47.9 | 48.3 | 48.1 | 47.9 |
| | % Basic | 11.3 | 10.9 | 10.9 | 10.2 | 10.1 | 10.2 |
| Charge Variant | % Acidic | 57.1 | NR | NR | NA | NR | NA |
| | % Main | 40.5 | NR | NR | NA | NR | NA |

TABLE 3-continued

Research Stability of 50 mg/mL H1H17203P Drug Product Stored at 5° C.

| | | | | | | | |
|---|---|---|---|---|---|---|---|
| Stability Study Number | | \multicolumn{6}{l}{H1H17203-SS004} |
| Source DS Lot Number | | \multicolumn{6}{l}{9018800002} |
| Formulation Lot Number | | \multicolumn{6}{l}{L15-0397} |
| Formulation | | \multicolumn{6}{l}{50 mg/mL H1H17203P, 10 mM histidine, 10% (w/v) sucrose, 0.1% (w/v) polysorbate 80, pH 6.0} |
| Fill Volume | | \multicolumn{6}{l}{0.4 mL} |
| Container/Closure | | \multicolumn{6}{l}{2 mL Type I borosilicate glass vial with West S2-F451 4432/50 GRY B2-40 stopper} |

| | | Length of Storage (months) | | | | | |
|---|---|---|---|---|---|---|---|
| Assay | | 0 | 1 | 3 | 6 | 9 | 12 |
| Analysis by ICIEF | % Basic | 2.4 | NR | NR | NA | NR | NA |
| Particulate Analysis by MFI (particles/mL) | 2-10 μm | 25573 | NR | NR | 9370 | NR | 1212 |
| | ≥10 μm | 1267 | NR | NR | 436 | NR | 24 |
| | ≥25 μm | 150 | NR | NR | 28 | NR | 3 |

TABLE 4

Research Stability of 50 mg/mL H1H17139P Drug Product Stored at 5° C.

| | |
|---|---|
| Stability Study Number | H1H17139 -SS004 |
| Source DS Lot Number | 9019300002 |
| Formulation Lot Number | L15-0396 |
| Formulation | 50 mg/mL H1H17139P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50GRY B2-40 stopper |

| | | Length of Storage (months) | | | | | |
|---|---|---|---|---|---|---|---|
| Assay | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.0 | 6.1 | 6.1 | 6.1 | 6.1 | 6.1 |
| % Total H1H17139P Recovered by RP-UPLC | | 100 | 100 | 103 | 94 | 101 | 100 |
| Purity by MCE-SDS | Non-reduced; % main peak | 100 | NR | NR | NA | NR | NA |
| | Reduced; % heavy + light chain | 98.7 | NR | NR | NA | NR | NA |
| Purity by SE-UPLC | % HMW | 0.6 | 0.6 | 0.7 | 0.8 | 0.9 | 0.9 |
| | % Native | 98.4 | 98.4 | 98.3 | 98.2 | 97.8 | 97.5 |
| | % LMW | 1.1 | 1.0 | 1.0 | 1.1 | 1.4 | 1.6 |
| Charge Variant Analysis by CEX-UPLC | % Acidic | 42.9 | 42.8 | 42.8 | 43.6 | 42.9 | 43.5 |
| | % Main | 53.2 | 53.2 | 52.9 | 52.1 | 52.8 | 51.6 |
| | % Basic | 4.0 | 4.0 | 4.3 | 4.3 | 4.4 | 4.9 |
| Charge Variant Analysis by iCIEF | % Acidic | 49.4 | NR | NR | NA | NR | NA |
| | % Main | 46.8 | NR | NR | NA | NR | NA |
| | % Basic | 3.2 | NR | NR | NA | NR | NA |
| Particulate Analysis by MFI (particles/mL) | 2-10 μm | 7332 | NR | NR | 654 | NR | 1153 |
| | ≥10 μm | 37 | NR | NR | 15 | NR | 24 |
| | ≥25 μm | 3 | NR | NR | 3 | NR | 3 |

TABLE 5

Research Stability of 50 mg/mL H1H17161P Drug Product Stored at 5° C.

| | |
|---|---|
| Stability Study Number | H1H17161-SS004 |
| Source DS Lot Number | 9019800002 |
| Formulation Lot Number | L15-0400 |
| Formulation | 50 mg/mL H1H17161P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 GRY B2-40 stopper |

| Assay | | Length of Storage (months) | | | | | |
|---|---|---|---|---|---|---|---|
| | | 0 | 1 | 3 | 6 | 9 | 12 |
| Color and Appearance | | Pass | Pass | Pass | Pass | Pass | Pass |
| Turbidity (Increase in OD at 405 nm) | | 0.00 | 0.00 | 0.00 | 0.00 | 0.00 | 0.00 |
| pH | | 6.1 | 6.1 | 6.1 | 6.1 | 6.1 | 6.1 |
| % Total H1H17161P Recovered by RP-UPLC | | 100 | 99 | 106 | 106 | 104 | 106 |
| Purity by MCE-SDS | Non-reduced; % main peak | 100 | NF | NR | NA | NR | NA |
| | Reduced; % heavy + light chain | 98.4 | NR | NR | NA | NR | NA |
| Purity by SE-UPLC | % HMW | 1.1 | 1.3 | 1.4 | 1.5 | 1.6 | 1.7 |
| | % Native | 97.4 | 97.3 | 97.2 | 97.1 | 96.6 | 96.2 |
| | % LMW | 1.5 | 1.5 | 1.4 | 1.4 | 1.8 | 2.0 |
| Charge Variant Analysis by CEX-UPLC | % Acidic | 60.5 | 60.3 | 59.8 | 59.2 | 61.0 | 59.8 |
| | % Main | 35.7 | 35.7 | 35.1 | 36.4 | 35.6 | 34.8 |
| | % Basic | 3.9 | 4.0 | 5.1 | 4.4 | 3.5 | 5.4 |
| Charge Variant Analysis by ICIEF | % Acidic | 54.1 | NR | NR | NA | NR | NA |
| | % Main | 42.7 | NR | NR | NA | NR | NA |
| | % Basic | 3.2 | NR | NR | NA | NR | NA |
| Particulate Analysis by MFI (particles/mL) | 2-10 μm | 7526 | NR | NR | 1274 | NR | 3066 |
| | ≥10 μm | 39 | NR | NR | 99 | NR | 148 |
| | ≥25 μm | 7 | NR | NR | 8 | NR | 22 |

TABLE 6

Research Stability of 50 mg/mL H1H17203P Drug Product - Effect of Accelerated Conditions

| | |
|---|---|
| Stability Study Number | H1H17203-SS004 |
| Source DS Lot Number | 9018800002 |
| Formulation Lot Number | L15-0397 |
| Formulation | 50 mg/mL H1H17203P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 |

| Assay | | No Storage | 25° C. (months) | | | 45° C. (days) | | |
|---|---|---|---|---|---|---|---|---|
| | | 0 | 0.5 | 1 | 3 | 7 | 14 | 28 |
| Color and Appearance | | Pass | Pass | Pass | Pass | Pass | Pass | Pass |
| Turbidity (Increase in OD at 405 | | 0.00 | 0.00 | 0.00 | 0.00 | 0.00 | 0.01 | 0.01 |
| pH | | 6.1 | 6.0 | 6.1 | 6.1 | 6.1 | 6.1 | 6.1 |
| % Total H1H17203P | | 100 | 100 | 101 | 102 | 99 | 99 | 101 |
| Purity by MCE-SDS | Non-reduced; % main peak | 100 | NR | NR | 100 | NR | NR | 98.2 |
| | Reduced; % heavy + light chain | 99.6 | NR | NR | 99.1 | NR | NR | 98.4 |
| Purity by SE-UPLC | % HMW | 0.6 | 0.7 | 0.8 | 0.9 | 1.4 | 1.8 | 2.7 |
| | % Native | 98.3 | 98.3 | 98.1 | 97.6 | 97.1 | 96.2 | 94.4 |
| | % LMW | 1.2 | 1.0 | 1.1 | 1.5 | 1.5 | 2.0 | 2.8 |
| Charge Variant | % Acidic | 42.2 | 42.3 | 43.0 | 45.1 | 46.2 | 50.3 | 57.3 |
| | % Main | 46.5 | 47.2 | 47.0 | 45.9 | 43.7 | 40.3 | 33.4 |

TABLE 6-continued

Research Stability of 50 mg/mL H1H17203P Drug Product - Effect of Accelerated Conditions

| Stability Study Number | H1H17203-SS004 |
| --- | --- |
| Source DS Lot Number | 9018800002 |
| Formulation Lot Number | L15-0397 |
| Formulation | 50 mg/mL H1H17203P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 |

Storage Condition/Length of Storage

| Assay | | No Storage | 25° C. (months) | | | 45° C. (days) | | |
| --- | --- | --- | --- | --- | --- | --- | --- | --- |
| | | 0 | 0.5 | 1 | 3 | 7 | 14 | 28 |
| Analysis by CEX-UPLC Charge Variant | % Basic | 11.3 | 10.5 | 10.0 | 9.0 | 10.1 | 9.4 | 9.3 |
| | % Acidic | 57.1 | NR | NR | 60.1 | NR | NR | 70.6 |
| | % Main | 40.5 | NR | NR | 37.0 | NR | NR | 26.3 |
| Analysis by ICIEF | % Basic | 2.4 | NR | NR | 3.0 | NR | NR | 3.1 |
| Particulate Analysis by MFI (particles/mL) | 2-10 μm | 25573 | NR | NR | 10568 | NR | NR | 2677 |
| | ≥10 μm | 1267 | NR | NR | 989 | NR | NR | 149 |
| | ≥25 μm | 150 | NR | NR | 187 | NR | NR | 25 |

TABLE 7

Research Stability of 50 mg/mL H1H17139P Drug Product - Effect of Accelerated Conditions

| Stability Study Number | H1H17139-SS004 |
| --- | --- |
| Source DS Lot Number | 9019300002 |
| Formulation Lot Number | L15-0396 |
| Formulation | 50 mg/mL H1H17139P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 |

Storage Condition/Length of Storage

| Assay | | No Storage | 25° C. (months) | | | 45° C. (days) | | |
| --- | --- | --- | --- | --- | --- | --- | --- | --- |
| | | 0 | 0.5 | 1 | 3 | 7 | 14 | 28 |
| Color and Appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.01 |
| pH | | 6.0 | 6.0 | 6.1 | 6.1 | 6.1 | 6.1 | 6.0 |
| % Total H1H17139P Recovered | | 100 | 100 | 100 | 104 | 100 | 100 | 99 |
| Purity by MCE-SDS | Non-reduced; % main peak | 100 | NR | NR | 99.5 | NR | NR | 98.8 |
| | Reduced; % heavy + light chain | 98.7 | NR | NR | 99.1 | NR | NR | 98.4 |
| Purity by SE-UPLC | % HMW | 0.6 | 0.7 | 0.8 | 1.0 | 0.9 | 1.1 | 1.4 |
| | % Native | 98.4 | 98.1 | 98.0 | 97.4 | 97.6 | 96.8 | 95.7 |
| | % LMW | 1.1 | 1.2 | 1.2 | 1.6 | 1.5 | 2.1 | 2.9 |
| Charge Variant Analysis by CEX-UPLC | % Acidic | 42.9 | 43.0 | 43.2 | 45.5 | 45.4 | 49.5 | 56.7 |
| | % Main | 53.2 | 52.8 | 52.4 | 49.6 | 49.9 | 45.6 | 38.5 |
| | % Basic | 4.0 | 4.3 | 4.4 | 4.9 | 4.8 | 5.0 | 4.8 |
| Charge Variant Analysis by ICIEF | % Acidic | 49.4 | NR | NR | 52.5 | NR | NR | 62.3 |
| | % Main | 46.8 | NR | NR | 43.0 | NR | NR | 32.2 |
| | % Basic | 3.2 | NR | NR | 3.9 | NR | NR | 4.8 |
| Particulate Analysis by MFI (particles/mL) | 2-10 μm | 7332 | NR | NR | 1279 | NR | NR | 4628 |
| | ≥10 μm | 37 | NR | NR | 65 | NR | NR | 170 |
| | ≥25 μm | 3 | NR | NR | 6 | NR | NR | 23 |

TABLE 8

Research Stability of 50 mg/mL H1H17161P Drug Product - Effect of Accelerated Conditions

| | |
|---|---|
| Stability Study Number | H1H17161-SS004 |
| Source DS Lot Number | 9019800002 |
| Formulation Lot Number | L15-0400 |
| Formulation | 50 mg/mL H1H17161P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 |

| | | Storage Condition/Length of Storage | | | | | |
|---|---|---|---|---|---|---|---|
| | | No Storage | 25° C. (months) | | | 45° C. (days) | | |
| Assay | | 0 | 0.5 | 1 | 3 | 7 | 14 | 28 |
| Color and Appearance | | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 |
| pH | | 6.1 | 6.1 | 6.1 | 6.1 | 6.1 | 6.1 | 6.1 |
| % Total H1H17161P Recovered by RP-UPLC | | 100 | 105 | 98 | 107 | 99 | 96 | 99 |
| Purity by MCE-SDS | Non-reduced; % main peak | 100 | NR | NR | 98.4 | NR | NR | 96.1 |
| | Reduced; % heavy + light chain | 98.4 | NR | NR | 97.6 | NR | NR | 97.8 |
| Purity by SE-UPLC | % HMW | 1.1 | 1.4 | 1.6 | 1.8 | 1.5 | 1.7 | 2.1 |
| | % Native | 97.4 | 97.0 | 96.8 | 96.2 | 96.5 | 95.6 | 94.6 |
| | % LMW | 1.5 | 1.7 | 1.7 | 2.0 | 2.0 | 2.6 | 3.3 |
| Charge Variant Analysis by CEX-UPLC | % Acidic | 60.5 | 61.0 | 61.7 | 64.7 | 64.7 | 69.1 | 76.1 |
| | % Main | 35.7 | 34.6 | 34.2 | 30.0 | 30.8 | 26.6 | 19.4 |
| | % Basic | 3.9 | 4.4 | 4.2 | 5.4 | 4.4 | 4.2 | 4.5 |
| Charge Variant Analysis by iCIEF | % Acidic | 54.1 | NR | NR | 57.5 | NR | NR | 67.3 |
| | % Main | 42.7 | NR | NR | 38.0 | NR | NR | 26.9 |
| | % Basic | 3.2 | NR | NR | 4.4 | NR | NR | 5.8 |
| Particulate Analysis by MFI (particles/mL) | 2-10 μm | 7526 | NR | NR | 468 | NR | NR | 2204 |
| | ≥10 μm | 39 | NR | NR | 33 | NR | NR | 98 |
| | ≥25 μm | 7 | NR | NR | 5 | NR | NR | 7 |

TABLE 9

Research Stability of 50 mg/mL H1H17203P Drug Product - Effect of Stress Conditions

| | |
|---|---|
| Stability Study Number | RG3470-SS004 |
| Source DS Lot Number | 9018800002 |
| Formulation Lot Number | L15-0397 |
| Formulation | 50 mg/mL H1H17203P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 |

| | | Stress Condition/Length of Stress | | | | |
|---|---|---|---|---|---|---|
| | | No Stress | Agitation (minutes) | | Freeze/Thaw (cycles) | |
| Assay | | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.1 | 6.1 | 6.1 | 6.1 | 6.1 |
| % Total H1H17203P Recovered by RP-UPLC | | 100 | 100 | 100 | 99 | 100 |
| Purity by MCE-SDS | Non-reduced; % main peak | 100 | NR | 100 | NR | 100 |
| | Reduced; % heavy + light chain | 99.6 | NR | 99.6 | NR | 99.2 |

TABLE 9-continued

Research Stability of 50 mg/mL H1H17203P Drug Product -
Effect of Stress Conditions

| | | | | | | |
|---|---|---|---|---|---|---|
| Stability Study Number | | RG3470-SS004 | | | | |
| Source DS Lot Number | | 9018800002 | | | | |
| Formulation Lot Number | | L15-0397 | | | | |
| Formulation | | 50 mg/mL H1H17203P, 10 mM histidine, 10% (w/v) sucrose, 0.1% (w/v) polysorbate 80, pH 6.0 | | | | |
| Fill Volume | | 0.4 mL | | | | |
| Container/Closure | | 2 mL Type I borosilicate glass vial with West S2-F451 4432/50 | | | | |

| | | Stress Condition/Length of Stress | | | | |
|---|---|---|---|---|---|---|
| | | No Stress | Agitation (minutes) | | Freeze/Thaw (cycles) | |
| Assay | | 0 | 60 | 120 | 4 | 8 |
| Purity by SE-UPLC | % Total HMW | 0.6 | 0.5 | 0.5 | 0.6 | 0.6 |
| | % Total Native | 98.3 | 98.3 | 98.3 | 98.3 | 98.3 |
| | % Total LMW | 1.2 | 1.2 | 1.2 | 1.1 | 1.1 |
| Charge Variant Analysis by CEX-UPLC | % Acidic | 42.2 | 42.3 | 42.3 | 42.3 | 42.4 |
| | % Main | 46.5 | 46.8 | 46.8 | 46.7 | 46.6 |
| | % Basic | 11.3 | 11.0 | 11.0 | 11.0 | 11.0 |
| Charge Variant Analysis by iCIEF | % Acidic | 57.1 | NR | 57.5 | NR | 57.1 |
| | % Main | 40.5 | NR | 39.8 | NR | 40.5 |
| | % Basic | 2.4 | NR | 2.6 | NR | 2.3 |

TABLE 10

Research Stability of 50 mg/mL H1H17139P Drug Product - Effect of Stress Conditions

| | | | | | | |
|---|---|---|---|---|---|---|
| Stability Study Number | | H1H17139-SS004 | | | | |
| Source DS Lot Number | | 9019300002 | | | | |
| Formulation Lot Number | | L15-0396 | | | | |
| Formulation | | 50 mg/mL H1H17139P, 10 mM histidine, 10% (w/v) sucrose, 0.1% (w/v) polysorbate 80, pH 6.0 | | | | |
| Fill Volume | | 0.4 mL | | | | |
| Container/Closure | | 2 mL Type I borosilicate glass vial with West S2-F451 4432/50 | | | | |

| | | Stress Condition/Length of Stress | | | | |
|---|---|---|---|---|---|---|
| | | No Stress | Agitation (minutes) | | Freeze/Thaw (cycles) | |
| Assay | | 0 | 60 | 120 | 4 | 8 |
| Color and Appearance | | Pass | Pass | Pass | Pass | Pass |
| Turbidity (Increase in OD at 405 nm) | | 0.00 | 0.00 | 0.00 | 0.00 | 0.00 |
| pH | | 6.0 | 6.1 | 6.0 | 6.0 | 6.1 |
| % Total H1H17139P Recovered by RP-UPLC | | 100 | 100 | 100 | 100 | 100 |
| Purity by MCE-SDS | Non-reduced; % main peak | 100 | NR | 100 | NR | 100 |
| | Reduced; % heavy + light chain | 98.7 | NR | 99.1 | NR | 99.3 |
| Purity by SE-UPLC | % Total HMW | 0.6 | 0.5 | 0.5 | 0.6 | 0.6 |
| | % Total Native | 98.4 | 98.4 | 98.4 | 98.4 | 98.4 |
| | % Total LMW | 1.1 | 1.1 | 1.1 | 1.1 | 1.1 |
| Charge Variant Analysis by CEX-UPLC | % Acidic | 42.9 | 42.9 | 42.9 | 43.1 | 42.9 |
| | % Main | 53.2 | 53.2 | 53.2 | 53.0 | 53.2 |
| | % Basic | 4.0 | 3.9 | 3.9 | 4.0 | 3.9 |
| Charge Variant Analysis by iCIEF | % Acidic | 49.4 | NR | 49.8 | NR | 49.5 |
| | % Main | 46.8 | NR | 46.0 | NR | 46.5 |
| | % Basic | 3.2 | NR | 3.7 | NR | 3.5 |

TABLE 11

Research Stability of 50 mg/mL H1H17161P Drug Product - Effect of Stress Conditions

| Stability Study Number | H1H17161-SS004 |
| --- | --- |
| Source H1H17161P DS Lot | 9019800002 |
| Formulation Lot Number | L15-0400 |
| Formulation | 50 mg/mL H1H17161P, 10 mM histidine, 10% (w/v) sucrose, 0.1% (w/v) polysorbate 80, pH 6.0 |
| Fill Volume | 0.4 mL |
| Container/Closure | 2 mL Type I borosilicate glass vial with West S2-F451 4432/50 |

| | | Stress Condition/Length of Stress | | | |
| --- | --- | --- | --- | --- | --- |
| | No Stress | Agitation (minutes) | | Freeze/Thaw (cycles) | |
| Assay | 0 | 60 | 120 | 4 | 8 |
| Color and Appearance | Pass | Pass | Pass | Pass | Pass |
| Turbidity (Increase in OD at 405 nm) | 0.00 | 0.00 | 0.00 | 0.00 | 0.00 |
| pH | 6.1 | 6.1 | 6.1 | 6.1 | 6.1 |
| % Total H1H17161P Recovered by RP-UPLC | 100 | 100 | 101 | 99 | 98 |
| Purity by MCE-SDS Non-reduced; % main peak | 100 | NR | 100 | NF | 100 |
| Purity by MCE-SDS Reduced; % heavy + light chain | 98.4 | NR | 98.7 | NR | 97.9 |
| Purity by SE-UPLC % Total HMW | 1.1 | 1.0 | 1.1 | 1.1 | 1.1 |
| Purity by SE-UPLC % Total Native | 97.4 | 97.4 | 97.5 | 97.4 | 97.3 |
| Purity by SE-UPLC % Total LMW | 1.5 | 1.5 | 1.5 | 1.5 | 1.5 |
| Charge Variant Analysis by CEX-UPLC % Acidic | 60.5 | 60.3 | 60.3 | 60.5 | 60.9 |
| Charge Variant Analysis by CEX-UPLC % Main | 35.7 | 35.9 | 35.8 | 35.6 | 35.2 |
| Charge Variant Analysis by CEX-UPLC % Basic | 3.9 | 3.8 | 3.9 | 4.0 | 4.0 |
| Charge Variant Analysis by iCIEF % Acidic | 54.1 | NR | 53.2 | NR | 54.4 |
| Charge Variant Analysis by iCIEF % Main | 42.7 | NR | 42.6 | NR | 42.3 |
| Charge Variant Analysis by iCIEF % Basic | 3.2 | NR | 4.3 | NP | 3.3 |

Conclusions

H1H17203P, H1H17139P, and H1H17161P antibodies are manufactured as a liquid DP for IV administration. The H1H17203P DP contains 50 mg/mL H1H17203P antibody formulated in a solution containing 10 mM histidine, pH 6.0, 0.1% (w/v) polysorbate 80, and 10% (w/v) sucrose. The H1H17139P DP contains 50 mg/mL H1H17139P antibody formulated in a solution containing 10 mM histidine, pH 6.0, 0.1% (w/v) polysorbate 80, and 10% (w/v) sucrose. The H1H17161P DP contains 50 mg/mL H1H17161P antibody formulated in a solution containing 10 mM histidine, pH 6.0, 0.1% (w/v) polysorbate 80, and 10% (w/v) sucrose.

Based on the results of the studies in this Example, 50 mg/mL H1H17203P DP, 50 mg/mL H1H17139P DP and 50 mg/mL H1H17161P DP are stable when stored at 2-8° C. for at least 12 months. In addition, the main degradation pathways identified under accelerated conditions were formation of HMW and LMW species and acidic charge variants.

Example 5: Stability Studies for Aqueous Formulation Containing 50 mg/mL Anti-EBOV Antibody Combination Three anti-EBOV monoclonal antibodies, H1H17203P, H1H17139P, and H1H17161P were formulated using 50 mg/mL total protein (16.7 mg/mL H1H17203P, 16.7 mg/mL H1H17139P, and 16.7 mg/mL H1H17161P), 10 mM histidine, pH 6.0, 0.1% (w/v) polysorbate 80, and 10% (w/v) sucrose. Three anti-EBOV monoclonal antibodies were formulated and combined into a single glass vial. Methods used to assess stability were developed to provide, where possible information on each component antibody. However, many of the analytical methods are incapable of providing information on each individual antibody. When not able to individually provide results for each antibody, the analytical method provides stability data for the total drug product.

The physical stability of a formulation refers to properties such as color, appearance, pH, turbidity and protein concentration. The presence of visible particulates in solution can be detected by visual inspection. A solution passes visual inspection if it is clear to slightly opalescent, essentially free from visible particulates, and colorless to pale yellow. Turbidity, measured by an increase in OD at 405 nm, can also be used to detect particulates in solution. An increase in OD at 405 nm may indicate the presence of particulates, an increase in opalescence, or color change of the test articles. MFI is used to measure subvisible particulates that are ≥2 μm in size. Total protein concentration is measured by a RP-UPLC assay and reported as percent protein recovery relative to the starting material.

In the RP-UPLC assay, H1H17203P, H1H17139P, and H1H17161P peaks cannot be resolved from each another following elution from the reversed-phase column (FIG. 1). The total protein concentration (H1H17203P, H1H17139P, and H1H17161P) is determined by comparing the peak area to a calibration curve generated using a H1H17203P standard. Because the extinction coefficient of H1H17203P, H1H17139P, and H1H17161P is 1.50, 1.57 and 1.36, respectively, the extinction coefficient of co-formulated H1H17203P, H1H17139P, and H1H17161P (1:1:1) would be approximately 1.48 (the average of the three extinction coefficients). Therefore, H1H17203P standard (extinction coefficient, 1.50) was chosen to generate the standard curve to determine the total protein concentration in the co-formulated formulation. Percent recovery is calculated based on the measured total protein concentration relative to the starting concentration.

Chemical stability refers to the formation of covalently modified forms (e.g. covalent aggregates, cleavage products or charge variant forms) and non-covalently modified forms (e.g. non-covalent aggregates) of protein. Higher and lower molecular weight degradation products can be separated from native molecular weight product using SE-UPLC and MCE-SDS methods. The three-way antibody formulations were characterized for total purity (native H1H17203P, H1H17139P, and H1H17161P) by SE-UPLC (i.e. molecular weight purity of H1H17203P, H1H17139P, and H1H17161P were not determined individually) because H1H17203P, H1H17139P, and H1H17161P native species cannot be resolved from each other (FIG. 2). Similarly, three-way antibody formulations will be characterized for total high molecular weight (HMW) species (H1H17203P HMW, H1H17139P HMW, and H1H17161P HMW) and total low molecular weight (LMW) species (H1H17203P LMW, H1H17139P LMW, and H1H17161P LMW) because HMW or LMW species of H1H17203P, H1H17139P, and H1H17161P cannot be resolved from each other (FIG. 2). The percentage of total HMW species or total LMW species in the 3-way formulation, determined using the SE-UPLC method, is calculated from the ratio of the area of total HMW species or total LMW species to the total area of all H1H17203P, H1H17139P, and H1H17161P peaks, respectively. Total purity, determined by non-reduced MCE-SDS is calculated from the ratio of the H1H17203P, H1H17139P, and H1H17161P main band intensity to the total intensity of all bands. Total purity, determined by reduced MCE-SDS is calculated from the ratio of the sum of the H1H17203P, H1H17139P, and H1H17161P heavy chain and light chain band intensities relative to the total intensity of all bands.

The iCIEF method did not have sufficient resolution to separate all charge variant forms of all three antibodies. Therefore, this analytical method was not used to assess changes in the charge variant profile for the three-way formulation samples. Charge variant forms of H1H17203P, H1H17139P, and H1H17161P that are co-formulated were able to be resolved using the CEX-UPLC method. For H1H17203P, H1H17139P, and H1H17161P, peaks with retention times earlier than that of the main peak are labeled as "acidic" peaks; peaks with retention times later than that of the main peak are labeled as "basic" peaks. The percentages of acidic, main, and basic peaks are calculated by comparing the individual peak area to the total peak areas of each antibody.

The Drug Product (DP) used for the storage, accelerated, and stress stability studies was created by filling 0.4 mL of FDS in 2 mL Type 1 glass vials. The DP was incubated under several elevated temperature conditions, relative to storage temperature conditions. These accelerated conditions were selected to simulate the conditions to which the DP may be subjected during manufacturing and handling in order to elucidate the degradation pathways for co-formulated H1H17203P, H1H17139P, and H1H17161P DP. An outline of the storage, accelerated, and stress stability conditions for the co-formulated DP are presented in Table 12 and the analysis plans are presented in Table 13.

TABLE 12

Research Stability Studies for H1H17203P, H1H17139P, and H1H17161P Combination DP

| Storage Stability | | Container/Closure |
|---|---|---|
| Storage Temperature | Length of Storage (months) | Type 1 borosilicate glass with FluroTec ® coated 4432/50 butyl rubber stopper |
| 5° C. | 0, 1, 3, 6, 9, 12, 18, 24, and 36 | |
| Accelerated Stability | | |
| Incubation Condition | Length of Incubation | |
| 25° C. | 0, 0.5, 1, and 3 months | |
| 45° C. | 0, 7, 14, and 28 days | |
| Stress Stability | | |
| Stress | Duration of Stress | |
| Agitation (vortex) | 0, 60, and 120 minutes | |
| Freeze/Thaw[a] | 0, 4, and 8 cycles | |

[a]Frozen at −30° C. and thawed at room temperature.

TABLE 13

Research Stability Studies, Analysis Plan for H1H17203P, H1H17139P, and H1H17161P Combination DP

| Assay | Samples to be Analyzed |
|---|---|
| Color and Appearance | All Samples |
| pH | All Samples |
| Turbidity (Increase in OD at 405 nm) | All Samples |
| % Total H1H17203P, H1H17139P, H1H17161P Recovered by RP-UPLC | All Samples |
| Total Purity (H1H17203P, H1H17139P, H1H17161P) by Non-Reduced and Reduced MCE-SDS | t = 0, 6, 12, 24 and 36 months at 5° C.; 6 months at 25° C.; 28 days at 45° C. 120 min Agitation, 8X Freeze/Thaw |
| Total (H1H17203P, H1H17139P, H1H17161P) Purity by SE-UPLC | All Samples |
| Charge variant analysis by CEX-UPLC | All samples |
| Particulate Matter Analysis by MFI | t = 0, 6, 12, 24 and 36 months at 5° C.; 6 months at 25° C.; 28 days at 45° C. 120 min Agitation, 8X Freeze/Thaw |
| % H1H17203P, H1H17139P, and H1H17161P Relative Potency by Bioassay | t = 0, 6, 12, 24 and 36 months at 5° C.; 6 months at 25° C.; 28 days at 45° C. 120 min Agitation, 8X Freeze/Thaw |

Research Storage Stability for Co-Formulated H1H17203P, H1H17139P, and H1H17161P OP (1:1:1, 50 mg/mL Total Protein)

Three months of research storage stability data are shown for the co-formulated H1H17203P, H1H17139P, and H1H17161P OP. Co-formulated H1H17203P, H1H17139P, and H1H17161P OP was physically stable when stored at 5° C. for 3 months. An increase of 0.2% in total HMW species was observed by SE-UPLC when co-formulated H1H17203P, H1H17139P, and H1H17161P OP (1:1:1, 50 mg/mL total protein) was stored at 5° C. for 3 months, and an increase of 0.6 in total HMW was observed by SE-UPLC after storage at 5° C. for 18 months. No appreciable change in the physical or chemical stability of the co-formulated H1H17203P, H1H17139P, and H1H17161P OP (1:1:1, 50 mg/mL total protein) was detected in any of the other monitored attributes. H1H17203P, H1H17139P, and H1H17161P maintained potency over the 3 month assessment interval as determined by bioassay analysis. See Table 14.

Research Accelerated Stability for Co-Formulated H1H17203P, H1H17139P, and H1H17161P DP (1:1:1, 50 mg/mL Total Protein)

Results from the analysis of the co-formulated H1H17203P, H1H17139P, and H1H17161P DP following incubation under accelerated conditions are provided in 4. After incubation for 28 days at 45° C., an increase of 1.3% in the relative amount of total HMW species (SE-UPLC) was observed. After incubation for 28 days at 45° C., an increase of 14.7%, 14.4% and 22.9% was observed in H1H17203P, H1H17139P, and H1H17161P acidic charge variant species (CEX-UPLC), respectively. After incubation for 3 months at 25° C., an increase of 2.6%, 2.5% and 5.6% was observed in H1H17203P, H1H17139P, and H1H17161P acidic charge variant species (CEX-UPLC), respectively. H1H17203P, H1H17139P, and H1H17161P maintained potency, as determined by bioassay analysis, after incubation under the accelerated conditions. The results from accelerated stability testing demonstrated that an increase in the relative amounts of total HMW species, total LMW species, and the formation of acidic charge variants for H1H17203P, H1H17139P, and H1H17161P were the main degradation pathways for the co-formulated H1H17203P, H1H17139P, and H1H17161P DP (1:1:1, 50 mg/mL total protein). See Table 15.

Research Stress Stability for Co-Formulated H1H17203P, H1H17139P, and H1H17161P DP (1:1:1, 50 mg/mL Total Protein)

Results from the co-formulated H1H17203P, H1H17139P, and H1H17161P DP stress stability studies are provided in Table 16. Co-formulated H1H17203P, H1H17139P, and H1H17161P DP was physically and chemically stable when agitated (vortexed at ambient temperature) for 120 minutes or when subjected to 8 freeze/thaw cycles (freezing at −30° C. and thawing at room temperature). No appreciable change in the physical or chemical stability was detected in any of the monitored attributes. H1H17203P, H1H17139P, and H1H17161P maintained potency when the DP was agitated for 120 minutes or when subjected to 8 freeze/thaw cycles. See Table 16.

Research Stability Conclusions for Co-Formulated H1H17203-3471-3479 Drug Product The results from storage, accelerated, and stress stability studies indicate that co-formulated H1H17203P, H1H17139P, and H1H17161P DP will be stable during manufacture (fill/finish and labeling operations). The H1H17203P, H1H17139P, and H1H17161P Combination DP formulation can withstand short exposures to room temperature without compromising physical or chemical stability. H1H17203P, H1H17139P, and H1H17161P Combination DP will be stored at 2° C. to 8° C. and exposure to temperatures greater than 8° C. will be limited.

The long-term storage of co-formulated H1H17203P, H1H17139P, and H1H17161P DP at 2-8° C. was determined over 36 months (Table 14). Increases of 0.7% each in total HMW species and total LMW species were observed following storage at 5° C. for 36 months. Changes of 1.1%, 1.2% and 7.3% in acidic species were observed for H1H17203P, H1H17139P and H1H17161P, respectively. No significant change in potency was observed over the 36-month duration of the study, indicating that the anti-EBOV formulation provided acceptable long term storage stability under refrigerated conditions.

TABLE 14

Research Stability of H1H17203P, H1H17139P, and H1H17161P Combination DP (1:1:1, 50 mg/mL total protein) Stored at 5° C.

| | |
|---|---|
| Stability Study Number | H1H17203P, H1H17139P, and H1H17161P-SS002 |
| Lot Number | 9018800002, 9019300002, 9019800002 |
| Formulation Lot Number | L15-401 |
| Formulation | 16.7 mg/mL H1H17203P, 16.7 mg/mL H1H17139P, 16.7 mg/mL H1H17161P, 10 mM histidine, pH 6.0, 0.1% (w/v) polysorbate 80, 10% (w/v) sucrose |
| Fill Volume | 0.4 mL |
| Container/Closure | 2 mL Type I borosilicate glass vial with West S2-F451 4432/50 GRY B2-40 stopper |

| | | Length of Storage (months) | | | | | | | | |
|---|---|---|---|---|---|---|---|---|---|---|
| Assay | | 0 | 1 | 3 | 6 | 9 | 12 | 18 | 24 | 36 |
| Color and Appearance | | Pass | Pass | Pass | Pass | Pass | Pass | Pass | Pass | Pass |
| Turbidity (Increase in OD at 405 nm) | | 0.00 | 0.00 | 0.00 | 0.00 | 0.00 | 0.00 | 0.00 | 0.01 | 0.01 |
| pH | | 6.1 | 6.1 | 6.1 | 6.1 | 6.0 | 6.1 | 6.0 | 6.1 | 6.1 |
| % Total Protein Recovered by | H1H17203P, H1H17139P, and H1H17161P | 100 | 101 | 104 | 104 | 103 | 103 | 101 | 103 | 102 |

TABLE 14-continued Research Stability of H1H17203P, H1H17139P, and H1H17161P Combination
DP (1:1:1, 50 mg/mL total protein) Stored at 5° C.

Stability Study Number: H1H17203P, H1H17139P, and H1H17161P-SS002
Lot Number: 9018800002, 9019300002, 9019800002
Formulation Lot Number: L15-401
Formulation: 16.7 mg/mL H1H17203P, 16.7 mg/mL H1H17139P, 16.7 mg/mL H1H17161P, 10 mM histidine, pH 6.0, 0.1% (w/v) polysorbate 80, 10% (w/v) sucrose
Fill Volume: 0.4 mL
Container/Closure: 2 mL Type I borosilicate glass vial with West S2-F451 4432/50 GRY B2-40 stopper

| Assay | | | 0 | 1 | 3 | 6 | 9 | 12 | 18 | 24 | 36 |
|---|---|---|---|---|---|---|---|---|---|---|---|
| RP-UPLC | | | | | | | | | | | |
| Total Purity by MCE-SDS | Non-reduced; % (H1H17203P, H1H17139P, and H1H17161P) main | | 100 | NR | NR | 99.6 | NR | 99.7 | NR | 99.7 | 100.0 |
| | Reduced; % (H1H17203P, H1H17139P, and H1H17161P) heavy chain + % (H1H17203P, H1H17139P, and H1H17161P) light chain | | 99.3 | NR | NR | 99.2 | NR | 99.2 | NR | 99.1 | 98.9 |
| Total Purity by SE-UPLC | % Total HMW | | 0.7 | 0.8 | 0.9 | 1.1 | 1.1 | 1.2 | 1.3 | 1.3 | 1.4 |
| | % Total Native | | 98.2 | 98.0 | 98.0 | 97.8 | 97.6 | 97.2 | 97.3 | 96.9 | 96.8 |
| | % Total LMW | | 1.1 | 1.1 | 1.1 | 1.1 | 1.3 | 1.7 | 1.5 | 1.8 | 1.8 |
| Charge variants by CEX-UPLC | H1H17203P | % Acidic | 37.3 | 37.2 | 36.6 | 36.0 | 36.9 | 37.1 | 37.9 | 38.2 | 38.4 |
| | | % Main | 41.3 | 41.3 | 41.8 | 42.8 | 42.1 | 42.1 | 41.3 | 41.1 | 42.6 |
| | | % Basic | 21.5 | 21.6 | 21.6 | 21.2 | 21.1 | 20.7 | 20.8 | 20.7 | 19.0 |
| | H1H17139P | % Acidic | 43.2 | 43.1 | 42.9 | 40.7 | 41.9 | 42.5 | 44.2 | 44.5 | 42.0 |
| | | % Main | 53.5 | 53.7 | 53.8 | 56.0 | 54.7 | 53.9 | 52.4 | 52.0 | 54.4 |
| | | % Basic | 3.2 | 3.2 | 3.3 | 3.4 | 3.4 | 3.6 | 3.5 | 3.5 | 3.6 |
| | H1H17161P | % Acidic | 50.3 | 50.5 | 48.3 | 50.5 | 52.4 | 50.9 | 54.3 | 55.2 | 57.6 |
| | | % Main | 44.6 | 44.4 | 45.0 | 46.0 | 43.8 | 43.7 | 41.9 | 40.2 | 38.1 |
| | | % Basic | 5.2 | 5.1 | 6.7 | 3.5 | 3.8 | 5.4 | 3.8 | 4.7 | 4.3 |
| Particulate Analysis by MFI (particles/mL) | 2-10 μm | | 16393 | NR | NR | 7081 | NR | 1472 | 4337 | 4506 | 8719 |
| | ≥10 μm | | 55 | NR | NR | 626 | NR | 35 | 359 | 951 | 1212 |
| | ≥25 μm | | 3 | NR | NR | 120 | NR | 5 | 26 | 129 | 210 |
| % Relative Potency (Bioassay) | Virus Neutralization assay | | 107 | NR | 80 | 80 | NR | 69 | NR | 72 | 86 |
| | ADCC assay | | 112 | NR | 105 | 126 | NR | 125 | NR | 111 | 116 |

NR, Not Required.

Results from the accelerated studies are provided below in Table 15. After incubation for 3 months at 25° C., an increase of 0.6% in the relative amount of total HMW species and total LMW species was observed. Increases in acidic charge variants of 2.6%, 2.5% and 5.6% were observed for H1H17203P, H1H17139P, and H1H17161P, respectively. Co-formulated H1H17203P, H1H17139P, and H1H17161P DP maintained potency after incubation under the accelerated conditions. After incubation for 28 days at 45° C., an increase of 1.3% in the relative amount of total HMW species was observed while the increase in total LMW species was 1.9%.

The results from stress and accelerated stability studies of co-formulated H1H17203P, H1H17139P, and H1H17161P DP demonstrated limited increases in the relative amounts of total HMW species, total LMW species, and acidic charge variants for co-formulated H1H17203P, H1H17139P, and H1H17161P DP similarly to those from the individual formulations.

TABLE 15

Research Stability of H1H17203P, H1H17139P, and H1H17161P Combination DP (1:1:1, 50 mg/mL total protein) - Effect of Accelerated Conditions

| Stability Study Number | | | H1H17203P, H1H17139P, and H1H17161P-SS002 | | | | | |
|---|---|---|---|---|---|---|---|---|
| Lot Number | | | 9018800002, 9019300002, 9019800002 | | | | | |
| Formulation Lot Number | | | L15-401 | | | | | |
| Formulation | | | 16.7 mg/mL H1H17203P, 16.7 mg/mL H1H17139P, 16.7 mg/mL H1H17161P, 10 mM histidine, pH 6.0, 0.1% (w/v) polysorbate 80, 10% (w/v) sucrose | | | | | |
| Fill Volume | | | 0.4 mL | | | | | |
| Container/Closure | | | 2 mL Type I borosilicate glass vial with West S2-F451 4432/50 GRY B2-40 stopper | | | | | |

| | | | No Storage | 25 °C. (months) | | | 45° C. (days) | | |
|---|---|---|---|---|---|---|---|---|---|
| Assay | | | 0 | 0.5 | 1 | 3 | 7 | 14 | 28 |
| Color and Appearance | | | Pass | Pass | Pass | Pass | Pass | Pass | Pass |
| Turbidity (Increase in OD at 405 nm) | | | 0.00 | 0.00 | 0.01 | 0.00 | 0.00 | 0.01 | 0.01 |
| pH | | | 6.1 | 6.0 | 6.1 | 6.1 | 6.0 | 6.1 | 6.1 |
| % Total Protein Recovered by RP-UPLC | H1H17203P, H1H17139P, and H1H17161P | | 100 | 100 | 101 | 104 | 99 | 98 | 101 |
| Total Purity by MCE-SDS | Non-reduced; % (H1H17203P, H1H17139P, and H1H17161P) main | | 100 | NR | NR | 100 | NR | NR | 98.5 |
| | Reduced; % (H1H17203P, H1H17139P, and H1H17161P heavy chain) + % (H1H17203P, H1H17139P, and H1H17161P) light chain | | 99.3 | NR | NR | 98.8 | NR | NR | 98.0 |
| Total Purity by SE-UPLC | % Total HMW | | 0.7 | 1.0 | 1.1 | 1.3 | 1.1 | 1.4 | 2.0 |
| | % Total Native | | 98.2 | 97.7 | 97.6 | 97.0 | 97.2 | 96.5 | 95.0 |
| | % Total LMW | | 1.1 | 1.3 | 1.3 | 1.7 | 1.7 | 2.2 | 3.0 |
| Charge variants by CEX-UPLC | H1H17203P | % Acidic | 37.3 | 37.5 | 38.0 | 39.9 | 40.2 | 43.7 | 52.0 |
| | | % Main | 41.3 | 41.6 | 41.5 | 40.4 | 39.2 | 36.4 | 31.7 |
| | | % Basic | 21.5 | 20.9 | 20.5 | 19.6 | 20.6 | 19.9 | 16.2 |
| | H1H17139P | % Acidic | 43.2 | 43.1 | 43.5 | 45.7 | 46.0 | 49.8 | 57.6 |
| | | % Main | 53.5 | 53.4 | 53.0 | 50.3 | 49.9 | 45.6 | 38.1 |
| | | % Basic | 3.2 | 3.5 | 3.5 | 4.0 | 4.0 | 4.6 | 4.4 |
| | H1H17161P | % Acidic | 50.3 | 51.7 | 53.2 | 55.9 | 56.2 | 61.5 | 73.2 |
| | | % Main | 44.6 | 43.1 | 42.3 | 37.0 | 38.9 | 33.2 | 22. |
| | | % Basic | 5.2 | 5.3 | 4.5 | 7.1 | 4.9 | 5.3 | 4.6 |
| Particulate Analysis by MFI (particles/mL) | 2-10 μm | | 16393 | NR | NR | 1785 | NR | NR | 1882 |
| | ≥10 μm | | 55 | NR | NR | 200 | NR | NR | 144 |
| | ≥25 μm | | 3 | NR | NR | 41 | NR | NR | 33 |
| % Relative Potency by Bioassay | Virus Neutralization assay | | 107 | NR | NR | 86 | NR | NR | 75 |
| | ADCC assay | | 112 | NF | NR | 116 | NR | NR | 123 |

NR, Not Required.

Results from the stress stability studies showed that co-formulated H1H17203P, H1H17139P, and H1H17161P DP was physically and chemically stable when agitated (vortexed at ambient room temperature) for 120 minutes or when subjected to eight freeze/thaw cycles (Table 16). No appreciable change in the physical or chemical stability was detected in any of the monitored attributes. Potency was maintained when the co-formulated H1H17203P, H1H17139P, and H1H17161P OP was agitated or when subjected to freeze/thaw cycles.

TABLE 16

Research Stability of H1H17203P, H1H17139P, and H1H17161P Combination DP (1:1:1, 50 mg/mL total protein) - Effect of Stress Conditions

| | | |
|---|---|---|
| Stability Study Number | | H1H17203P, H1H17139P, and H1H17161P -SS002 |
| Lot Number | | 9018800002, 9019300002, 9019800002 |
| Formulation Lot Number | | L15-401 |
| Formulation | | 16.7 mg/mL H1H17203P, 16.7 mg/mL H1H17139P, 16.7 mg/mL H1H17161P, 10 mM histidine, pH 6.0, 0.1% (w/v) polysorbate 80, 10% (w/v) sucrose |
| Fill Volume | | 0.4 mL |
| Container/Closure | | 2 mL Type I borosilicate glass vial with West S2-F451 4432/50 GRY B2-40 stopper |

| | | | No Stress | Agitation (minutes) | | Freeze/Thaw (cycles) | |
|---|---|---|---|---|---|---|---|
| Assay | | | 0 | 60 | 120 | 4 | 8 |
| Color and Appearance | | | Pass | Pass | Pass | Pass | Pass |
| Turbidity (Increase in OD at 405 nm) | | | 0.00 | 0.00 | 0.00 | 0.00 | 0.00 |
| pH | | | 6.1 | 6.0 | 6.0 | 6.1 | 6.1 |
| % Total Protein Recovered by RP-UPLC | H1H17203P, H1H17139P, and H1H17161P | | 100 | 100 | 100 | 101 | 101 |
| Total Purity by MCE-SDS | Non-reduced; % Native (H1H17203P, H1H17139P, and H1H17161P) | | 100 | NR | 99.7 | NR | 100 |
| | Reduced; % (H1H17203P, H1H17139P, and H1H17161P heavy chain) + % (H1H17203P, H1H17139P, and H1H17161P) light chain | | 99.3 | NR | 99.1 | NR | 98.8 |
| Total Purity by SE-UPLC | % Total HMW | | 0.7 | 0.7 | 0.7 | 0.7 | 0.8 |
| | % Total Native | | 98.2 | 98.1 | 98.1 | 98.2 | 98.1 |
| | % Total LMW | | 1.1 | 1.2 | 1.2 | 1.1 | 1.1 |
| Charge variants by CEX-UPLC | H1H17203P | % Acidic | 37.3 | 37.1 | 37.3 | 37.2 | 37.4 |
| | | % Main | 41.3 | 41.3 | 41.2 | 41.2 | 41.0 |
| | | % Basic | 21.5 | 21.6 | 21.5 | 21.6 | 21.6 |
| | H1H17139P | % Acidic | 43.2 | 43.1 | 43.4 | 43.3 | 43.5 |
| | | % Main | 53.5 | 53.6 | 53.5 | 53.4 | 53.3 |
| | | % Basic | 3.2 | 3.3 | 3.2 | 3.3 | 3.2 |
| | H1H17161P | % Acidic | 50.3 | 50.4 | 50.5 | 50.3 | 50.6 |
| | | % Main | 44.6 | 44.6 | 44.3 | 44.5 | 44.2 |
| | | % Basic | 5.2 | 5.0 | 5.2 | 5.2 | 5.2 |
| % Relative Potency (Bioassay) | Virus Neutralization assay | | 107 | NR | 116 | NR | 94 |
| | ADCC assay | | 112 | NR | 87 | NR | 127 |

NR, Not Required

Conclusions

Co-formulated H1H17203P, H1H17139P, and H1H17161P DP is manufactured as a liquid DP for IV administration. The H1H17203P, H1H17139P, and H1H17161P DP can contain 16.7 mg/mL H1H17203P, 16.7 mg/mL H1H17139P and 16.7 mg/mL H1H17161P formulated in a solution containing 10 mM histidine, pH 6.0, 0.1% (w/v) polysorbate 80, and 10% (w/v) sucrose. Based on the results of the studies herein:

Co-formulated H1H17203P, H1H17139P, and H1H17161P DP is stable when stored at 2-8° C. for at least 3 months.

The main degradation pathways identified under accelerated conditions were formation of HMW and LMW species and acidic charge variants.

Example 6: Effect of Different Buffers and pH

The effect of buffer and pH on the thermal stability of the three anti-EBOV antibodies was examined in liquid formulations by incubating 100 mg/mL total antibody at 45° C. for 28 days in a series of buffer systems at varying pH ranges. The following pH and buffer systems were studied: citrate (pH 5.2, 6.0, 6.8) and histidine (pH 5.2, 6.0, 6.8). Based on results from SE-UPLC analysis, maximum protein stability was observed when the antibodies were formulated at pH 6.0 in histidine buffer (Tables 17-20 and 22-25). Presence of sub-visible particles was determined in the three-way antibody formulation using micro fluid imaging (MFI) (Table 21).

TABLE 17

Effect of Buffer and pH on the Stability of 100 mg/mL H1H17203P Incubated at 45° C. for 28 Days - Visual, OD, pH, SE-UPLC, and RP-UPLC Results

| Buffer/pH | Days | Visual | OD @ 405 nm | ΔOD | pH | % HMW | % Native | % LMW | Protein Conc. (mg/mL) | % Recovery |
|---|---|---|---|---|---|---|---|---|---|---|
| 10 mM | t = 0 | pass | 0.085 | 0.00 | 5.4 | 1.0 | 97.8 | 1.2 | 31.8 | 100.0 |
| Histidine | 7 | pass | 0.084 | 0.00 | 5.4 | 2.2 | 96.0 | 1.8 | 32.3 | 101.7 |
| pH 5.2 | 14 | pass | 0.089 | 0.00 | 5.4 | 3.2 | 94.2 | 2.6 | 31.9 | 100.4 |
|  | 21 | pass | 0.089 | 0.00 | 5.4 | 4.9 | 92.2 | 2.9 | 32.3 | 101.7 |
|  | 28 | pass | 0.091 | 0.01 | 5.5 | 6.0 | 90.6 | 3.4 | 32.5 | 102.1 |
| 10 mM | t = 0 | pass | 0.088 | 0.00 | 6.1 | 1.3 | 97.6 | 1.1 | 33.3 | 100.0 |
| Histidine | 7 | pass | 0.087 | 0.00 | 6.1 | 1.3 | 97.0 | 1.7 | 33.9 | 101.9 |
| pH 6.0 | 14 | pass | 0.090 | 0.00 | 6.1 | 1.6 | 96.0 | 2.3 | 33.3 | 100.2 |
|  | 21 | pass | 0.093 | 0.01 | 6.1 | 2.2 | 95.3 | 2.5 | 33.9 | 101.8 |
|  | 28 | pass | 0.094 | 0.01 | 6.1 | 2.7 | 94.4 | 3.0 | 34.0 | 102.1 |
| 10 mM | t = 0 | pass | 0.087 | 0.00 | 7.0 | 1.7 | 97.1 | 1.2 | 33.0 | 100.0 |
| Histidine | 7 | pass | 0.088 | 0.00 | 7.0 | 1.7 | 96.6 | 1.7 | 33.7 | 102.0 |
| pH 6.8 | 14 | pass | 0.089 | 0.00 | 7.0 | 2.2 | 95.5 | 2.4 | 33.0 | 100.0 |
|  | 21 | pass | 0.092 | 0.01 | 7.0 | 2.8 | 94.6 | 2.6 | 33.3 | 100.9 |
|  | 28 | pass | 0.095 | 0.01 | 7.1 | 3.4 | 93.4 | 3.1 | 33.6 | 101.8 |
| 10 mM | t = 0 | pass | 0.101 | 0.00 | 5.3 | 1.6 | 97.2 | 1.2 | 32.8 | 100.0 |
| Citrate | 7 | pass | 0.154 | 0.05 | 5.3 | 16.2 | 82.1 | 1.8 | 33.4 | 101.6 |
| pH 5.2 | 14 | pass | 0.347 | 0.25 | 5.3 | 30.1 | 67.7 | 2.3 | 32.5 | 99.1 |
|  | 21 | pass | 1.320 | 1.22 | 5.3 | 32.2 | 64.7 | 3. | 23.3 | 71.0 |
|  | 28 | pass | 2.332 | 2.23 | 5.3 | NP | NP | NP | NP | NP |
| 10 mM | t = 0 | pass | 0.102 | 0.00 | 6.1 | 1.9 | 97.0 | 1.2 | 31.1 | 100.0 |
| Citrate | 7 | pass | 0.103 | 0.00 | 6.1 | 3.0 | 95.3 | 1.7 | 31.2 | 100.4 |
| pH 6.0 | 14 | pass | 0.106 | 0.00 | 6.1 | 4.4 | 93.4 | 2.2 | 30.8 | 99.1 |
|  | 21 | pass | 0.118 | 0.02 | 6.1 | 6.3 | 91.3 | 2.4 | 31.6 | 101.6 |
|  | 28 | pass | 0.131 | 0.03 | 6.1 | 7.7 | 89.4 | 2.9 | 31.7 | 101.9 |
| 10 mM | t = 0 | pass | 0.103 | 0.00 | 6.8 | 2.6 | 96.3 | 1.2 | 32.1 | 100.0 |
| Citrate | 7 | pass | 0.105 | 0.00 | 6.9 | 3.3 | 95.0 | 1.7 | 32.1 | 100.0 |
| pH 6.8 | 14 | pass | 0.109 | 0.01 | 6.8 | 4.4 | 93.3 | 2.3 | 31.9 | 99.5 |
|  | 21 | pass | 0.117 | 0.01 | 6.9 | 5.8 | 91.7 | 2.5 | 32.5 | 101.4 |
|  | 28 | pass | 0.123 | 0.02 | 6.9 | 7.1 | 90.0 | 3.0 | 32.7 | 102.1 |

10 mM citrate, pH 5.2, 28 d samples were not run on UPLC instruments due to visual failures

TABLE 18

Effect of Buffer and pH on the Stability of 100 mg/mL H1H17139P Incubated at 45° C. for 28 Days - Visual, OD, pH, SE-UPLC and RP-UPLC Results

| Buffer/pH | Days | Visual | OD @ 405 nm | ΔOD | pH | % HMW | % Native | % LMW | Protein Conc. (mg/mL) | % Recovery |
|---|---|---|---|---|---|---|---|---|---|---|
| 10 mM | t = 0 | pass | 0.085 | 0.00 | 5.4 | 0.8 | 97.8 | 1.4 | 33.4 | 100.0 |
| Histidine | 7 | pass | 0.083 | 0.00 | 5.4 | 0.6 | 97.3 | 2.1 | 33.7 | 100.9 |
| pH 5.2 | 14 | pass | 0.085 | 0.00 | 5.4 | 0.7 | 96.5 | 2.8 | 33.8 | 101.0 |
|  | 21 | pass | 0.085 | 0.00 | 5.4 | 0.8 | 96.1 | 3.1 | 33.8 | 101.1 |
|  | 28 | pass | 0.088 | 0.00 | 5.4 | 0.9 | 95.4 | 3.7 | 33.9 | 101.4 |
| 10 mM | t = 0 | pass | 0.087 | 0.00 | 6.1 | 1.1 | 97.5 | 1.4 | 33.9 | 100.0 |
| Histidine | 7 | pass | 0.085 | 0.00 | 6.1 | 0.8 | 97.3 | 1.9 | 34.1 | 100.6 |
| pH 6.0 | 14 | pass | 0.088 | 0.00 | 6.1 | 0.9 | 96.7 | 2.5 | 34.3 | 101.0 |

TABLE 18-continued

Effect of Buffer and pH on the Stability of 100 mg/mL H1H17139P Incubated at 45° C.
for 28 Days - Visual, OD, pH, SE-UPLC and RP-UPLC Results

| Buffer/pH | Days | Visual | OD @ 405 nm | ΔOD | pH | % HMW | % Native | % LMW | Protein Conc. (mg/mL) | % Recovery |
|---|---|---|---|---|---|---|---|---|---|---|
| | 21 | pass | 0.091 | 0.00 | 6.1 | 1.0 | 96.3 | 2.7 | 34.5 | 101.6 |
| | 28 | pass | 0.091 | 0.00 | 6.2 | 1.1 | 95.8 | 3.2 | 34.5 | 101.6 |
| 10 mM | t = 0 | pass | 0.085 | 0.00 | 6.9 | 1.4 | 97.3 | 1.4 | 32.6 | 100.0 |
| Histidine | 7 | pass | 0.085 | 0.00 | 6.9 | 1.1 | 96.9 | 2.0 | 32.9 | 100.8 |
| pH 6.8 | 14 | pass | 0.088 | 0.00 | 6.9 | 1.3 | 96.2 | 2.5 | 32.8 | 100.7 |
| | 21 | pass | 0.090 | 0.00 | 7.0 | 1.4 | 95.8 | 2.8 | 32.9 | 101.0 |
| | 28 | pass | 0.091 | 0.01 | 7.0 | 1.6 | 95.0 | 3.4 | 32.8 | 100.8 |
| 10 mM | t = 0 | pass | 0.093 | 0.00 | 5.3 | 1.1 | 97.5 | 1.4 | 32.1 | 100.0 |
| Citrate | 7 | pass | 0.093 | 0.00 | 5.3 | 1.2 | 96.7 | 2.2 | 32.5 | 101.2 |
| pH 5.2 | 14 | pass | 0.095 | 0.00 | 5.3 | 1.4 | 95.5 | 3.0 | 32.5 | 101.0 |
| | 21 | pass | 0.097 | 0.00 | 5.2 | 1.8 | 94.8 | 3.4 | 32.4 | 100.7 |
| | 28 | pass | 0.097 | 0.00 | 5.3 | 2.1 | 93.9 | 4.1 | 32.5 | 101.1 |
| 10 mM | t = 0 | pass | 0.096 | 0.00 | 6.1 | 1.6 | 97.1 | 1.4 | 31.2 | 100.0 |
| Citrate | 7 | pass | 0.094 | 0.00 | 6.1 | 1.5 | 96.5 | 1.9 | 31.4 | 100.7 |
| pH 6.0 | 14 | pass | 0.096 | 0.00 | 6.0 | 1.8 | 95.7 | 2.5 | 31.1 | 99.9 |
| | 21 | pass | 0.097 | 0.00 | 6.1 | 2.0 | 95.3 | 2.7 | 31.3 | 100.4 |
| | 28 | pass | 0.098 | 0.00 | 6.1 | 2.2 | 94.6 | 3.2 | 31.6 | 101.3 |
| 10 mM | t = 0 | pass | 0.099 | 0.00 | 6.8 | 2.2 | 96.4 | 1.3 | 31.9 | 100.0 |
| Citrate | 7 | pass | 0.097 | 0.00 | 6.8 | 2.1 | 95.9 | 2.0 | 32.2 | 100.7 |
| pH 6.8 | 14 | pass | 0.099 | 0.00 | 6.8 | 2.4 | 95.1 | 2.5 | 32.0 | 100.4 |
| | 21 | pass | 0.102 | 0.00 | 6.8 | 2.6 | 94.7 | 2.8 | 31.9 | 100.0 |
| | 28 | pass | 0.101 | 0.00 | 6.9 | 2.8 | 93.9 | 3.3 | 32.2 | 100.9 |

TABLE 19

Effect of Buffer and pH on the Stability of 100 mg/mL H1H17161P Incubated at 45° C.
for 28 Days - Visual, OD, pH, SE-UPLC, and RP-UPLC Results

| Buffer/pH | Days | Visual | OD @ 405 nm | ΔOD | pH | % HMW | % Native | % LMW | Protein Conc. (mg/mL) | % Recovery |
|---|---|---|---|---|---|---|---|---|---|---|
| 10 mM | t = 0 | pass | 0.104 | 0.00 | 5.3 | 1.9 | 96.6 | 1.5 | 31.1 | 100% |
| Histidine | 7 | pass | 0.100 | 0.00 | 5.4 | 1.4 | 96.4 | 2.3 | 31.3 | 101% |
| pH 5.2 | 14 | pass | 0.102 | 0.00 | 5.4 | 1.4 | 95.7 | 2.9 | 31.1 | 100% |
| | 21 | pass | 0.103 | 0.00 | 5.4 | 1.5 | 95.3 | 3.2 | 31.2 | 100% |
| | 28 | pass | 0.108 | 0.00 | 5.5 | 1.5 | 94.7 | 3.8 | 31.3 | 101% |
| 10 mM | t = 0 | pass | 0.107 | 0.00 | 6.1 | 2.3 | 96.3 | 1.5 | 32.1 | 100% |
| Histidine | 7 | pass | 0.106 | 0.00 | 6.1 | 1.7 | 96.3 | 2.1 | 32.6 | 102% |
| pH 6.0 | 14 | pass | 0.112 | 0.01 | 6.1 | 1.7 | 95.6 | 2.7 | 32.1 | 100% |
| | 21 | pass | 0.106 | 0.00 | 6.2 | 1.8 | 95.4 | 2.8 | 32.4 | 101% |
| | 28 | pass | 0.108 | 0.00 | 6.2 | 1.9 | 94.9 | 3.3 | 32.6 | 101% |
| 10 mM | t = 0 | pass | 0.106 | 0.00 | 7.0 | 2.8 | 95.8 | 1.5 | 31.1 | 100% |
| Histidine | 7 | pass | 0.108 | 0.00 | 7.0 | 2.2 | 95.7 | 2.1 | 31.4 | 101% |
| pH 6.8 | 14 | pass | 0.109 | 0.00 | 7.0 | 2.4 | 94.8 | 2.7 | 31.0 | 100% |
| | 21 | pass | 0.109 | 0.00 | 7.0 | 2.6 | 94.5 | 2.9 | 31.4 | 101% |
| | 28 | pass | 0.108 | 0.00 | 7.1 | 2.8 | 93.7 | 3.5 | 31.4 | 101% |
| 10 mM | t = 0 | pass | 0.112 | 0.00 | 5.2 | 2.2 | 96.3 | 1.5 | 30.0 | 100% |
| Citrate | 7 | pass | 0.117 | 0.01 | 5.2 | 1.9 | 95.7 | 2.4 | 30.3 | 101% |
| pH 5.2 | 14 | pass | 0.111 | 0.00 | 5.2 | 2.2 | 94.6 | 3.3 | 30.2 | 101% |
| | 21 | pass | 0.110 | 0.00 | 5.3 | 2.4 | 94.0 | 3.6 | 30.2 | 101% |
| | 28 | pass | 0.110 | 0.00 | 5.2 | 2.6 | 93.1 | 4.3 | 30.3 | 101% |
| 10 mM | t = 0 | pass | 0.120 | 0.00 | 6.0 | 3.1 | 95.5 | 1.5 | 31.6 | 100% |
| Citrate | 7 | pass | 0.122 | 0.00 | 6.0 | 2.8 | 95.1 | 2.1 | 31.9 | 101% |
| pH 6.0 | 14 | pass | 0.119 | 0.00 | 6.0 | 3.1 | 94.3 | 2.6 | 31.9 | 101% |
| | 21 | pass | 0.118 | 0.00 | 6.0 | 3.3 | 93.9 | 2.8 | 32.0 | 101% |
| | 28 | pass | 0.116 | 0.00 | 6.0 | 3.6 | 93.2 | 3.3 | 31.9 | 101% |
| 10 mM | t = 0 | pass | 0.123 | 0.00 | 6.8 | 4.0 | 94.6 | 1.5 | 31.9 | 100% |
| Citrate | 7 | pass | 0.123 | 0.00 | 6.9 | 3.8 | 94.1 | 2.1 | 32.3 | 102% |
| pH 6.8 | 14 | pass | 0.125 | 0.00 | 6.8 | 4.3 | 93.1 | 2.7 | 31.9 | 100% |
| | 21 | pass | 0.123 | 0.00 | 6.9 | 4.6 | 92.5 | 2.9 | 32.2 | 101% |
| | 28 | pass | 0.121 | 0.00 | 6.9 | 4.9 | 91.6 | 3.4 | 32.1 | 101% |

TABLE 20

Effect of Buffer and pH on the Stability of 100 mg/mL Total H1H17203P, H1H17139P, and H1H17161P Combination Incubated at 45° C. for 28 Days - Visual, OD, pH, SE-UPLC, and RP-UPLC Results

| Buffer/pH | Days | Visual | OD @ 405 nm | ΔOD | pH | % HMW | % Native | % LMW | Protein Conc. (mg/mL) | % Recovery |
|---|---|---|---|---|---|---|---|---|---|---|
| 10 mM Histidine pH 5.2 | t = 0 | pass | 0.168 | 0.00 | 5.5 | 1.3 | 97.3 | 1.4 | 95.2 | 100% |
| | 7 | pass | 0.168 | 0.00 | 5.5 | 2.3 | 95.7 | 2 | 94.1 | 99% |
| | 14 | pass | 0.175 | 0.01 | 5.5 | 3.2 | 94.0 | 2.8 | 93.2 | 98% |
| | 21 | pass | 0.176 | 0.01 | 5.5 | 4.2 | 92.9 | 2.9 | 94.7 | 99% |
| | 28 | pass | 0.181 | 0.01 | 5.6 | 4.8 | 91.9 | 3.4 | 94.9 | 100% |
| 10 mM Histidine pH 6.0 | t = 0 | pass | 0.177 | 0.00 | 6.2 | 1.7 | 97.0 | 1.4 | 98.2 | 100% |
| | 7 | pass | 0.177 | 0.00 | 6.3 | 2.3 | 95.8 | 1.9 | 96.9 | 99% |
| | 14 | pass | 0.183 | 0.01 | 6.2 | 2.9 | 94.6 | 2.5 | 94.4 | 96% |
| | 21 | pass | 0.190 | 0.01 | 6.3 | 3.4 | 94. | 2.6 | 95.6 | 97% |
| | 28 | pass | 0.193 | 0.02 | 6.3 | 3.8 | 93.2 | 3 | 97.8 | 100% |
| 10 mM Histidine pH 6.8 | t = 0 | pass | 0.180 | 0.00 | 7.1 | 2.1 | 96.4 | 1.6 | 95.9 | 100% |
| | 7 | pass | 0.186 | 0.01 | 7.2 | 3.3 | 94.8 | 1.9 | 95.2 | 99% |
| | 14 | pass | 0.194 | 0.01 | 7.1 | 4.1 | 93.3 | 2.6 | 92.6 | 97% |
| | 21 | pass | 0.196 | 0.02 | 7.1 | 4.8 | 92.4 | 2.7 | 92.9 | 97% |
| | 28 | pass | 0.199 | 0.02 | 7.1 | 5.4 | 91.3 | 3.3 | 95.7 | 100% |
| 10 mM Citrate pH 5.2 | t = 0 | pass | 0.189 | 0.00 | 5.4 | 1.7 | 96.9 | 1.3 | 94.7 | 100% |
| | 7 | pass | 0.219 | 0.03 | 5.4 | 7.6 | 90.4 | 2 | 94.2 | 99% |
| | 14 | pass | 0.362 | 0.17 | 5.4 | 14 | 83.3 | 2.7 | 91.1 | 96% |
| | 21 | fail | 0.737 | 0.55 | 5.4 | 17.7 | 79.3 | 2.9 | 92.9 | 98% |
| | 28 | pass | 1.267 | 1.08 | 5.4 | NA | NA | NA | NA | NA |
| 10 mM Citrate pH 6.0 | t = 0 | pass | 0.201 | 0.00 | 6.2 | 2.3 | 96.4 | 1.3 | 93.3 | 100% |
| | 7 | pass | 0.201 | 0.00 | 6.2 | 3.6 | 94.6 | 1.9 | 93.0 | 100% |
| | 14 | pass | 0.208 | 0.01 | 6.2 | 4.7 | 92.9 | 2.5 | 92.8 | 99% |
| | 21 | pass | 0.220 | 0.02 | 6.2 | 5.7 | 91.8 | 2.5 | 92.6 | 99% |
| | 28 | pass | 0.226 | 0.03 | 6.2 | 6.6 | 90.4 | 3 | 94.5 | 101% |
| 10 mM Citrate pH 6.8 | t = 0 | pass | 0.212 | 0.00 | 6.9 | 3 | 95.7 | 1.3 | 96.1 | 100% |
| | 7 | pass | 0.213 | 0.00 | 6.9 | 4.4 | 93.7 | 1.9 | 95.7 | 100% |
| | 14 | pass | 0.225 | 0.01 | 6.9 | 5.6 | 91.8 | 2.6 | 95.5 | 99% |
| | 21 | pass | 0.224 | 0.01 | 6.9 | 6.5 | 90.9 | 2.6 | 95.7 | 100% |
| | 28 | pass | 0.234 | 0.02 | 6.9 | 7.4 | 89.5 | 3.2 | 96.4 | 100% |

TABLE 21

MFI Results for Total H1H17203P, H1H17139P, and H1H17161P Combination Formulation

| Sample | 2-10 μm Conc.(#/ml) | ≥2 μm Conc.(#/ml) | ≥10 μm Conc.(#/ml) | ≥25 μm Conc.(#/ml) |
|---|---|---|---|---|
| 10 mM Histidine pH 5.2 t = 0 | 468 | 507 | 40 | 2 |
| 10 mM Histidine pH 6.0 t = 0 | 557 | 570 | 13 | 0 |
| 10 mM Histidine pH 6.8 t = 0 | 607 | 641 | 33 | 6 |
| 10 mM Citrate pH 5.2 t = 0 | 973 | 1017 | 44 | 6 |
| 10 mM Citrate pH 6.0 t = 0 | 741 | 770 | 29 | 10 |
| 10 mM Citrate pH 6.8 t = 0 | 710 | 802 | 92 | 21 |
| 10 mM Histidine pH 5.2 t = 28 d at 45 C. | 1380 | 1439 | 58 | 2 |
| 10 mM Histidine pH 6.0 t = 28 d at 45 C. | 1396 | 1463 | 67 | 8 |
| 10 mM Histidine pH 6.8 t = 28 d at 45 C. | 1959 | 2024 | 65 | 6 |
| 10 mM Citrate pH 5.2 t = 28 d at 45 C. | 50767 | 57378 | 6611 | 582 |
| 10 mM Citrate pH 6.0 t = 28 d at 45 C. | 1326 | 1359 | 33 | 0 |
| 10 mM Citrate pH 6.8 t = 28 d at 45 C. | 1508 | 1600 | 92 | 10 |

Based on results from CEX-UPLC analysis, maximum protein stability was observed when the antibodies were formulated between pH 5.2 and 6.8 in histidine buffer or between pH 5.2 and 6.8 in acetate buffer. These analyses also revealed that aggregation (i.e. formation of HMW species), fragmentation (i.e. formation of LMW species), and formation of charge variants were the main degradation pathways. Histidine buffer was selected as the formulation buffer because it provided the best overall level of protein stabilization with respect to formation of HMW and LMW species and formation of charge variants. A pH of 6.0 was chosen for the formulation because formation of HMW species and charge variants, which are the major degradation pathways, were minimized at this pH. Based on these results, 10 mM histidine buffer at pH 6.0 was chosen for the anti-EBOV individual and combination formulations. See Tables 22-25.

TABLE 22

Effect of Buffer and pH on the Stability of 100 mg/mL H1H17203P Incubated at 45° C. for 28 Days - CEX-UPLC Results

| Formulation | Stress | Days | H1H17203P % Acidic | % Main | % Basic |
|---|---|---|---|---|---|
| 10 mM Histidine pH 5.2 | 45° C. | 0 | 34.7 | 52.2 | 13.1 |
| | | 7 | 37.1 | 45.8 | 17.1 |
| | | 14 | 41.9 | 39.9 | 18.2 |
| | | 21 | 45.4 | 35.1 | 19.5 |
| | | 28 | 48.9 | 32.4 | 18.7 |
| 10 mM Histidine pH 6.0 | 45° C. | 0 | 35.2 | 51.9 | 12.9 |
| | | 7 | 39.2 | 49.3 | 11.6 |
| | | 14 | 45.0 | 44.4 | 10.6 |
| | | 21 | 49.9 | 39.9 | 10.1 |
| | | 28 | 54.0 | 36.3 | 9.8 |
| 10 mM Histidine pH 6.8 | 45° C. | 0 | 35.6 | 51.5 | 13.0 |
| | | 7 | 44.2 | 47.1 | 8.8 |
| | | 14 | 53.3 | 40.1 | 6.7 |
| | | 21 | 60.2 | 33.9 | 6.0 |
| | | 28 | 65.6 | 29.0 | 5.5 |
| 10 mM Citrate pH 5.2 | 45° C. | 0 | 34.5 | 52.4 | 13.2 |
| | | 7 | 37.3 | 40.7 | 22.0 |
| | | 14 | 33.4 | 25.6 | 41.1 |
| | | 21 | 47.7 | 27.3 | 25.1 |
| | | 28 | NP | NP | NP |
| 10 mM Citrate pH 6.0 | 45° C. | 0 | 34.8 | 52.0 | 13.2 |
| | | 7 | 41.7 | 49.9 | 8.5 |
| | | 14 | 48.5 | 43.0 | 8.5 |
| | | 21 | 53.7 | 37.5 | 8.8 |
| | | 28 | 58.1 | 33.2 | 8.7 |
| 10 mM Citrate pH 6.8 | 45° C. | 0 | 34.8 | 51.6 | 13.6 |
| | | 7 | 44.0 | 48.5 | 7.5 |
| | | 14 | 52.3 | 41.0 | 6.7 |
| | | 21 | 58.6 | 34.6 | 6.7 |
| | | 28 | 63.6 | 29.9 | 6.6 |

Citrate, pH 5.2, 28 d samples were not run on UPLC instruments due to visual failures

TABLE 23

Effect of Buffer and pH on the Stability of 100 mg/mL H1H17139P Incubated at 45° C. for 28 Days - CEX-UPLC Results

| Formulation | Stress | Days | H1H17139P % Acidic | % Main | % Basic |
|---|---|---|---|---|---|
| 10 mM Histidine pH 5.2 | 45° C. | 0 | 36.9 | 58.8 | 4.3 |
| | | 7 | 40.8 | 53.3 | 5.9 |
| | | 14 | 51.6 | 44.0 | 4.5 |
| | | 21 | 51.6 | 41.4 | 7.1 |
| | | 28 | 55.6 | 37.3 | 7.1 |
| 10 mM Histidine pH 6.0 | 45° C. | 0 | 37.3 | 58.5 | 4.3 |
| | | 7 | 40.9 | 54.2 | 4.8 |
| | | 14 | 48.6 | 46.3 | 5.1 |
| | | 21 | 50.9 | 44.5 | 4.7 |
| | | 28 | 55.2 | 40.4 | 4.4 |
| 10 mM Histidine pH 6.8 | 45° C. | 0 | 37.5 | 58.2 | 4.3 |
| | | 7 | 44.8 | 51.3 | 4.0 |
| | | 14 | 51.2 | 41.8 | 7.0 |
| | | 21 | 58.9 | 38.0 | 3.1 |
| | | 28 | 64.4 | 32.9 | 2.8 |
| 10 mM Citrate pH 5.2 | 45° C. | 0 | 36.8 | 58.7 | 4.5 |
| | | 7 | 44.0 | 49.3 | 6.7 |
| | | 14 | 52.5 | 44.0 | 3.5 |
| | | 21 | 57.7 | 35.3 | 7.0 |
| | | 28 | 62.6 | 30.7 | 6.8 |
| 10 mM Citrate pH 6.0 | 45° C. | 0 | 36.7 | 58.6 | 4.6 |
| | | 7 | 41.8 | 52.8 | 5.4 |
| | | 14 | 46.2 | 49.0 | 4.8 |
| | | 21 | 53.9 | 41.2 | 4.9 |
| | | 28 | 58.7 | 36.8 | 4.5 |
| 10 mM Citrate pH 6.8 | 45° C. | 0 | 36.8 | 58.2 | 5.1 |
| | | 7 | 43.9 | 51.2 | 4.9 |
| | | 14 | 46.4 | 47.0 | 6.6 |
| | | 21 | 57.7 | 38.1 | 4.1 |
| | | 28 | 63.0 | 33.3 | 3.7 |

TABLE 24

Effect of Buffer and pH on the Stability of 100 mg/mL H1H17161P Incubated at 45° C. for 28 Days - CEX-UPLC Results

| Formulation | Stress | Days | H1H17161P % Acidic | % Main | % Basic |
|---|---|---|---|---|---|
| 10 mM Histidine pH 5.2 | 45° C. | 0 | 52.0 | 42.0 | 6.0 |
| | | 7 | 59.4 | 35.4 | 5.2 |
| | | 14 | 72.8 | 22.4 | 4.9 |
| | | 21 | 73.0 | 21.7 | 5.3 |
| | | 28 | 73.1 | 21.3 | 5.7 |
| 10 mM Histidine pH 6.0 | 45° C. | 0 | 52.0 | 42.2 | 5.9 |
| | | 7 | 59.4 | 36.1 | 4.5 |
| | | 14 | 72.1 | 23.7 | 4.2 |
| | | 21 | 75.7 | 20.1 | 4.2 |
| | | 28 | 74.8 | 20.9 | 4.3 |
| 10 mM Histidine pH 6.8 | 45° C. | 0 | 52.1 | 41.9 | 6.0 |
| | | 7 | 65.2 | 30.2 | 4.5 |
| | | 14 | 78.5 | 17.5 | 4.0 |
| | | 21 | 83.2 | 13.1 | 3.7 |
| | | 28 | 84.6 | 11.8 | 3.7 |
| 10 mM Citrate pH 5.2 | 45° C. | 0 | 51.7 | 42.4 | 5.9 |
| | | 7 | 69.2 | 25.5 | 5.3 |
| | | 14 | 71.2 | 23.0 | 5.9 |
| | | 21 | 81.4 | 13.4 | 5.2 |
| | | 28 | 78.7 | 15.5 | 5.8 |
| 10 mM Citrate pH 6.0 | 45° C. | 0 | 51.5 | 42.3 | 6.1 |
| | | 7 | 58.8 | 35.9 | 5.3 |
| | | 14 | 69.8 | 24.9 | 5.3 |
| | | 21 | 78.6 | 16.4 | 5.0 |
| | | 28 | 74.6 | 19.9 | 5.5 |
| 10 mM Citrate pH 6.8 | 45° C. | 0 | 52.2 | 41.3 | 6.4 |
| | | 7 | 63.2 | 31.8 | 5.0 |
| | | 14 | 74.5 | 19.8 | 5.7 |
| | | 21 | 85.3 | 9.7 | 5.0 |
| | | 28 | 80.2 | 13.8 | 6.0 |

TABLE 25

Effect of Buffer and pH on the Stability of 100 mg/mL Total H1H17203P, H1H17139P, and H1H17161P Combination Incubated at 45° C. for 28 Days - CEX-UPLC Results

| Formulation | Days | H1H17139P % Acidic | H1H17139P % Main | H1H17139P % Basic | H1H17203P % Acidic | H1H17203P % Main | H1H17203P % Basic | H1H17161P % Acidic | H1H17161P % Main | H1H17161P % Basic |
|---|---|---|---|---|---|---|---|---|---|---|
| 10 mM Histidine pH 5.2 | 0 | 36.2 | 61.1 | 2.6 | 31.5 | 47.1 | 21.4 | 41.7 | 54.3 | 4.0 |
|  | 7 | 41.5 | 54.2 | 4.4 | 38.3 | 45.6 | 16.1 | 55.2 | 39.1 | 5.7 |
|  | 14 | 47.1 | 47.8 | 5.2 | 42.0 | 39.5 | 18.5 | 65.1 | 28.8 | 6.1 |
|  | 21 | 51.9 | 42.5 | 5.6 | 45.2 | 34.9 | 19.9 | 70.4 | 23.4 | 6.2 |
|  | 28 | 55.8 | 38.5 | 5.7 | 47.6 | 32.0 | 20.4 | 67.6 | 25.0 | 7.3 |
| 10 mM Histidine pH 6.0 | 0 | 36.6 | 60.8 | 2.6 | 31.9 | 46.8 | 21.2 | 44.0 | 51.4 | 4.5 |
|  | 7 | 41.5 | 54.7 | 3.7 | 38.8 | 47.2 | 14.0 | 56.5 | 38.7 | 4.8 |
|  | 14 | 46.7 | 49.2 | 4.1 | 43.0 | 41.7 | 15.3 | 69.3 | 25.8 | 4.9 |
|  | 21 | 51.7 | 44.2 | 4.1 | 46.8 | 37.1 | 16.1 | 73.3 | 21.9 | 4.8 |
|  | 28 | 55.1 | 40.5 | 4.3 | 49.5 | 34.0 | 16.5 | 70.7 | 24.5 | 4.8 |
| 10 mM Histidine pH 6.8 | 0 | 37.1 | 60.4 | 2.5 | 32.4 | 46.2 | 21.4 | 42.7 | 52.8 | 4.5 |
|  | 7 | 46.5 | 50.9 | 2.6 | 43.3 | 43.2 | 13.6 | 63.0 | 31.8 | 5.2 |
|  | 14 | 54.9 | 42.6 | 2.5 | 50.0 | 34.8 | 15.2 | 76.7 | 18.5 | 4.8 |
|  | 21 | 61.7 | 36.0 | 2.3 | 57.8 | 30.0 | 12.2 | 89.1 | 7.3 | 3.6 |
|  | 28 | 65.9 | 31.9 | 2.2 | 57.2 | 25.3 | 17.4 | 83.2 | 12.5 | 4.4 |
| 10 mM Citrate pH 5.2 | 0 | 36.2 | 61.0 | 2.8 | 31.9 | 47.4 | 20.7 | 42.9 | 52.6 | 4.6 |
|  | 7 | 43.8 | 51.7 | 4.5 | 40.1 | 43.8 | 16.1 | 55.9 | 37.9 | 6.2 |
|  | 14 | 50.9 | 43.8 | 5.2 | 44.7 | 35.9 | 19.4 | 77.0 | 15.8 | 7.2 |
|  | 21 | 57.1 | 37.5 | 5.5 | 54.0 | 34.0 | 12.0 | 82.8 | 11.8 | 5.4 |
|  | 28 | NA | NA | NA | NA | NA | NA | NA | NA | NA |
| 10 mM Citrate pH 6.0 | 0 | 36.4 | 60.9 | 2.6 | 37.1 | 54.6 | 8.3 | 53.0 | 43.3 | 3.7 |
|  | 7 | 42.0 | 54.2 | 3.8 | 39.4 | 46.9 | 13.8 | 54.3 | 40.0 | 5.7 |
|  | 14 | 47.9 | 48.0 | 4.1 | 44.0 | 40.8 | 15.2 | 60.3 | 34.0 | 5.6 |
|  | 21 | 53.2 | 42.3 | 4.5 | 52.1 | 38.6 | 9.3 | 81.5 | 14.0 | 4.5 |
|  | 28 | 57.7 | 38.6 | 3.7 | 50.8 | 31.3 | 17.9 | 69.1 | 24.9 | 6.0 |
| 10 mM Citrate pH 6.8 | 0 | 37.2 | 60.0 | 2.8 | 37.4 | 53.3 | 9.3 | 52.8 | 42.0 | 5.3 |
|  | 7 | 44.3 | 52.9 | 2.8 | 41.8 | 45.4 | 12.8 | 57.8 | 36.2 | 6.0 |
|  | 14 | 51.8 | 45.5 | 2.7 | 47.5 | 38.2 | 14.3 | 66.0 | 27.5 | 6.5 |
|  | 21 | 58.0 | 39.5 | 2.5 | 54.5 | 33.8 | 11.7 | 78.7 | 16.6 | 4.7 |
|  | 28 | 62.6 | 35.0 | 2.4 | 55.4 | 28.4 | 16.3 | 76.1 | 17.6 | 6.2 |

Example 7: Selection of Stabilizer Under Stress Conditions

From Example 6, pH 6.0 and 10 mM L-histidine was identified as the optimal buffer system for the individually formulated antibodies and the 100 mg/mL 3 way co-formulation. Additional excipients such as thermal stabilizers, surfactants, and anti-oxidants were assessed in this Example for effects on forced degradation and stability. Stabilizers such as sucrose, surfactants, proline, or methionine are often added to antibody formulations to increase the thermal stability of the protein in liquid formulations. Anti-EBOV antibodies formulated separately or in combination in a liquid formulation exhibited improved stability under accelerated conditions when formulated with 5% w/v sucrose and 0.1% w/v Polysorbate 80 or 0.1% Polysorbate 20 and show comparable stability outcomes under vortex stress. (Tables 27-32). Table 26 provides the excipient variables and the respective formulations for Tables 16-21. Base formulations contain 33.3 mg/mL Anti-EBOV Antibody 5% w/v Sucrose and 10 mM Histidine.

TABLE 26

Excipients Tested and Formulation Components

| Formulations | Buffer pH | Additional Sucrose % W/V | Surfactant PS20 % W/V | Surfactant PS80 % W/V | Arginine, mM | Proline, mM | Methionine, mM |
|---|---|---|---|---|---|---|---|
| F1 | 10 mM L-histidine pH 6.0 | 0.0% | 0.00% | 0.00% | 0 | 0 | 0 |
| F2 | 10 mM L-histidine pH 6.0 | 5.0% | 0.10% | 0.00% | 0 | 0 | 20 |
| F3 | 10 mM L-histidine pH 6.0 | 5.0% | 0.00% | 0.00% | 0 | 0 | 0 |
| F4 | 10 mM L-histidine pH 6.0 | 0.0% | 0.00% | 0.10% | 0 | 0 | 20 |
| F5 | 10 mM L-histidine pH 6.0 | 5.0% | 0.10% | 0.00% | 100 | 0 | 0 |
| F6 | 10 mM L-histidine pH 6.0 | 0.0% | 0.10% | 0.00% | 100 | 0 | 20 |
| F7 | 10 mM L-histidine pH 6.0 | 0.0% | 0.00% | 0.10% | 100 | 0 | 0 |
| F8 | 10 mM L-histidine pH 6.0 | 5.0% | 0.00% | 0.00% | 100 | 0 | 20 |
| F9 | 10 mM L-histidine pH 6.0 | 5.0% | 0.00% | 0.10% | 0 | 200 | 0 |
| F10 | 10 mM L-histidine pH 6.0 | 0.0% | 0.10% | 0.00% | 0 | 200 | 0 |
| F11 | 10 mM L-histidine pH 6.0 | 0.0% | 0.00% | 0.00% | 0 | 200 | 20 |
| F12 | 10 mM L-histidine pH 6.0 | 5.0% | 0.00% | 0.10% | 0 | 200 | 20 |

TABLE 27

Effect of Excipients on the Stability of 33 mg/mL H1H17203P Antibody Incubated at 40° C. for up to Two Months - Visual, OD, pH, SE-UPLC, RP-UPLC Concentration, CEX-UPLC

| Formulation | Sample | Visual | OD @ 405 nm | pH | % HMW | % Native | % LMW | Con, mg/ml | % Acidic | % Main | % Basic |
|---|---|---|---|---|---|---|---|---|---|---|---|
| F1 | t = 0 | 0 | 0.087 | 6.1 | 1.0 | 98.1 | 0.9 | 34.9 | 33.57 | 54.25 | 12.19 |
|  | VTX 120 minutes | 0 | 0.086 | 6.1 | 1.0 | 98.1 | 0.9 | 34.7 | 33.44 | 54.28 | 12.26 |
|  | F/T 8 cycles | 0 | 0.090 | 6.1 | 1.0 | 98.2 | 0.9 | 33.4 | 33.47 | 54.5 | 12.03 |
|  | 40° C. 8 days | 0 | 0.087 | 6.2 | 0.9 | 97.9 | 1.3 | 33.4 | 35.36 | 53.43 | 11.22 |
|  | 40° C. 14 days | 0 | 0.088 | 6.0 | 0.9 | 97.6 | 1.5 | 33.3 | 37.3 | 51.88 | 10.81 |
|  | 40° C. 28 days | 0 | 0.092 | 6.1 | 1.0 | 97.1 | 1.9 | 33.8 | 43.52 | 46.39 | 10.09 |
|  | 40° C. 2 month | 0 | 0.093 | 6.1 | 1.3 | 95.6 | 3.1 | 34.5 | 53.22 | 37.88 | 8.9 |
| F2 | t = 0 | 0 | 0.089 | 6.1 | 0.9 | 98.2 | 0.9 | 34.6 | 33.56 | 54.22 | 12.21 |
|  | VTX 120 minutes | 0 | 0.091 | 6.1 | 0.9 | 98.2 | 0.9 | 34.3 | 33.46 | 54.33 | 12.21 |
|  | F/T 8 cycles | 0 | 0.089 | 6.0 | 0.9 | 98.2 | 0.9 | 33.6 | 33.49 | 54.43 | 12.08 |
|  | 40° C. 8 days | 0 | 0.089 | 6.1 | 0.8 | 98.0 | 1.2 | 33.7 | 35.19 | 53.66 | 11.16 |
|  | 40° C. 14 days | 0 | 0.090 | 6.0 | 0.8 | 97.7 | 1.5 | 33.7 | 37.14 | 52.06 | 10.8 |
|  | 40° C. 28 days | 0 | 0.091 | 6.1 | 0.9 | 97.1 | 1.9 | 33.7 | 43.38 | 46.39 | 10.23 |
|  | 40° C. 2 month | 0 | 0.094 | 6.0 | 1.2 | 95.7 | 3.1 | 34.6 | 52.95 | 38.02 | 9.03 |
| F3 | t = 0 | 0 | 0.087 | 6.1 | 0.9 | 98.2 | 0.9 | 33.9 | 33.46 | 54.56 | 11.97 |
|  | VTX 120 minutes | 0 | 0.086 | 6.1 | 1.0 | 98.1 | 0.9 | 33.8 | 33.38 | 54.63 | 12 |
|  | F/T 8 cycles | 0 | 0.091 | 6.0 | 0.9 | 98.2 | 0.9 | 33.0 | 33.41 | 54.5 | 12.08 |
|  | 40° C. 8 days | 0 | 0.087 | 6.1 | 0.8 | 98.0 | 1.2 | 32.9 | 35.15 | 53.59 | 11.27 |
|  | 40° C. 14 days | 0 | 0.087 | 6.0 | 0.8 | 97.8 | 1.4 | 32.7 | 37.07 | 52.09 | 10.84 |
|  | 40° C. 28 days | 0 | 0.089 | 6.1 | 0.9 | 97.2 | 1.9 | 33.1 | 43.25 | 46.52 | 10.22 |
|  | 40° C. 2 month | 0 | 0.092 | 6.1 | 1.2 | 95.8 | 3.1 | 34.0 | 52.67 | 38.19 | 9.14 |
| F4 | t = 0 | 0 | 0.088 | 6.1 | 0.9 | 98.2 | 0.9 | 33.6 | 33.57 | 54.61 | 11.82 |
|  | VTX 120 minutes | 0 | 0.089 | 6.1 | 0.9 | 98.2 | 1.0 | 33.4 | 33.45 | 54.55 | 12.01 |
|  | F/T 8 cycles | 0 | 0.089 | 6.0 | 0.9 | 98.2 | 0.9 | 32.9 | 33.43 | 54.4 | 12.18 |
|  | 40° C. 8 days | 0 | 0.089 | 6.1 | 0.8 | 98.0 | 1.2 | 32.6 | 35.29 | 53.64 | 11.06 |
|  | 40° C. 14 days | 0 | 0.088 | 6.1 | 0.8 | 97.7 | 1.5 | 32.6 | 37.35 | 52.02 | 10.63 |
|  | 40° C. 28 days | 0 | 0.090 | 6.1 | 0.9 | 97.1 | 1.9 | 33.1 | 43.71 | 46.4 | 9.88 |
|  | 40° C. 2 month | 0 | 0.094 | 6.1 | 1.2 | 95.7 | 3.1 | 34.4 | 53.4 | 37.85 | 8.76 |
| F5 | t = 0 | 0 | 0.098 | 6.1 | 0.9 | 98.2 | 0.9 | 33.3 | 33.23 | 54.61 | 12.16 |
|  | VTX 120 minutes | 0 | 0.098 | 6.1 | 0.9 | 98.2 | 0.9 | 33.4 | 33.01 | 54.87 | 12.13 |
|  | F/T 8 cycles | 0 | 0.099 | 6.1 | 0.9 | 98.2 | 0.9 | 33.0 | 33.12 | 54.53 | 12.36 |
|  | 40° C. 8 days | 0 | 0.098 | 6.1 | 0.8 | 98.0 | 1.2 | 32.9 | 33.5 | 54.31 | 12.21 |
|  | 40° C. 14 days | 0 | 0.098 | 6.1 | 0.9 | 97.6 | 1.5 | 33.0 | 34.66 | 53.21 | 12.13 |
|  | 40° C. 28 days | 0 | 0.100 | 6.1 | 1.2 | 96.9 | 2.0 | 33.1 | 40.01 | 48.03 | 11.95 |
|  | 40° C. 2 month | 0 | 0.101 | 6.1 | 1.8 | 95.1 | 3.1 | 34.2 | 48.34 | 41.07 | 10.59 |
| F6 | t = 0 | 0 | 0.098 | 6.1 | 0.9 | 98.2 | 0.9 | 32.6 | 33.21 | 54.7 | 12.08 |
|  | VTX 120 minutes | 0 | 0.098 | 6.1 | 0.8 | 98.2 | 0.9 | 32.5 | 33.15 | 54.67 | 12.18 |
|  | F/T 8 cycles | 0 | 0.100 | 6.1 | 0.9 | 98.2 | 0.9 | 32.0 | 33.23 | 54.5 | 12.27 |
|  | 40° C. 8 days | 0 | 0.099 | 6.1 | 0.9 | 97.9 | 1.2 | 31.8 | 33.61 | 54.42 | 11.97 |
|  | 40° C. 14 days | 0 | 0.097 | 6.1 | 1.0 | 97.6 | 1.5 | 32.0 | 34.91 | 53.31 | 11.77 |
|  | 40° C. 28 days | 0 | 0.099 | 6.1 | 1.3 | 96.8 | 2.0 | 32.1 | 40.39 | 48.17 | 11.45 |
|  | 40° C. 2 month | 0 | 0.100 | 6.1 | 2.0 | 95.0 | 3.1 | 33.1 | 48.96 | 41.05 | 9.99 |
| F7 | t = 0 | 0 | 0.099 | 6.1 | 0.9 | 98.1 | 1.0 | 33.1 | 33.3 | 54.63 | 12.07 |
|  | VTX 120 minutes | 0 | 0.102 | 6.1 | 0.9 | 98.2 | 1.0 | 33.3 | 33.13 | 54.53 | 12.33 |
|  | F/T 8 cycles | 0 | 0.100 | 6.1 | 0.9 | 98.2 | 1.0 | 33.0 | 33.27 | 54.49 | 12.23 |
|  | 40° C. 8 days | 0 | 0.099 | 6.1 | 0.9 | 97.9 | 1.3 | 33.1 | 33.64 | 54.23 | 12.13 |
|  | 40° C. 14 days | 0 | 0.098 | 6.1 | 0.9 | 97.6 | 1.5 | 32.7 | 35.05 | 52.89 | 12.06 |
|  | 40° C. 28 days | 0 | 0.100 | 6.1 | 1.2 | 96.9 | 1.9 | 32.9 | 40.34 | 48.1 | 11.57 |
|  | 40° C. 2 month | 0 | 0.103 | 6.1 | 1.8 | 95.1 | 3.1 | 33.9 | 48.94 | 40.76 | 10.29 |
| F8 | t = 0 | 0 | 0.097 | 6.1 | 0.9 | 98.2 | 0.9 | 34.4 | 33.36 | 54.61 | 12.03 |
|  | VTX 120 minutes | 0 | 0.101 | 6.1 | 1.0 | 98.1 | 0.9 | 34.0 | 33.09 | 54.58 | 12.34 |
|  | F/T 8 cycles | 0 | 0.098 | 6.1 | 0.9 | 98.2 | 0.9 | 33.5 | 33.21 | 54.47 | 12.33 |
|  | 40° C. 8 days | 0 | 0.097 | 6.1 | 0.8 | 98.0 | 1.3 | 33.5 | 33.52 | 54.38 | 12.1 |
|  | 40° C. 14 days | 0 | 0.098 | 6.1 | 0.8 | 97.8 | 1.5 | 33.3 | 34.92 | 53.05 | 12.05 |
|  | 40° C. 28 days | 0 | 0.100 | 6.1 | 0.9 | 97.2 | 2.0 | 33.4 | 40.11 | 48.22 | 11.67 |
|  | 40° C. 2 month | 0 | 0.102 | 6.1 | 1.2 | 95.8 | 3.1 | 34.5 | 48.51 | 41.2 | 10.29 |
| F9 | t = 0 | 0 | 0.089 | 6.1 | 0.9 | 98.2 | 0.9 | 34.6 | 33.6 | 54.38 | 12.01 |
|  | VTX 120 minutes | 0 | 0.091 | 6.1 | 0.9 | 98.2 | 1.0 | 34.8 | 33.61 | 54.3 | 12.1 |
|  | F/T 8 cycles | 0 | 0.090 | 6.0 | 0.9 | 98.2 | 0.9 | 34.1 | 33.64 | 54.07 | 12.29 |
|  | 40° C. 8 days | 0 | 0.090 | 6.1 | 0.7 | 98.1 | 1.2 | 34.0 | 35.24 | 53.74 | 11.02 |
|  | 40° C. 14 days | 0 | 0.091 | 6.1 | 0.7 | 97.8 | 1.4 | 33.6 | 37.17 | 52.17 | 10.67 |
|  | 40° C. 28 days | 0 | 0.091 | 6.1 | 0.8 | 97.3 | 1.9 | 34.0 | 43.32 | 46.82 | 9.85 |
|  | 40° C. 2 month | 0 | 0.096 | 6.1 | 1.0 | 95.9 | 3.1 | 35.2 | 52.79 | 38.64 | 8.57 |
| F10 | t = 0 | 0 | 0.088 | 6.1 | 0.9 | 98.2 | 0.9 | 33.1 | 33.47 | 54.48 | 12.05 |
|  | VTX 120 minutes | 0 | 0.092 | 6.1 | 0.9 | 98.2 | 0.9 | 33.3 | 33.47 | 54.22 | 12.31 |
|  | F/T 8 cycles | 0 | 0.090 | 6.1 | 0.9 | 98.2 | 0.9 | 32.9 | 33.64 | 54.22 | 12.14 |
|  | 40° C. 8 days | 0 | 0.090 | 6.1 | 0.8 | 98.0 | 1.2 | 33.1 | 35.4 | 53.71 | 10.89 |
|  | 40° C. 14 days | 0 | 0.090 | 6.1 | 0.8 | 97.8 | 1.4 | 32.4 | 37.37 | 52.15 | 10.47 |
|  | 40° C. 28 days | 0 | 0.090 | 6.1 | 0.9 | 97.1 | 2.0 | 32.9 | 43.57 | 46.76 | 9.65 |
|  | 40° C. 2 month | 0 | 0.093 | 6.1 | 1.2 | 95.7 | 3.1 | 34.2 | 53.03 | 38.64 | 8.33 |
| F11 | t = 0 | 0 | 0.087 | 6.1 | 0.9 | 98.2 | 0.9 | 33.3 | 33.51 | 54.53 | 11.98 |
|  | VTX 120 minutes | 0 | 0.088 | 6.1 | 0.9 | 98.2 | 0.9 | 33.6 | 33.48 | 54.66 | 11.87 |
|  | F/T 8 cycles | 0 | 0.088 | 6.1 | 0.9 | 98.2 | 0.9 | 32.7 | 33.75 | 54.16 | 12.08 |
|  | 40° C. 8 days | 0 | 0.088 | 6.1 | 0.7 | 98.1 | 1.2 | 32.4 | 35.31 | 53.79 | 10.9 |
|  | 40° C. 14 days | 0 | 0.090 | 6.1 | 0.7 | 97.9 | 1.4 | 32.6 | 37.4 | 52.26 | 10.34 |

TABLE 27-continued

Effect of Excipients on the Stability of 33 mg/mL H1H17203P Antibody Incubated at
40° C. for up to Two Months - Visual, OD, pH, SE-UPLC, RP-UPLC Concentration, CEX-UPLC

| Formulation | Sample | Visual | OD @ 405 nm | pH | % HMW | % Native | % LMW | Con, mg/ml | % Acidic | % Main | % Basic |
|---|---|---|---|---|---|---|---|---|---|---|---|
|  | 40° C. 28 days | 0 | 0.090 | 6.1 | 0.8 | 97.3 | 2.0 | 32.6 | 43.56 | 46.89 | 9.56 |
|  | 40° C. 2 month | 0 | 0.094 | 6.1 | 0.9 | 96.0 | 3.1 | 34.0 | 53.08 | 38.74 | 8.16 |
| F12 | t = 0 | 1 | 0.087 | 6.1 | 0.9 | 98.2 | 1.0 | 33.5 | 33.48 | 54.38 | 12.14 |
|  | VTX 120 minutes | 1 | 0.088 | 6.1 | 0.9 | 98.2 | 0.9 | 33.6 | 33.49 | 54.56 | 11.95 |
|  | F/T 8 cycles | 0 | 0.089 | 6.0 | 0.9 | 98.2 | 0.9 | 32.8 | 33.72 | 54.22 | 12.06 |
|  | 40° C. 8 days | 0 | 0.089 | 6.1 | 0.7 | 98.1 | 1.2 | 32.5 | 35.29 | 53.69 | 11.02 |
|  | 40° C. 14 days | 0 | 0.090 | 6.1 | 0.7 | 97.9 | 1.4 | 32.7 | 37.14 | 52.24 | 10.62 |
|  | 40° C. 28 days | 0 | 0.091 | 6.1 | 0.8 | 97.3 | 1.9 | 32.9 | 43.38 | 46.9 | 9.73 |
|  | 40° C. 2 month | 0 | 0.095 | 6.1 | 0.9 | 96.0 | 3.1 | 34.1 | 52.74 | 38.78 | 8.47 |

TABLE 28

Effect of Excipients on the Stability of 33 mg/mL H1H17139P Antibody Incubated at
40° C. for up to Two Months - Visual, OD, pH, SE-UPLC, RP-UPLC Concentration, CEX-UPLC

| Formulation | Sample | Visual | OD @ 405 nm | pH | % HMW | % Native | % LMW | Con, mg/ml | % Acidic | % Main | % Basic |
|---|---|---|---|---|---|---|---|---|---|---|---|
| F1 | t = 0 | 0 | 0.084 | 6.1 | 0.7 | 98.2 | 1.1 | 31.1 | 36.5 | 60.0 | 3.6 |
|  | VTX 120 minutes | 0 | 0.082 | 6.1 | 0.7 | 98.2 | 1.1 | 31.5 | 36.4 | 59.9 | 3.7 |
|  | F/T 8 cycles | 0 | 0.083 | 6.0 | 0.7 | 98.1 | 1.1 | 31.1 | 36.7 | 59.6 | 3.7 |
|  | 40° C. 8 days | 0 | 0.083 | 6.1 | 0.6 | 97.9 | 1.4 | 31.3 | 38.4 | 57.2 | 4.3 |
|  | 40° C. 14 days | 0 | 0.083 | 6.1 | 0.7 | 97.7 | 1.6 | 31.6 | 39.6 | 56.2 | 4.2 |
|  | 40° C. 28 days | 0 | 0.083 | 6.2 | 0.7 | 97.2 | 2.1 | 31.9 | 43.9 | 51.8 | 4.3 |
|  | 40° C. 2 month | 0 | 0.089 | 6.1 | 0.9 | 95.8 | 3.3 | 31.8 | 52.4 | 43.9 | 3.8 |
| F2 | t = 0 | 0 | 0.086 | 6.1 | 0.7 | 98.2 | 1.2 | 32.5 | 36.5 | 60.0 | 3.5 |
|  | VTX 120 minutes | 0 | 0.085 | 6.1 | 0.7 | 98.2 | 1.1 | 32.5 | 36.5 | 59.8 | 3.7 |
|  | F/T 8 cycles | 0 | 0.085 | 6.0 | 0.7 | 98.2 | 1.1 | 32.4 | 36.8 | 59.5 | 3.7 |
|  | 40° C. 8 days | 0 | 0.086 | 6.1 | 0.6 | 98.0 | 1.4 | 32.3 | 38.5 | 57.2 | 4.3 |
|  | 40° C. 14 days | 0 | 0.086 | 6.0 | 0.6 | 97.8 | 1.6 | 32.4 | 39.5 | 56.3 | 4.2 |
|  | 40° C. 28 days | 0 | 0.086 | 6.1 | 0.6 | 97.2 | 2.2 | 32.7 | 43.8 | 51.9 | 4.3 |
|  | 40° C. 2 month | 0 | 0.092 | 6.0 | 0.7 | 96.0 | 3.3 | 32.9 | 52.3 | 44.0 | 3.7 |
| F3 | t = 0 | 0 | 0.085 | 6.1 | 0.7 | 98.1 | 1.1 | 32.4 | 36.4 | 60.0 | 3.6 |
|  | VTX 120 minutes | 0 | 0.086 | 6.1 | 0.7 | 98.2 | 1.1 | 32.7 | 36.4 | 59.9 | 3.7 |
|  | F/T 8 cycles | 0 | 0.084 | 6.0 | 0.7 | 98.1 | 1.1 | 32.3 | 36.8 | 59.5 | 3.8 |
|  | 40° C. 8 days | 0 | 0.083 | 6.1 | 0.6 | 98.0 | 1.4 | 32.3 | 38.4 | 57.3 | 4.3 |
|  | 40° C. 14 days | 0 | 0.084 | 6.0 | 0.6 | 97.7 | 1.6 | 32.2 | 39.3 | 56.4 | 4.2 |
|  | 40° C. 28 days | 0 | 0.084 | 6.1 | 0.7 | 97.2 | 2.1 | 32.9 | 43.6 | 52.1 | 4.3 |
|  | 40° C. 2 month | 0 | 0.090 | 6.0 | 0.8 | 95.9 | 3.3 | 32.8 | 52.4 | 43.7 | 4.0 |
| F4 | t = 0 | 0 | 0.086 | 6.1 | 0.7 | 98.2 | 1.1 | 32.7 | 36.5 | 60.0 | 3.6 |
|  | VTX 120 minutes | 1 | 0.087 | 6.1 | 0.7 | 98.2 | 1.1 | 32.9 | 36.5 | 59.9 | 3.7 |
|  | F/T 8 cycles | 0 | 0.088 | 6.0 | 0.7 | 98.2 | 1.1 | 32.8 | 36.8 | 59.4 | 3.8 |
|  | 40° C. 8 days | 0 | 0.088 | 6.1 | 0.6 | 98.0 | 1.4 | 32.4 | 38.5 | 57.3 | 4.2 |
|  | 40° C. 14 days | 0 | 0.087 | 6.1 | 0.6 | 97.8 | 1.6 | 32.9 | 39.6 | 56.3 | 4.2 |
|  | 40° C. 28 days | 0 | 0.087 | 6.1 | 0.7 | 97.2 | 2.1 | 33.2 | 43.9 | 52.0 | 4.2 |
|  | 40° C. 2 month | 0 | 0.092 | 6.1 | 0.8 | 96.0 | 3.3 | 33.4 | 52.8 | 43.4 | 3.8 |
| F5 | t = 0 | 0 | 0.094 | 6.1 | 0.7 | 98.2 | 1.2 | 32.2 | 36.1 | 60.2 | 3.7 |
|  | VTX 120 minutes | 0 | 0.094 | 6.1 | 0.7 | 98.2 | 1.2 | 32.3 | 36.1 | 60.1 | 3.8 |
|  | F/T 8 cycles | 0 | 0.094 | 6.1 | 0.7 | 98.2 | 1.1 | 32.0 | 36.4 | 59.7 | 3.9 |
|  | 40° C. 8 days | 0 | 0.094 | 6.1 | 0.6 | 98.0 | 1.5 | 31.9 | 37.2 | 58.1 | 4.8 |
|  | 40° C. 14 days | 0 | 0.092 | 6.1 | 0.6 | 97.8 | 1.7 | 32.2 | 37.8 | 57.5 | 4.7 |
|  | 40° C. 28 days | 0 | 0.093 | 6.1 | 0.7 | 97.2 | 2.2 | 32.5 | 41.4 | 53.5 | 5.1 |
|  | 40° C. 2 month | 0 | 0.095 | 6.1 | 0.8 | 95.9 | 3.3 | 33.0 | 48.6 | 46.3 | 5.1 |
| F6 | t = 0 | 0 | 0.095 | 6.1 | 0.7 | 98.2 | 1.2 | 31.6 | 36.1 | 60.3 | 3.7 |
|  | VTX 120 minutes | 0 | 0.094 | 6.1 | 0.7 | 98.2 | 1.2 | 31.9 | 36.2 | 60.0 | 3.8 |
|  | F/T 8 cycles | 0 | 0.096 | 6.1 | 0.7 | 98.2 | 1.2 | 31.5 | 36.3 | 59.8 | 3.9 |
|  | 40° C. 8 days | 0 | 0.096 | 6.1 | 0.6 | 98.0 | 1.5 | 31.6 | 37.3 | 58.1 | 4.6 |
|  | 40° C. 14 days | 0 | 0.095 | 6.1 | 0.6 | 97.8 | 1.7 | 31.8 | 38.2 | 57.3 | 4.5 |
|  | 40° C. 28 days | 0 | 0.093 | 6.1 | 0.6 | 97.2 | 2.2 | 32.0 | 41.7 | 53.4 | 4.9 |
|  | 40° C. 2 month | 0 | 0.097 | 6.1 | 0.7 | 96.0 | 3.3 | 32.6 | 49.4 | 46.0 | 4.7 |
| F7 | t = 0 | 0 | 0.095 | 6.1 | 0.7 | 98.1 | 1.2 | 32.1 | 36.1 | 60.3 | 3.7 |
|  | VTX 120 minutes | 0 | 0.096 | 6.1 | 0.7 | 98.1 | 1.2 | 32.5 | 36.1 | 60.1 | 3.8 |
|  | F/T 8 cycles | 0 | 0.097 | 6.1 | 0.7 | 98.1 | 1.2 | 32.0 | 36.4 | 59.7 | 3.9 |
|  | 40° C. 8 days | 0 | 0.098 | 6.1 | 0.6 | 98.0 | 1.5 | 32.5 | 37.3 | 58.0 | 4.7 |
|  | 40° C. 14 days | 0 | 0.095 | 6.1 | 0.6 | 97.7 | 1.6 | 32.3 | 37.9 | 57.4 | 4.7 |
|  | 40° C. 28 days | 0 | 0.096 | 6.1 | 0.7 | 97.2 | 2.1 | 32.6 | 41.6 | 53.4 | 5.0 |
|  | 40° C. 2 month | 0 | 0.096 | 6.1 | 0.8 | 95.8 | 3.4 | 33.1 | 49.1 | 46.1 | 4.9 |

TABLE 28-continued

Effect of Excipients on the Stability of 33 mg/mL H1H17139P Antibody Incubated at 40° C. for up to Two Months - Visual, OD, pH, SE-UPLC, RP-UPLC Concentration, CEX-UPLC

| Formulation | Sample | Visual | OD @ 405 nm | pH | % HMW | % Native | % LMW | Con, mg/ml | % Acidic | % Main | % Basic |
|---|---|---|---|---|---|---|---|---|---|---|---|
| F8 | t = 0 | 0 | 0.093 | 6.1 | 0.7 | 98.2 | 1.1 | 32.7 | 36.1 | 60.2 | 3.6 |
|  | VTX 120 minutes | 0 | 0.100 | 6.1 | 0.7 | 98.2 | 1.2 | 32.6 | 36.1 | 60.2 | 3.7 |
|  | F/T 8 cycles | 0 | 0.097 | 6.1 | 0.7 | 98.2 | 1.2 | 32.6 | 36.4 | 59.7 | 3.9 |
|  | 40° C. 8 days | 0 | 0.098 | 6.1 | 0.6 | 98.0 | 1.5 | 32.6 | 37.2 | 58.2 | 4.7 |
|  | 40° C. 14 days | 0 | 0.095 | 6.1 | 0.6 | 97.8 | 1.7 | 32.9 | 38.1 | 57.3 | 4.6 |
|  | 40° C. 28 days | 0 | 0.101 | 6.1 | 0.6 | 97.3 | 2.1 | 33.0 | 41.4 | 53.6 | 5.0 |
|  | 40° C. 2 month | 0 | 0.096 | 6.1 | 0.6 | 96.1 | 3.3 | 33.4 | 48.9 | 46.2 | 4.9 |
| F9 | t = 0 | 0 | 0.086 | 6.1 | 0.7 | 98.1 | 1.2 | 32.9 | 36.5 | 59.9 | 3.6 |
|  | VTX 120 minutes | 0 | 0.087 | 6.1 | 0.7 | 98.2 | 1.2 | 32.8 | 36.6 | 59.7 | 3.7 |
|  | F/T 8 cycles | 0 | 0.087 | 6.1 | 0.7 | 98.2 | 1.1 | 32.7 | 36.8 | 59.4 | 3.8 |
|  | 40° C. 8 days | 0 | 0.090 | 6.1 | 0.5 | 98.0 | 1.5 | 32.6 | 38.4 | 57.2 | 4.3 |
|  | 40° C. 14 days | 0 | 0.088 | 6.1 | 0.6 | 97.9 | 1.6 | 33.1 | 39.6 | 56.3 | 4.2 |
|  | 40° C. 28 days | 0 | 0.090 | 6.1 | 0.6 | 97.3 | 2.1 | 33.2 | 43.9 | 51.8 | 4.4 |
|  | 40° C. 2 month | 0 | 0.092 | 6.1 | 0.7 | 96.1 | 3.2 | 33.6 | 52.1 | 43.9 | 3.9 |
| F10 | t = 0 | 1 | 0.087 | 6.1 | 0.7 | 98.2 | 1.1 | 33.0 | 36.5 | 59.9 | 3.6 |
|  | VTX 120 minutes | 0 | 0.089 | 6.1 | 0.7 | 98.2 | 1.1 | 33.5 | 36.6 | 59.7 | 3.7 |
|  | F/T 8 cycles | 0 | 0.088 | 6.1 | 0.7 | 98.2 | 1.1 | 33.1 | 36.8 | 59.4 | 3.8 |
|  | 40° C. 8 days | 0 | 0.090 | 6.1 | 0.6 | 98.0 | 1.4 | 33.0 | 38.1 | 58.0 | 4.0 |
|  | 40° C. 14 days | 0 | 0.088 | 6.1 | 0.6 | 97.8 | 1.6 | 33.1 | 39.7 | 56.1 | 4.2 |
|  | 40° C. 28 days | 0 | 0.090 | 6.1 | 0.6 | 97.3 | 2.1 | 33.6 | 44.1 | 51.7 | 4.2 |
|  | 40° C. 2 month | 0 | 0.093 | 6.1 | 0.7 | 96.0 | 3.3 | 34.2 | 52.6 | 43.7 | 3.8 |
| F11 | t = 0 | 0 | 0.084 | 6.1 | 0.7 | 98.2 | 1.1 | 31.8 | 36.6 | 59.8 | 3.6 |
|  | VTX 120 minutes | 0 | 0.085 | 6.1 | 0.7 | 98.2 | 1.1 | 32.2 | 36.6 | 59.7 | 3.7 |
|  | F/T 8 cycles | 0 | 0.085 | 6.1 | 0.7 | 98.2 | 1.1 | 31.9 | 36.9 | 59.3 | 3.8 |
|  | 40° C. 8 days | 0 | 0.088 | 6.1 | 0.5 | 98.1 | 1.4 | 31.6 | 38.2 | 57.8 | 4.0 |
|  | 40° C. 14 days | 0 | 0.085 | 6.1 | 0.5 | 97.9 | 1.6 | 32.0 | 39.6 | 56.3 | 4.1 |
|  | 40° C. 28 days | 0 | 0.088 | 6.1 | 0.6 | 97.3 | 2.1 | 32.3 | 44.1 | 51.8 | 4.1 |
|  | 40° C. 2 month | 0 | 0.093 | 6.1 | 0.6 | 96.1 | 3.3 | 32.7 | 52.5 | 43.8 | 3.7 |
| F12 | t = 0 | 0 | 0.086 | 6.1 | 0.7 | 98.2 | 1.2 | 33.1 | 36.6 | 59.7 | 3.6 |
|  | VTX 120 minutes | 0 | 0.086 | 6.1 | 0.7 | 98.2 | 1.1 | 33.4 | 36.7 | 59.6 | 3.7 |
|  | F/T 8 cycles | 0 | 0.089 | 6.1 | 0.7 | 98.2 | 1.2 | 33.0 | 37.0 | 59.2 | 3.8 |
|  | 40° C. 8 days | 0 | 0.089 | 6.1 | 0.5 | 98.1 | 1.4 | 32.8 | 38.1 | 57.9 | 4.1 |
|  | 40° C. 14 days | 0 | 0.086 | 6.1 | 0.5 | 97.9 | 1.6 | 33.0 | 39.7 | 56.2 | 4.2 |
|  | 40° C. 28 days | 0 | 0.900 | 6.1 | 0.6 | 97.3 | 2.1 | 33.3 | 43.9 | 51.9 | 4.2 |
|  | 40° C. 2 month | 0 | 0.095 | 6.1 | 0.6 | 96.1 | 3.3 | 33.8 | 52.3 | 44.0 | 3.7 |

TABLE 29

Effect of Excipients on the Stability of 33 mg/mL H1H17161P Antibody Incubated at 40° C. for up to Two Months - Visual, OD, pH, SE-UPLC, RP-UPLC Concentration, CEX-UPLC

| Formulation | Sample | Visual | OD @ 405 nm | pH | % HMW | % Native | % LMW | Con, mg/ml | % Acidic | % Main | % Basic |
|---|---|---|---|---|---|---|---|---|---|---|---|
| F1 | t = 0 | 0 | 0.109 | 6.1 | 1.6 | 97.2 | 1.2 | 34 | 53.5 | 42.6 | 4.0 |
|  | VTX 120 minutes | 0 | 0.109 | 6.1 | 1.6 | 97.2 | 1.2 | 34 | 54.1 | 42.2 | 3.7 |
|  | F/T 8 cycles | 0 | 0.108 | 6.0 | 1.7 | 97.2 | 1.2 | 34 | 54.3 | 42.2 | 3.5 |
|  | 40° C. 8 days | 0 | 0.105 | 6.0 | 1.4 | 97.1 | 1.5 | 34 | 57.4 | 38.8 | 3.9 |
|  | 40° C. 14 days | 0 | 0.107 | 6.0 | 1.4 | 96.9 | 1.7 | 34 | 59.6 | 36.4 | 3.9 |
|  | 40° C. 28 days | 0 | 0.109 | 6.1 | 1.6 | 96.1 | 2.3 | 34 | 63.5 | 31.2 | 5.3 |
|  | 40° C. 2 month | 0 | 0.112 | 6.2 | 1.7 | 95.0 | 3.3 | 33 | 74.3 | 22.4 | 3.3 |
| F2 | t = 0 | 0 | 0.111 | 6.1 | 1.6 | 97.2 | 1.2 | 33 | 53.1 | 43.0 | 4.0 |
|  | VTX 120 minutes | 0 | 0.100 | 6.1 | 1.6 | 97.2 | 1.3 | 33 | 53.7 | 42.8 | 3.5 |
|  | F/T 8 cycles | 0 | 0.112 | 6.0 | 1.6 | 97.2 | 1.2 | 34 | 53.5 | 42.9 | 3.6 |
|  | 40° C. 8 days | 0 | 0.106 | 6.0 | 1.3 | 97.2 | 1.5 | 34 | 55.5 | 40.5 | 4.0 |
|  | 40° C. 14 days | 0 | 0.110 | 6.0 | 1.3 | 97.0 | 1.7 | 34 | 57.5 | 38.4 | 4.1 |
|  | 40° C. 28 days | 0 | 0.110 | 6.1 | 1.4 | 96.3 | 2.3 | 34 | 59.9 | 34.7 | 5.5 |
|  | 40° C. 2 month | 0 | 0.114 | 6.1 | 1.5 | 95.2 | 3.3 | 33 | 69.7 | 26.5 | 3.8 |
| F3 | t = 0 | 0 | 0.110 | 6.1 | 1.6 | 97.2 | 1.2 | 34 | 53.5 | 42.7 | 3.9 |
|  | VTX 120 minutes | 0 | 0.109 | 6.1 | 1.8 | 96.9 | 1.3 | 33 | 54.0 | 42.3 | 3.7 |
|  | F/T 8 cycles | 0 | 0.109 | 6.0 | 1.6 | 97.1 | 1.2 | 34 | 54.3 | 42.3 | 3.4 |
|  | 40° C. 8 days | 0 | 0.105 | 6.0 | 1.3 | 97.1 | 1.5 | 34 | 57.2 | 39.0 | 3.8 |
|  | 40° C. 14 days | 0 | 0.107 | 6.0 | 1.4 | 96.9 | 1.7 | 34 | 59.8 | 36.2 | 4.1 |
|  | 40° C. 28 days | 0 | 0.109 | 6.1 | 1.5 | 96.2 | 2.3 | 34 | 63.2 | 31.7 | 5.2 |
|  | 40° C. 2 month | 0 | 0.111 | 6.1 | 1.6 | 95.1 | 3.3 | 33 | 74.0 | 22.9 | 3.1 |
| F4 | t = 0 | 0 | 0.110 | 6.1 | 1.6 | 97.2 | 1.3 | 34 | 53.3 | 43.3 | 3.4 |
|  | VTX 120 minutes | 0 | 0.109 | 6.1 | 1.6 | 97.1 | 1.3 | 34 | 53.5 | 42.9 | 3.7 |
|  | F/T 8 cycles | 0 | 0.113 | 6.1 | 1.6 | 97.2 | 1.2 | 34 | 53.9 | 42.5 | 3.6 |
|  | 40° C. 8 days | 0 | 0.106 | 6.0 | 1.3 | 97.2 | 1.5 | 34 | 55.5 | 40.6 | 3.9 |
|  | 40° C. 14 days | 0 | 0.113 | 6.0 | 1.4 | 96.9 | 1.7 | 34 | 57.8 | 38.2 | 4.0 |
|  | 40° C. 28 days | 0 | 0.110 | 6.1 | 1.4 | 96.3 | 2.3 | 34 | 60.0 | 34.8 | 5.3 |
|  | 40° C. 2 month | 0 | 0.114 | 6.1 | 1.6 | 95.1 | 3.4 | 33 | 70.2 | 26.4 | 3.4 |

TABLE 29-continued

Effect of Excipients on the Stability of 33 mg/mL H1H17161P Antibody Incubated at
40° C. for up to Two Months - Visual, OD, pH, SE-UPLC, RP-UPLC Concentration, CEX-UPLC

| Formulation | Sample | Visual | OD @ 405 nm | pH | % HMW | % Native | % LMW | Con, mg/ml | % Acidic | % Main | % Basic |
|---|---|---|---|---|---|---|---|---|---|---|---|
| F5 | t = 0 | 0 | 0.121 | 6.1 | 1.6 | 97.2 | 1.2 | 33 | 53.6 | 43.0 | 3.5 |
| | VTX 120 minutes | 0 | 0.122 | 6.1 | 1.6 | 97.1 | 1.3 | 34 | 53.9 | 42.4 | 3.7 |
| | F/T 8 cycles | 0 | 0.124 | 6.1 | 1.6 | 97.2 | 1.2 | 34 | 54.3 | 41.9 | 3.8 |
| | 40° C. 8 days | 0 | 0.114 | 6.1 | 1.4 | 97.1 | 1.6 | 34 | 56.0 | 39.8 | 4.2 |
| | 40° C. 14 days | 0 | 0.118 | 6.1 | 1.5 | 96.8 | 1.8 | 34 | 59.0 | 36.6 | 4.5 |
| | 40° C. 28 days | 0 | 0.116 | 6.2 | 1.5 | 96.1 | 2.4 | 34 | 61.9 | 32.5 | 5.6 |
| | 40° C. 2 month | 0 | 0.117 | 6.1 | 1.7 | 95.0 | 3.4 | 33 | 72.6 | 23.9 | 3.5 |
| F6 | t = 0 | 0 | 0.121 | 6.1 | 1.6 | 97.2 | 1.2 | 33 | 53.0 | 43.1 | 3.8 |
| | VTX 120 minutes | 0 | 0.121 | 6.1 | 1.6 | 97.1 | 1.3 | 33 | 53.1 | 43.1 | 3.8 |
| | F/T 8 cycles | 0 | 0.123 | 6.1 | 1.6 | 97.2 | 1.2 | 33 | 53.3 | 42.8 | 3.9 |
| | 40° C. 8 days | 0 | 0.117 | 6.1 | 1.4 | 97.1 | 1.6 | 34 | 53.8 | 41.9 | 4.3 |
| | 40° C. 14 days | 0 | 0.121 | 6.1 | 1.4 | 96.8 | 1.8 | 33 | 56.2 | 39.2 | 4.6 |
| | 40° C. 28 days | 0 | 0.118 | 6.2 | 1.5 | 96.1 | 2.4 | 33 | 57.1 | 36.8 | 6.1 |
| | 40° C. 2 month | 0 | 0.119 | 6.1 | 1.6 | 95.0 | 3.4 | 33 | 66.1 | 30.0 | 3.9 |
| F7 | t = 0 | 0 | 0.121 | 6.1 | 1.6 | 97.1 | 1.3 | 34 | 53.7 | 42.6 | 3.7 |
| | VTX 120 minutes | 0 | 0.122 | 6.1 | 1.6 | 97.0 | 1.4 | 34 | 53.9 | 42.3 | 3.9 |
| | F/T 8 cycles | 0 | 0.123 | 6.1 | 1.6 | 97.2 | 1.2 | 34 | 54.1 | 42.2 | 3.7 |
| | 40° C. 8 days | 0 | 0.115 | 6.1 | 1.5 | 97.0 | 1.6 | 34 | 56.3 | 39.5 | 4.2 |
| | 40° C. 14 days | 0 | 0.120 | 6.1 | 1.5 | 96.7 | 1.8 | 34 | 59.1 | 36.4 | 4.6 |
| | 40° C. 28 days | 0 | 0.117 | 6.2 | 1.6 | 96.0 | 2.4 | 34 | 63.2 | 31.1 | 5.7 |
| | 40° C. 2 month | 0 | 0.119 | 6.1 | 1.7 | 94.9 | 3.4 | 33 | 73.7 | 22.5 | 3.9 |
| F8 | t = 0 | 0 | 0.120 | 6.1 | 1.6 | 97.2 | 1.2 | 33 | 53.3 | 43.2 | 3.5 |
| | VTX 120 minutes | 0 | 0.120 | 6.1 | 2.5 | 96.1 | 1.3 | 33 | 53.1 | 43.1 | 3.8 |
| | F/T 8 cycles | 0 | 0.121 | 6.1 | 1.6 | 97.2 | 1.2 | 34 | 52.9 | 43.1 | 4.0 |
| | 40° C. 8 days | 0 | 0.117 | 6.1 | 1.4 | 97.1 | 1.5 | 34 | 53.8 | 41.9 | 4.3 |
| | 40° C. 14 days | 0 | 0.119 | 6.1 | 1.4 | 96.8 | 1.8 | 34 | 55.8 | 39.5 | 4.7 |
| | 40° C. 28 days | 0 | 0.115 | 6.2 | 1.5 | 96.2 | 2.3 | 34 | 56.6 | 37.5 | 6.0 |
| | 40° C. 2 month | 0 | 0.117 | 6.1 | 1.5 | 95.1 | 3.4 | 33 | 65.4 | 30.4 | 4.3 |
| F9 | t = 0 | 0 | 0.112 | 6.1 | 1.6 | 97.2 | 1.3 | 33 | 53.9 | 42.5 | 3.6 |
| | VTX 120 minutes | 0 | 0.112 | 6.1 | 1.6 | 97.2 | 1.3 | 33 | 54.2 | 42.2 | 3.6 |
| | F/T 8 cycles | 0 | 0.114 | 6.1 | 1.6 | 97.2 | 1.2 | 34 | 54.4 | 42.0 | 3.6 |
| | 40° C. 8 days | 0 | 0.107 | 6.1 | 1.2 | 97.3 | 1.5 | 34 | 57.1 | 39.1 | 3.8 |
| | 40° C. 14 days | 0 | 0.114 | 6.0 | 1.3 | 97.0 | 1.8 | 34 | 59.9 | 36.0 | 4.1 |
| | 40° C. 28 days | 0 | 0.110 | 6.2 | 1.3 | 96.4 | 2.3 | 34 | 63.0 | 31.5 | 5.6 |
| | 40° C. 2 month | 0 | 0.114 | 6.1 | 1.4 | 95.2 | 3.4 | 33 | 73.5 | 23.1 | 3.4 |
| F10 | t = 0 | 0 | 0.113 | 6.1 | 1.6 | 97.2 | 1.2 | 33 | 54.2 | 42.8 | 3.1 |
| | VTX 120 minutes | 0.112 | 0.000 | FDG | 1.6 | 97.2 | 1.2 | 33 | 54.3 | 42.3 | 3.5 |
| | F/T 8 cycles | 0.114 | 0.001 | FDG | 1.6 | 97.2 | 1.2 | 33 | 54.5 | 42.0 | 3.6 |
| | 40° C. 8 days | 0 | 0.112 | 6.1 | 1.3 | 97.2 | 1.6 | 34 | 57.1 | 39.1 | 3.7 |
| | 40° C. 14 days | 0 | 0.111 | 6.1 | 1.3 | 97.0 | 1.7 | 33 | 59.9 | 36.0 | 4.1 |
| | 40° C. 28 days | 0 | 0.111 | 6.2 | 1.4 | 96.3 | 2.4 | 34 | 62.9 | 31.7 | 5.4 |
| | 40° C. 2 month | 0 | 0.115 | 6.1 | 1.5 | 95.2 | 3.4 | 33 | 73.0 | 23.7 | 3.3 |
| F11 | t = 0 | 0 | 0.110 | 6.1 | 1.6 | 97.2 | 1.3 | 33 | 53.6 | 43.1 | 3.4 |
| | VTX 120 minutes | 0 | 0.112 | 6.1 | 1.7 | 97.1 | 1.2 | 33 | 53.6 | 42.8 | 3.6 |
| | F/T 8 cycles | 0 | 0.111 | 6.1 | 1.6 | 97.3 | 1.2 | 34 | 53.6 | 42.8 | 3.6 |
| | 40° C. 8 days | 0 | 0.107 | 6.1 | 1.2 | 97.2 | 1.5 | 34 | 55.6 | 40.6 | 3.8 |
| | 40° C. 14 days | 0 | 0.112 | 6.1 | 1.3 | 97.0 | 1.7 | 34 | 57.9 | 38.0 | 4.1 |
| | 40° C. 28 days | 0 | 0.114 | 6.1 | 1.3 | 96.4 | 2.3 | 34 | 59.7 | 34.9 | 5.4 |
| | 40° C. 2 month | 0 | 0.118 | 6.1 | 1.4 | 95.3 | 3.3 | 33 | 69.5 | 27.1 | 3.5 |
| F12 | t = 0 | 0 | 0.114 | 6.1 | 1.6 | 97.1 | 1.3 | 34 | 53.8 | 42.8 | 3.4 |
| | VTX 120 minutes | 0 | 0.114 | 6.1 | 1.5 | 97.2 | 1.3 | 34 | 53.8 | 42.6 | 3.6 |
| | F/T 8 cycles | 0 | 0.113 | 6.1 | 1.6 | 97.2 | 1.2 | 34 | 53.8 | 42.7 | 3.6 |
| | 40° C. 8 days | 0 | 0.109 | 6.1 | 1.2 | 97.3 | 1.5 | 34 | 55.5 | 40.7 | 3.8 |
| | 40° C. 14 days | 0 | 0.113 | 6.0 | 1.2 | 97.0 | 1.7 | 34 | 57.9 | 37.9 | 4.2 |
| | 40° C. 28 days | 0 | 0.113 | 6.1 | 1.3 | 96.4 | 2.4 | 34 | 60.0 | 34.4 | 5.7 |
| | 40° C. 2 month | 0 | 0.120 | 6.1 | 1.4 | 95.3 | 3.3 | 33 | 69.4 | 26.8 | 3.8 |

TABLE 30

Effect of Excipients on the Stability of 100 mg/mL H1H17203P, H1H17139P, and
H1H17161P Antibodies (ratio at 1:1:1) Incubated at 40° C. for up to Two Months -
Visual, OD, pH, SE-UPLC, RP-UPLC Concentration

| Formulation | Sample | Visual | OD @ 405 nm | ΔOD | pH | % HMW | % Native | % LMW | Con, mg/mL |
|---|---|---|---|---|---|---|---|---|---|
| F1 | t = 0 | 0 | 0.178 | 0.00 | 6.1 | 1.24 | 97.70 | 1.06 | 99 |
| | 120 minutes | 0 | 0.175 | 0.00 | 6.1 | 1.76 | 96.83 | 1.41 | 100 |
| | 8 cycles | 0 | 0.176 | 0.00 | 6.1 | 1.95 | 96.41 | 1.64 | 99 |
| | 40° C. 8 days | 0 | 0.176 | 0.00 | 6.1 | 2.29 | 95.56 | 2.16 | 98 |

TABLE 30-continued

Effect of Excipients on the Stability of 100 mg/mL H1H17203P, H1H17139P, and H1H17161P Antibodies (ratio at 1:1:1) Incubated at 40° C. for up to Two Months - Visual, OD, pH, SE-UPLC, RP-UPLC Concentration

| Formulation | Sample | Visual | OD @ 405 nm | ΔOD | pH | % HMW | % Native | % LMW | Con, mg/mL |
|---|---|---|---|---|---|---|---|---|---|
| | 40° C. 14 days | 0 | 0.179 | 0.00 | 6.1 | 2.91 | 93.82 | 3.27 | 99 |
| | 40° C. 28 days | 0 | 0.189 | 0.01 | 6.1 | 4.01 | 91.58 | 4.41 | 103 |
| | 40° C. 2 month | 0 | 0.191 | 0.01 | 6.1 | 1.32 | 97.63 | 1.04 | 98 |
| | 40° C. 3 months | 0 | 0.203 | 0.02 | 6.3 | 1.25 | 97.68 | 1.07 | 99 |
| | Light Stress Control | 0 | 0.177 | 0.00 | 6.1 | 1.43 | 97.19 | 1.39 | 98 |
| | Light Stress Mild | 0 | 0.178 | 0.00 | 6.1 | 5.56 | 93.21 | 1.24 | 99 |
| | Light Stress Extreme | 0 | 0.286 | 0.11 | 6.1 | 21.67 | 76.26 | 2.07 | 98 |
| F2 | t = 0 | 0 | 0.177 | 0.00 | 6.1 | 1.15 | 97.79 | 1.06 | 97 |
| | 120 minutes | 0 | 0.179 | 0.00 | 6.1 | 1.52 | 97.08 | 1.41 | 98 |
| | 8 cycles | 0 | 0.177 | 0.00 | 6.1 | 1.68 | 96.67 | 1.65 | 97 |
| | 40° C. 8 days | 0 | 0.175 | 0.00 | 6.1 | 1.96 | 95.88 | 2.16 | 97 |
| | 40° C. 14 days | 0 | 0.180 | 0.00 | 6.1 | 2.47 | 94.24 | 3.30 | 97 |
| | 40° C. 28 days | 0 | 0.185 | 0.01 | 6.1 | 3.33 | 92.34 | 4.33 | 102 |
| | 40° C. 2 month | 0 | 0.193 | 0.02 | 6.1 | 1.14 | 97.81 | 1.04 | 97 |
| | 40° C. 3 months | 0 | 0.203 | 0.03 | 6.2 | 1.17 | 97.76 | 1.08 | 97 |
| F3 | t = 0 | 0 | 0.173 | 0.00 | 6.1 | 1.21 | 97.71 | 1.08 | 97 |
| | 120 minutes | 0 | 0.174 | 0.00 | 6.1 | 1.64 | 96.97 | 1.40 | 101 |
| | 8 cycles | 0 | 0.181 | 0.01 | 6.1 | 1.81 | 96.57 | 1.63 | 98 |
| | 40° C. 8 days | 0 | 0.171 | 0.00 | 6.1 | 2.11 | 95.74 | 2.15 | 97 |
| | 40° C. 14 days | 0 | 0.178 | 0.00 | 6.1 | 2.65 | 94.13 | 3.23 | 97 |
| | 40° C. 28 days | 0 | 0.185 | 0.01 | 6.1 | 3.37 | 92.40 | 4.23 | 102 |
| | 40° C. 2 month | 0 | 0.188 | 0.02 | 6.1 | 1.30 | 97.62 | 1.08 | 97 |
| | 40° C. 3 months | 0 | 0.203 | 0.03 | 6.3 | 1.22 | 97.70 | 1.08 | 100 |
| F4 | t = 0 | 0 | 0.180 | 0.00 | 6.1 | 1.18 | 97.75 | 1.08 | 97 |
| | 120 minutes | 0 | 0.182 | 0.00 | 6.1 | 1.57 | 97.04 | 1.38 | 97 |
| | 8 cycles | 0 | 0.178 | 0.00 | 6.1 | 1.76 | 96.62 | 1.62 | 97 |
| | 40° C. 8 days | 0 | 0.172 | 0.00 | 6.1 | 2.09 | 95.76 | 2.15 | 98 |
| | 40° C. 14 days | 0 | 0.179 | 0.00 | 6.1 | 2.68 | 94.07 | 3.24 | 99 |
| | 40° C. 28 days | 0 | 0.187 | 0.01 | 6.1 | 3.48 | 92.26 | 4.26 | 104 |
| | 40° C. 2 month | 0 | 0.194 | 0.01 | 6.1 | 1.17 | 97.77 | 1.07 | 99 |
| | 40° C. 3 months | 0 | 0.205 | 0.02 | 6.3 | 1.19 | 97.73 | 1.08 | 98 |
| | Light Stress Control | 0 | 0.178 | 0.00 | 6.1 | 1.27 | 97.47 | 1.26 | 98 |
| | Light Stress Mild | 0 | 0.178 | 0.00 | 6.1 | 4.60 | 94.18 | 1.22 | 98 |
| | Light Stress Extreme | 0 | 0.233 | 0.05 | 6.1 | 17.01 | 81.07 | 1.92 | 97 |

TABLE 30-continued

Effect of Excipients on the Stability of 100 mg/mL H1H17203P, H1H17139P, and H1H17161P Antibodies (ratio at 1:1:1) Incubated at 40° C. for up to Two Months - Visual, OD, pH, SE-UPLC, RP-UPLC Concentration

| Formulation | Sample | Visual | OD @ 405 nm | ΔOD | pH | % HMW | % Native | % LMW | Con, mg/mL |
|---|---|---|---|---|---|---|---|---|---|
| F5 | t = 0 | 0 | 0.194 | 0.00 | 6.1 | 1.12 | 97.78 | 1.10 | 96 |
| | 120 minutes | 0 | 0.196 | 0.00 | 6.1 | 1.30 | 97.26 | 1.44 | 96 |
| | 8 cycles | 0 | 0.198 | 0.00 | 6.1 | 1.43 | 96.89 | 1.68 | 96 |
| | 40° C. 8 days | 0 | 0.187 | 0.00 | 6.1 | 1.65 | 96.14 | 2.22 | 98 |
| | 40° C. 14 days | 0 | 0.190 | 0.00 | 6.1 | 2.07 | 94.59 | 3.34 | 97 |
| | 40° C. 28 days | 0 | 0.195 | 0.00 | 6.1 | 2.88 | 92.77 | 4.35 | 102 |
| | 40° C. 2 month | 0 | 0.198 | 0.00 | 6.1 | 1.11 | 97.79 | 1.10 | 96 |
| | 40° C. 3 months | 0 | 0.204 | 0.01 | 6.3 | 1.13 | 97.78 | 1.10 | 97 |
| F6 | t = 0 | 0 | 0.197 | 0.00 | 6.1 | 1.10 | 97.82 | 1.07 | 96 |
| | 120 minutes | 0 | 0.197 | 0.00 | 6.2 | 1.31 | 97.25 | 1.44 | 96 |
| | 8 cycles | 0 | 0.200 | 0.00 | 6.1 | 1.44 | 96.86 | 1.70 | 96 |
| | 40° C. 8 days | 0 | 0.191 | 0.00 | 6.1 | 1.69 | 96.09 | 2.22 | 96 |
| | 40° C. 14 days | 0 | 0.195 | 0.00 | 6.1 | 2.28 | 94.37 | 3.35 | 96 |
| | 40° C. 28 days | 0 | 0.200 | 0.00 | 6.2 | 3.02 | 92.66 | 4.32 | 102 |
| | 40° C. 2 month | 0 | 0.199 | 0.00 | 6.1 | 1.10 | 97.78 | 1.13 | 96 |
| | 40° C. 3 months | 0 | 0.208 | 0.01 | 6.3 | 1.12 | 97.77 | 1.11 | 96 |
| F7 | t = 0 | 0 | 0.198 | 0 | 6.13 | 1.13 | 97.82 | 1.05 | 95 |
| | 120 minutes | 0 | 0.196 | 0 | 6.14 | 1.38 | 97.19 | 1.43 | 97 |
| | 8 cycles | 0 | 0.209 | 0.011 | 6.13 | 1.53 | 96.79 | 1.69 | 96 |
| | 40° C. 8 days | 0 | 0.189 | 0 | 6.09 | 1.75 | 96.04 | 2.22 | 98 |
| | 40° C. 14 days | 0 | 0.1917 | 0 | 6.08 | 2.26 | 94.41 | 3.34 | 97 |
| | 40° C. 28 days | 0 | 0.1973 | 0 | 6.15 | 3.38 | 92.08 | 4.54 | 104 |
| | 40° C. 2 month | 0 | 0.1994 | 0.0014 | 6.15 | 1.14 | 97.79 | 1.08 | 97 |
| | 40° C. 3 months | 0 | 0.2086 | 0.0106 | 6.28 | 1.14 | 97.76 | 1.09 | 97 |
| | Light Stress Control | 0 | 0.1977 | 0 | 6.12 | 1.15 | 97.56 | 1.28 | 98 |
| | Light Stress Mild | 0 | 0.2001 | 0.0021 | 6.11 | 4.87 | 93.85 | 1.28 | 98 |
| | Light Stress Extreme | 0 | 0.287 | 0.089 | 6.11 | 17.14 | 80.69 | 2.17 | 97 |
| F8 | t = 0 | 0 | 0.191 | 0.00 | 6.1 | 1.10 | 97.84 | 1.06 | 97 |
| | 120 minutes | 0 | 0.192 | 0.00 | 6.1 | 1.24 | 97.33 | 1.44 | 96 |
| | 8 cycles | 0 | 0.195 | 0.00 | 6.1 | 1.32 | 97.00 | 1.67 | 96 |
| | 40° C. 8 days | 0 | 0.184 | 0.00 | 6.1 | 1.49 | 96.29 | 2.22 | 97 |
| | 40° C. 14 days | 0 | 0.189 | 0.00 | 6.1 | 1.85 | 94.82 | 3.32 | 97 |
| | 40° C. 28 days | 0 | 0.198 | 0.01 | 6.2 | 2.35 | 93.33 | 4.32 | 102 |
| | 40° C. 2 month | 0 | 0.194 | 0.00 | 6.2 | 1.26 | 97.69 | 1.06 | 97 |
| | 40° C. 3 months | 0 | 0.204 | 0.01 | 6.3 | 1.11 | 97.79 | 1.10 | 101 |
| F9 | t = 0 | 0 | 0.177 | 0 | 6.11 | 1.15 | 97.77 | 1.09 | 97 |
| | 120 minutes | 0 | 0.18 | 0.003 | 6.11 | 1.38 | 97.25 | 1.38 | 97 |
| | 8 cycles | 0 | 0.181 | 0.004 | 6.1 | 1.51 | 96.87 | 1.63 | 96 |
| | 40° C. 8 days | 0 | 0.177 | 0 | 6.08 | 1.71 | 96.12 | 2.17 | 97 |

TABLE 30-continued

Effect of Excipients on the Stability of 100 mg/mL H1H17203P, H1H17139P, and H1H17161P Antibodies (ratio at 1:1:1) Incubated at 40° C. for up to Two Months - Visual, OD, pH, SE-UPLC, RP-UPLC Concentration

| Formulation | Sample | Visual | OD @ 405 nm | ΔOD | pH | % HMW | % Native | % LMW | Con, mg/mL |
|---|---|---|---|---|---|---|---|---|---|
| | 40° C. 14 days | 0 | 0.1813 | 0.0043 | 6.08 | 2.09 | 94.63 | 3.28 | 97 |
| | 40° C. 28 days | 0 | 0.187 | 0.01 | 6.13 | 2.63 | 93.08 | 4.29 | 103 |
| | 40° C. 2 month | 0 | 0.1914 | 0.0144 | 6.11 | 1.12 | 97.84 | 1.03 | 97 |
| | 40° C. 3 months | 0 | 0.1987 | 0.0217 | 6.23 | 1.15 | 97.78 | 1.08 | 98 |
| | Light Stress Control | 0 | 0.1776 | 0.0006 | 6.12 | 1.19 | 97.56 | 1.26 | 99 |
| | Light Stress Mild | 0 | 0.1777 | 0.0007 | 6.12 | 4.15 | 94.59 | 1.26 | 98 |
| | Light Stress Extreme | 0 | 0.2888 | 0.1118 | 6.11 | 15.33 | 82.28 | 2.39 | 99 |
| F10 | t = 0 | 0 | 0.18 | 0 | 6.11 | 1.17 | 97.77 | 1.07 | 96 |
| | 120 minutes | 0 | 0.179 | 0 | 6.12 | 1.45 | 97.13 | 1.41 | 96 |
| | 8 cycles | 0 | 0.184 | 0.004 | 6.1 | 1.59 | 96.76 | 1.65 | 96 |
| | 40° C. 8 days | 0 | 0.177 | 0 | 6.08 | 1.83 | 95.99 | 2.19 | 97 |
| | 40° C. 14 days | 0 | 0.1812 | 0.0012 | 6.09 | 2.28 | 94.43 | 3.30 | 96 |
| | 40° C. 28 days | 0 | 0.1892 | 0.0092 | 6.143 | 2.95 | 92.76 | 4.28 | 102 |
| | 40° C. 2 month | 0 | 0.1873 | 0.0073 | 6.11 | 1.15 | 97.81 | 1.04 | 96 |
| | 40° C. 3 months | 0 | 0.1982 | 0.0182 | 6.23 | 1.17 | 97.76 | 1.07 | 97 |
| F11 | t = 0 | 0 | 0.177 | 0 | 6.12 | 1.13 | 97.79 | 1.08 | 100 |
| | 120 minutes | 0 | 0.178 | 0.001 | 6.12 | 1.34 | 97.25 | 1.40 | 97 |
| | 8 cycles | 0 | 0.18 | 0.003 | 6.1 | 1.46 | 96.90 | 1.65 | 97 |
| | 40° C. 8 days | 0 | 0.177 | 0 | 6.09 | 1.67 | 96.16 | 2.18 | 96 |
| | 40° C. 14 days | 0 | 0.1807 | 0.0037 | 6.08 | 2.02 | 94.66 | 3.31 | 97 |
| | 40° C. 28 days | 0 | 0.1897 | 0.0127 | 6.14 | 2.48 | 93.26 | 4.26 | 102 |
| | 40° C. 2 month | 0 | 0.1886 | 0.0116 | 6.13 | 1.20 | 97.75 | 1.04 | 97 |
| | 40° C. 3 months | 0 | 0.1934 | 0.0164 | 6.24 | 1.15 | 97.80 | 1.06 | 101 |
| F12 | t = 0 | 0 | 0.178 | 0 | 6.1 | 1.13 | 97.78 | 1.10 | 99 |
| | 120 minutes | 0 | 0.178 | 0 | 6.11 | 1.30 | 97.30 | 1.40 | 96 |
| | 8 cycles | 0 | 0.181 | 0.003 | 6.09 | 1.40 | 96.96 | 1.64 | 97 |
| | 40° C. 8 days | 0 | 0.176 | 0 | 6.07 | 1.59 | 96.25 | 2.16 | 98 |
| | 40° C. 14 days | 0 | 0.1815 | 0.0035 | 6.07 | 1.92 | 94.82 | 3.26 | 97 |
| | 40° C. 28 days | 0 | 0.1895 | 0.0115 | 6.1 | 2.35 | 93.42 | 4.24 | 102 |
| | 40° C. 2 month | 0 | 0.1955 | 0.0175 | 6.11 | 1.10 | 97.86 | 1.04 | 97 |
| | 40° C. 3 months | 0 | 0.2008 | 0.0228 | 6.22 | 1.12 | 97.78 | 1.10 | 98 |
| | Light Stress Control | 0 | 0.1786 | 0.0006 | 6.12 | 1.13 | 97.60 | 1.26 | 99 |
| | Light Stress Mild | 0 | 0.179 | 0.001 | 6.11 | 3.37 | 95.38 | 1.26 | 98 |
| | Light Stress Extreme | 0 | 0.241 | 0.063 | 6.12 | 11.99 | 85.85 | 2.16 | 99 |

TABLE 31

Effect of Excipients on the Stability of 100 mg/mL H1H17203P, H1H17139P, and H1H17161P Antibodies (at ratio 1:1:1) Incubated at 40° C. for up to Two Months - CEX-UPLC

|  |  | H1H17139P | | | H1H17203P | | | H1H17161P | | |
|---|---|---|---|---|---|---|---|---|---|---|
| Formulation | Sample | % Acidic | % Main | % Basic | % Acidic | % Main | % Basic | % Acidic | % Main | % Basic |
| F1 | t = 0 | 36.1 | 61.2 | 2.7 | 31.9 | 47.6 | 20.6 | 41.2 | 49.9 | 8.9 |
|  | 120 minutes | 36.0 | 61.3 | 2.7 | 31.8 | 47.8 | 20.4 | 40.9 | 49.5 | 9.7 |
|  | 8 cycles | 36.2 | 61.1 | 2.7 | 31.8 | 47.7 | 20.5 | 40.3 | 49.8 | 9.8 |
|  | 40° C. 8 days | 38.2 | 58.6 | 3.3 | 33.9 | 46.8 | 19.3 | 46.1 | 44.1 | 9.9 |
|  | 40° C. 14 days | 39.9 | 56.6 | 3.5 | 35.9 | 45.3 | 18.8 | 48.4 | 42.2 | 9.4 |
|  | 40° C. 28 days | 44.8 | 51.3 | 3.9 | 39.6 | 41.1 | 19.3 | 56.8 | 37.0 | 6.2 |
|  | 40° C. 2 month | 54.5 | 42.0 | 3.5 | 46.7 | 32.6 | 20.7 | 68.5 | 27.6 | 3.8 |
|  | 40° C. 3 months | 62.2 | 32.8 | 5.0 | 54.2 | 27.0 | 18.8 | 78.3 | 16.9 | 4.8 |
| F2 | t = 0 | 36.2 | 61.1 | 2.7 | 31.7 | 47.8 | 20.5 | 40.6 | 50.2 | 9.1 |
|  | 120 minutes | 36.0 | 61.4 | 2.6 | 31.6 | 48.1 | 20.3 | 41.2 | 51.2 | 7.6 |
|  | 8 cycles | 36.3 | 61.1 | 2.7 | 31.8 | 47.8 | 20.4 | 39.6 | 49.6 | 10.7 |
|  | 40° C. 8 days | 38.1 | 58.6 | 3.3 | 33.6 | 46.9 | 19.4 | 42.2 | 46.7 | 11.1 |
|  | 40° C. 14 days | 39.8 | 56.7 | 3.5 | 35.4 | 45.6 | 19.0 | 44.9 | 45.1 | 10.0 |
|  | 40° C. 28 days | 44.9 | 51.1 | 4.0 | 39.3 | 41.2 | 19.5 | 56.7 | 36.8 | 6.4 |
|  | 40° C. 2 month | 54.2 | 42.3 | 3.5 | 46.1 | 32.6 | 21.3 | 62.9 | 32.7 | 4.4 |
|  | 40° C. 3 months | 61.5 | 33.9 | 4.7 | 54.5 | 28.3 | 17.2 | 71.3 | 23.5 | 5.2 |
| F3 | t = 0 | 36.1 | 61.2 | 2.7 | 31.7 | 47.8 | 20.5 | 41.4 | 50.2 | 8.4 |
|  | 120 minutes | 36.0 | 61.4 | 2.6 | 31.6 | 48.1 | 20.3 | 41.2 | 50.4 | 8.4 |
|  | 8 cycles | 36.2 | 61.2 | 2.6 | 31.8 | 47.8 | 20.4 | 40.3 | 49.6 | 10.0 |
|  | 40° C. 8 days | 38.1 | 58.7 | 3.3 | 33.6 | 46.9 | 19.4 | 44.8 | 45.5 | 9.6 |
|  | 40° C. 14 days | 39.6 | 56.8 | 3.6 | 35.4 | 45.6 | 19.0 | 47.4 | 42.5 | 10.1 |
|  | 40° C. 28 days | 44.5 | 51.5 | 4.0 | 39.3 | 41.2 | 19.5 | 56.6 | 37.3 | 6.1 |
|  | 40° C. 2 month | 53.9 | 42.5 | 3.6 | 46.1 | 32.6 | 21.3 | 67.8 | 27.8 | 4.5 |
|  | 40° C. 3 months | 61.6 | 34.9 | 3.5 | 54.5 | 28.3 | 17.2 | 77.8 | 17.7 | 4.4 |
| F4 | t = 0 | 36.2 | 61.1 | 2.7 | 31.9 | 47.8 | 20.3 | 40.5 | 50.7 | 8.8 |
|  | 120 minutes | 35.9 | 61.5 | 2.6 | 31.7 | 48.2 | 20.1 | 40.2 | 51.5 | 8.3 |
|  | 8 cycles | 36.2 | 61.1 | 2.7 | 31.8 | 47.9 | 20.3 | 39.2 | 50.8 | 10.0 |
|  | 40° C. 8 days | 38.1 | 58.6 | 3.4 | 33.8 | 47.1 | 19.1 | 42.6 | 47.8 | 9.6 |
|  | 40° C. 14 days | 40.0 | 56.6 | 3.5 | 35.7 | 45.9 | 18.4 | 44.9 | 45.6 | 9.6 |
|  | 40° C. 28 days | 45.1 | 51.1 | 3.8 | 40.0 | 41.1 | 18.9 | 53.0 | 40.4 | 6.6 |
|  | 40° C. 2 month | 54.6 | 42.1 | 3.4 | 47.3 | 32.7 | 20.0 | 63.9 | 32.2 | 3.9 |
|  | 40° C. 3 months | 61.5 | 34.0 | 4.6 | 54.7 | 28.4 | 16.9 | 72.6 | 23.0 | 4.4 |
| F5 | t = 0 | 35.9 | 61.4 | 2.7 | 31.5 | 48.0 | 20.5 | 41.5 | 50.7 | 7.9 |
|  | 120 minutes | 35.7 | 61.8 | 2.5 | 31.2 | 48.5 | 20.2 | 41.6 | 50.1 | 8.3 |
|  | 8 cycles | 35.9 | 61.5 | 2.7 | 31.4 | 48.1 | 20.5 | 40.3 | 50.1 | 9.6 |
|  | 40° C. 8 days | 36.8 | 59.8 | 3.3 | 32.4 | 48.0 | 19.6 | 45.2 | 46.5 | 8.3 |
|  | 40° C. 14 days | 38.4 | 57.7 | 3.8 | 34.0 | 46.4 | 19.6 | 46.6 | 42.1 | 11.3 |
|  | 40° C. 28 days | 42.4 | 53.3 | 4.3 | 37.1 | 43.0 | 19.9 | 55.9 | 37.5 | 6.5 |
|  | 40° C. 2 month | 50.5 | 45.7 | 3.8 | 43.7 | 36.0 | 20.3 | 68.8 | 27.3 | 3.9 |
|  | 40° C. 3 months | 56.9 | 38.2 | 4.9 | 51.0 | 32.3 | 16.7 | 76.8 | 17.9 | 5.4 |
| F6 | t = 0 | 36.0 | 61.2 | 2.8 | 31.7 | 47.8 | 20.5 | 40.3 | 50.2 | 9.6 |
|  | 120 minutes | 36.2 | 60.9 | 2.9 | 31.6 | 47.8 | 20.6 | 39.1 | 50.5 | 10.4 |
|  | 8 cycles | 35.8 | 61.4 | 2.8 | 31.5 | 48.0 | 20.4 | 39.2 | 50.5 | 10.3 |
|  | 40° C. 8 days | 37.0 | 59.6 | 3.4 | 32.7 | 47.9 | 19.4 | 41.7 | 48.4 | 9.9 |
|  | 40° C. 14 days | 38.8 | 57.5 | 3.8 | 34.3 | 46.7 | 19.0 | 43.0 | 45.7 | 11.3 |
|  | 40° C. 28 days | 42.7 | 53.2 | 4.1 | 37.6 | 43.2 | 19.1 | 50.3 | 42.8 | 6.9 |
|  | 40° C. 2 month | 51.2 | 45.1 | 3.7 | 44.7 | 36.1 | 19.2 | 60.1 | 35.4 | 4.5 |
|  | 40° C. 3 months | 57.5 | 37.8 | 4.7 | 52.1 | 32.5 | 15.5 | 68.3 | 26.4 | 5.4 |
| F7 | t = 0 | 36.0 | 61.2 | 2.8 | 31.6 | 47.8 | 20.5 | 41.0 | 49.4 | 9.6 |
|  | 120 minutes | 36.1 | 61.2 | 2.8 | 31.6 | 47.8 | 20.7 | 40.0 | 50.2 | 9.9 |
|  | 8 cycles | 35.9 | 61.3 | 2.7 | 31.5 | 48.1 | 20.4 | 40.1 | 49.6 | 10.3 |
|  | 40° C. 8 days | 37.1 | 59.4 | 3.5 | 32.8 | 47.6 | 19.5 | 44.9 | 44.8 | 10.3 |
|  | 40° C. 14 days | 38.8 | 57.4 | 3.8 | 34.3 | 46.5 | 19.2 | 47.2 | 42.8 | 10.1 |
|  | 40° C. 28 days | 42.8 | 53.0 | 4.1 | 37.5 | 43.0 | 19.5 | 56.3 | 37.3 | 6.4 |
|  | 40° C. 2 month | 51.2 | 45.1 | 3.7 | 44.8 | 36.2 | 19.0 | 69.5 | 27.1 | 3.4 |
|  | 40° C. 3 months |  |  |  |  |  |  |  |  |  |
| F8 | t = 0 | 35.8 | 61.5 | 2.7 | 31.5 | 48.0 | 20.5 | 40.5 | 51.5 | 8.0 |
|  | 120 minutes | 36.0 | 61.2 | 2.7 | 31.6 | 47.9 | 20.6 | 39.5 | 50.9 | 9.7 |
|  | 8 cycles | 35.7 | 61.8 | 2.5 | 31.3 | 48.7 | 19.9 | 40.2 | 49.9 | 10.0 |
|  | 40° C. 8 days | 36.9 | 59.6 | 3.5 | 32.7 | 47.6 | 19.7 | 41.5 | 48.0 | 10.5 |
|  | 40° C. 14 days | 38.7 | 57.5 | 3.9 | 34.3 | 46.5 | 19.2 | 43.2 | 45.7 | 11.1 |
|  | 40° C. 28 days | 42.6 | 53.3 | 4.2 | 37.4 | 43.1 | 19.5 | 50.4 | 42.9 | 6.7 |
|  | 40° C. 2 month | 50.8 | 45.5 | 3.7 | 44.3 | 36.0 | 19.7 | 60.1 | 35.7 | 4.2 |
|  | 40° C. 3 months | 57.8 | 37.3 | 4.9 | 52.1 | 32.1 | 15.9 | 68.8 | 25.8 | 5.4 |
| F9 | t = 0 | 36.2 | 61.1 | 2.7 | 31.9 | 47.8 | 20.2 | 41.3 | 49.7 | 9.0 |
|  | 120 minutes | 36.4 | 60.9 | 2.7 | 31.9 | 47.7 | 20.5 | 40.0 | 50.2 | 9.9 |
|  | 8 cycles | 36.1 | 61.3 | 2.7 | 31.8 | 47.9 | 20.3 | 39.2 | 51.0 | 9.9 |
|  | 40° C. 8 days | 37.9 | 58.8 | 3.3 | 33.6 | 47.3 | 19.1 | 44.9 | 45.8 | 9.3 |
|  | 40° C. 14 days | 40.0 | 56.3 | 3.7 | 35.7 | 45.5 | 18.8 | 46.8 | 42.2 | 11.0 |
|  | 40° C. 28 days | 44.7 | 51.3 | 4.0 | 39.5 | 41.5 | 19.0 | 56.3 | 37.9 | 5.8 |
|  | 40° C. 2 month | 53.8 | 42.6 | 3.6 | 46.2 | 33.3 | 20.5 | 67.7 | 28.9 | 3.3 |
|  | 40° C. 3 months | 60.8 | 34.4 | 4.9 | 54.3 | 29.2 | 16.5 | 76.9 | 18.2 | 4.9 |

TABLE 31-continued

Effect of Excipients on the Stability of 100 mg/mL H1H17203P, H1H17139P, and H1H17161P Antibodies (at ratio 1:1:1) Incubated at 40° C. for up to Two Months - CEX-UPLC

| Formulation | Sample | H1H17139P % Acidic | H1H17139P % Main | H1H17139P % Basic | H1H17203P % Acidic | H1H17203P % Main | H1H17203P % Basic | H1H17161P % Acidic | H1H17161P % Main | H1H17161P % Basic |
|---|---|---|---|---|---|---|---|---|---|---|
| F10 | t = 0 | 36.0 | 61.5 | 2.5 | 31.9 | 47.7 | 20.4 | 41.1 | 50.5 | 8.4 |
| | 120 minutes | 36.4 | 60.9 | 2.7 | 31.9 | 47.8 | 20.3 | 40.1 | 50.8 | 9.1 |
| | 8 cycles | 36.2 | 61.2 | 2.6 | 31.8 | 48.0 | 20.2 | 39.1 | 51.1 | 9.8 |
| | 40° C. 8 days | 37.9 | 58.8 | 3.3 | 33.8 | 47.2 | 18.9 | 44.8 | 46.0 | 9.2 |
| | 40° C. 14 days | 40.2 | 56.4 | 3.5 | 35.8 | 45.6 | 18.7 | 46.3 | 42.0 | 11.6 |
| | 40° C. 28 days | 44.9 | 51.1 | 3.9 | 39.7 | 41.7 | 18.6 | 56.9 | 37.5 | 5.6 |
| | 40° C. 2 month | 54.2 | 42.4 | 3.4 | 46.6 | 33.2 | 20.2 | 67.5 | 29.2 | 3.3 |
| | 40° C. 3 months | 60.9 | 34.6 | 4.5 | 53.9 | 29.0 | 17.1 | 75.8 | 19.5 | 4.7 |
| F11 | t = 0 | 36.0 | 61.5 | 2.5 | 31.7 | 48.4 | 20.0 | 41.0 | 51.8 | 7.2 |
| | 120 minutes | 36.4 | 60.9 | 2.7 | 31.8 | 47.8 | 20.4 | 39.9 | 50.5 | 9.6 |
| | 8 cycles | 36.2 | 61.2 | 2.6 | 31.7 | 48.1 | 20.2 | 38.9 | 50.8 | 10.3 |
| | 40° C. 8 days | 37.9 | 58.8 | 3.3 | 33.8 | 47.3 | 18.9 | 42.4 | 47.5 | 10.1 |
| | 40° C. 14 days | 40.2 | 56.4 | 3.5 | 35.7 | 45.8 | 18.5 | 44.2 | 44.8 | 10.9 |
| | 40° C. 28 days | 44.9 | 51.1 | 3.9 | 39.8 | 41.7 | 18.5 | 52.5 | 41.6 | 5.9 |
| | 40° C. 2 month | 54.2 | 42.4 | 3.4 | 45.0 | 32.1 | 22.9 | 59.7 | 36.2 | 4.1 |
| | 40° C. 3 months | 60.9 | 34.6 | 4.5 | 54.5 | 29.4 | 16.1 | 72.0 | 24.3 | 3.7 |
| F12 | t = 0 | 36.1 | 61.3 | 2.6 | 31.9 | 48.1 | 20.0 | 40.8 | 51.5 | 7.7 |
| | 120 minutes | 36.1 | 61.2 | 2.7 | 31.8 | 47.8 | 20.4 | 39.5 | 49.5 | 11.0 |
| | 8 cycles | 36.1 | 61.2 | 2.7 | 31.8 | 47.9 | 20.3 | 38.4 | 50.8 | 10.8 |
| | 40° C. 8 days | 38.2 | 58.4 | 3.4 | 33.8 | 47.3 | 19.0 | 42.6 | 47.0 | 10.3 |
| | 40° C. 14 days | 40.0 | 56.4 | 3.6 | 35.6 | 45.9 | 18.5 | 44.1 | 45.4 | 10.4 |
| | 40° C. 28 days | 44.7 | 51.3 | 4.0 | 39.6 | 41.7 | 18.7 | 52.4 | 41.7 | 5.9 |
| | 40° C. 2 month | 53.9 | 42.6 | 3.5 | 44.2 | 32.0 | 23.8 | 58.9 | 36.6 | 4.6 |
| | 40° C. 3 months | 60.2 | 35.1 | 4.7 | 53.2 | 29.4 | 17.4 | 71.3 | 25.1 | 3.5 |

TABLE 32

Effect of Excipients on the Stability of 100 mg/mL H1H17203P, H1H17139P, and H1H17161P Antibodies (at ratio 1:1:1) Incubated at 40° C. for up to Two Months - MFI Results

| Sample | Stressed Condition | 2-10 μm Conc. (#/ml) | ≥2 μm Conc. (#/ml) | ≥10 μm Conc. (#/ml) | ≥25 μm Conc. (#/ml) |
|---|---|---|---|---|---|
| F1 | t = 0 | 1127 | 1150 | 23 | 0 |
| F2 | | 4778 | 1044 | 79 | 13 |
| F3 | | 4112 | 4201 | 90 | 6 |
| F4 | | 1459 | 1509 | 50 | 10 |
| F5 | | 649 | 695 | 46 | 8 |
| F6 | | 831 | 929 | 98 | 27 |
| F7 | | 1136 | 1249 | 113 | 13 |
| F8 | | 2311 | 2414 | 102 | 13 |
| F9 | | 632 | 655 | 23 | 0 |
| F10 | | 990 | 1028 | 38 | 4 |
| F11 | | 1845 | 1931 | 86 | 4 |
| F12 | | 678 | 722 | 44 | 4 |
| F1 | VTX | 4778 | 4995 | 217 | 31 |
| F2 | | 2461 | 2544 | 83 | 8 |
| F3 | | 3003 | 3064 | 61 | 0 |
| F4 | | 2497 | 2553 | 56 | 6 |
| F5 | | 1744 | 1771 | 27 | 0 |
| F6 | | 4427 | 4540 | 113 | 8 |
| F7 | | 2734 | 2797 | 63 | 13 |
| F8 | | 3874 | 4066 | 192 | 21 |
| F9 | | 1697 | 1730 | 33 | 4 |
| F10 | | 1876 | 1926 | 50 | 4 |
| F11 | | 2464 | 2530 | 67 | 6 |
| F12 | | 1104 | 1154 | 50 | 8 |
| F1 | F/T | 6406 | 6657 | 250 | 42 |
| F2 | | 2011 | 2074 | 63 | 6 |
| F3 | | 2572 | 2616 | 44 | 17 |
| F4 | | 2864 | 2960 | 96 | 25 |
| F5 | | 1354 | 1396 | 42 | 2 |
| F6 | | 4141 | 4379 | 238 | 23 |
| F7 | | 3905 | 3982 | 77 | 4 |
| F8 | | 3377 | 3471 | 94 | 4 |
| F9 | | 1965 | 1996 | 31 | 2 |
| F10 | | 1746 | 1792 | 46 | 2 |
| F11 | | 5040 | 5134 | 94 | 6 |
| F12 | | 1304 | 1323 | 19 | 2 |

Example 8: Selection of Organic Cosolvent Against Agitation Stress

Stabilizers such as surfactants and organic cosolvents are often added to the antibody formulations to protect the protein from agitation-induced aggregation. The effect of organic cosolvents and surfactants on the agitation stress stability and thermal stability of 33.3 mg/mL individual anti-EBOV antibody, and 100 mg/mL of the three antibody co-formulated cocktail (ratio at 1:1:1) were examined in liquid formulations. The previous example identified Polysorbate 80 as a critical excipient component. The present Example evaluates different Polysorbate 80 by % w/v under agitation stress induced by orbital shaking at 250 rpm for 48 hours. See Tables 33-40. Base formulations contain 33.3. mg/mL single antibody (or 100 mg/mL total antibody in co-formulation), 10 mM histidine, pH 6.0, 5% w/v sucrose, with 0.04% to 0.2% Polysorbate 80 as shown. Formulations containing no surfactant are less stable under agitation stress in comparison to formulation with ≥0.04% w/v PS80. In addition, there are no significant differences in the MFI and SE-UPLC results among formulations containing ≥0.04% w/v Polysorbate 80.

TABLE 33

Effect of Polysorbate 80 on Agitation Stress in Formulation Containing H1H17203P Anti-EBOV - Visual, OD, pH, % HMW, % Native, % LMW, and PS80 % w/v concentration

| Base Formulation+ | Stress | Visual | OD @ 405 nm | pH | % HMW | % Native | % LMW | Con, mg/mL |
|---|---|---|---|---|---|---|---|---|
| 0.04% w/v PS80 | t = 0 | 0 | 0.087 | 6.1 | 1.3 | 97.7 | 1.0 | 33.9 |
| | OB 250 rpm 48 hr | 0 | 0.088 | 6.0 | 1.2 | 97.8 | 1.0 | 34.5 |
| 0.08% w/v PS80 | t = 0 | 0 | 0.087 | 6.0 | 1.3 | 97.7 | 1.0 | 33.8 |
| | OB 250 rpm 48 hr | 0 | 0.087 | 6.0 | 1.2 | 97.8 | 1.0 | 34.8 |
| 0.12% w/v PS80 | t = 0 | 0 | 0.086 | 6.0 | 1.9 | 97.0 | 1.1 | 33.4 |
| | OB 250 rpm 48 hr | 0 | 0.086 | 6.0 | 1.8 | 97.2 | 1.1 | 33.8 |
| 0.20% w/v PS80 | t = 0 | 0 | 0.087 | 6.0 | 1.3 | 97.6 | 1.1 | 33.3 |
| | OB 250 rpm 48 hr | 0 | 0.087 | 6.0 | 1.2 | 97.8 | 1.1 | 34.2 |
| 0.00% w/v PS80 | t = 0 | 0 | 0.086 | 6.0 | 2.4 | 96.7 | 1.0 | 32.5 |
| | OB 250 rpm 48 hr | 2 | 0.365 | 6.0 | 55.2 | 44.1 | 0.7 | 32.6 |

TABLE 34

Effect of Polysorbate 80 on Agitation Stress in Formulation Containing H1H17139P Anti-EBOV - Visual, OD, pH, % HMW, % Native, % LMW, and PS80 % w/v Concentration

| Base Formulation+ | Stress | Visual | OD @ 405 nm | pH | % HMW | % Native | % LMW | Con, mg/mL |
|---|---|---|---|---|---|---|---|---|
| 0.04% w/v PS80 | t = 0 | 0 | 0.084 | 6.0 | 0.9 | 97.8 | 1.2 | 32.4 |
| | OB 250 rpm 48 hr | 0 | 0.083 | 6.0 | 0.8 | 97.9 | 1.2 | 32.6 |
| 0.08% w/v PS80 | t = 0 | 0 | 0.083 | 6.0 | 0.9 | 97.8 | 1.2 | 32.4 |
| | OB 250 rpm 48 hr | 0 | 0.082 | 6.0 | 0.8 | 97.9 | 1.2 | 32.5 |
| 0.12% w/v PS80 | t = 0 | 0 | 0.084 | 6.0 | 0.9 | 97.8 | 1.2 | 32.5 |
| | OB 250 rpm 48 hr | 0 | 0.083 | 6.0 | 0.8 | 97.9 | 1.2 | 32.8 |
| 0.20% w/v PS80 | t = 0 | 0 | 0.084 | 6.0 | 0.9 | 97.8 | 1.3 | 32.7 |
| | OB 250 rpm 48 hr | 0 | 0.082 | 6.0 | 0.8 | 97.9 | 1.3 | 32.9 |
| 0.00% w/v PS80 | t = 0 | 0 | 0.090 | 6.0 | 1.6 | 97.3 | 1.1 | 32.3 |
| | OB 250 rpm 48 hr | 0 | 0.086 | 6.0 | 3.3 | 95.6 | 1.1 | 32.0 |

TABLE 35

Effect of Polysorbate 80 on Agitation Stress in Formulation Containing H1H17161P Anti-EBOV - Visual, OD, pH, % HMW, % Native, % LMW, and PS80 % w/v Concentration

| Base Formulation+ | Stress | Visual | OD @ 405 nm | pH | % HMW | % Native | % LMW | Con, mg/mL |
|---|---|---|---|---|---|---|---|---|
| 0.04% w/v PS80 | t = 0 | 0 | 0.114 | 6.0 | 1.9 | 96.8 | 1.3 | 33 |
| | OB 250 rpm 48 hr | 0 | 0.111 | 6.1 | 1.8 | 96.9 | 1.3 | 33 |
| 0.08% w/v PS80 | t = 0 | 0 | 0.112 | 6.0 | 1.9 | 96.8 | 1.3 | 33 |
| | OB 250 rpm 48 hr | 0 | 0.111 | 6.1 | 1.8 | 97.0 | 1.3 | 33 |
| 0.12% w/v PS80 | t = 0 | 0 | 0.110 | 6.0 | 1.9 | 96.8 | 1.3 | 33 |
| | OB 250 rpm 48 hr | 0 | 0.110 | 6.0 | 1.8 | 97.0 | 1.3 | 34 |
| 0.20% w/v PS80 | t = 0 | 0 | 0.106 | 6.0 | 1.9 | 96.8 | 1.3 | 33 |
| | OB 250 rpm 48 hr | 0 | 0.111 | 6.1 | 1.8 | 96.9 | 1.3 | 33 |
| 0.00% w/v PS80 | t = 0 | 0 | 0.111 | 6.0 | 1.9 | 96.9 | 1.2 | 33 |
| | OB 250 rpm 48 hr | 0 | 0.112 | 6.0 | 10.7 | 88.2 | 1.1 | 33 |

TABLE 36

Effect of Polysorbate 80 on Agitation Stress in Formulation Containing H1H17203P, H1H17139P, and H1H17161P Anti-EBOV - Visual, OD, pH, % HMW, % Native, % LMW, and PS80 % w/v concentration

| Formulation | Stress | Visual | OD @ 405 nm | pH | % HMW | % Native | % LMW | Con, mg/ml | PS 80 % w/v |
|---|---|---|---|---|---|---|---|---|---|
| F1 | t = 0 | 0 | 0.182 | 6.1 | 1.6 | 97.3 | 1.2 | 98 | 0.058 |
|  | OB 250 rpm 48 hr | 0 | 0.188 | 6.1 | 1.6 | 97.3 | 1.1 | 98 | 0.059 |
| F2 | t = 0 | 0 | 0.180 | 6.1 | 1.6 | 97.3 | 1.1 | 97 | 0.095 |
|  | OB 250 rpm 48 hr | 0 | 0.180 | 6.1 | 1.6 | 97.3 | 1.1 | 98 | 0.095 |
| F3 | t = 0 | 0 | 0.175 | 6.1 | 1.8 | 97.1 | 1.1 | 93 | 0.13 |
|  | OB 250 rpm 48 hr | 0 | 0.176 | 6.1 | 1.7 | 97.2 | 1.1 | 93 | 0.129 |
| F4 | t = 0 | 0 | 0.179 | 6.1 | 1.6 | 97.3 | 1.1 | 97 | 0.207 |
|  | OB 250 rpm 48 hr | 0 | 0.182 | 6.1 | 1.6 | 97.3 | 1.1 | 97 | 0.207 |
| F5 | t = 0 | 0 | 0.191 | 6.1 | 2.1 | 96.9 | 1.1 | 99 |  |
|  | OB 250 rpm 48 hr | 0 | 0.178 | 6.0 | 8.8 | 90.2 | 1.0 | 98 |  |

TABLE 37

Effect of Polysorbate 80 on Agitation Stress in Formulation Containing H1H17203P Anti-EBOV - MFI Results

| Base Formulation+ | Stress | 10-300 μm (#/mL) | 25-300 μm (#/mL) |
|---|---|---|---|
| 0.04% w/v PS80 | t = 0 | 405.12 | 10.44 |
|  | OB 250 rpm 48 hr | 513.71 | 20.88 |
| 0.08% w/v PS80 | t = 0 | 279.82 | 4.18 |
|  | OB 250 rpm 48 hr | 743.41 | 31.32 |
| 0.12% w/v PS80 | t = 0 | 281.91 | 12.53 |
|  | OB 250 rpm 48 hr | 1150.62 | 18.79 |
| 0.20% w/v PS80 | t = 0 | 524.15 | 12.53 |
|  | OB 250 rpm 48 hr | 657.45 | 8.35 |
| 0.00% w/v PS80 | t = 0 | 389.9 | 22.94 |
|  | OB 250 rpm 48 hr | 1524.14 | 129.27 |

TABLE 38

Effect of Polysorbate 80 on Agitation Stress in Formulation Containing H1H17139P Anti-EBOV - MFI Results

| Base Formulation+ | Stress | 10-300 μm (#/mL) | 25-300 μm (#/mL) |
|---|---|---|---|
| 0.04% w/v PS80 | t = 0 | 1675.63 | 37.61 |
|  | OB 250 rpm 48 hr | 421.82 | 18.79 |
| 0.08% w/v PS80 | t = 0 | 208.82 | 10.44 |
|  | OB 250 rpm 48 hr | 355 | 12.53 |
| 0.12% w/v PS80 | t = 0 | 402.82 | 64.70 |
|  | OB 250 rpm 48 hr | 1002.87 | 22.98 |
| 0.20% w/v PS80 | t = 0 | 421.82 | 18.79 |
|  | OB 250 rpm 48 hr | 1423.56 | 10.45 |
| 0.00% w/v PS80 | t = 0 | 98 | 8.34 |
|  | OB 250 rpm 48 hr | 369.24 | 6.26 |

TABLE 39

Effect of Polysorbate 80 on Agitation Stress in Formulation Containing H1H17161P Anti-EBOV - MFI Results

| Base Formulation+ | Stress | 10-300 μm (#/mL) | 25-300 μm (#/mL) |
|---|---|---|---|
| 0.04% w/v PS80 | t = 0 | 17 | 0 |
|  | OB 250 rpm 48 hr | 2 | 0 |
| 0.08% w/v PS80 | t = 0 | 6 | 0 |
|  | OB 250 rpm 48 hr | 25 | 4 |
| 0.12% w/v PS80 | t = 0 | 8 | 4 |
|  | OB 250 rpm 48 hr | 17 | 8 |
| 0.20% w/v PS80 | t = 0 | 33 | 4 |
|  | OB 250 rpm 48 hr | 10 | 2 |
| 0.00% w/v PS80 | t = 0 | 15 | 2 |
|  | OB 250 rpm 48 hr | 8 | 4 |

TABLE 40

Effect of Polysorbate 80 on Agitation Stress in Formulation Containing H1H17203P, H1H17139P, and H1H17161P Anti-EBOV - MFI Results

| Base Formulation+ | Stress | 10-300 μm (#/mL) | 25-300 μm (#/mL) |
|---|---|---|---|
| 0.04% w/v PS80 | t = 0 | 21 | 6 |
|  | OB 250 rpm 48 hr | 15 | 0 |
| 0.08% w/v PS80 | t = 0 | 8 | 0 |
|  | OB 250 rpm 48 hr | 2 | 0 |
| 0.12% w/v PS80 | t = 0 | 25 | 2 |
|  | OB 250 rpm 48 hr | 15 | 0 |
| 0.20% w/v PS80 | t = 0 | 8 | 0 |
|  | OB 250 rpm 48 hr | 19 | 2 |
| 0.00% w/v PS80 | t = 0 | 2 | 0 |
|  | OB 250 rpm 48 hr | 25 | 6 |

The anti-EBOV antibodies were unstable when agitated by orbital shaking at 250 rpm in the absence of an organic cosolvent or surfactant. After agitation by orbital shaking at 250 rpm in the absence of cosolvent or surfactant, the solution became cloudy, exhibited a substantial increase in turbidity, and had an increase in aggregates as determined by SE-UPLC, as well as loss in protein recovery by RP-UPLC. In contrast, 0.1% polysorbate 80 protected the antibodies from agitation-induced instability.

Example 9: Selection of Stabilizer Concentration

The goal of the present Example was to identify the levels of stabilizing component that could be used to develop a drug product formulation supporting 33.3 mg/mL individual anti-EBOV antibody, and 100 mg/mL of the three antibody co-formulated cocktail (ratio at 1:1:1). 10% sucrose was selected in the initial formulation, and tested at varying amounts to assess any change in antibody stability: 5%, 10%, 15%, and 20%. Base formulations contained 100 mg/mL antibody, 10 mM histidine at pH 6.0, and 0.1% polysorbate 80.

Sucrose was chosen as the thermal stabilizer for anti-EBOV antibodies during the low concentration formulation development. For the high concentration formulation development, different concentrations of sucrose were evaluated on the stability of the antibodies at 100 mg/mL concentrations at 25° C. for 0 to 6 months and at 40° C. for 0 to 3 months. The formation of HMW species decreased with increasing sucrose concentrations when the formulations were incubated at 40° C. for 28 days.

This study demonstrated that the protein stability is comparable for the formulation containing 10% w/v sucrose as compared to formulations containing 15% or 20% sucrose, and as such, no additional sucrose was needed beyond 10% w/v. See Tables 41-48.

TABLE 41

Accelerated Stability of High Concentration (100 mg/mL) H1H17203P Anti-EBOV Antibody with Thermal Stabilizers - Visual, OD, and pH

| Base Formulation+ | Stress | Visual | OD @ 405 nm | pH |
|---|---|---|---|---|
| 5% sucrose | t = 0 | 0 | 0.085 | 6.0 |
| | 25° C. 0.5 m | 0 | 0.084 | 6.0 |
| | 25° C. 1 m | 0 | 0.085 | 6.1 |
| | 25° C. 3 m | 0 | 0.082 | 6.1 |
| | 25° C. 6 m | 0 | 0.091 | 6.1 |
| | 40° C. 7 d | 0 | 0.085 | 6.0 |
| | 40° C. 14 d | 0 | 0.086 | 6.0 |
| | 40° C. 21 d | 0 | 0.086 | 6.1 |
| | 40° C. 28 d | 0 | 0.087 | 6.1 |
| 10% sucrose | t = 0 | 0 | 0.085 | 6.0 |
| | 25° C. 0.5 m | 0 | 0.084 | 6.0 |
| | 25° C. 1 m | 0 | 0.085 | 6.1 |
| | 25° C. 3 m | 0 | 0.084 | 6.0 |
| | 25° C. 6 m | 0 | 0.093 | 6.0 |
| | 40° C. 7 d | 0 | 0.086 | 6.0 |
| | 40° C. 14 d | 0 | 0.085 | 6.0 |
| | 40° C. 21 d | 0 | 0.086 | 6.0 |
| | 40° C. 28 d | 0 | 0.088 | 6.1 |
| 15% sucrose | t = 0 | 0 | 0.086 | 6.0 |
| | 25° C. 0.5 m | 0 | 0.084 | 6.0 |
| | 25° C. 1 m | 0 | 0.084 | 6.0 |
| | 25° C. 3 m | 0 | 0.083 | 6.0 |
| | 25° C. 6 m | 0 | 0.090 | 6.0 |
| | 40° C. 7 d | 0 | 0.086 | 6.0 |
| | 40° C. 14 d | 0 | 0.086 | 6.0 |
| | 40° C. 21 d | 0 | 0.087 | 6.0 |
| | 40° C. 28 d | 0 | 0.086 | 6.0 |
| 20% sucrose | t = 0 | 0 | 0.086 | 5.9 |
| | 25° C. 0.5 m | 0 | 0.087 | 5.9 |
| | 25° C. 1 m | 0 | 0.084 | 6.0 |
| | 25° C. 3 m | 0 | 0.095 | 6.0 |
| | 25° C. 6 m | 0 | 0.089 | 6.0 |
| | 40° C. 7 d | 0 | 0.086 | 6.0 |
| | 40° C. 14 d | 0 | 0.085 | 6.0 |
| | 40° C. 21 d | 0 | 0.085 | 6.0 |
| | 40° C. 28 d | 0 | 0.086 | 6.0 |

TABLE 42

Accelerated Stability of High Concentration (100 mg/mL) H1H17203P Anti-EBOV Antibody with Thermal Stabilizers - SE-UPLC, RP-UPLC and CEX-UPLC Results

| Base Formulation+ | Stress | SE-UPLC % HMW | SE-UPLC % Monomer | SE-UPLC % LMW | RP-UPLC, mg/mL | CEX % Acidic | CEX % Main | CEX % Basic |
|---|---|---|---|---|---|---|---|---|
| 5% sucrose | t = 0 | 2.4 | 96.6 | 1.0 | 32.9 | 33.7 | 53.4 | 12.9 |
| | 25° C. 0.5 m | 2.1 | 96.9 | 1.1 | 32.4 | 33.9 | 53.7 | 12.4 |
| | 25° C. 1 m | 2.1 | 96.8 | 1.2 | 32.7 | 35.0 | 52.8 | 12.2 |
| | 25° C. 3 m | 2.1 | 96.3 | 1.6 | 32.6 | 38.6 | 50.9 | 10.5 |
| | 25° C. 6 m | 2.2 | 95.7 | 2.1 | 32.8 | 42.9 | 47.1 | 9.9 |
| | 40° C. 7 d | 2.0 | 96.7 | 1.3 | 32.3 | 35.3 | 52.3 | 12.5 |
| | 40° C. | 2.0 | 96.5 | 1.5 | 32.4 | 37.5 | 50.7 | 11.8 |

TABLE 42-continued

Accelerated Stability of High Concentration (100 mg/mL) H1H17203P Anti-EBOV Antibody with Thermal Stabilizers - SE-UPLC, RP-UPLC and CEX-UPLC Results

| Base Formulation+ | Stress | SE-UPLC % HMW | SE-UPLC % Monomer | SE-UPLC % LMW | RP-UPLC, mg/mL | CEX % Acidic | CEX % Main | CEX % Basic |
|---|---|---|---|---|---|---|---|---|
| | 40° C. 14 d | 2.1 | 96.1 | 1.8 | 32.5 | 40.0 | 48.7 | 11.3 |
| | 40° C. 21 d | 2.2 | 95.8 | 2.0 | 32.8 | 42.9 | 46.2 | 10.9 |
| 10% sucrose | t = 0 | 2.4 | 96.6 | 1.0 | 33.1 | 33.7 | 53.3 | 13.0 |
| | 25° C. 0.5 m | 2.0 | 96.9 | 1.1 | 32.7 | 33.9 | 53.6 | 12.5 |
| | 25° C. 1 m | 2.0 | 96.8 | 1.2 | 33.0 | 35.0 | 52.7 | 12.3 |
| | 25° C. 3 m | 2.1 | 96.3 | 1.6 | 32.8 | 38.4 | 50.8 | 10.8 |
| | 25° C. 6 m | 2.2 | 95.7 | 2.2 | 33.1 | 42.7 | 47.3 | 10.1 |
| | 40° C. 7 d | 2.0 | 96.8 | 1.2 | 32.5 | 35.1 | 52.3 | 12.6 |
| | 40° C. 14 d | 2.0 | 96.5 | 1.5 | 32.7 | 37.6 | 50.6 | 11.9 |
| | 40° C. 21 d | 2.1 | 96.2 | 1.8 | 32.8 | 39.8 | 48.7 | 11.5 |
| | 40° C. 28 d | 2.1 | 95.9 | 2.0 | 32.9 | 42.6 | 46.3 | 11.2 |
| 15% sucrose | t = 0 | 2.4 | 96.7 | 1.0 | 33. | 33.7 | 53.3 | 13.0 |
| | 25° C. 0.5 m | 2.0 | 96.9 | 1.1 | 33.0 | 33.9 | 53.5 | 12.6 |
| | 25° C. 1 m | 2.0 | 96.8 | 1.2 | 32.6 | 34.8 | 52.7 | 12.5 |
| | 25° C. 3 m | 2.1 | 96.4 | 1.6 | 32.8 | 38.2 | 50.9 | 10.9 |
| | 25° C. 6 m | 2.1 | 95.8 | 2.2 | 32.8 | 42.4 | 47.1 | 10.4 |
| | 40° C. 7 d | 2.0 | 96.8 | 1.2 | 32.9 | 35.1 | 52.4 | 12.6 |
| | 40° C. 14 d | 2.0 | 96.5 | 1.5 | 32.4 | 37.3 | 50.6 | 12.2 |
| | 40° C. 21 d | 2.0 | 96.2 | 1.8 | 32.6 | 39.5 | 48.8 | 11.7 |
| | 40° C. 28 d | 2.1 | 96.0 | 1.9 | 32.8 | 42.3 | 46.3 | 11.4 |
| 20% sucrose | t = 0 | 2.4 | 96.6 | 1.0 | 33.0 | 33.7 | 53.4 | 12.9 |
| | 25° C. 0.5 m | 2.0 | 96.9 | 1.1 | 32.5 | 33.9 | 53.6 | 12.5 |
| | 25° C. 1 m | 2.0 | 96.8 | 1.2 | 32.8 | 34.8 | 52.7 | 12.5 |
| | 25° C. 3 m | 2.0 | 96.4 | 1.6 | 32.7 | 37.9 | 50.8 | 11.3 |
| | 25° C. 6 m | 2.1 | 95.8 | 2.1 | 33.1 | 41.9 | 47.5 | 10.7 |
| | 40° C. 7 d | 2.0 | 96.8 | 1.2 | 32.4 | 34.9 | 52.5 | 12.6 |
| | 40° C. 14 d | 1.9 | 96.6 | 1.5 | 32.5 | 37.3 | 50.6 | 12.2 |
| | 40° C. 21 d | 2.0 | 96.3 | 1.7 | 32.7 | 39.1 | 49.0 | 11.9 |
| | 40° C. 28 d | 2.0 | 96.0 | 1.9 | 32.8 | 41.9 | 46.4 | 11.7 |

TABLE 43

Accelerated Stability of High Concentration (100 mg/mL) H1H17139P Anti-EBOV Antibody with Thermal Stabilizers - Visual, OD, and pH

| Base Formulation + | Stress | Visual | OD @ 405 nm | pH |
|---|---|---|---|---|
| 5% sucrose | t = 0 | 0 | 0.083 | 6.0 |
| | 25° C. 0.5 m | 0 | 0.083 | 6.0 |
| | 25° C. 1 m | 0 | 0.083 | 6.0 |
| | 25° C. 3 m | 0 | 0.086 | 6.0 |
| | 25° C. 6 m | 0 | 0.085 | 6.0 |
| | 40° C. 7 d | 0 | 0.084 | 6.0 |
| | 40° C. 14 d | 0 | 0.084 | 6.0 |
| | 40° C. 21 d | 0 | 0.084 | 6.0 |
| | 40° C. 28 d | 0 | 0.082 | 6.1 |
| 10% sucrose | t = 0 | 0 | 0.083 | 6.0 |
| | 25° C. 0.5 m | 0 | 0.082 | 6.0 |
| | 25° C. 1 m | 0 | 0.081 | 6.1 |
| | 25° C. 3 m | 0 | 0.087 | 6.0 |
| | 25° C. 6 m | 0 | 0.084 | 6.0 |
| | 40° C. 7 d | 0 | 0.083 | 6.0 |
| | 40° C. 14 d | 0 | 0.084 | 6.0 |
| | 40° C. 21 d | 0 | 0.084 | 6.0 |
| | 40° C. 28 d | 0 | 0.083 | 6.0 |
| 15% sucrose | t = 0 | 0 | 0.083 | 6.0 |
| | 25° C. 0.5 m | 0 | 0.082 | 6.0 |
| | 25° C. 1 m | 0 | 0.080 | 6.0 |
| | 25° C. 3 m | 0 | 0.085 | 6.0 |
| | 25° C. 6 m | 0 | 0.084 | 6.0 |
| | 40° C. 7 d | 0 | 0.084 | 6.0 |
| | 40° C. 14 d | 0 | 0.082 | 6.0 |
| | 40° C. 21 d | 0 | 0.083 | 6.0 |
| | 40° C. 28 d | 0 | 0.082 | 6.0 |
| 20% sucrose | t = 0 | 0 | 0.083 | 5.9 |
| | 25° C. 0.5 m | 0 | 0.083 | 5.9 |
| | 25° C. 1 m | 0 | 0.082 | 6.0 |
| | 25° C. 3 m | 0 | 0.085 | 6.0 |
| | 25° C. 6 m | 0 | 0.084 | 6.0 |
| | 40° C. 7 d | 0 | 0.085 | 6.0 |
| | 40° C. 14 d | 0 | 0.083 | 5.9 |

TABLE 43-continued

Accelerated Stability of High Concentration (100 mg/mL) H1H17139P Anti-EBOV Antibody with Thermal Stabilizers - Visual, OD, and pH

| Base Formulation + | Stress | Visual | OD @ 405 nm | pH |
|---|---|---|---|---|
| | 40° C. 21 d | 0 | 0.085 | 6.0 |
| | 40° C. 28 d | 0 | 0.082 | 6.0 |

TABLE 44

Accelerated Stability of High Concentration (100 mg/mL) H1H17139P Anti-EBOV Antibody with Thermal Stabilizers - SE-UPLC, RP-UPLC and CEX-UPLC Results

| Base Formulation+ | Stress | SE-UPLC % HMW | SE-UPLC % Monomer | SE-UPLC % LMW | RP-UPLC, mg/mL | CEX % Acidic | CEX % Main | CEX % Basic |
|---|---|---|---|---|---|---|---|---|
| 5% sucrose | t = 0 | 1.6 | 97.2 | 1.1 | 32.1 | 35.9 | 59.6 | 4.5 |
| | 25° C. 0.5 m | 1.4 | 97.4 | 1.3 | 32.3 | 35.8 | 59.7 | 4.6 |
| | 25° C. 1 m | 1.3 | 97.3 | 1.3 | 32.5 | 37.1 | 58.2 | 4.7 |
| | 25° C. 3 m | 1.4 | 96.9 | 1.7 | 32.4 | 39.9 | 55.2 | 4.9 |
| | 25° C. 6 m | 1.4 | 96.3 | 2.3 | 32.4 | 43.0 | 51.8 | 5.1 |
| | 40° C. 7 d | 1.3 | 97.4 | 1.4 | 32.2 | 37.0 | 58.1 | 4.9 |
| | 40° C. 14 d | 1.3 | 97.1 | 1.6 | 32.3 | 39.0 | 56.0 | 5.0 |
| | 40° C. 21 d | 1.3 | 96.9 | 1.9 | 32.5 | 40.8 | 54.1 | 5.1 |
| | 40° C. 28 d | 1.3 | 96.7 | 2.1 | 32.4 | 43.9 | 51.0 | 5.2 |
| 10% sucrose | t = 0 | 1.6 | 97.2 | 1.2 | 32.3 | 35.7 | 59.8 | 4.5 |
| | 25° C. 0.5 m | 1.3 | 97.4 | 1.2 | 32.5 | 35.7 | 59.7 | 4.6 |
| | 25° C. 1 m | 1.3 | 97.4 | 1.3 | 32.6 | 37.1 | 58.1 | 4.8 |
| | 25° C. 3 m | 1.4 | 96.9 | 1.8 | 32.8 | 39.5 | 55.6 | 4.9 |
| | 25° C. 6 m | 1.4 | 96.4 | 2.3 | 32.8 | 42.7 | 52.2 | 5.2 |
| | 40° C. 7 d | 1.3 | 97.4 | 1.4 | 32.4 | 36.8 | 58.4 | 4.9 |
| | 40° C. 14 d | 1.3 | 97.1 | 1.6 | 32.6 | 38.8 | 56.1 | 5.1 |
| | 40° C. 21 d | 1.2 | 96.9 | 1.9 | 32.8 | 40.6 | 54.2 | 5.2 |
| | 40° C. 28 d | 1.3 | 96.7 | 2.1 | 32.6 | 43.8 | 51.0 | 5.3 |
| 15% sucrose | t = 0 | 1.6 | 97.2 | 1.1 | 32.3 | 35.7 | 59.8 | 4.5 |
| | 25° C. 0.5 m | 1.3 | 97.5 | 1.2 | 32.4 | 35.7 | 59.7 | 4.6 |
| | 25° C. 1 m | 1.3 | 97.4 | 1.3 | 32.6 | 37.0 | 58.2 | 4.8 |
| | 25° C. 3 m | 1.3 | 96.9 | 1.8 | 32.8 | 39.6 | 55.3 | 5.1 |
| | 25° C. 6 m | 1.4 | 96.4 | 2.3 | 32.6 | 42.5 | 52.3 | 5.3 |
| | 40° C. 7 d | 1.3 | 97.4 | 1.4 | 32.4 | 36.6 | 58.5 | 4.9 |
| | 40° C. 14 d | 1.3 | 97.1 | 1.6 | 32.5 | 38.7 | 56.2 | 5.1 |
| | 40° C. 21 d | 1.2 | 96.9 | 1.9 | 32.8 | 40.5 | 54.2 | 5.3 |
| | 40° C. 28 d | 1.3 | 96.7 | 2.1 | 32.7 | 43.3 | 51.2 | 5.5 |
| | t = 0 | 1.6 | 97.2 | 1.2 | 32.6 | 35.8 | 59.7 | 4.5 |
| | 25° C. 0.5 m | 1.3 | 97.5 | 1.2 | 32.7 | 35.6 | 59.7 | 4.7 |
| | 25° C. 1 m | 1.3 | 97.4 | 1.3 | 32.9 | 36.7 | 58.5 | 4.8 |
| | 25° C. 3 m | 1.3 | 96.9 | 1.8 | 33.1 | 39.4 | 55.6 | 5.1 |
| | 25° C. 6 m | 1.3 | 96.4 | 2.3 | 33.1 | 42.4 | 52.3 | 5.4 |
| | 40° C. 7 d | 1.3 | 97.4 | 1.4 | 32.7 | 36.6 | 58.4 | 5.0 |
| | 40° C. 14 d | 1.3 | 97.1 | 1.6 | 32.9 | 38.4 | 56.4 | 5.3 |
| | 40° C. 21 d | 1.3 | 96.9 | 1.9 | 33.0 | 40.2 | 54.3 | 5.5 |
| | 40° C. 28 d | 1.3 | 96.7 | 2.0 | 33.0 | 42.9 | 51.5 | 5.6 |

TABLE 45

Accelerated Stability of High Concentration (100 mg/mL) H1H17161P Anti-EBOV Antibody with Thermal Stabilizers - Visual, OD, and pH

| Base Formulation + | Stress | Visual | OD @ 405 nm | pH |
|---|---|---|---|---|
| 5% sucrose | t = 0 | 0 | 0.114 | 6.0 |
| | 25° C. 0.5 m | 0 | 0.113 | 6.0 |
| | 25° C. 1 m | 0 | 0.112 | 6.1 |
| | 25° C. 3 m | 0 | 0.109 | 6.0 |
| | 25° C. 6 m | 0 | 0.110 | 6.1 |
| | 40° C. 7 d | 0 | 0.110 | 6.1 |
| | 40° C. 14 d | 0 | 0.112 | 6.0 |
| | 40° C. 21 d | 0 | 0.115 | 6.0 |
| | 40° C. 28 d | 0 | 0.111 | 6.1 |
| 10% sucrose | t = 0 | 0 | 0.116 | 6.0 |
| | 25° C. 0.5 m | 0 | 0.113 | 6.0 |
| | 25° C. 1 m | 0 | 0.114 | 6.0 |
| | 25° C. 3 m | 0 | 0.111 | 6.0 |
| | 25° C. 6 m | 0 | 0.110 | 6.1 |
| | 40° C. 7 d | 0 | 0.113 | 6.1 |
| | 40° C. 14 d | 0 | 0.114 | 6.0 |
| | 40° C. 21 d | 0 | 0.112 | 6.0 |
| | 40° C. 28 d | 0 | 0.114 | 6.0 |
| 15% sucrose | t = 0 | 0 | 0.114 | 6.0 |
| | 25° C. 0.5 m | 0 | 0.113 | 6.0 |
| | 25° C. 1 m | 0 | 0.113 | 6.0 |
| | 25° C. 3 m | 0 | 0.111 | 6.0 |
| | 25° C. 6 m | 0 | 0.113 | 6.1 |
| | 40° C. 7 d | 0 | 0.110 | 6.1 |
| | 40° C. 14 d | 0 | 0.110 | 6.0 |
| | 40° C. 21 d | 0 | 0.112 | 6.0 |
| | 40° C. 28 d | 0 | 0.113 | 6.0 |
| 20% sucrose | t = 0 | 0 | 0.113 | 6.0 |
| | 25° C. 0.5 m | 0 | 0.113 | 6.0 |
| | 25° C. 1 m | 0 | 0.113 | 6.0 |
| | 25° C. 3 m | 0 | 0.109 | 6.0 |
| | 25° C. 6 m | 0 | 0.113 | 6.0 |
| | 40° C. 7 d | 0 | 0.109 | 6.0 |
| | 40° C. 14 d | 0 | 0.114 | 6.0 |
| | 40° C. 21 d | 0 | 0.112 | 6.0 |
| | 40° C. 28 d | 0 | 0.112 | 6.0 |

TABLE 46

Accelerated Stability of High Concentration (100 mg/mL) H1H17161P Anti-EBOV Antibody with Thermal Stabilizers - SE-UPLC, RP-UPLC and CEX-UPLC Results

| Base Formulation+ | Stress | SE-UPLC % HMW | SE-UPLC % Monomer | SE-UPLC % LMW | RP-UPLC, mg/mL | CEX % Acidic | CEX % Main | CEX % Basic |
|---|---|---|---|---|---|---|---|---|
| 5% sucrose | t = 0 | 1.9 | 96.9 | 1.3 | 33 | 53.9 | 41.3 | 4.8 |
| | 40° C. 7 d | 1.4 | 97.2 | 1.5 | 33 | 56.5 | 39.0 | 4.5 |
| | 40° C. 14 d | 1.4 | 96.9 | 1.7 | 33 | 59.1 | 36.4 | 4.5 |
| | 40° C. 21 d | 1.5 | 96.5 | 2.0 | 34 | 61.5 | 33.9 | 4.7 |
| | 40° C. 28 d | 1.5 | 96.2 | 2.3 | 34 | 64.3 | 30.1 | 5.6 |
| | 25° C. 0.5 m | 1.5 | 97.2 | 1.3 | 33 | 55.7 | 40.5 | 3.8 |
| | 25° C. 1 m | 1.5 | 97.1 | 1.5 | 34 | 55.8 | 38.6 | 5.7 |
| | 25° C. 3 m | 1.6 | 96.6 | 1.9 | 33 | 62.1 | 35.3 | 2.6 |
| | 25° C. 6 m | 1.7 | 95.9 | 2.4 | 33 | 69.6 | 26.9 | 3.5 |
| 10% sucrose | t = 0 | 1.9 | 96.9 | 1.3 | 33 | 53.9 | 41.6 | 4.6 |
| | 40° C. 7 d | 1.3 | 97.2 | 1.5 | 34 | 56.3 | 39.0 | 4.7 |
| | 40° C. 14 d | 1.4 | 96.9 | 1.7 | 34 | 58.9 | 36.4 | 4.7 |
| | 40° C. 21 d | 1.5 | 96.6 | 2.0 | 34 | 61.5 | 33.8 | 4.7 |
| | 40° C. 28 d | 1.5 | 96.3 | 2.2 | 34 | 64.3 | 30.9 | 4.8 |
| | 25° C. 0.5 m | 1.4 | 97.3 | 1.3 | 34 | 54.0 | 41.6 | 4.4 |
| | 25° C. 1 m | 1.5 | 97. | 1.5 | 34 | 56.0 | 38.3 | 5.7 |
| | 25° C. 3 m | 1.5 | 96.6 | 1.9 | 34 | 62.3 | 35.0 | 2.7 |
| | 25° C. 6 m | 1.6 | 96.0 | 2.4 | 34 | 69.4 | 27.4 | 3.2 |
| 15% sucrose | t = 0 | 1.9 | 96.9 | 1.2 | 33 | 54.6 | 41.7 | 3.8 |
| | 40° C. 7 d | 1.3 | 97.2 | 1.5 | 33 | 56.5 | 39.6 | 3.9 |
| | 40° C. 14 d | 1.4 | 97.0 | 1.7 | 33 | 59.1 | 36.6 | 4.3 |
| | 40° C. 21 d | 1.4 | 96.6 | 2.0 | 34 | 61.4 | 33.5 | 5.1 |
| | 40° C. 28 d | 1.4 | 96.3 | 2.3 | 34 | 64.2 | 30.5 | 5.3 |
| | 25° C. 0.5 m | 1.4 | 97.3 | 1.3 | 33 | 54.6 | 40.5 | 4.9 |
| | 25° C. 1 m | 1.4 | 97. | 1.5 | 34 | 55.7 | 38.7 | 5.6 |
| | 25° C. 3 m | 1.5 | 96.7 | 1.9 | 34 | 61.9 | 35.3 | 2.8 |
| | 25° C. 6 m | 1.5 | 96.0 | 2.4 | 34 | 69.0 | 27.6 | 3.4 |
| 20% sucrose | t = 0 | 1.9 | 96.9 | 1.3 | 33 | 54.4 | 42.0 | 3.6 |
| | 40° C. 7 d | 1.3 | 97.2 | 1.5 | 33 | 56.3 | 38.8 | 4.9 |
| | 40° C. 14 d | 1.3 | 97.0 | 1.7 | 33 | 59.0 | 36.3 | 4.7 |

TABLE 46-continued

Accelerated Stability of High Concentration (100 mg/mL) H1H17161P Anti-EBOV
Antibody with Thermal Stabilizers - SE-UPLC, RP-UPLC and CEX-UPLC Results

| Base Formulation+ | Stress | SE-UPLC % HMW | SE-UPLC % Monomer | SE-UPLC % LMW | RP-UPLC, mg/mL | CEX % Acidic | CEX % Main | CEX % Basic |
|---|---|---|---|---|---|---|---|---|
| | 40° C. 21 d | 1.4 | 96.1 | 2.0 | 34 | 61.4 | 33.8 | 4.8 |
| | 40° C. 28 d | 1.4 | 96.4 | 2.2 | 34 | 64.1 | 30.6 | 5.3 |
| | 25° C. 0.5 m | 1.4 | 97.3 | 1.3 | 33 | 54.2 | 41.5 | 4.3 |
| | 25° C. 1 m | 1.4 | 97.1 | 1.5 | 34 | 55.7 | 38.4 | 5.9 |
| | 25° C. 3 m | 1.5 | 96.7 | 1.9 | 34 | 61.6 | 36.1 | 2.3 |
| | 25° C. 6 m | 1.5 | 96.1 | 2.5 | 34 | 68.9 | 27.6 | 3.6 |

TABLE 47

Accelerated Stability of High Concentration H1H17203P, H1H17139P, and
H1H17161P Anti-EBOV Antibodies with Thermal Stabilizers - Visual, OD,
pH, SE-UPLC, and RP-UPLC

| Base Formulation+ | Stress | Visual | OD @ 405 nm | pH | % HMW | % Native | % LMW | Con, mg/ml |
|---|---|---|---|---|---|---|---|---|
| 5% sucrose | t = 0 | 0 | 0.182 | 6.0 | 2.08 | 96.9 | 1.03 | 96 |
| | 25° C. 0.5 m | 0 | 0.183 | 6.1 | 2.2 | 96.66 | 1.14 | 98 |
| | 25° C. 1 m | 0 | 0.187 | 6.1 | 2.34 | 96.39 | 1.26 | 96 |
| | 25° C. 3 m | 0 | 0.177 | 6.1 | 2.65 | 95.6 | 1.75 | 95 |
| | 25° C. 6 m | 0 | 0.184 | 6.1 | 2.95 | 94.84 | 2.2 | 94 |
| | 40° C. 7 d | 0 | 0.179 | 6.1 | 2.29 | 96.39 | 1.31 | 98 |
| | 40° C. 14 d | 0 | 0.182 | 6.1 | 2.51 | 95.96 | 1.54 | 98 |
| | 40° C. 21 d | 0 | 0.191 | 6.1 | 2.68 | 95.45 | 1.87 | 95 |
| | 40° C. 28 d | 0 | 0.191 | 6.1 | 2.83 | 95.11 | 2.06 | 96 |
| | 40° C. 2 m | 0 | 0.193 | 6.1 | 3.56 | 93.35 | 3.09 | 96 |
| | 40° C. 3 m | 0 | 0.205 | 6.1 | 4.22 | 91.61 | 4.17 | 93 |
| 10% sucrose | t = 0 | 0 | 0.175 | 6.0 | 2.06 | 96.89 | 1.04 | 97 |
| | 25° C. 0.5 m | 0 | 0.180 | 6.0 | 2.14 | 96.71 | 1.15 | 99 |
| | 25° C. 1 m | 0 | 0.195 | 6.1 | 2.26 | 96.44 | 1.29 | 96 |
| | 25° C. 3 m | 0 | 0.177 | 6.1 | 2.56 | 95.68 | 1.76 | 95 |
| | 25° C. 6 m | 0 | 0.182 | 6.1 | 2.84 | 94.93 | 2.22 | 95 |
| | 40° C. 7 d | 0 | 0.180 | 6.1 | 2.23 | 96.44 | 1.33 | 97 |
| | 40° C. 14 d | 0 | 0.184 | 6.0 | 2.42 | 96.04 | 1.55 | 98 |
| | 40° C. 21 d | 0 | 0.187 | 6.1 | 2.57 | 95.57 | 1.85 | 96 |
| | 40° C. 28 d | 0 | 0.187 | 6.1 | 2.69 | 95.26 | 2.05 | 96 |
| | 40° C. 2 m | 0 | 0.194 | 6.1 | 3.29 | 93.66 | 3.05 | 97 |
| | 40° C. 3 m | 0 | 0.208 | 6.1 | 3.93 | 91.89 | 4.18 | 95 |
| 15% sucrose | t = 0 | 0 | 0.175 | 6.0 | 2.06 | 96.9 | 1.04 | 96 |
| | 25° C. 0.5 m | 0 | 0.177 | 6.0 | 2.11 | 96.73 | 1.16 | 98 |
| | 25° C. 1 m | 0 | 0.178 | 6.1 | 2.22 | 96.52 | 1.26 | 96 |
| | 25° C. 3 m | 0 | 0.179 | 6.1 | 2.49 | 95.78 | 1.73 | 96 |
| | 25° C. 6 m | 0 | 0.179 | 6.1 | 2.72 | 95.09 | 2.19 | 95 |
| | 40° C. 7 d | 0 | 0.181 | 6.1 | 2.17 | 96.5 | 1.32 | 98 |
| | 40° C. 14 d | 0 | 0.179 | 6.0 | 2.34 | 96.13 | 1.54 | 99 |
| | 40° C. 21 d | 0 | 0.183 | 6.1 | 2.48 | 95.72 | 1.81 | 95 |
| | 40° C. 28 d | 0 | 0.189 | 6.1 | 2.6 | 95.33 | 2.06 | 96 |
| | 40° C. 2 m | 0 | 0.194 | 6.1 | 3.12 | 93.85 | 3.03 | 96 |
| | 40° C. 3 m | 0 | 0.201 | 6.1 | 3.71 | 92.13 | 4.15 | 95 |
| 20% sucrose | t = 0 | 0 | 0.178 | 6.0 | 2.05 | 96.91 | 1.03 | 96 |
| | 25° C. 0.5 m | 0 | 0.174 | 6.0 | 2.07 | 96.78 | 1.14 | 99 |
| | 25° C. 1 m | 0 | 0.178 | 6.1 | 2.2 | 96.51 | 1.31 | 96 |
| | 25° C. 3 m | 0 | 0.181 | 6.0 | 2.42 | 95.81 | 1.77 | 95 |
| | 25° C. 6 m | 0 | 0.175 | 6.1 | 2.64 | 95.13 | 2.22 | 95 |
| | 40° C. 7 d | 0 | 0.184 | 6.1 | 2.15 | 96.53 | 1.33 | 98 |
| | 40° C. 14 d | 0 | 0.178 | 6.0 | 2.28 | 96.18 | 1.54 | 99 |
| | 40° C. 21 d | 0 | 0.185 | 6.1 | 2.42 | 95.71 | 1.87 | 96 |
| | 40° C. 28 d | 0 | 0.192 | 6.1 | 2.53 | 95.41 | 2.06 | 96 |
| | 40° C. 2 m | 0 | 0.192 | 6.0 | 3.02 | 93.93 | 3.05 | 96 |
| | 40° C. 2 m | 0 | 0.199 | 6.1 | 3.51 | 92.37 | 4.13 | 95 |

TABLE 48

Accelerated Stability of High Concentration (100 mg/mL) H1H17203P, H1H17139P, and H1H17161P Anti-EBOV Antibodies with Thermal Stabilizers - CEX-UPLC Results

| | | H1H17139P | | | H1H17203P | | | H1H17161P | | |
|---|---|---|---|---|---|---|---|---|---|---|
| Formulation | Stress | % Acidic | % Main | % Basic | % Acidic | % Main | % Basic | % Acidic | % Main | % Basic |
| 5% sucrose | t = 0 | 35.7 | 61.4 | 2.9 | 31.1 | 46.4 | 22.5 | 46.1 | 48.8 | 5.1 |
| | 40° C. | 37.0 | 59.5 | 3.5 | 32.5 | 45.6 | 21.9 | 50.4 | 44.3 | 5.3 |
| | 40° C. | 39.1 | 57.1 | 3.8 | 34.7 | 44.1 | 21.3 | 53.8 | 41.1 | 5.1 |
| | 40° C. | 41.2 | 55.0 | 3.8 | 36.7 | 43.0 | 20.4 | 54.8 | 39.0 | 6.2 |
| | 40° C. | 43.7 | 52.2 | 4.1 | 38.7 | 41.1 | 20.2 | 56.7 | 36.2 | 7.1 |
| | 40° C. | 53.2 | 42.5 | 4.3 | 46.1 | 31.7 | 22.2 | 71.2 | 24.4 | 4.4 |
| | 40° C. | 60.6 | 35.0 | 4.4 | 53.6 | 28.3 | 18.1 | 79.8 | 16.2 | 4.0 |
| | 25° C. | 35.7 | 61.2 | 3.2 | 31.3 | 46.4 | 22.3 | 48.0 | 46.5 | 5.5 |
| | 25° C. | 36.3 | 60.4 | 3.3 | 31.8 | 46.8 | 21.3 | 46.7 | 46.7 | 6.5 |
| | 25° C. | 39.3 | 57.6 | 3.1 | 35.3 | 45.3 | 19.4 | 56.9 | 40.4 | 2.6 |
| | 25° C. | 43.8 | 52.5 | 3.8 | 39.3 | 42.1 | 18.5 | 63.3 | 32.3 | 4.4 |
| 10% sucrose | t = 0 | 35.9 | 61.2 | 2.9 | 31.1 | 46.4 | 22.5 | 46.1 | 48.8 | 5.1 |
| | 40° C. | 36.9 | 59.5 | 3.6 | 32.5 | 45.5 | 22.0 | 50.2 | 44.0 | 5.8 |
| | 40° C. | 38.9 | 57.2 | 3.9 | 34.5 | 44.1 | 21.5 | 53.6 | 41.3 | 5.1 |
| | 40° C. | 41.1 | 54.9 | 4.0 | 36.6 | 43.0 | 20.4 | 54.1 | 38.6 | 7.3 |
| | 40° C. | 43.4 | 52.4 | 4.2 | 38.6 | 41.3 | 20.1 | 56.8 | 35.7 | 7.5 |
| | 40° C. | 52.7 | 42.9 | 4.4 | 45.8 | 32.4 | 21.8 | 71.0 | 24.6 | 4.5 |
| | 40° C. | 59.5 | 36.5 | 4.1 | 52.9 | 28.4 | 18.6 | 81.0 | 15.3 | 3.8 |
| | 25° C. | 35.6 | 61.2 | 3.2 | 31.3 | 46.3 | 22.4 | 48.0 | 46.6 | 5.4 |
| | 25° C. | 36.2 | 60.3 | 3.5 | 31.7 | 46.9 | 21.3 | 46.5 | 46.5 | 7.0 |
| | 25° C. | 39.1 | 57.7 | 3.2 | 35.1 | 45.1 | 19.8 | 56.7 | 40.2 | 3.1 |
| | 25° C. | 44.0 | 52.3 | 3.7 | 39.2 | 41.8 | 19.1 | 62.6 | 32.7 | 4.7 |
| 15% sucrose | t = 0 | 35.9 | 61.2 | 2.9 | 31.1 | 46.5 | 22.4 | 46.0 | 48.7 | 5.4 |
| | 40° C. | 36.7 | 59.5 | 3.8 | 32.5 | 45.6 | 21.9 | 50.5 | 43.9 | 5.6 |
| | 40° C. | 38.7 | 57.4 | 3.9 | 34.5 | 44.1 | 21.4 | 53.1 | 41.2 | 5.6 |
| | 40° C. | 40.9 | 54.9 | 4.1 | 36.4 | 42.9 | 20.7 | 53.4 | 38.9 | 7.7 |
| | 40° C. | 43.1 | 52.7 | 4.2 | 38.4 | 41.5 | 20.1 | 57.1 | 36.0 | 6.9 |
| | 40° C. | 52.4 | 43.0 | 4.6 | 45.5 | 32.8 | 21.8 | 70.1 | 24.9 | 4.9 |
| | 40° C. | 59.4 | 36.3 | 4.4 | 54.2 | 29.4 | 16.4 | 81.2 | 15.5 | 3.2 |
| | 25° C. | 35.6 | 61.2 | 3.2 | 31.3 | 46.5 | 22.2 | 47.9 | 46.7 | 5.4 |
| | 25° C. | 36.2 | 60.5 | 3.3 | 31.7 | 47.0 | 21.3 | 46.7 | 46.6 | 6.7 |
| | 25° C. | 39.0 | 57.7 | 3.3 | 35.0 | 44.9 | 20.1 | 56.1 | 39.6 | 4.3 |
| | 25° C. | 43.5 | 52.7 | 3.8 | 38.6 | 41.8 | 19.6 | 62.2 | 33.4 | 4.4 |
| 20% sucrose | t = 0 | 35.9 | 61.2 | 2.9 | 31.1 | 46.2 | 22.7 | 46.1 | 48.9 | 5.0 |
| | 40° C. | 36.7 | 59.6 | 3.6 | 32.4 | 45.1 | 22.5 | 50.1 | 44.5 | 5.4 |
| | 40° C. | 38.6 | 57.4 | 4.0 | 34.2 | 43.9 | 21.9 | 53.5 | 41.1 | 5.4 |
| | 40° C. | 40.6 | 55.2 | 4.2 | 36.2 | 43.0 | 20.8 | 53.5 | 38.9 | 7.6 |
| | 40° C. | 42.9 | 52.7 | 4.4 | 37.8 | 41.3 | 20.9 | 57.0 | 36.7 | 6.3 |
| | 40° C. | 51.7 | 43.6 | 4.7 | 44.8 | 32.5 | 22.7 | 66.4 | 27.4 | 6.2 |
| | 40° C. | 58.8 | 36.8 | 4.5 | 55.3 | 30.7 | 14.0 | 79.7 | 14.4 | 5.8 |
| | 25° C. | 35.6 | 61.2 | 3.2 | 31.3 | 46.4 | 22.3 | 47.9 | 46.7 | 5.5 |
| | 25° C. | 35.7 | 60.9 | 3.4 | 31.6 | 46.8 | 21.6 | 46.6 | 45.8 | 7.7 |
| | 25° C. | 38.6 | 58.1 | 3.3 | 34.7 | 45.4 | 20.0 | 56.9 | 40.6 | 2.5 |
| | 25° C. | 43.1 | 53.0 | 3.9 | 38.4 | 42.0 | 19.7 | 61.7 | 33.3 | 5.1 |

Example 10: Formulated Drug Substance (FDS) Research Stability Studies (12 months) for Individually Formulated H1H17203P C21P1 FDS, H1H17139P C21P1 FDS, and H1H17161P C2P11 FDS Research and clinical FDS are manufactured using comparable processes, and the methods used to assess the stability of research material are similar to the methods used to assess the stability of material intended for clinical studies. Consequently, the results obtained from the research stability studies can be used to assess the stability of material intended for clinical studies.

The present long-term storage stability study evaluated H1H17203P C2P1 FDS, H1H17139P C2P1 FDS, and H1H17161P C2P1 FDS stability through 12 months of storage at −80° C. and −30° C. H1H17203P C2P1 FDS, H1H17139P C2P1 FDS, and H1H17161P C2P1 FDS are stable for at least 12 months when stored at −80° C. and −30° C.

The long-term, ongoing stability studies continue for the duration of the stability protocol, as presented in Table 49. Samples were analyzed following the analysis plan outlined in Table 50. The analysis plan, preliminary acceptance criteria, and sampling plan are provided in Table 50.

TABLE 49

Summary of Formulated Drug Substance Stability Studies for H1H17203P, H1H17139P, and H1H17161P

| Study No. | Study Type | Container Closure | Storage Conditions | Study Duration | Available Data |
|---|---|---|---|---|---|
| H1H17203P-SS018 | Research | 5 mL gamma-irradiated polycarbonate vial with silicone lined closure | −80° C. | 84 months | 12 months |
| | | | −30° C. | 84 months | 12 months |
| | | | −20° C. | 3 months | 3 months |
| | | | 5° C. | 56 days | 56 days |
| | | | 25° C./60% RH | 28 days | 28 days |
| | | | 40° C./75% RH | 28 days | 28 days |
| | | | Agitation | 120 minutes | 120 minutes |
| | | | Freeze/Thaw | 8 cycles | 8 cycles |
| H1H17139P-SS018 | Research | 5 mL gamma-irradiated polycarbonate vial with silicone lined closure | −80° C. | 84 months | 12 months |
| | | | −30° C. | 84 months | 12 months |
| | | | −20° C. | 3 months | 3 months |
| | | | 5° C. | 56 days | 56 days |
| | | | 25° C./60% RH | 28 days | 28 days |
| | | | 40° C./75% RH | 28 days | 28 days |
| | | | Agitation | 120 minutes | 120 minutes |
| | | | Freeze/Thaw | 8 cycles | 8 cycles |
| H1H17161P-SS018 | Research | 5 mL gamma-irradiated polycarbonate vial with silicone lined closure | −80° C. | 84 months | 12 months |
| | | | −30° C. | 84 months | 12 months |
| | | | −20° C. | 3 months | 3 months |
| | | | 5° C. | 56 days | 56 days |
| | | | 25° C./60% RH | 28 days | 28 days |
| | | | 40° C./75% RH | 28 days | 28 days |
| | | | Agitation | 120 minutes | 120 minutes |
| | | | Freeze/Thaw | 8 cycles | 8 cycles |

RH, relative humidity

TABLE 50

Analysis Plan and Preliminary Acceptance Criteria for H1H17203P, H1H17139P, H1H17161P Formulated Drug Substance Research Stability Studies

| Assay | Preliminary Acceptance Criteria | Research Samples to be Analyzed |
|---|---|---|
| Physical form/Condition | Liquid essentially free from visible particulates | All samples |
| Clarity | Not more turbid than Reference Suspension IV | All samples |
| Color | Not more intensely colored than Reference Solution BY2 | All samples |
| pH | 5.8 to 6.2 | All samples |
| Total Protein Content (A280) | 90 to 110 mg/mL | N/A |
| Total Protein Content (RP-UPLC) | 90 to 110 mg/mL | All samples |
| Potency: Pseudovirus Neutralization Assay | 50% to 150% of reference standard | t = 0, 6, 12, 24, 36, 48, 60, 72 and 84 months at −80° C., and −30° C., 3 months (−20° C.), 56 days (5° C.), 28 days (25° C./60% RH), and 28 days (40° C./75% RH) |
| Potency: ADCC assay | 50% to 150% of reference standard | t = 0, 6, 12, 24, 36, 48, 60, 72 and 84 months at −80° C., and −30° C., 3 months (−20° C.), 56 days (5° C.), 28 days (25° C./60% RH), and 28 days (40° C./75% RH) |
| Purity by Reduced MCE a. % Purity b. % NGHC c. % LMW | a. HC peak + LC peak ≥80% total peak area b. ≤15% NGHC c. ≤10% LMW species | t = 0, 6, 12, 24, 36, 48, 60, 72 and 84 months at −80° C., and −30° C., 3 months (−20° C.), 56 days (5° C.), 28 days (25° C./60% RH), and 28 days (40° C./75% RH) |
| Purity by Non-reduced MCE a. % Purity b. % LMW c. % HMW | a. MP + PGMP ≥80% total peak area b. ≤15% LMW species c. N/A | t = 0, 6, 12, 24, 36, 48, 60, 72 and 84 months at −80° C., and −30° C., 3 months (−20° C.), 56 days (5° C.), 28 days (25° C./60% RH), and 28 days (40° C./75% RH) |
| Purity by SE-UPLC a. % Main Peak Purity b. % LMW c. % HMW | a. ≥90% total peak area b. ≤5% LMW species c. ≤7% HMW species | All samples |
| Charge Variant Analysis by CEX-UPLC a. % Region 1 b. % Region 2 c. % Region 3 | a. ≤65% Region 1 b. ≥35% Region 2 c. ≤20% Region 3 | All samples |

$A_{280}$, absorbance at 280 nm; CEX, cation-exchange chromatography; SE-UPLC, size-exclusion ultra performance liquid chromatography; HMW, high molecular weight; HC, heavy chain; LC, light chain; LMW, low molecular weight; MCE, microchip capillary electrophoresis; NGHC, non-glycosylated heavy chain Formulated Drug Substance Stability Study Results Long-Term Storage Research Stability Study Results of H1H17203P FDS In the research stability studies, C2P1 FDS was found to be physically and chemically stable when stored at −80° C. and −30° C. (Table 51 and Table 52, respectively). No appreciable change in the physical or chemical stability was detected in any of the monitored attributes. Research stability studies examining C2P1 FDS under the long-term storage conditions will continue through 84 months.

Accelerated Stability Study Results of H1H17203P FDS

The research stability studies indicated that C2P1 FDS was physically and chemically stable when stored at −20° C. for 3 months and 5° C. for 56 days (Table 53 and Table 54). No appreciable change in the physical or chemical stability was detected in any of the monitored attributes. Following storage at 25° C./60% RH (Table 54) for 28 days, a minor increase of 0.3% in HMW species was observed by SE-UPLC for H1H17203P. No meaningful change was observed in other monitored attributes following incubation at 25° C./60% RH for 28 days. Research studies examining C2P1 FDS under the accelerated storage condition of −20° C., 5° C. and 25° C./60% RH are complete.

Stress Stability Study Results of H1H17203P FDS

Research stability study results from the analysis of C2P1 FDS under stress conditions of 40° C./75% RH are provided in Table 55. Increase of 1.2% in HMW and 0.4% in LMW species were observed by SE-UPLC; and increases of 11.1% in Region 1 were observed by CEX-UPLC. No meaningful change in other monitored attributes was observed. The C2P1 FDS maintained potency following incubation at 40° C./75% RH for 28 days. Research studies examining C2P1 FDS under the stress storage condition of 40° C./75% RH are complete.

Research stability results from the analysis of C2P1 FDS following agitation and freeze/thaw conditions are provided in Table 56. C2P1 FDS was physically and chemically stable when agitated (vortexed at ambient temperature) for 120 minutes or when subjected to 8 freeze/thaw cycles (freezing at −30° C. and thawing at room temperature). No appreciable change in the physical or chemical stability of H1H17203P was observed in any of the monitored attributes. Research studies examining C2P1 FDS under agitation and freeze/thaw conditions are complete.

Long-Term Storage Research Stability Study Results of H1H17139P FDS

In the research stability studies, C2P1 FDS was found to be physically and chemically stable when stored at −80° C. and −30° C. (Table 57 and Table 58). No appreciable change in the physical or chemical stability was detected in any of the monitored attributes. Research stability studies examining C2P1 FDS under the long-term storage conditions will continue through 84 months.

Accelerated Stability Study Results of H1H17139P FDS

The research stability studies indicated that C2P1 FDS was physically and chemically stable when stored at −20° C. for 3 months and 5° C. for 56 days (Table 59 and Table 60). No appreciable change in the physical or chemical stability was detected in any of the monitored attributes. Following storage at 25° C./60% RH (Table 60) for 28 days, a minor increase of 0.3% in HMW species was observed by SE-UPLC. No meaningful change was observed in other monitored attributes following incubation at 25° C./60% RH for 28 days. Research studies examining C2P1 FDS under the accelerated storage condition of −20° C., 5° C. and 25° C./60% RH are complete.

Stress Stability Study Results of H1H17139P FDS

Research stability study results from the analysis of C2P1 FDS under stress conditions of 40° C./75% RH are provided in Table 61. An increase of 0.9% in HMW species and 0.4% in LMW species were observed by SE-UPLC; and an increase of 11.1% in Region 1 and decrease of 12.9% in Region 2 was observed by CEX-UPLC. No meaningful change in other monitored attributes was observed. The C2P1 FDS maintained potency following incubation at 40° C./75% RH for 28 days. Research studies examining C2P1 FDS under the stress storage condition of 40° C./75% RH are complete.

Research stability results from the analysis of C2P1 FDS following agitation and freeze/thaw conditions are provided in Table 62. C2P1 FDS was physically and chemically stable when agitated (vortexed at ambient temperature) for 120 minutes or when subjected to 8 freeze/thaw cycles (freezing at −30° C. and thawing at room temperature). No appreciable change in the physical or chemical stability of H1H17139P was observed in any of the monitored attributes. Research studies examining C2P1 FDS under agitation and freeze/thaw conditions are complete.

Long-Term Storage Research Stability Study Results of H1H17161P FDS

In the research stability studies, C2P1 FDS was found to be physically and chemically stable when stored at −80° C. and −30° C. (Table 63 and Table 64). No appreciable change in the physical or chemical stability was detected in any of the monitored attributes. Research stability studies examining C2P1 FDS under the long-term storage conditions will continue through 84 months.

Accelerated Stability Study Results of H1H17161P FDS

The research stability studies indicated that C2P1 FDS was physically and chemically stable when stored at −20° C. for 3 months and 5° C. for 56 days (Table 65 and Table 66). No appreciable change in the physical or chemical stability was detected in any of the monitored attributes. Following storage at 25° C./60% RH (Table 66) for 28 days, a minor increase of 0.4% in HMW species was observed by SE-UPLC. No meaningful change was observed in other monitored attributes following incubation at 25° C./60% RH for 28 days. Research studies examining C2P1 FDS under the accelerated storage condition of −20° C., 5° C., and 25° C./60% RH are complete.

Stress Stability Study Results of H1H17161P FDS

Research stability study results from the analysis of C2P1 FDS under stress conditions of 40° C./75% RH are provided in Table 67. An increase of 1.0% in HMW species and 0.4% in LMW species were observed by SE-UPLC; and an increase of 14.4% in Region 1 was observed by CEX-UPLC. No meaningful change in other monitored attributes was observed. The C2P1 FDS maintained potency following incubation at 40° C./75% RH for 28 days. Research studies examining C2P1 FDS under the stress storage condition of 40° C./75% RH are complete.

Research stability results from the analysis of C2P1 FDS following agitation and freeze/thaw conditions are provided in Table 68. C2P1 FDS was physically and chemically stable when agitated (vortexed at ambient temperature) for 120 minutes or when subjected to 8 freeze/thaw cycles (freezing at −30° C. and thawing at room temperature). No appreciable change in the physical or chemical stability of H1H17161P was observed in any of the monitored attributes. Research studies examining C2P1 FDS under agitation and freeze/thaw conditions are complete.

Stability Conclusions

H1H17203P C2P1 FDS, H1H17139P C2P1 FDS, and H1H17161P C2P1 FDS can each withstand short exposures to refrigeration, room temperature, and agitation stress, and can be frozen and thawed without compromising either the physical or chemical stability of the protein. These results indicate that the H1H17203P C2P1 FDS, H1H17139P C2P1 FDS, and H1H17161P C2P1 FDS are stable during the manufacture of the three-way combination drug product (DP). Exposure of H1H17203P C2P1 FDS, H1H17139P C2P1 FDS, and H1H17161P C2P1 FDS to temperatures above room temperature should be avoided.

Recommended Storage Conditions

The recommended long-term storage temperature for H1H17203P C2P1 FDS, H1H17139P C2P1 FDS, and H1H17161P C2P1 FDS is −30° C.

TABLE 51

Research Stability of 100 mg/mL H1H17203P C2P1 Formulated Drug Substance Stored at −80° C.

| Formulation | 100 mg/mL H1H17203P, 10 mM L-histidine, 10% (w/v) sucrose, 0.1% (w/v) polysorbate 80, pH 6.0 | | | | | |
|---|---|---|---|---|---|---|
| Container/Closure | 5 mL gamma-irradiated polycarbonate vial with HDPE closure | | | | | |
| | Length of Storage at −80° C. (months) | | | | | |
| Assay | 0 | 1 | 3 | 6 | 9 | 12 |
| Physical form/Condition | LEFVP | LEFVP | LEFVP | LEFVP | LEFVP | LEFVP |
| Clarity | ≤6 NTU | ≤6 NTU | ≤6 NTU | ≤6 NTU | ≤6 NTU | ≤6 NTU |
| Color | ≤BY4 | ≤BY4 | ≤BY4 | ≤BY4 | ≤BY4 | ≤BY4 |
| pH | 6.0 | 6.0 | 6.0 | 6.1 | 6.0 | 6.0 |
| Total Protein Content by RP-UPLC (mg/mL) | 98.7 | 99.7 | 98.7 | 98.1 | 99.0 | 99.2 |
| Non-reduced MCE (%) Purity | 95.9 | NR | NR | 95.9 | NR | 95.7 |
| Non-reduced MCE (%) LMW | 3.6 | NR | NR | 3.5 | NR | 4.0 |
| Reduced MCE (%) Purity | 91.1 | NR | NR | 92.0 | NR | 92.1 |
| Reduced MCE (%) NGHC | 7.2 | NR | NR | 7.0 | NR | 7.2 |
| Reduced MCE (%) LMW | 0.4 | NR | NR | 0.2 | NR | 0.2 |
| Purity by SE-UPLC (%) Main | 99.1 | 99.1 | 99.1 | 99.1 | 99.1 | 99.1 |
| Purity by SE-UPLC (%) LMW | 0.1 | 0.1 | 0.1 | 0.1 | 0.1 | 0.1 |
| Purity by SE-UPLC (%) HMW | 0.8 | 0.8 | 0.8 | 0.8 | 0.8 | 0.8 |
| Charge Variant Analysis by CEX-UPLC (%) Region 1 | 34.7 | 34.7 | 34.5 | 34.5 | 34.7 | 34.7 |
| Charge Variant Analysis by CEX-UPLC (%) Region 2 | 53.5 | 53.5 | 53.7 | 53.6 | 54.0 | 54.0 |
| Charge Variant Analysis by CEX-UPLC (%) Region 3 | 11.8 | 11.8 | 11.8 | 11.9 | 11.3 | 11.3 |
| Relative Potency (%) Pseudovirus Neutralization Assay | 90 | NR | NR | 96 | NR | 104 |
| Relative Potency (%) ADCC assay | 80 | NR | NR | 118 | NR | 91 |

CEX, cation exchange;
FDS, formulated drug substance;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
RP, reversed-phase;
SE, size exclusion;
UPLC, ultra performance liquid chromatography;
ADCC, Antibody-Dependent Cellular Cytotoxicity;

TABLE 52

Research Stability of 100 mg/mL H1H17203P C2P1 Formulated Drug Substance Stored at −30° C.

| Formulation | 100 mg/mL H1H17203P, 10 mM L-histidine, 10% (w/v) sucrose, 0.1% (w/v) polysorbate 80, pH 6.0 | | | | | |
|---|---|---|---|---|---|---|
| Container/Closure | 5 mL gamma-irradiated polycarbonate vial with HDPE closure | | | | | |
| | Length of Storage at −30° C. (months) | | | | | |
| Assay | 0 | 1 | 3 | 6 | 9 | 12 |
| Physical form/Condition | LEFVP | LEFVP | LEFVP | LEFVP | LEFVP | LEFVP |
| Clarity | ≤6 NTU | ≤6 NTU | ≤6 NTU | ≤6 NTU | ≤6 NTU | ≤6 NTU |
| Color | ≤BY4 | ≤BY4 | ≤BY4 | ≤BY4 | ≤BY4 | ≤BY4 |
| pH | 6.0 | 6.0 | 6.0 | 6.1 | 6.0 | 6.0 |
| Total Protein Content by RP-UPLC (mg/mL) | 98.7 | 99.2 | 98.0 | 98.3 | 99.0 | 99.6 |
| Non-reduced MCE (%) Purity | 95.9 | NR | NR | 96.0 | NR | 95.6 |
| Non-reduced MCE (%) LMW | 3.6 | NR | NR | 3.5 | NR | 4.1 |
| Reduced MCE (%) Purity | 91.1 | NR | NR | 91.1 | NR | 92.2 |
| Reduced MCE (%) NGHC | 7.2 | NR | NR | 7.3 | NR | 7.0 |
| Reduced MCE (%) LMW | 0.4 | NR | NR | 0.4 | NR | 0.2 |
| Purity by SE-UPLC (%) Main | 99.1 | 99.1 | 99.1 | 99.1 | 99.1 | 99.1 |
| Purity by SE-UPLC (%) LMW | 0.1 | 0.1 | 0.1 | 0.1 | 0.1 | 0.1 |
| Purity by SE-UPLC (%) HMW | 0.8 | 0.8 | 0.8 | 0.8 | 0.8 | 0.8 |

TABLE 52-continued

Research Stability of 100 mg/mL H1H17203P C2P1 Formulated Drug Substance Stored at −30° C.

| Formulation | 100 mg/mL H1H17203P, 10 mM L-histidine, 10% (w/v) sucrose, 0.1% (w/v) polysorbate 80, pH 6.0 |
| --- | --- |
| Container/Closure | 5 mL gamma-irradiated polycarbonate vial with HDPE closure |

| | | Length of Storage at −30° C. (months) | | | | | |
| --- | --- | --- | --- | --- | --- | --- | --- |
| Assay | | 0 | 1 | 3 | 6 | 9 | 12 |
| Charge Variant | Region 1 | 34.7 | 34.8 | 34.5 | 34.5 | 34.7 | 34.7 |
| Analysis by | Region 2 | 53.5 | 53.5 | 53.7 | 53.5 | 53.9 | 54.0 |
| CEX-UPLC (%) | Region 3 | 11.8 | 11.8 | 11.8 | 12.0 | 11.4 | 11.3 |
| Relative Potency (%) | Pseudovirus Neutralization Assay | 90 | NR | NR | 90 | NR | 106 |
| | ADCC assay | 80 | NR | NR | 101 | NR | 84 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography;
ADCC, Antibody-dependent cellular cytotoxicity

TABLE 53

Research Stability of 100 mg/mL H1H17203P C2P1 Formulated Drug Substance - Effect of Accelerated Conditions at −20° C.

| Formulation | 100 mg/mL H1H17203P, 10 mM L-histidine, 10% (w/v) sucrose, 0.1% (w/v) polysorbate 80, pH 6.0 |
| --- | --- |
| Container/Closure | 5 mL gamma-irradiated polycarbonate vial with HDPE closure |

| | | Length of Storage at −20° C. (months) | | | |
| --- | --- | --- | --- | --- | --- |
| Assay | | 0 | 1 | 2 | 3 |
| Physical form/Condition | | LEFVP | LEFVP | LEFVP | LEFVP |
| Clarity | | ≤6 NTU | ≤6 NTU | ≤6 NTU | ≤6 NTU |
| Color | | ≤BY4 | ≤BY4 | ≤BY4 | ≤BY4 |
| pH | | 6.0 | 6.0 | 6.0 | 6.0 |
| Total Protein Content by RP-UPLC (mg/mL) | | 98.7 | 99.8 | 98.2 | 99.0 |
| Non-reduced MCE (%) | Purity | 95.9 | NR | NR | 95.9 |
| | LMW | 3.6 | NR | NR | 3.4 |
| Reduced MCE (%) | Purity | 91.1 | NR | NR | 91.9 |
| | NGHC | 7.2 | NR | NR | 6.9 |
| | LMW | 0.4 | NR | NR | 0.4 |
| Purity by SE-UPLC (%) | Main | 99.1 | 99.1 | 99.1 | 99.1 |
| | LMW | 0.1 | 0.1 | 0.1 | 0.1 |
| | HMW | 0.8 | 0.8 | 0.8 | 0.8 |
| CEX-UPLC (%) | Region 1 | 34.7 | 34.7 | 34.5 | 34.5 |
| | Region 2 | 53.5 | 53.5 | 53.8 | 53.6 |
| | Region 3 | 11.8 | 11.8 | 11.7 | 11.9 |
| Relative Potency (%) | Pseudovirus Neutralization Assay | 90 | NR | NR | 92 |
| | ADCC assay | 80 | NR | NR | 102 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size exclusion; UPLC, ultra performance liquid chromatography; ADCC, Antibody-Dependent Cellular Cytotoxicity;

TABLE 54

Research Stability of 100 mg/mL H1H17203P C2P1 Formulated Drug Substance - Effect of Accelerated Conditions

| Formulation | 100 mg/mL H1H17203P, 10 mM L-histidine, 10% (w/v) sucrose, 0.1% (w/v) polysorbate 80, pH 6.0 |
| --- | --- |
| Container/Closure | 5 mL gamma-irradiated polycarbonate vial with HDPE closure |

| | | 5° C. Storage (days) | | | | 25° C./60% RH Storage (days) | | |
| --- | --- | --- | --- | --- | --- | --- | --- | --- |
| Assay | t = 0 | 14 | 28 | 56 | 7 | 14 | 28 |
| Physical form/Condition | LEFVP | LEFVP | LEFVP | LEFVP | LEFVP | LEFVP | LEFVP |
| Clarity | ≤6 NTU | ≤6 NTU | ≤6 NTU | ≤6 NTU | ≤6 NTU | ≤6 NTU | ≤6 NTU |
| Color | ≤BY4 | ≤BY4 | ≤BY4 | ≤BY4 | ≤BY4 | ≤BY4 | ≤BY4 |

TABLE 54-continued

Research Stability of 100 mg/mL H1H17203P C2P1 Formulated Drug Substance - Effect of Accelerated Conditions Formulation: 100 mg/mL H1H17203P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | t = 0 | 5° C. Storage (days) 14 | 28 | 56 | 25° C./60% RH Storage (days) 7 | 14 | 28 |
|---|---|---|---|---|---|---|---|---|
| pH | | 6.0 | 6.0 | 6.0 | 6.0 | 6.0 | 6.0 | 6.0 |
| Total Protein Content by RP-UPLC (mg/mL) | | 98.7 | 98.2 | 100.0 | 99.0 | 99.6 | 98.0 | 100.9 |
| Non-reduced MCE (%) | Purity | 95.9 | NR | NR | 95.5 | NR | NR | 95.5 |
| | LMW | 3.6 | NR | NR | 3.5 | NR | NR | 3.8 |
| Reduced MCE (%) | Purity | 91.1 | NR | NR | 92.2 | NR | NR | 91.6 |
| | NGHC | 7.2 | NR | NR | 7.0 | NR | NR | 7.1 |
| | LMW | 0.4 | NR | NR | 0.1 | NR | NR | 0.5 |
| Purity by SE-UPLC (%) | Main | 99.1 | 99.1 | 99.0 | 99.0 | 99.0 | 98.9 | 98.8 |
| | LMW | 0.1 | 0.1 | 0.1 | 0.1 | 0.1 | 0.1 | 0.2 |
| | HMW | 0.8 | 0.8 | 0.8 | 0.9 | 0.9 | 0.9 | 1.1 |
| CEX-UPLC (%) | Region 1 | 34.7 | 34.7 | 34.7 | 34.4 | 34.6 | 34.9 | 35.5 |
| | Region 2 | 53.5 | 53.6 | 53.6 | 53.9 | 53.8 | 53.8 | 53.7 |
| | Region 3 | 11.8 | 11.7 | 11.7 | 11.7 | 11.6 | 11.3 | 10.9 |
| Relative Potency (%) | Pseudovirus Neutralization Assay | 90 | NR | NR | 87 | NR | NR | 86 |
| | ADCC assay | 80 | NR | NR | 142 | NR | NR | 98 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography;
ADCC, Antibody-dependent cellular cytotoxicity

TABLE 55

Research Stability of 100 mg/mL H1H17203P C2P1 Formulated Drug Substance - Effects of Stress Conditions Formulation: 100 mg/mL H1H17203P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | t = 0 | 40° C./75% RH Storage (days) 7 | 14 | 28 |
|---|---|---|---|---|---|
| Physical form/Condition | | LEFVP | LEFVP | LEFVP | LEFVP |
| Clarity | | ≤6 NTU | ≤6 NTU | ≤6 NTU | ≤6 NTU |
| Color | | ≤BY4 | ≤BY4 | ≤BY4 | ≤BY4 |
| pH | | 6.0 | 6.0 | 6.0 | 6.0 |
| Total Protein Content by RP-UPLC (mg/mL) | | 98.7 | 100.8 | 99.2 | 102.3 |
| Non-reduced MCE (%) | Purity | 95.9 | NR | NR | 93.6 |
| | LMW | 3.6 | NR | NR | 5.6 |
| Reduced MCE (%) | Purity | 91.1 | NR | NR | 91.5 |
| | NGHC | 7.2 | NR | NR | 6.9 |
| | LMW | 0.4 | NR | NR | 0.4 |
| Purity by SE-UPLC (%) | Main | 99.1 | 98.8 | 98.4 | 97.5 |
| | LMW | 0.1 | 0.2 | 0.3 | 0.5 |
| | HMW | 0.8 | 1.0 | 1.4 | 2.0 |
| CEX-UPLC (%) | Region 1 | 34.7 | 36.0 | 39.5 | 45.8 |
| | Region 2 | 53.5 | 52.7 | 49.8 | 43.8 |
| | Region 3 | 11.8 | 11.3 | 10.7 | 10.4 |
| Relative Potency (%) | Pseudovirus Neutralization Assay | 90 | NR | NR | 85 |
| | ADCC assay | 80 | NR | NR | 103 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size-exclusion; UPLC, ultra performance liquid chromatography; ADCC, Antibody-dependent cellular cytotoxicity

TABLE 56

Research Stability of 100 mg/mL H1H17203P C2P1 Formulation Drug Substance - Effect of Agitation, and Freezing and Thawing Formulation: 100 mg/mL H1H17203P, 10 mM L-histidine, 10% (w/v) sucrose, 0.1% (w/v) polysorbate 80, pH 6.0
Container/Closure: 5 mL gamma-irradiated polycarbonate vial with HDPE

| Assay | | t = 0 | Agitation (minutes) 60 | 120 | Freeze/Thaw (cycles) 4 | 8 |
|---|---|---|---|---|---|---|
| Physical form/Condition | | LEFVP | LEFVP | LEFVP | LEFVP | LEFVP |
| Clarity | | ≤6 NTU | ≤6 NTU | ≤6 NTU | ≤6 NTU | ≤6 NTU |
| Color | | ≤BY4 | ≤BY4 | ≤BY4 | ≤BY4 | ≤BY4 |
| pH | | 6.0 | 6.0 | 6.0 | 6.0 | 6.0 |
| Total Protein Content by RP-UPLC (mg/mL) | | 98.7 | 100.2 | 100.3 | 99.7 | 100.2 |
| Non-reduced MCE (%) | Purity | 95.9 | NR | 96.2 | NR | 95.9 |
| | LMW | 3.6 | NR | 3.4 | NR | 3.5 |
| Reduced MCE (%) | Purity | 91.1 | NR | 91.5 | NR | 91.4 |
| | NGHC | 7.2 | NR | 7.3 | NR | 7.0 |
| | LMW | 0.4 | NR | 0.2 | NR | 0.3 |
| Purity by SE-UPLC (%) | Main | 99.1 | 99.1 | 99.1 | 99.1 | 99.1 |
| | LMW | 0.1 | 0.1 | 0.1 | 0.1 | 0.1 |
| | HMW | 0.8 | 0.8 | 0.8 | 0.8 | 0.8 |
| CEX-UPLC (%) | Region 1 | 34.7 | 34.8 | 34.7 | 34.8 | 34.8 |
| | Region 2 | 53.5 | 53.5 | 53.6 | 53.5 | 53.5 |
| | Region 3 | 11.8 | 11.8 | 11.7 | 11.8 | 11.7 |
| Relative Potency (%) | Pseudovirus Neutralization Assay | 90 | NR | 89 | NR | 86 |
| | ADCC assay | 80 | NR | 109 | NR | 96 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography;
ADCC, Antibody-dependent cellular cytotoxicity

TABLE 57

Research Stability of 100 mg/mL H1H17139P C2P1 Formulated Drug Substance Stored at −80° C.

Formulation: 100 mg/mL H1H17139P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | Length of Storage at −80° C. (months) 0 | 1 | 3 | 6 | 9 | 12 |
|---|---|---|---|---|---|---|---|
| Physical form/Condition | | LEFVP | LEFVP | LEFVP | LEFVP | LEFVP | LEFVP |
| Clarity | | ≤6 NTU | ≤6 NTU | ≤6 NTU | ≤6 NTU | ≤6 NTU | ≤6 NTU |
| Color | | ≤BY4 | ≤BY4 | ≤BY4 | ≤BY4 | ≤BY4 | ≤BY4 |
| pH | | 6.0 | 6.0 | 6.1 | 6.0 | 6.0 | 6.0 |
| Total Protein Content by RP-UPLC (mg/mL) | | 94.4 | 93.8 | 96.8 | 95.3 | 97.0 | 96.8 |
| Non-reduced MCE (%) | Purity | 95.0 | NR | NR | 95.2 | NR | 94.9 |
| | LMW | 4.8 | NR | NR | 4.7 | NR | 4.8 |
| Reduced MCE (%) | Purity | 95.6 | NR | NR | 95.7 | NR | 95.7 |
| | NGHC | 3.4 | NR | NR | 3.4 | NR | 3.5 |
| | LMW | 0.2 | NR | NR | 0.2 | NR | 0.1 |
| Purity by SE-UPLC (%) | Main | 99.3 | 99.4 | 99.3 | 99.3 | 99.4 | 99.3 |
| | LMW | 0.1 | 0.0 | 0.1 | 0.1 | 0.1 | 0.1 |
| | HMW | 0.6 | 0.6 | 0.6 | 0.6 | 0.6 | 0.6 |
| Charge Variant | Region 1 | 34.3 | 34.2 | 34.2 | 32.9 | 32.8 | 34.1 |
| | Region 2 | 62.1 | 62.2 | 62.2 | 64.0 | 64.0 | 62.2 |

TABLE 57-continued

Research Stability of 100 mg/mL H1H17139P C2P1 Formulated Drug Substance Stored at −80° C.

| Formulation | 100 mg/mL H1H17139P, 10 mM L-histidine, 10% (w/v) sucrose, 0.1% (w/v) polysorbate 80, pH 6.0 | | | | | |
|---|---|---|---|---|---|---|
| Container/Closure | 5 mL gamma-irradiated polycarbonate vial with HDPE closure | | | | | |
| | | Length of Storage at −80° C. (months) | | | | |
| Assay | | 0 | 1 | 3 | 6 | 9 | 12 |
| Analysis by CEX-UPLC (%) | Region 3 | 3.6 | 3.6 | 3.6 | 3.1 | 3.1 | 3.6 |
| Relative Potency (%) | ADCC assay | 92 | NR | NR | 99 | NR | 91 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography;
ADCC, Antibody-dependent cellular cytotoxicity

TABLE 58

Research Stability of 100 mg/mL H1H17139P C2P1 Formulated Drug Substance Stored at −30° C.

| Formulation | | 100 mg/mL H1H17139P, 10 mM L-histidine, 10% (w/v) sucrose, 0.1% (w/v) polysorbate 80, pH 6.0 | | | | | |
|---|---|---|---|---|---|---|---|
| Container/Closure | | 5 mL gamma-irradiated polycarbonate vial with HDPE closure | | | | | |
| | | Length of Storage at −30° C. (months) | | | | | |
| Assay | | 0 | 1 | 3 | 6 | 9 | 12 |
| Physical form/Condition | | LEFVP | LEFVP | LEFVP | LEFVP | LEFVP | LEFVP |
| Clarity | | ≤6 NTU | ≤6 NTU | ≤6 NTU | ≤6 NTU | ≤6 NTU | ≤6 NTU |
| Color | | ≤BY4 | ≤BY4 | ≤BY4 | ≤BY4 | ≤BY4 | ≤BY4 |
| pH | | 6.0 | 6.0 | 6.1 | 6.0 | 6.0 | 6.0 |
| Total Protein Content by RP-UPLC (mg/mL) | | 94.4 | 94.2 | 96.4 | 95.9 | 96.2 | 97.4 |
| Non-reduced MCE (%) | Purity | 95.0 | NR | NR | 94.7 | NR | 94.9 |
| | LMW | 4.8 | NR | NR | 5.0 | NR | 4.9 |
| Reduced MCE (%) | Purity | 95.6 | NR | NR | 95.8 | NR | 96.0 |
| | NGHC | 3.4 | NR | NR | 3.3 | NR | 3.3 |
| | LMW | 0.2 | NR | NR | 0.2 | NR | 0.1 |
| Purity by SE-UPLC (%) | Main | 99.3 | 99.3 | 99.3 | 99.3 | 99.3 | 99.3 |
| | LMW | 0.1 | 0.1 | 0.1 | 0.1 | 0.1 | 0.1 |
| | HMW | 0.6 | 0.6 | 0.6 | 0.6 | 0.6 | 0.6 |

TABLE 58-continued

Research Stability of 100 mg/mL H1H17139P C2P1 Formulated Drug Substance Stored at −30° C.

| Formulation | 100 mg/mL H1H17139P, 10 mM L-histidine, 10% (w/v) sucrose, 0.1% (w/v) polysorbate 80, pH 6.0 |
| --- | --- |
| Container/Closure | 5 mL gamma-irradiated polycarbonate vial with HDPE closure |

| Assay | | Length of Storage at −30° C. (months) | | | | | |
| --- | --- | --- | --- | --- | --- | --- | --- |
| | | 0 | 1 | 3 | 6 | 9 | 12 |
| Charge Variant Analysis by CEX-UPLC (%) | Region 1 | 34.3 | 34.2 | 34.2 | 33.1 | 32.8 | 34.2 |
| | Region 2 | 62.1 | 62.2 | 62.2 | 63.9 | 64.1 | 62.1 |
| | Region 3 | 3.6 | 3.6 | 3.6 | 3.0 | 3.1 | 3.8 |
| Relative Potency (%) | ADCC assay | 92 | NR | NR | 79 | NR | 94 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography;
ADCC, Antibody-dependent cellular cytotoxicity

TABLE 59

Research Stability of 100 mg/mL H1H17139P C2P1 Formulated Drug Substance - Effect of Accelerated Conditions at −20° C.

| Formulation | 100 mg/mL H1H17139P, 10 mM L-histidine, 10% (w/v) sucrose, 0.1% (w/v) polysorbate 80, pH 6.0 |
| --- | --- |
| Container/Closure | 5 mL gamma-irradiated polycarbonate vial with HDPE closure |

| Assay | | Length of Storage at −20° C. (months) | | | |
| --- | --- | --- | --- | --- | --- |
| | | 0 | 1 | 2 | 3 |
| Physical form/Condition | | LEFVP | LEFVP | LEFVP | LEFVP |
| Clarity | | ≤6 NTU | ≤6 NTU | ≤6 NTU | ≤6 NTU |
| Color | | ≤BY4 | ≤BY4 | ≤BY4 | ≤BY4 |
| pH | | 6.0 | 6.0 | 6.0 | 6.1 |
| Total Protein Content by RP-UPLC (mg/mL) | | 94.4 | 94.7 | 94.4 | 96.8 |
| Non-reduced MCE (%) | Purity | 95.0 | NR | NR | 95.1 |
| | LMW | 4.8 | NR | NR | 4.8 |
| | HMW | 0.2 | NR | NR | 0.2 |
| Reduced MCE (%) | Purity | 95.6 | NR | NR | 95.7 |
| | NGHC | 3.4 | NR | NR | 3.4 |
| | LMW | 0.2 | NR | NR | 0.1 |
| Purity by SE-UPLC (%) | Main | 99.3 | 99.3 | 99.3 | 99.3 |
| | LMW | 0.1 | 0.1 | 0.1 | 0.1 |
| | HMW | 0.6 | 0.6 | 0.6 | 0.6 |
| CEX-UPLC (%) | Region 1 | 34.3 | 34.2 | 34.3 | 34.2 |
| | Region 2 | 62.1 | 62.2 | 62.1 | 62.2 |
| | Region 3 | 3.6 | 3.6 | 3.6 | 3.6 |
| Relative Potency (%) | ADCC Assay | 92 | NR | NR | 107 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size exclusion; UPLC, ultra performance liquid chromatography; ADCC, Antibody-Dependent Cellular Cytotoxicity

TABLE 60

Research Stability of 100 mg/mL H1H17139P C2P1 Formulated Drug Substance - Effect of Accelerated Conditions

| Formulation | 100 mg/mL H1H17139P, 10 mM L-histidine, 10% (w/v) sucrose, 0.1% (w/v) polysorbate 80, pH 6.0 |
| --- | --- |
| Container/Closure | 5 mL gamma-irradiated polycarbonate vial with HDPE closure |

| Assay | 5° C. Storage (days) | | | | 25° C./60% RH Storage (days) | | |
| --- | --- | --- | --- | --- | --- | --- | --- |
| | t = 0 | 14 | 28 | 56 | 7 | 14 | 28 |
| Physical form/Condition | LEFVP | LEFVP | LEFVP | LEFVP | LEFVP | LEFVP | LEFVP |
| Clarity | ≤6 NTU | ≤6 NTU | ≤6 NTU | ≤6 NTU | ≤6 NTU | ≤6 NTU | ≤6 NTU |
| Color | ≤BY4 | ≤BY4 | ≤BY4 | ≤BY4 | ≤BY4 | ≤BY4 | ≤BY4 |
| pH | 6.0 | 5.9 | 6.1 | 6.0 | 6.1 | 6.0 | 6.0 |
| Total Protein Content by RP-UPLC (mg/mL) | 94.4 | 94.2 | 94.7 | 99.5 | 93.7 | 94.7 | 94.9 |

TABLE 60-continued

Research Stability of 100 mg/mL H1H17139P C2P1 Formulated Drug Substance - Effect of Accelerated Conditions Formulation: 100 mg/mL H1H17139P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | 5° C. Storage (days) | | | 25° C./60% RH Storage (days) | | |
|---|---|---|---|---|---|---|---|
| | | t = 0 | 14 | 28 | 56 | 7 | 14 | 28 |
| Non-reduced MCE (%) | Purity | 95.0 | NR | NR | 94.9 | NR | NR | 94.8 |
| | LMW | 4.8 | NR | NR | 4.8 | NR | NR | 5.1 |
| Reduced MCE (%) | Purity | 95.6 | NR | NR | 95.9 | NR | NR | 95.7 |
| | NGHC | 3.4 | NR | NR | 3.2 | NR | NR | 3.4 |
| | LMW | 0.2 | NR | NR | 0.1 | NR | NR | 0.2 |
| Purity by SE-UPLC (%) | Main | 99.3 | 99.3 | 99.3 | 99.2 | 99.2 | 99.1 | 99.0 |
| | LMW | 0.1 | 0.1 | 0.1 | 0.1 | 0.1 | 0.1 | 0.1 |
| | HMW | 0.6 | 0.6 | 0.7 | 0.7 | 0.7 | 0.8 | 0.9 |
| CEX-UPLC (%) | Region 1 | 34.3 | 34.1 | 34.1 | 34.1 | 33.9 | 34.2 | 34.7 |
| | Region 2 | 62.1 | 62.2 | 62.2 | 62.2 | 62.2 | 61.7 | 61.1 |
| | Region 3 | 3.6 | 3.7 | 3.7 | 3.8 | 3.9 | 4.1 | 4.3 |
| Relative Potency (%) | ADCC Assay | 92 | NR | NR | 113 | NR | NR | 100 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography;
ADCC, Antibody-dependent cellular cytotoxicity

TABLE 61

Research Stability of 100 mg/mL H1H17139P C2P1 Formulated Drug Substance - Effects of Stress Conditions Formulation: 100 mg/mL H1H17139P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | Length of storage at 40° C./75% RH (days) | | | |
|---|---|---|---|---|---|
| | | T = 0 | 7 | 14 | 28 |
| Physical form/Condition | | LEFVP | LEFVP | LEFVP | LEFVP |
| Clarity | | ≤6 NTU | ≤6 NTU | ≤6 NTU | ≤6 NTU |
| Color | | ≤BY4 | ≤BY4 | ≤BY4 | ≤BY4 |
| pH | | 6.0 | 6.0 | 6.0 | 6.0 |
| Total Protein Content by RP-UPLC (mg/mL) | | 94.4 | 95.3 | 95.4 | 96.7 |
| Non-reduced MCE (%) | Purity | 95.0 | NR | NR | 92.3 |
| | LMW | 4.8 | NR | NR | 6.8 |
| Reduced MCE (%) | Purity | 95.6 | NR | NR | 94.7 |
| | NGHC | 3.4 | NR | NR | 3.4 |
| | LMW | 0.2 | NR | NR | 0.7 |
| Purity by SE-UPLC (%) | Main | 99.3 | 98.8 | 98.5 | 98.0 |
| | LMW | 0.1 | 0.2 | 0.3 | 0.5 |
| | HMW | 0.6 | 1.0 | 1.2 | 1.5 |
| CEX-UPLC (%) | Region 1 | 34.3 | 36.3 | 39.3 | 45.4 |
| | Region 2 | 62.1 | 59.0 | 55.6 | 49.2 |
| | Region 3 | 3.6 | 4.7 | 5.1 | 5.5 |
| Relative Potency (%) | ADCC Assay | 92 | NR | NR | 97 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size-exclusion; UPLC, ultra performance liquid chromatography; ADCC, Antibody-dependent cellular cytotoxicity

TABLE 62

Research Stability of 100 mg/mL H1H17139P C2P1 Formulation Drug Substance - Effect of Agitation and Freezing and Thawing Formulation: 100 mg/mL H1H17139P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | Agitation (minutes) | | | Freeze/Thaw (cycles) | |
|---|---|---|---|---|---|---|
| | | t = 0 | 60 | 120 | 4 | 8 |
| Physical form/Condition | | LEFVP | LEFVP | LEFVP | LEFVP | LEFVP |
| Clarity | | ≤6 NTU | ≤6 NTU | ≤6 NTU | ≤6 NTU | ≤6 NTU |
| Color | | ≤BY4 | ≤BY4 | ≤BY4 | ≤BY4 | ≤BY4 |
| pH | | 6.0 | 6.0 | 6.0 | 6.0 | 6.0 |
| Total Protein Content by RP-UPLC (mg/mL) | | 94.4 | 94.0 | 94.4 | 94.4 | 94.9 |

TABLE 62-continued

Research Stability of 100 mg/mL H1H17139P C2P1 Formulation Drug Substance - Effect of Agitation and Freezing and Thawing

| | | | | | | |
|---|---|---|---|---|---|---|
| Non-reduced MCE (%) | Purity | 95.0 | NR | 95.0 | NR | 94.9 |
| | LMW | 4.8 | NR | 4.9 | NR | 4.8 |
| Reduced MCE (%) | Purity | 95.6 | NR | 95.9 | NR | 95.8 |
| | NGHC | 3.4 | NR | 3.3 | NR | 3.2 |
| | LMW | 0.2 | NR | 0.1 | NR | 0.2 |
| Purity by SE-UPLC (%) | Main | 99.3 | 99.3 | 99.3 | 99.3 | 99.4 |
| | LMW | 0.1 | 0.1 | 0.1 | 0.1 | 0.1 |
| | HMW | 0.6 | 0.6 | 0.6 | 0.6 | 0.6 |
| CEX-UPLC (%) | Region 1 | 34.3 | 34.3 | 34.2 | 34.1 | 34.3 |
| | Region 2 | 62.1 | 62. | 62.2 | 62.2 | 62.1 |
| | Region 3 | 3.6 | 3.6 | 3.7 | 3.7 | 3.6 |
| Relative Potency (%) | ADCC Assay | 92 | NR | 120 | NR | 92 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size exclusion; UPLC, ultra performance liquid chromatography; ADCC, Antibody-dependent cellular cytotoxicity

TABLE 63

Research Stability of 100 mg/mL H1H17161P C2P1 Formulated Drug Substance Stored at −80° C.

| | |
|---|---|
| Formulation | 100 mg/mL H1H17161P, 10 mM L-histidine, 10% (w/v) sucrose, 0.1% (w/v) polysorbate 80, pH 6.0 |
| Container/Closure | 5 mL gamma-irradiated polycarbonate vial with HDPE closure |

| | | Length of Storage at −80° C. (months) | | | | | |
|---|---|---|---|---|---|---|---|
| Assay | | 0 | 1 | 3 | 6 | 9 | 12 |
| Physical form/Condition | | LEFVP | LEFVP | LEFVP | LEFVP | LEFVP | LEFVP |
| Clarity | | ≤6 NTU | ≤6 NTU | ≤6 NTU | ≤6 NTU | ≤6 NTU | ≤6 NTU |
| Color | | ≤BY3 | ≤BY3 | ≤BY3 | ≤BY3 | ≤BY3 | ≤BY3 |
| pH | | 6.0 | 6.0 | 6.1 | 6.0 | 6.0 | 6.0 |
| Total Protein Content by RP-UPLC (mg/mL) | | 95.8 | 95.8 | 95.8 | 97.0 | 99.1 | 97.3 |
| Non-reduced MCE (%) | Purity | 95.7 | NR | NR | 95.7 | NR | 95.6 |
| | LMW | 3.9 | NR | NR | 3.9 | NR | 3.9 |
| Reduced MCE (%) | Purity | 96.0 | NR | NR | 96.2 | NR | 96.2 |
| | NGHC | 3.5 | NR | NR | 3.3 | NR | 3.5 |
| | LMW | 0.0 | NR | NR | 0.0 | NR | 0.0 |
| Purity by SE-UPLC (%) | Main | 98.8 | 98.8 | 98.8 | 98.7 | 98.5 | 98.8 |
| | LMW | 0.1 | 0.2 | 0.1 | 0.2 | 0.3 | 0.1 |
| | HMW | 1.1 | 1.1 | 1.1 | 1.1 | 1.2 | 1.1 |
| Charge Variant Analysis by CEX-UPLC (%) | Region 1 | 48.2 | 47.9 | 47.7 | 47.7 | 48.2 | 48.7 |
| | Region 2 | 45.2 | 45.5 | 46. | 46.9 | 45.3 | 45.3 |
| | Region 3 | 6.7 | 6.6 | 6.2 | 5.4 | 6.6 | 6.1 |
| Relative Potency (%) | Pseudovirus Neutralization assay | 110 | NR | NR | 137 | NR | 112 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography

TABLE 64

Research Stability of 100 mg/mL H1H17161P C2P1 Formulated Drug Substance Stored at −30° C.

Formulation: 100 mg/mL H1H17161P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | Length of Storage at −30° C. (months) | | | | | |
|---|---|---|---|---|---|---|---|
| | | 0 | 1 | 3 | 6 | 9 | 12 |
| Physical form/Condition | | LEFVP | LEFVP | LEFVP | LEFVP | LEFVP | LEFVP |
| Clarity | | ≤6 NTU | ≤6 NTU | ≤6 NTU | ≤6 NTU | ≤6 NTU | ≤6 NTU |
| Color | | ≤BY3 | ≤BY3 | ≤BY3 | ≤BY3 | ≤BY3 | ≤BY3 |
| pH | | 6.0 | 6.0 | 6.1 | 6.0 | 6.0 | 6.0 |
| Total Protein Content by RP-UPLC (mg/mL) | | 95.8 | 95.8 | 95.8 | 96.8 | 99.4 | 97.5 |
| Non-reduced MCE (%) | Purity | 95.7 | NR | NR | 95.7 | NR | 95.7 |
| | LMW | 3.9 | NR | NR | 3.9 | NR | 3.9 |
| Reduced MCE (%) | Purity | 96.0 | NR | NR | 96.1 | NR | 96.2 |
| | NGHC | 3.5 | NR | NR | 3.4 | NR | 3.3 |
| | LMW | 0.0 | NR | NR | 0.0 | NR | 0.0 |
| Purity by SE-UPLC (%) | Main | 98.8 | 98.8 | 98.8 | 98.7 | 98.5 | 98.8 |
| | LMW | 0.1 | 0.1 | 0.1 | 0.2 | 0.2 | 0.2 |
| | HMW | 1.1 | 1.1 | 1.1 | 1.1 | 1.2 | 1.1 |
| Charge Variant Analysis by CEX-UPLC (%) | Region 1 | 48.2 | 48.0 | 47.7 | 47.6 | 48.3 | 48.9 |
| | Region 2 | 45.2 | 45.4 | 46.2 | 47.1 | 45.1 | 45.1 |
| | Region 3 | 6.7 | 6.6 | 6.2 | 5.3 | 6.6 | 6.0 |
| Relative Potency (%) | Pseudovirus Neutralization Assay | 110 | NR | NR | 132 | NR | 106 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography

TABLE 65

Research Stability of 100 mg/mL H1H17161P C2P1 Formulated Drug Substance - Effect of Accelerated Conditions at −20° C.

Formulation: 100 mg/mL H1H17161P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | Length of Storage at −20° C. (months) | | | |
|---|---|---|---|---|---|
| | | 0 | 1 | 2 | 3 |
| Physical form/Condition | | LEFVP | LEFVP | LEFVP | LEFVP |
| Clarity | | ≤6 NTU | ≤6 NTU | ≤6 NTU | ≤6 NTU |
| Color | | ≤BY3 | ≤BY3 | ≤BY3 | ≤BY3 |
| pH | | 6.0 | 6.0 | 6.0 | 6.1 |
| Total Protein Content by RP-UPLC (mg/mL) | | 95.8 | 96.3 | 95.9 | 95.6 |
| Non-reduced MCE (%) | Purity | 95.7 | NR | NR | 95.6 |
| | LMW | 3.9 | NR | NR | 3.9 |
| Reduced MCE (%) | Purity | 96.0 | NR | NR | 95.9 |
| | NGHC | 3.5 | NR | NR | 3.7 |
| | LMW | 0.0 | NR | NR | 0.0 |
| Purity by SE-UPLC (%) | Main | 98.8 | 98.8 | 98.7 | 98.8 |
| | LMW | 0.1 | 0.1 | 0.2 | 0.1 |
| | HMW | 1.1 | 1.1 | 1.1 | 1.1 |
| CEX-UPLC (%) | Region 1 | 48.2 | 47.8 | 47.7 | 47.8 |
| | Region 2 | 45.2 | 45.5 | 46.1 | 46.0 |
| | Region 3 | 6.6 | 6.7 | 6.2 | 6.2 |
| Relative Potency (%) | Pseudovirus Neutralization Assay | 110 | NR | NR | 126 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size-exclusion; UPLC, ultra performance liquid chromatography

TABLE 66

Research Stability of 100 mg/mL H1H17161P C2P1 Formulated Drug Substance - Effect of Accelerated Conditions Formulation: 100 mg/mL H1H17161P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | 5° C. Storage (days) | | | | 25° C./60% RH Storage (days) | | |
|---|---|---|---|---|---|---|---|---|
| | | t = 0 | 14 | 28 | 56 | 7 | 14 | 28 |
| Physical form/Condition | | LEFVP | LEFVP | LEFVP | LEFVP | LEFVP | LEFVP | LEFVP |
| Clarity | | ≤6 NTU | ≤6 NTU | ≤6 NTU | ≤6 NTU | ≤6 NTU | ≤6 NTU | ≤6 NTU |
| Color | | ≤BY3 | ≤BY3 | ≤BY3 | ≤BY3 | ≤BY3 | ≤BY3 | ≤BY3 |
| pH | | 6.0 | 6.0 | 6.0 | 6.0 | 6.0 | 6.0 | 6.0 |
| Total Protein Content by RP-UPLC (mg/mL) | | 95.8 | 97.2 | 97.1 | 96.9 | 95.1 | 97.2 | 96.7 |
| Non-reduced MCE (%) | Purity | 95.7 | NR | NR | 95.5 | NR | NR | 95.1 |
| | LMW | 3.9 | NR | NR | 3.9 | NR | NR | 4.0 |
| Reduced MCE (%) | Purity | 96.0 | NR | NR | 96.1 | NR | NR | 95.7 |
| | NGHC | 3.5 | NR | NR | 3.4 | NR | NR | 3.5 |
| | LMW | 0.0 | NR | NR | 0.0 | NR | NR | 0.1 |
| Purity by SE-UPLC (%) | Main | 98.8 | 98.8 | 98.7 | 98.5 | 98.6 | 98.5 | 98.3 |
| | LMW | 0.1 | 0.1 | 0.2 | 0.2 | 0.2 | 0.2 | 0.2 |
| | HMW | 1.1 | 1.1 | 1.2 | 1.3 | 1.2 | 1.4 | 1.5 |
| CEX-UPLC (%) | Region 1 | 48.2 | 48.1 | 48.4 | 48.0 | 49.0 | 49.3 | 50.1 |
| | Region 2 | 45.2 | 45.3 | 44.9 | 45.6 | 44.3 | 43.6 | 42.8 |
| | Region 3 | 6.6 | 6.7 | 6.8 | 6.4 | 6.6 | 7.0 | 7.1 |
| Relative Potency (%) | Pseudovirus Neutralization Assay | 110 | NR | NR | 108 | NR | NR | 111 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography

TABLE 67

Research Stability of 100 mg/mL H1H17161P C2P1 Formulated Drug Substance - Effects of Stress Conditions Formulation: 100 mg/mL H1H17161P, 10 mM L-histidine, 10% (w/v) sucrose, 0.1% (w/v) polysorbate 80, pH 6.0
Container/Closure: 5 mL gamma-irradiated polycarbonate vial with HDPE closure

| Assay | | Length of storage at 40° C./75% RH (days) | | | |
|---|---|---|---|---|---|
| | | T = 0 | 7 | 14 | 28 |
| Physical form/Condition | | LEFVP | LEFVP | LEFVP | LEFVP |
| Clarity | | ≤6 NTU | ≤6 NTU | ≤6 NTU | ≤6 NTU |
| Color | | ≤BY3 | ≤BY3 | ≤BY3 | ≤BY3 |
| pH | | 6.0 | 6.0 | 6.0 | 6.0 |
| Total Protein Content by RP-UPLC (mg/mL) | | 95.8 | 97.0 | 96.4 | 97.4 |
| Non-reduced MCE (%) | Purity | 95.7 | NR | NR | 93.0 |
| | LMW | 3.9 | NR | NR | 5.7 |
| Reduced MCE (%) | Purity | 96.0 | NR | NR | 95.0 |
| | NGHC | 3.5 | NR | NR | 3.5 |
| | LMW | 0.0 | NR | NR | 0.4 |
| Purity by SE-UPLC (%) | Main | 98.8 | 98.2 | 97.9 | 97.4 |
| | LMW | 0.1 | 0.2 | 0.3 | 0.5 |
| | HMW | 1.1 | 1.5 | 1.8 | 2.1 |
| CEX-UPLC (%) | Region 1 | 48.2 | 52.1 | 56.2 | 62.6 |
| | Region 2 | 45.2 | 40.5 | 36.4 | 30.3 |
| | Region 3 | 6.6 | 7.4 | 7.4 | 7.1 |
| Relative Potency (%) | Pseudovirus Neutralization Assay | 110 | NR | NR | 114 |

CEX, cation exchange; FDS, formulated drug substance; FDG, Formulation Development Group; HDPE, high-density polyethylene; HMW, high molecular weight; LEFVP, liquid essentially free from visible particulates; LMW, low molecular weight; MCE, microchip capillary electrophoresis; NGHC, Non-glycosylated Heavy Chain; NR, not required per protocol; OD, optical density; RP, reversed-phase; SE, size-exclusion; UPLC, ultra performance liquid chromatography

TABLE 68

Research Stability of 100 mg/mL H1H17161P C2P1 Formulation Drug Substance - Effect of Agitation, and Freezing and Thawing Formulation: 100 mg/mL H1H17161P, 10 mM L-histidine, 10% (w/v), sucrose 0.1% (w/v) polysorbate 80, pH 6.0
Container/Closure: 5 mL gamma-irradiated polycarbonate vial with HDPE closure

| Assay | | t = 0 | Agitation (minutes) | | Freeze/Thaw (cycles) | |
|---|---|---|---|---|---|---|
| | | | 60 | 120 | 4 | 8 |
| Physical form/Condition | | 0 | 0 | 0 | 0 | 0 |
| Clarity | | ≤6 NTU | ≤6 NTU | ≤6 NTU | ≤6 NTU | ≤6 NTU |
| Color | | ≤BY3 | ≤BY3 | ≤BY3 | ≤BY3 | ≤BY3 |
| pH | | 6.0 | 6.0 | 6.0 | 6.0 | 5.9 |
| Total Protein Content by RP-UPLC (mg/mL) | | 95.8 | 96.5 | 94.0 | 96.2 | 96.2 |
| Non-reduced MCE (%) | Purity | 95.7 | NR | 95.8 | NR | 95.7 |
| | LMW | 3.9 | NR | 3.8 | NR | 3.8 |
| Reduced MCE (%) | Purity | 96.0 | NR | 96.2 | NR | 96.1 |
| | NGHC | 3.5 | NR | 3.4 | NR | 3.4 |
| | LMW | 0.0 | NR | 0.0 | NR | 0.0 |
| Purity by SE-UPLC (%) | Main | 98.8 | 98.8 | 98.8 | 98.8 | 98.8 |
| | LMW | 0.1 | 0.2 | 0.2 | 0.1 | 0.1 |
| | HMW | 1.1 | 1.1 | 1.1 | 1.1 | 1.1 |
| CEX-UPLC (%) | Region 1 | 48.2 | 48.7 | 48.6 | 48.6 | 48.6 |
| | Region 2 | 45.2 | 44.9 | 44.9 | 44.9 | 44.8 |
| | Region 3 | 6.6 | 6.5 | 6.5 | 6.6 | 6.6 |
| Relative Potency (%) | Pseudovirus Neutralization Assay | 110 | NR | 114 | NR | 115 |

CEX, cation exchange;
FDS, formulated drug substance;
FDG, Formulation Development Group;
HDPE, high-density polyethylene;
HMW, high molecular weight;
LEFVP, liquid essentially free from visible particulates;
LMW, low molecular weight;
MCE, microchip capillary electrophoresis;
NGHC, Non-glycosylated Heavy Chain;
NR, not required per protocol;
OD, optical density;
RP, reversed-phase;
SE, size-exclusion;
UPLC, ultra performance liquid chromatography

Example 11: Formulated Drug Substance Research Stability Studies for Co-Formulated H1H17203P, H1H17139P, and H1H17161P C2P1 DP Research stability studies were performed to evaluate the long-term storage, accelerated, and stress conditions for the Combination C2P1 OP manufactured for research and developmental use. Six months of research stability data are available at the long-term storage condition of 5° C., 6 months at the accelerated condition of 25° C./60% RH. Studies examining the stress conditions of 3 months at 40° C./75% RH, agitation, and freezing and thawing are complete.

Table 69 describes all stability studies examining the Combination C2P1 OP. The analysis plan, preliminary acceptance criteria, and sampling plan for the stability samples are provided in Table 70.
The stability studies will continue for the entire duration of the stability protocol as presented in Table 69. Samples were analyzed following the analysis plan outlined in Table 70.

TABLE 69

Summary of Combination Drug Product Stability Studies

| Study Type | Concentration (mg/mL) | Container Closure | Storage Conditions | Study Duration | Available Data |
|---|---|---|---|---|---|
| Research | 100 | 20 mL USP/EP glass vial with FluroTec-coated butyl stopper and Flip-Off seal | 5° C. | 84 months | 6 months |
| | | | 25° C./60% RH | 12 months | 6 months |
| | | | 40° C./75% RH | 3 months | 3 months |
| | | | Agitation | 120 minutes | 120 minutes |
| | | | Freezing and Thawing | 8 cycles | 8 cycles |

DP, drug product; USP, United States Pharmacopeia; EP, European Pharmacopoeia; RH, relative humidity

TABLE 70

Analysis Plan for Drug Product Research Stability Studies

| Assay | Research Samples to be Analyzed |
|---|---|
| Physical form/Condition | All samples |
| Clarity | All samples |
| Color | All samples |
| pH | All samples |
| Total Protein Content (RP-UPLC) | All samples |
| Purity by Reduced MCE<br>a. % Purity<br>b. % NGHC<br>c. % LMW | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |
| Purity by Non-reduced MCE<br>a. % Purity<br>b. % LMW<br>c. % HMW | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |
| Purity by SE-UPLC<br>a. % Main peak purity<br>b. % LMW<br>c. % HMW | All samples |
| Charge Variant Analysis by CEX-UPLC<br>a. % Region 1c<br>b. % Region 2c<br>c. % Region 3c<br>d. % Main Peak H1H17203P<br>e. % Main Peak H1H17139P<br>f. % Main Peak H1H17161P | All samples |
| Potency: ADCC Assay | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |
| Potency: Pseudovirus Neutralization Assay | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |
| Particulate Matter (light obscuration) | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |
| Particulate Matter (MFI) 2 μm ≤ x < 10 μm | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |
| Polysorbate 80 | T = 0, 6, 12, 24, 36, 48, 60, 72 and 84 months at 5° C.;<br>3 and 6 months at 25° C./60% RH;<br>1 and 3 months at 40° C./75% RH<br>Agitation and Freeze/Thaw samples |

$A_{280}$, absorbance at 280 nm; CEX, cation-exchange chromatography; EU, endotoxin units; HC, heavy chain; HMW, high molecular weight; LC, light chain; LMW, low molecular weight; MCE, microchip capillary electrophoresis; MFI, Micro-Flow Imaging ™; N/A, Not applicable; NGHC, non-glycosylated heavy chain; Ph. Eur., European Pharmacopeia; RH, relative humidity; SE-UPLC, size-exclusion ultra high-performance liquid chromatography; USP, United States Pharmacopeia Long-term Stability Study Results In the research long-term stability study, the Combination OP was physically and chemically stable when stored at 5° C. throughout the assessment period (Table 71). No appreciable change in the physical or chemical stability was detected in any of the monitored attributes after 6 months at 5° C. The research stability study examining OP under the long-term storage condition will continue through 84 months.

Accelerated Stability Study Results

Research stability study results from the analysis of OP under accelerated condition of 25° C./60% RH are provided in Table 72. Throughout the 6 month assessment period, increases of 0.9% in HMW species and 0.3% in LMW were observed by SE-UPLC. Reduction of 2.0%, 3.1%, and 5.1% in main peaks corresponding to the H1H17203P, H1H17139P and H1H17161P, respectively, were observed by CEX-UPLC. The OP maintained potency following incubation at 25° C./60% RH for 6 months. Sub-visible particle level as determined by HIAC was within the acceptance criteria. No meaningful change in other monitored attributes was observed. Research studies examining DP under the accelerated storage condition of 25° C./60% RH are complete.

Stress Stability Study Results

Research stability study results from the analysis of DP under stress conditions of 40° C./75% RH are provided in Table 72. Throughout the 3 month assessment period, increases of 3.0% in HMW and 1.3% in LMW were observed by SE-UPLC; reductions in purity of 3.8% or 7.8% and increases in LMW species of 1.8% or 6.4% were observed by reduced or non-reduced MCE, respectively; and reduction of 9.3%, 11.5%, and 11.4% in main peaks corresponding to the H1H17203P, H1H17139P and H1H17161P, respectively, were observed by CEX-UPLC. The DP maintained potency as determined by the pseudovirus neutralization assay. The DP maintained potency following the incubation at 40° C./75% RH for 28 days but showed reduced potency after incubation for 3 months as determined by the ADCC assay. Sub-visible particle level as determined by HIAC was within the acceptance criteria. No meaningful change in other monitored attributes was observed. Research studies examining DP under the stress storage condition of 40° C./75% RH are complete.

Research stability results from the analysis of DP following agitation and freeze/thaw conditions are provided in Table 73. DP was physically and chemically stable when agitated (vortexed at ambient temperature) for 120 minutes or when subjected to 4 freeze/thaw cycles (freezing at −30° C. and thawing at room temperature). No meaningful change in the physical or chemical stability of the DP was observed in any of the monitored attributes. Research studies examining DP under agitation and freeze/thaw conditions are complete.

Stability Conclusions

The recommended storage for the Combination DP is 2° C. to 8° C. Data from DP stability studies demonstrate that the product will remain stable when stored at 2° C. to 8° C.

TABLE 71

Research Stability of H1H17203P- H1H17139P-H1H17161P Co-Formulated Drug Product 100 mg/mL, Stored at 5° C.

| Formulation | 33.3 mg/mL H1H17203P, 33.3 mg/mL H1H17139P, and 33.3 mg/mL H1H17161P recombinant proteins, in an aqueous buffered solution, pH 6.0, containing 10 mM L-histidine, 10% (w/v) sucrose, and 0.1% (w/v) polysorbate 80 |
|---|---|
| Container Closure | 20 mL USP/Ph. Eur. Type 1 borosilicate glass vial; 20 mm FluroTec ®-coated butyl single-vent stopper; 20 mm Flip-Off ® seal |
| Storage Condition | 5° C. |

| | Length of Storage (months) | | | |
|---|---|---|---|---|
| Assay | T = 0 | 1 | 3 | 6 |
| Physical form/Condition | LEFVP | LEFVP | LEFVP | LEFVP |
| Clarity | ≤6 NTU | ≤6 NTU | ≤6 NTU | ≤6 NTU |
| Color | ≤BY4 | ≤BY4 | ≤BY4 | ≤BY4 |
| pH | 6.0 | 6.0 | 6.0 | 6.0 |

TABLE 71-continued

Research Stability of H1H17203P- H1H17139P-H1H17161P Co-Formulated Drug Product 100 mg/mL, Stored at 5° C.

| | | | | | |
|---|---|---|---|---|---|
| Total Protein Content by RP-UPLC (mg/mL) | | 98.5 | 98.4 | 97.3 | 96.6 |
| Polysorbate 80 (% w/v) | | 0.09 | NR | NR | 0.09 |
| % Relative Potency by Bioassay | ADCC | 89 | NR | NR | 95 |
| | Pseudovirus Neutralization | 105 | NR | NR | 120 |
| Reduced MCE (%) | Purity | 94.4 | NR | NR | 94.7 |
| | NGHC | 4.7 | NR | NR | 4.5 |
| | LMW | 0.1 | NR | NR | 0.2 |
| Non-reduced MCE (%) | Purity | 95.4 | NR | NR | 95.6 |
| | LMW | 4.1 | NR | NR | 4.0 |
| SE-UPLC (%) | Main | 99.1 | 99.0 | 98.8 | 98.8 |
| | LMW | 0.1 | 0.1 | 0.1 | 0.1 |
| | HMW | 0.9 | 0.9 | 1.2 | 1.1 |
| Charge Variant Analysis by CEX-UPLC (%) | Region 1C | 10.9 | 10.8 | 11.0 | 11.5 |
| | Region 2C | 13.3 | 13.2 | 13.3 | 13.5 |
| | Region 3C | 18.4 | 18.4 | 18.0 | 18.6 |
| | H1H17203P Main | 19.3 | 19.4 | 19.4 | 19.2 |
| | H1H17139P Main | 21.1 | 21.2 | 21.1 | 20.9 |
| | H1H17161P Main | 17.0 | 16.9 | 17.2 | 16.4 |
| Particulate Matter (light obscuration) (particles/container) | ≥10 µm | 39 | NR | NR | 5 |
| | ≥25 µm | 15 | NR | NR | 0 |
| Particulate Matter (MFI) (particles/mL) | 2 to 10 µm | 195 | NR | NR | 90 |

HMW, high molecular weight; LEFVP, liquid essentially free from visible particulates; LMW, low molecular weight; MCE, microchip capillary electrophoresis; MFI, Micro-Flow Imaging ™; NGHC, non-glycosylated heavy chain; SE, Size-exclusion; UPLC, Ultra-high pressure liquid chromatography; CEX, Cation exchange chromatography; RP, reversed-phase; ADCC, Antibody-dependent cellular cytotoxicity; NR, Not required

TABLE 72

Research Stability of H1H17203P-H1H17139P-H1H17161P Co-Formulated Drug Product 100 mg/mL, Stored at 25° C./60% RH and 40° C./75% RH

| | |
|---|---|
| Formulation | 33.3 mg/mL H1H17203P, 33.3 mg/mL H1H17139P, and 33.3 mg/mL H1H17161P recombinant proteins, in an aqueous buffered solution, pH 6.0, containing 10 mM L-histidine, 10% (w/v) sucrose, and 0.1% (w/v) polysorbate 80 |
| Container | 20 mL USP/Ph. Eur. Type 1 borosilicate glass vial; 20 mm FluroTec ®-coated butyl |
| Closure | single-vent stopper; 20 mm Flip-Off ® seal |

| | | | 25° C./60% RH Storage (months) | | | | | 40° C./75% RH Storage (months) | | | |
|---|---|---|---|---|---|---|---|---|---|---|---|
| Assay | | T = 0 | 0.5 | 1 | 3 | 6 | 0.25 | 0.5 | 1 | 3 |
| Physical form/Condition | | LEFVP | LEFVP | LEFVP | LEFVP | LEFVP | LEFVP | LEFVP | LEFVP | LEFVP |
| Clarity | | ≤6 NTU | ≤6 NTU | ≤6 NTU | ≤6 NTU | ≤6 NTU | ≤6 NTU | ≤6 NTU | ≤6 NTU | ≤6 NTU |
| Color | | ≤BY4 | ≤BY4 | ≤BY4 | ≤BY4 | ≤BY4 | ≤BY4 | ≤BY4 | <BY4 | ≤BY4 |
| pH | | 6.0 | 6.0 | 6.0 | 6.0 | 6.0 | 6.0 | 6.0 | 6.0 | 6.0 |
| Total Protein Content by RP-UPLC (mg/mL) | | 98.5 | 98.7 | 98.2 | 96.9 | 96.1 | 98.2 | 98.3 | 98.8 | 96.8 |
| Polysorbate 80 (% w/v) | | 0.09 | NR | NR | 0.09 | 0.09 | NR | NR | 0.09 | 0.09 |
| % Relative Potency by Bioassay | ADCC | 89 | NR | NR | 93 | 82 | NR | NR | 83 | 45 |
| | Pseudovirus Neutralization | 105 | NR | NR | 112 | 124 | NR | NR | 101 | 99 |
| Reduced MCE (%) | Purity | 94.4 | NR | NR | 93.2 | 93.7 | NR | NR | 93.7 | 90.6 |
| | NGHC | 4.7 | NR | NR | 4.4 | 4.6 | NR | NR | 4.6 | 5.2 |
| | LMW | 0.1 | NR | NR | 0.3 | 0.7 | NR | NR | 0.5 | 1.9 |
| Non-reduced MCE (%) | Purity | 95.4 | NR | NR | 94.2 | 93.4 | NR | NR | 93.1 | 87.6 |
| | LMW | 4.1 | NR | NR | 4.9 | 5.5 | NR | NR | 6.0 | 10.5 |
| SE-UPLC (%) | Main | 99.1 | 98.9 | 98.7 | 98.2 | 97.8 | 98.6 | 98.3 | 97.7 | 94.7 |
| | LMW | 0.1 | 0.1 | 0.2 | 0.3 | 0.4 | 0.2 | 0.3 | 0.5 | 1.4 |
| | HMW | 0.9 | 1.1 | 1.2 | 1.6 | 1.8 | 1.3 | 1.4 | 1.8 | 3.9 |
| Charge Variant Analysis by CEX-UPLC (%) | Region 1C | 10.9 | 10.8 | 11.0 | 12.2 | 14.1 | 11.7 | 12.6 | 14.7 | 20.9 |
| | Region 2C | 13.3 | 13.3 | 13.7 | 15.1 | 16.8 | 14.5 | 15.7 | 18.1 | 25.0 |
| | Region 3C | 18.4 | 18.6 | 19.0 | 19.8 | 22.0 | 19.6 | 20.7 | 23.1 | 28.9 |
| | H1H17203P Main | 19.3 | 19.5 | 19.4 | 18.7 | 17.3 | 18.8 | 18.0 | 15.9 | 10.0 |
| | H1H17139P Main | 21.1 | 21.2 | 20.9 | 19.6 | 18.0 | 20.0 | 19.0 | 16.5 | 9.6 |
| | H1H17161P Main | 17.0 | 16.5 | 16.0 | 14.7 | 11.9 | 15.4 | 14.1 | 11.7 | 5.6 |

TABLE 72-continued

Research Stability of H1H17203P-H1H17139P-H1H17161P Co-Formulated Drug
Product 100 mg/mL, Stored at 25° C./60% RH and 40° C./75% RH

| Formulation | 33.3 mg/mL H1H17203P, 33.3 mg/mL H1H17139P, and 33.3 mg/mL H1H17161P recombinant proteins, in an aqueous buffered solution, pH 6.0, containing 10 mM L-histidine, 10% (w/v) sucrose, and 0.1% (w/v) polysorbate 80 |
| --- | --- |
| Container Closure | 20 mL USP/Ph. Eur. Type 1 borosilicate glass vial; 20 mm FluroTec ®-coated butyl single-vent stopper; 20 mm Flip-Off ® seal |

| | | | 25° C./60% RH Storage (months) | | | | 40° C./75% RH Storage (months) | | | |
| --- | --- | --- | --- | --- | --- | --- | --- | --- | --- | --- |
| Assay | | T = 0 | 0.5 | 1 | 3 | 6 | 0.25 | 0.5 | 1 | 3 |
| Particulate Matter (light obscuration) (particles/container) | ≥10 μm | 39 | NR | NR | 10 | 10 | NR | NR | 131 | 121 |
|  | ≥25 μm | 15 | NR | NR | 0 | 0 | NR | NR | 0 | 5 |
| Particulate Matter (MFI) (particles/mL) | 2 to 10 μm | 195 | NR | NR | 450 | 275 | NR | NR | 637 | 409 |

HMW, high molecular weight;
LEFVP, liquid essentially free from visible particulates;
LMW, low molecular weight;
MCE, microchip capillary electrophoresis;
MFI, Micro-Flow Imaging ™;
NGHC, non-glycosylated heavy chain;
SE, Size-exclusion;
UPLC, Ultra-high pressure liquid chromatography;
CEX, Cation exchange chromatography;
DCC, Antibody-dependent cellular cytotoxicity;
NR, Not required

TABLE 73

Research Stability of H1H17203P-H1H17139P-H1H17161P Co-Formulated Drug
Product - Effect of Agitation, and Freezing and Thawing

| Formulation | 33.3 mg/mL H1H17203P, 33.3 mg/mL H1H17139P, and 33.3 mg/mL H1H17161P recombinant proteins, in an aqueous buffered solution, pH 6.0, containing 10 mM L-histidine, 10% (w/v) sucrose, and 0.1% (w/v) polysorbate 80 |
| --- | --- |
| Container/Closure | 20 mL USP/Ph. Eur. Type 1 borosilicate glass vial; 20 mm FluroTec ®-coated butyl single-vent stopper; 20 mm Flip-Off ® seal |

| | | | Agitation (minutes) | | Freezing/Thawing (cycles) | |
| --- | --- | --- | --- | --- | --- | --- |
| Assay | | T = 0 | 60 | 120 | 4 | 8 |
| Physical form/Condition | | LEFVP | LEFVP | LEFVP | LEFVP | LEFVP |
| Clarity | | ≤6 NTU | ≤6 NTU | ≤6 NTU | ≤6 NTU | ≤6 NTU |
| Color | | ≤BY4 | <BY4 | ≤BY4 | ≤BY4 | ≤BY4 |
| pH | | 6.0 | 6.0 | 6.0 | 6.0 | 6.0 |
| Total Protein Content by RP-UPLC (mg/mL) | | 98.5 | 98.4 | 98.6 | 98.8 | 97.6 |
| Polysorbate 80 (% w/v) | | 0.09 | NR | 0.09 | 0.09 | 0.09 |
| % Relative Potency by Bioassay | ADCC | 89 | NR | 102 | 85 | 87 |
|  | Pseudovirus Neutralization | 105 | NR | 119 | 123 | 119 |
| Reduced MCE (%) | Purity | 94.4 | NR | 94.9 | 95.0 | 94.5 |
|  | NGHC | 4.7 | NR | 4.3 | 4.2 | 4.7 |
|  | LMW | 0.1 | NR | 0.2 | 0.2 | 0.1 |
| Non-reduced MCE (%) | Purity | 95.4 | NR | 95.4 | 95.4 | 95.4 |
|  | LMW | 4.1 | NR | 4.2 | 4.2 | 4.2 |
| Purity by SE-UPLC (%) | Main | 99.1 | 99.1 | 99.1 | 99.1 | 99.0 |
|  | LMW | 0.1 | 0.1 | 0.1 | 0.1 | 0.1 |
|  | HMW | 0.9 | 0.9 | 0.9 | 0.9 | 0.9 |
| Charge Variant Analysis by CEX-UPLC (%) | Region 1C | 10.9 | 10.8 | 10.9 | 10.9 | 10.4 |
|  | Region 2C | 13.3 | 13.2 | 13.2 | 13.3 | 13.3 |
|  | Region 3C | 18.4 | 18.4 | 18.4 | 18.5 | 18.4 |
|  | H1H17203P Main | 19.3 | 19.4 | 19.4 | 19.4 | 19.4 |
|  | H1H17139P Main | 21.1 | 21.2 | 21.2 | 21.2 | 21.3 |
|  | H1H17161P Main | 17.0 | 16.9 | 17.0 | 16.7 | 17.2 |

TABLE 73-continued

Research Stability of H1H17203P-H1H17139P-H1H17161P Co-Formulated Drug Product - Effect of Agitation, and Freezing and Thawing

| Formulation | 33.3 mg/mL H1H17203P, 33.3 mg/mL H1H17139P, and 33.3 mg/mL H1H17161P recombinant proteins, in an aqueous buffered solution, pH 6.0, containing 10 mM L-histidine, 10% (w/v) sucrose, and 0.1% (w/v) polysorbate 80 |
|---|---|
| Container/Closure | 20 mL USP/Ph. Eur. Type 1 borosilicate glass vial; 20 mm FluroTec ®-coated butyl single-vent stopper; 20 mm Flip-Off ® seal |

| Assay | | T = 0 | Agitation (minutes) 60 | 120 | Freezing/Thawing (cycles) 4 | 8 |
|---|---|---|---|---|---|---|
| Particulate Matter (light obscuration) (particles/container) | ≥10 μm | 39 | NR | 102 | 39 | 53 |
| | ≥25 μm | 15 | NR | 5 | 0 | 0 |
| Particulate Matter (MFI) (particles/mL) | 2 to 10 μm | 195 | NR | 372 | 534 | 494 |

HMW, high molecular weight;
LEFVP, liquid essentially free from visible particulates;
LMW, low molecular weight;
MCE, microchip capillary electrophoresis;
MFI, Micro-Flow Imaging ™;
NGHC, non-glycosylated heavy chain;
SE, Size-exclusion;
UPLC, Ultra-high pressure liquid chromatography;
CEX, Cation exchange chromatography;
DCC, Antibody-dependent cellular cytotoxicity;
NR, Not required Antibody Sequences Table 74 sets forth the amino acid sequence identifiers of the heavy and light chain variable regions and CDRs of selected anti-Ebola virus antibodies. Table 75 provides sequence identifiers for full length heavy and light chain amino acid sequences.

TABLE 74

Amino Acid Sequence Identifiers

| Antibody Designation | SEQ ID NOS: | | | | | | | |
|---|---|---|---|---|---|---|---|---|
| | HCVR | HCDR1 | HCDR2 | HCDR3 | LCVR | LCDR1 | LCDR2 | LCDR3 |
| H1H17203P | 2 | 4 | 6 | 8 | 10 | 12 | 14 | 16 |
| H1H17139P | 20 | 22 | 24 | 26 | 28 | 30 | 32 | 34 |
| H1H17161P | 38 | 40 | 42 | 44 | 46 | 48 | 50 | 52 |

TABLE 75

Sequence Identifiers for Full Length Heavy and Light Chain Sequences

| Antibody Designation | SEQ ID NOs: | |
| --- | --- | --- |
| | Full length Heavy Chain Amino Acid | Full length Light Chain Amino Acid |
| H1H17203P | 17 | 18 |
| H1H17139P | 35 | 36 |
| H1H17161P | 53 | 54 |

The present disclosure is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A stable liquid pharmaceutical formulation comprising:
   (a) sucrose at a concentration from 10%±2% to 20%±4% w/v;
   (b) a buffer comprising histidine at a concentration from 5 mM±1 mM to 20 mM±4 mM;
   (c) an organic cosolvent comprising polysorbate at a concentration from 0.01%±0.005% to 0.5%±0.25% w/v; and
   (d) at least one antibody which binds specifically to Ebola virus (EBOV) and comprises three heavy chain complementarity determining regions (CDRs) (HCDR1, HCDR2 and HCDR3) and three light chain CDRs (LCDR1, LCDR2 and LCDR3) contained in a heavy chain variable region/light chain variable region (HCVR/LCVR) amino acid sequence pair selected from the group consisting of (i) SEQ ID NOs: 2/10, (ii) SEQ ID NOs: 20/28, and (iii) SEQ ID NOs: 38/46;
   wherein the formulation comprises the following: (i), (ii), (iii), (i)+(ii), (i)+(iii), (ii)+(iii), or (i)+(ii)+(iii), at a total antibody concentration from 5 mg/mL±0.75 mg/mL to 250 mg/mL±37.5 mg/mL; and
   wherein the formulation has a pH of 6.0±0.3; and
   wherein the formulation maintains ADCC potency of at least about 90% in an ADCC bioassay and/or demonstrates that at least 90% of the antibody is the native species after storage at a temperature from about 40° C. to about 45° C. for no less than 20 days.

2. The pharmaceutical formulation of claim 1, wherein the total antibody concentration is 50 mg/mL±7.5 mg/mL.

3. The pharmaceutical formulation of claim 1, wherein the total antibody concentration is 100 mg/mL±15.0 mg/mL.

4. The pharmaceutical formulation of claim 1, wherein the polysorbate is polysorbate 80.

5. The pharmaceutical formulation of claim 1, comprising:
(a) from 10%±2% to 15%±3% w/v sucrose,
(b) from 5 mM±1 mM to 20 mM±4 mM histidine buffer,
(c) from 0.01%±0.005% to 0.5%±0.25% w/v polysorbate 80, and
(d) (i)+(ii)+(iii) in an amount of 50 mg/mL±7.5 mg/mL total antibody,
at pH 6.0±0.3.

6. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10.

7. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28.

8. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

9. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28.

10. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

11. The pharmaceutical formulation of claim 1 comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

12. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 50 mg/mL±7.5 mg/mL total antibody,
at pH 6.0±0.3;
wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

13. The pharmaceutical formulation of claim 1, comprising:
(a) from 10%±2% to 15%±3% w/v sucrose,
(b) from 5 mM±1 mM to 20 mM±4 mM histidine buffer,
(c) from 0.01%±0.005% to 0.5%±0.25% w/v polysorbate 80, and
(d) (i)+(ii)+(iii) in an amount of 100 mg/mL±15 mg/mL total antibody,
at pH 6.0±0.3.

14. The pharmaceutical formulation of claim 1, comprising:
(a) 10%±2% w/v sucrose,
(b) 10 mM±2 mM histidine buffer,
(c) 0.1%±0.05% w/v polysorbate 80, and
(d) 100 mg/mL±15 mg/mL total antibody,
at pH 6.0±0.3;
wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10.

15. The pharmaceutical formulation of claim 1, comprising:
    (a) 10%±2% w/v sucrose,
    (b) 10 mM±2 mM histidine buffer,
    (c) 0.1%±0.05% w/v polysorbate 80, and
    (d) 100 mg/mL±15 mg/mL total antibody,
    at pH 6.0±0.3;
    wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28.

16. The pharmaceutical formulation of claim 1, comprising:
    (a) 10%±2% w/v sucrose,
    (b) 10 mM±2 mM histidine buffer,
    (c) 0.1%±0.05% w/v polysorbate 80, and
    (d) 100 mg/mL±15 mg/mL total antibody,
    at pH 6.0±0.3;
    wherein the antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

17. The pharmaceutical formulation of claim 1, comprising:
    (a) 10%±2% w/v sucrose,
    (b) 10 mM±2 mM histidine buffer,
    (c) 0.1%±0.05% w/v polysorbate 80, and
    (d) 100 mg/mL±15 mg/mL total antibody,
    at pH 6.0±0.3;
    wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28.

18. The pharmaceutical formulation of claim 1, comprising:
    (a) 10%±2% w/v sucrose,
    (b) 10 mM±2 mM histidine buffer,
    (c) 0.1%±0.05% w/v polysorbate 80, and
    (d) 100 mg/mL±15 mg/mL total antibody,
    at pH 6.0±0.3;
    wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10 and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

19. The pharmaceutical formulation of claim 1, comprising:
    (a) 10%±2% w/v sucrose,
    (b) 10 mM±2 mM histidine buffer,
    (c) 0.1%±0.05% w/v polysorbate 80, and
    (d) 100 mg/mL±15 mg/mL total antibody,
    at pH 6.0±0.3;
    wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

20. The pharmaceutical formulation of claim 1, comprising:
    (a) 10%±2% w/v sucrose,
    (b) 10 mM±2 mM histidine buffer,
    (c) 0.1%±0.05% w/v polysorbate 80, and
    (d) 100 mg/mL±15 mg/mL total antibody,
    at pH 6.0±0.3;
    wherein a first antibody comprises three heavy chain CDRs (HCDR1, HCDR2 and HCDR3) and three light chain CDRs (LCDR1, LCDR2 and LCDR3) contained in the HCVR/LCVR amino acid sequence pair of (i) SEQ ID NOs: 2/10, a second antibody comprises three heavy chain CDRs (HCDR1, HCDR2 and HCDR3) and three light chain CDRs (LCDR1, LCDR2 and LCDR3) contained in the HCVR/LCVR amino acid sequence pair of (ii) SEQ ID NOs: 20/28, and a third antibody comprises three heavy chain CDRs (HCDR1, HCDR2 and HCDR3) and three light chain CDRs (LCDR1, LCDR2 and LCDR3) contained in the HCVR/LCVR amino acid sequence pair of (iii) SEQ ID NOs: 38/46.

21. The pharmaceutical formulation of claim 1 comprising:
    (a) a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46, respectively, and wherein the total antibody concentration is 50 mg/mL±7.5 mg/mL,
    (b) 10 mM±2 mM histidine buffer, pH 6.0±0.3,
    (c) 0.1%±0.05% w/v polysorbate 80, and
    (d) 10%±2% w/v sucrose; wherein:
    (i) at least 96% of the antibody is the native species after 12 months at 5° C.;
    (ii) at least 97% of the antibody is the native species after 120 minutes agitation; and
    (iii) at least 97% of the antibody is the native species after 8 freeze thaw cycles.

22. The pharmaceutical formulation of claim 1 comprising:
    (a) a combination of three antibodies that bind specifically to EBOV, wherein the three antibodies comprise a heavy chain variable region/light chain variable region (HCVR/LCVR) amino acid sequence pair of (i) SEQ ID NOs: 2/10, (ii) SEQ ID NOs: 20/28, and (iii) SEQ ID NOs: 38/46, respectively, and wherein the total antibody concentration is 100 mg/mL±15 mg/mL,
    (b) 10 mM±2 mM histidine buffer, pH 6.0±0.3,
    (c) 0.1%±0.05% w/v polysorbate 80, and
    (d) 10%±2% w/v sucrose; wherein:
    (i) at least 96% of the antibody is the native species after 12 months at 5° C.;
    (ii) at least 97% of the antibody is the native species after 120 minutes agitation; and
    (iii) at least 97% of the antibody is the native species after 8 freeze thaw cycles.

23. The pharmaceutical formulation of claim 1, wherein the antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16.

24. The pharmaceutical formulation of claim 1, wherein the antibody comprises an HCVR of SEQ ID NO: 2 and an LCVR of SEQ ID NO: 10.

25. The pharmaceutical formulation of claim 1, wherein the antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34.

26. The pharmaceutical formulation of claim 1, wherein the antibody comprises an HCVR of SEQ ID NO: 20 and an LCVR of SEQ ID NO: 28.

27. The pharmaceutical formulation of claim 1, wherein the antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

28. The pharmaceutical formulation of claim 1, wherein the antibody comprises an HCVR of SEQ ID NO: 38 and an LCVR of SEQ ID NO: 46.

29. A kit comprising the pharmaceutical formulation of claim 1, a container, and instructions.

30. The kit of claim 29, wherein the container is a glass vial.

31. The kit of claim 29, wherein the container is a prefilled syringe.

32. The kit of claim 29, wherein the container is an autoinjector.

33. The pharmaceutical formulation of claim 1, wherein the antibodies or antigen-binding fragments thereof of (i)+(ii)+(iii) are present in a ratio of 1:1:1.

34. The pharmaceutical formulation of claim 1, formulated for intravenous administration, intramuscular administration, subcutaneous administration, intraperitoneal administration, percutaneous administration, mucosal administration, nasal administration, pulmonary administration, or oral administration.

35. A stable liquid pharmaceutical formulation comprising:
  (a) sucrose at a concentration of 10%±2% w/v;
  (b) a buffer comprising histidine at a concentration less than 10 mM±2 mM;
  (c) an organic cosolvent comprising polysorbate at a concentration less than 0.2%±0.1% w/v; and
  (d) a first antibody comprising three heavy chain CDRs (HCDR1, HCDR2 and HCDR3) and three light chain CDRs (LCDR1, LCDR2 and LCDR3) contained in the HCVR/LCVR amino acid sequence pair of SEQ ID NOs: 2/10;
  a second antibody comprising three heavy chain CDRs (HCDR1, HCDR2 and HCDR3) and three light chain CDRs (LCDR1, LCDR2 and LCDR3) contained in the HCVR/LCVR amino acid sequence pair of SEQ ID NOs: 20/28, and
  a third antibody comprising three heavy chain CDRs (HCDR1, HCDR2 and HCDR3) and three light chain CDRs (LCDR1, LCDR2 and LCDR3) contained in the HCVR/LCVR amino acid sequence pair of SEQ ID NOs: 38/46,
  wherein the concentration of each of the first antibody, the second antibody and the third antibody in the formulation is from 10 mg/ml±0.75 mg/mL to 40 mg/ml±7.5 mg/mL;
  wherein the formulation has a pH of 6.0±0.3; and
  wherein the formulation maintains ADCC potency of at least about 90% in an ADCC bioassay and/or demonstrates that at least 90% of the antibody is the native species after storage at a temperature from about 40° C. to about 45° C. for no less than 20 days.

36. The pharmaceutical formulation of claim 35, wherein the concentration of each of the first antibody, the second antibody and the third antibody is 16.67 mg/mL±1.25 mg/ml.

37. The pharmaceutical formulation of claim 35, wherein the concentration of each of the first antibody, the second antibody and the third antibody is 33.33 mg/mL±2.5 mg/ml.

38. The pharmaceutical formulation of claim 35, further comprising L-histidine monohydrochloride monohydrate at a concentration of no more than 25 mM±5 mM.

39. The pharmaceutical formulation of claim 35, wherein the first antibody comprises an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16.

40. The pharmaceutical formulation of claim 39, wherein the first antibody comprises an HCVR of SEQ ID NO: 2 and an LCVR of SEQ ID NO: 10.

41. The pharmaceutical formulation of claim 40, wherein the first antibody comprises a heavy chain of SEQ ID NO: 17 and a light chain of SEQ ID NO: 18.

42. The pharmaceutical formulation of claim 35, wherein the second antibody comprises an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34.

43. The pharmaceutical formulation of claim 42, wherein the second antibody comprises an HCVR of SEQ ID NO: 20 and an LCVR of SEQ ID NO: 28.

44. The pharmaceutical formulation of claim 43, wherein the second antibody comprises a heavy chain of SEQ ID NO: 35 and a light chain of SEQ ID NO: 36.

45. The pharmaceutical formulation of claim 35, wherein the third antibody comprises an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52.

46. The pharmaceutical formulation of claim 45, wherein the third antibody comprises an HCVR of SEQ ID NO: 38 and an LCVR of SEQ ID NO: 46.

47. The pharmaceutical formulation of claim 46, wherein the third antibody comprises a heavy chain of SEQ ID NO: 53 and a light chain of SEQ ID NO: 54.

48. The pharmaceutical formulation of claim 35, wherein said formulation is contained in a container.

49. The pharmaceutical formulation of claim 48, wherein the container is a vial and the total volume of the pharmaceutical formulation contained in each vial is 14.5 mL±0.5 mL.

50. The pharmaceutical formulation of claim 49, wherein the pharmaceutical formulation contained in each vial comprises 0.74 mg/mL±0.05 mg/mL of L-histidine, 1.09 mg/mL±0.05 mg/mL of L-histidine monohydrochloride monohydrate, 1 mg/mL±0.05 mg/mL of polysorbate 80, 100 mg/mL±5 mg/mL of sucrose and water.

51. The pharmaceutical formulation of claim 35, formulated for intravenous administration.

52. The pharmaceutical formulation of claim 35, wherein the first antibody, the second antibody and the third antibody in the formulation are at a 1:1:1 ratio and the final dose of the three antibodies to be administered is 150 mg/kg±15 mg/kg of body weight.

53. The pharmaceutical formulation of claim 51, wherein the formulation is diluted in a PVC intravenous (IV) bag containing 0.9% Sodium Chloride, 5% Dextrose or Lactated Ringer's prior to the intravenous administration.

54. The pharmaceutical formulation of claim 53, wherein the final concentration of each of the first antibody, the second antibody and the third antibody after dilution is between about 2 mg/mL to about 30 mg/mL.

55. The pharmaceutical formulation of claim 53, wherein the duration of the intravenous administration of the diluted formulation is between about 2 hours to about 4 hours.

56. A stable liquid pharmaceutical formulation at a volume of 14.5 mL comprising:
   (a) 16.67 mg/mL of a first antibody comprising an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16,
   (b) 16.67 mg/mL of a second antibody comprising an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34, and
   (c) 16.67 mg/mL of a third antibody comprising an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52,
   (d) sucrose at a concentration of 10%±2% w/v,
   (e) a buffer comprising histidine at a concentration less than 10 mM±2 mM,
   (f) an organic cosolvent comprising polysorbate at a concentration less than 0.2%±0.1% w/v,
wherein the formulation maintains ADCC potency of at least about 90% in an ADCC bioassay and/or demonstrates that at least 90% of the antibody is the native species after storage at a temperature from about 40° C. to about 45° C. for no less than 20 days.

57. The stable liquid pharmaceutical formulation of claim 56, wherein
   the first antibody comprises an HCVR of SEQ ID NO: 2 and an LCVR of SEQ ID NO: 10,
   the second antibody comprises an HCVR of SEQ ID NO: 20 and an LCVR of SEQ ID NO: 28,
   and the third antibody comprises an HCVR of SEQ ID NO: 38 and an LCVR of SEQ ID NO: 46.

58. The stable liquid pharmaceutical formulation of claim 56, wherein the first antibody comprises a heavy chain of SEQ ID NO: 17 and a light chain of SEQ ID NO: 18,
   the second antibody comprises a heavy chain of SEQ ID NO: 35 and a light chain of SEQ ID NO: 36; and
   the third antibody comprises a heavy chain of SEQ ID NO: 53 and a light chain of SEQ ID NO: 54.

59. The stable liquid pharmaceutical formulation of claim 56 comprising:
   0.74 mg/mL of L-histidine,
   1.09 mg/mL of L-histidine monohydrochloride monohydrate,
   1 mg/mL of polysorbate 80,
   100 mg/mL of sucrose, and
   water;
   wherein the formulation has a pH of 6.0.

60. A stable liquid pharmaceutical formulation at a volume of 14.5 mL comprising:
   (a) 33.33 mg/mL of a first antibody comprising an HCDR1 of SEQ ID NO: 4, an HCDR2 of SEQ ID NO: 6, an HCDR3 of SEQ ID NO: 8, an LCDR1 of SEQ ID NO: 12, an LCDR2 of SEQ ID NO: 14, and an LCDR3 of SEQ ID NO: 16,
   (b) 33.33 mg/mL of a second antibody comprising an HCDR1 of SEQ ID NO: 22, an HCDR2 of SEQ ID NO: 24, an HCDR3 of SEQ ID NO: 26, an LCDR1 of SEQ ID NO: 30, an LCDR2 of SEQ ID NO: 32, and an LCDR3 of SEQ ID NO: 34, and
   (c) 33.33 mg/mL of a third antibody comprising an HCDR1 of SEQ ID NO: 40, an HCDR2 of SEQ ID NO: 42, an HCDR3 of SEQ ID NO: 44, an LCDR1 of SEQ ID NO: 48, an LCDR2 of SEQ ID NO: 50, and an LCDR3 of SEQ ID NO: 52,
   (d) sucrose at a concentration of 10%±2% w/v,
   (e) a buffer comprising histidine at a concentration less than 10 mM±2 mM,
   (f) an organic cosolvent comprising polysorbate at a concentration less than 0.2%±0.1% w/v,
wherein the formulation maintains ADCC potency of at least about 90% in an ADCC bioassay and/or demonstrates that at least 90% of the antibody is the native species after storage at a temperature from about 40° C. to about 45° C. for no less than 20 days.

61. The stable liquid pharmaceutical formulation of claim 60, wherein
   the first antibody comprises an HCVR of SEQ ID NO: 2 and an LCVR of SEQ ID NO: 10;
   the second antibody comprises an HCVR of SEQ ID NO: 20 and an LCVR of SEQ ID NO: 28,
   and the third antibody comprises an HCVR of SEQ ID NO: 38 and an LCVR of SEQ ID NO: 46.

62. The stable liquid pharmaceutical formulation of claim 60, wherein
   the first antibody comprises a heavy chain of SEQ ID NO: 17 and a light chain of SEQ ID NO: 18;
   the second antibody comprises a heavy chain of SEQ ID NO: 35 and a light chain of SEQ ID NO: 36; and
   the third antibody comprises a heavy chain of SEQ ID NO: 53 and a light chain of SEQ ID NO: 54.

63. The stable liquid pharmaceutical formulation of claim 60, comprising:
   0.74 mg/mL of L-histidine,
   1.09 mg/mL of L-histidine monohydrochloride monohydrate,
   1 mg/mL of polysorbate 80,
   100 mg/mL of sucrose, and
   water;
   wherein the formulation has a pH of 6.0.

* * * * *